(12) United States Patent
Herz et al.

(10) Patent No.: US 6,428,967 B1
(45) Date of Patent: Aug. 6, 2002

(54) LDL RECEPTOR SIGNALING PATHWAYS

(75) Inventors: Joachim Herz; Michael Gotthardt, both of Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/562,737

(22) Filed: May 1, 2000

(51) Int. Cl.[7] .................. G01N 33/53; G01N 33/68; C07K 14/705; C07K 14/775
(52) U.S. Cl. .................. 435/7.1; 435/69.6; 435/7.2; 530/350; 530/300; 530/301; 530/324
(58) Field of Search ................ 435/7.1, 69.6; 514/2, 4; 530/350, 300, 301, 324

(56) References Cited

FOREIGN PATENT DOCUMENTS

WO   WO 01/84159 A2 * 11/2001 .......... G01N/33/68

OTHER PUBLICATIONS

Liao et al. 2000, Neurochem. vol. 75, pp. 282–287. The postsynaptic density protein PSD–95 differentially regulates insulin–and src–mediated current modulation of mouse NMDA receptors expressed in Xenopus oocytes.*
Yamada et al. 1999, J Biol Chem vol. 274, pp. 6647–6652. Modulation of the channel activity of the epsilon2/eta 1 subtype N–MDA receptor by PSD–95.*
Arnold DB et al. 1999, Neuron vol. 23, pp. 149–157. Molecular determinants for sub–cellular localization of PSD–95 with an interacting K channel.*
Gotthardt et al. 2000, J Biol Chem. vol. 275: 25616–25624. Interactions of the low desnsity lipoprotein receptor gene family with cytosolic adaptor and scaffold proteins suggest diverse biological functions in ncellular communication and signal transductio.*

* cited by examiner

*Primary Examiner*—Yvonne Eyler
*Assistant Examiner*—Sarada C Prasad
(74) *Attorney, Agent, or Firm*—Richard Aron Osman

(57) ABSTRACT

The invention provides methods and compositions for inducing and detecting signal transduction through LDL receptors, including specifically detecting a stress that alters a functional interaction of a low density lipoprotein (LDL) receptor binding polypeptide with an LDL receptor interaction domain, by (a) introducing a predetermined stress into a system which provides a physical interaction of an LDL receptor binding polypeptide with an LDL receptor intracellular binding polypeptide interaction domain, whereby the system provides a stress-biased interaction of the binding polypeptide and the interaction domain, wherein the absence of the stress, the system provides a unbiased interaction of the binding polypeptide and the interaction domain; and (b) detecting the stress-biased interaction of the binding polypeptide and the interaction domain, wherein the binding polypeptide is selected from SEMCAP-1, JIP-1, PSD-95, JIP-2, Talin, OMP25, CAPON, PIP4,5 kinase, Na channel brain 3, Mint1, ICAP-1 and APC subunit10.

16 Claims, No Drawings

SEQUENCE LISTING

```
<160> NUMBER OF SEQ ID NOS:  132

<210> SEQ ID NO 1
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 1

Met Pro Leu Gly Leu Gly Arg Arg Lys Lys Ala Pro Pro Leu Val Glu
  1               5                  10                  15

Asn Glu Glu Ala Glu Pro Ser Arg Ser Gly Leu Gly Val Gly Glu Pro
                 20                  25                  30

Gly Pro Leu Gly Gly Ser Ala Ala Gly Glu Ser Gln Met Gly Leu Pro
             35                  40                  45

Pro Pro Pro Ala Ala Leu Arg Pro Arg Leu Val Phe His Thr Gln Leu
         50                  55                  60
```

Ala His Gly Ser Pro Thr Gly Arg Ile Glu Gly Phe Thr Asn Val Lys
65                  70                  75                  80

Glu Leu Tyr Gly Lys Ile Ala Glu Ala Phe Arg Leu Pro Ala Ala Glu
            85                  90                  95

Val Met Phe Cys Thr Leu Asn Thr His Lys Val Asp Met Asp Lys Leu
                100                 105                 110

Leu Gly Gly Gln Ile Gly Leu Glu Asp Phe Ile Phe Ala His Val Lys
            115                 120                 125

Gly Gln Arg Lys Glu Val Glu Val Phe Lys Ser Glu Ala Leu Gly
130                 135                 140

Leu Thr Ile Thr Asp Asn Gly Ala Gly Tyr Ala Phe Ile Lys Arg Ile
145                 150                 155                 160

Lys Glu Gly Ser Val Ile Asp His Ile Gln Leu Ile Ser Val Gly Asp
                165                 170                 175

Met Ile Glu Ala Ile Asn Gly Gln Ser Leu Leu Gly Cys Arg His Tyr
            180                 185                 190

Glu Val Ala Arg Leu Leu Lys Glu Leu Pro Arg Gly Arg Thr Phe Thr
            195                 200                 205

Leu Lys Leu Thr Glu Pro Arg Lys Ala Phe Asp Met Ile Ser Gln Arg
210                 215                 220

Ser Ala Gly Gly His Pro Gly Ser Gly Pro Gln Leu Gly Thr Gly Arg
225                 230                 235                 240

Gly Thr Leu Arg Leu Arg Ser Arg Gly Pro Ala Thr Val Glu Asp Leu
                245                 250                 255

Pro Ser Ala Phe Glu Glu Lys Ala Ile Glu Lys Val Asp Asp Leu Leu
            260                 265                 270

Glu Ser Tyr Met Gly Ile Arg Asp Thr Glu Leu Ala Ala Thr Met Val
            275                 280                 285

Glu Leu Gly Lys Asp Lys Arg Asn Pro Asp Glu Leu Ala Glu Ala Leu
            290                 295                 300

Asp Glu Arg Leu Gly Asp Phe Ala Phe Pro Asp Glu Phe Val Phe Asp
305                 310                 315                 320

Val Trp Gly Ala Ile Gly Asp Ala Lys Val Gly Arg Tyr
                325                 330

<210> SEQ ID NO 2
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 2

Met Ala Leu Gly Leu Gly Arg Arg Lys Lys Ala Asp Pro Leu Val Glu
1               5                   10                  15

Asn Glu Glu Ala Glu Glu Ser Arg Ser Gly Leu Gly Val Gly Glu Phe
            20                  25                  30

Gly Pro Leu Gly Gly Ser Ala Ala Gly Gly Ser Gln Met Gly Leu Pro
            35                  40                  45

Pro Pro Pro His Ala Leu Arg Pro Arg Leu Val Phe His Ile Gln Leu
            50                  55                  60

Ala His Gly Ser Pro Thr Gly Lys Ile Glu Gly Phe Thr Asn Val Lys
65                  70                  75                  80

Glu Met Tyr Gly Lys Ile Ala Glu Ala Phe Arg Asn Pro Ala Ala Glu

```
                    85                  90                  95
Val Met Phe Cys Thr Gln Asn Thr His Lys Val Asp Met Asp Lys Ser
                100                 105                 110

Leu Gly Gly Gln Ile Gly Leu Glu Asp Thr Ile Phe Ala His Val Lys
            115                 120                 125

Gly Gln Arg Val Glu Val Glu Val Phe Lys Ser Glu Glu Trp Leu Gly
        130                 135                 140

Leu Thr Ile Thr Asp Asn Gly Tyr Gly Tyr Ala Phe Ile Lys Arg Ile
145                 150                 155                 160

Lys Ala Gly Ser Val Ile Asp His Ile Gln Leu Asp Ser Val Gly Asp
                165                 170                 175

Met Ile Glu Ala Ile Glu Gly Gln Ser Leu Leu Gly Cys Arg His Phe
            180                 185                 190

Glu Val Ala Arg Leu Leu Lys Glu Leu Gly Arg Gly Arg Thr Phe Thr
        195                 200                 205

Leu Lys Leu His Glu Pro Arg Lys Ala Phe Asp Met Ile Ile Gln Arg
210                 215                 220

Ser Ala Gly Gly His Pro Gly Lys Gly Pro Gln Leu Gly Thr Gly Arg
225                 230                 235                 240

Gly Leu Leu Arg Leu Arg Ser Arg Gly Pro Ala Met Val Glu Asp Leu
                245                 250                 255

Pro Ser Ala Phe Glu Asn Lys Ala Ile Glu Lys Val Asp Asp Leu Gln
            260                 265                 270

Glu Ser Tyr Met Gly Ile Arg Asp Thr Arg Leu Ala Ala Thr Met Val
        275                 280                 285

Glu Leu Gly Ser Asp Lys Arg Asn Pro Asp Glu Leu Ala Thr Ala Leu
        290                 295                 300

Asp Glu Arg Leu Gly Asp Phe Val Phe Pro Asp Glu Phe Val Phe Asp
305                 310                 315                 320

Val Tyr Gly Ala Ile Gly Asp Ala Lys Val Gly Ala Tyr
                325                 330

<210> SEQ ID NO 3
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 3

Met Pro Ala Gly Leu Gly Arg Arg Lys Lys Ala Pro Asp Leu Val Glu
1               5                   10                  15

Asn Glu Glu Ala Glu Pro Glu Arg Ser Gly Leu Gly Val Gly Glu Pro
                20                  25                  30

Phe Pro Leu Gly Gly Ser Ala Ala Gly Glu Gly Gln Met Gly Leu Pro
            35                  40                  45

Pro Pro Pro Ala His Leu Arg Pro Arg Leu Val Phe His Thr Ile Leu
        50                  55                  60

Ala His Gly Ser Pro Thr Gly Arg Lys Glu Gly Phe Thr Asn Val Lys
65                  70                  75                  80

Glu Leu Leu Gly Lys Ile Ala Glu Ala Phe Arg Leu Met Ala Ala Glu
                85                  90                  95

Val Met Phe Cys Thr Leu Gln Thr His Lys Val Asp Met Asp Lys Leu
                100                 105                 110
```

```
Arg Gly Gly Gln Ile Gly Leu Glu Asp Phe Ser Phe Ala His Val Lys
        115                 120                 125

Gly Gln Arg Lys Thr Val Glu Val Phe Lys Ser Glu Glu Ala Val Gly
130                 135                 140

Leu Thr Ile Thr Asp Asn Gly Ala Trp Tyr Ala Phe Ile Lys Arg Ile
145                 150                 155                 160

Lys Glu Tyr Ser Val Ile Asp His Ile Gln Leu Ile Ala Val Gly Asp
                165                 170                 175

Met Ile Glu Ala Ile Asn Asp Gln Ser Leu Leu Gly Cys Arg His Tyr
            180                 185                 190

Phe Val Ala Arg Leu Leu Lys Glu Leu Pro Gly Gly Arg Thr Phe Thr
        195                 200                 205

Leu Lys Leu Thr His Pro Arg Lys Ala Phe Asp Met Ile Ser Ile Arg
    210                 215                 220

Ser Ala Gly Gly His Pro Gly Ser Lys Pro Gln Leu Gly Thr Gly Arg
225                 230                 235                 240

Gly Thr Leu Arg Leu Arg Ser Arg Gly Pro Ala Thr Met Glu Asp Leu
                245                 250                 255

Pro Ser Ala Phe Glu Glu Asn Ala Ile Glu Lys Val Asp Asp Leu Leu
            260                 265                 270

Gln Ser Tyr Met Gly Ile Arg Asp Thr Glu Arg Ala Ala Thr Met Val
        275                 280                 285

Glu Leu Gly Lys Ser Lys Arg Asn Pro Asp Glu Leu Ala Glu Thr Leu
    290                 295                 300

Asp Glu Arg Leu Gly Asp Phe Ala Val Pro Asp Glu Phe Val Phe Asp
305                 310                 315                 320

Val Trp Trp Ala Ile Gly Asp Ala Lys Val Gly Arg Ala
                325                 330

<210> SEQ ID NO 4
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 4

Met Pro Leu Ala Leu Gly Arg Arg Lys Lys Ala Pro Pro Asp Val Glu
1               5                   10                  15

Asn Glu Glu Ala Glu Pro Ser Glu Ser Gly Leu Gly Val Gly Glu Pro
            20                  25                  30

Gly Phe Leu Gly Gly Ser Ala Ala Gly Glu Ser Gly Met Gly Leu Pro
        35                  40                  45

Pro Pro Pro Ala Ala His Arg Pro Arg Leu Val Phe His Thr Gln Ile
    50                  55                  60

Ala His Gly Ser Pro Thr Gly Arg Ile Lys Gly Phe Thr Asn Val Lys
65                  70                  75                  80

Glu Leu Tyr Leu Lys Ile Ala Glu Ala Phe Arg Leu Pro Met Ala Glu
                85                  90                  95

Val Met Phe Cys Thr Leu Asn Asn His Lys Val Asp Met Asp Lys Leu
            100                 105                 110

Leu Gln Gly Gln Ile Gly Leu Glu Asp Phe Ile Arg Ala His Val Lys
        115                 120                 125

Gly Gln Arg Lys Glu Ser Glu Val Phe Lys Ser Glu Glu Ala Leu Thr
130                 135                 140
```

```
Leu Thr Ile Thr Asp Asn Gly Ala Gly Val Ala Phe Ile Lys Arg Ile
145                 150                 155                 160

Lys Glu Gly Trp Val Ile Asp His Ile Gln Leu Ile Ser Tyr Gly Asp
            165                 170                 175

Met Ile Glu Ala Ile Asn Gly Ala Ser Leu Leu Gly Cys Arg His Tyr
        180                 185                 190

Glu Asp Ala Arg Leu Leu Lys Glu Leu Pro Arg Glu Arg Thr Phe Thr
    195                 200                 205

Leu Lys Leu Thr Glu Phe Arg Lys Ala Phe Asp Met Ile Ser Gln Gly
210                 215                 220

Ser Ala Gly Gly His Pro Gly Ser Gly His Gln Leu Gly Thr Gly Arg
225                 230                 235                 240

Gly Thr Leu Ile Leu Arg Ser Arg Gly Pro Ala Thr Val Lys Asp Leu
                245                 250                 255

Pro Ser Ala Phe Glu Glu Lys Leu Ile Glu Lys Val Asp Asp Leu Leu
                260                 265                 270

Glu Met Tyr Met Gly Ile Arg Asp Thr Glu Leu Asn Ala Thr Met Val
            275                 280                 285

Glu Leu Gly Lys Asp Gln Arg Asn Pro Asp Glu Leu Ala Glu Ala Arg
290                 295                 300

Asp Glu Arg Leu Gly Asp Phe Ala Phe Ser Asp Glu Phe Val Phe Asp
305                 310                 315                 320

Val Trp Gly Thr Ile Gly Asp Ala Lys Val Gly Arg Tyr
                325                 330

<210> SEQ ID NO 5
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 5

Met Pro Leu Gly Ala Gly Arg Arg Lys Lys Ala Pro Pro Leu Asp Glu
  1               5                  10                  15

Asn Glu Glu Ala Glu Pro Ser Arg Glu Gly Leu Gly Val Gly Glu Pro
            20                  25                  30

Gly Pro Phe Gly Gly Ser Ala Ala Gly Glu Ser Gln Gly Gly Leu Pro
        35                  40                  45

Pro Pro Pro Ala Ala Leu His Pro Arg Leu Val Phe His Thr Gln Leu
    50                  55                  60

Ile His Gly Ser Pro Thr Gly Arg Ile Glu Lys Phe Thr Asn Val Lys
 65                  70                  75                  80

Glu Leu Tyr Gly Leu Ile Ala Glu Ala Phe Arg Leu Pro Ala Met Glu
                85                  90                  95

Val Met Phe Cys Thr Leu Asn Thr Asn Lys Val Asp Met Asp Lys Leu
            100                 105                 110

Leu Gly Gln Gln Ile Gly Leu Glu Asp Phe Ile Phe Arg His Val Lys
        115                 120                 125

Gly Gln Arg Lys Glu Val Ser Val Phe Lys Ser Glu Glu Ala Leu Gly
    130                 135                 140

Thr Thr Ile Thr Asp Asn Gly Ala Gly Tyr Val Phe Ile Lys Arg Ile
145                 150                 155                 160

Lys Glu Gly Ser Trp Ile Asp His Ile Gln Leu Ile Ser Val Tyr Asp
```

```
            165                 170                 175
Met Ile Glu Ala Ile Asn Gly Gln Ala Leu Leu Gly Cys Arg His Tyr
                180                 185                 190

Glu Val Asp Arg Leu Leu Lys Glu Leu Pro Arg Gly Glu Thr Phe Thr
            195                 200                 205

Leu Lys Leu Thr Glu Pro Phe Lys Ala Phe Asp Met Ile Ser Gln Arg
    210                 215                 220

Gly Ala Gly Gly His Pro Gly Ser Gly Pro His Leu Gly Thr Gly Arg
225                 230                 235                 240

Gly Thr Leu Arg Ile Arg Ser Arg Gly Pro Ala Thr Val Glu Lys Leu
                245                 250                 255

Pro Ser Ala Phe Glu Glu Lys Ala Leu Glu Lys Val Asp Asp Leu Leu
            260                 265                 270

Glu Ser Met Met Gly Ile Arg Asp Thr Glu Leu Ala Asn Thr Met Val
        275                 280                 285

Glu Leu Gly Lys Asp Lys Gln Asn Pro Asp Glu Leu Ala Glu Ala Leu
    290                 295                 300

Arg Glu Arg Leu Gly Asp Phe Ala Phe Pro Ser Glu Phe Val Phe Asp
305                 310                 315                 320

Val Trp Gly Ala Thr Gly Asp Ala Lys Val Gly Arg Tyr
                325                 330

<210> SEQ ID NO 6
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 6

Met Pro Leu Gly Leu Ala Arg Arg Lys Lys Ala Pro Pro Leu Val Asp
1               5                   10                  15

Asn Glu Glu Ala Glu Pro Ser Arg Ser Glu Leu Gly Val Gly Glu Pro
            20                  25                  30

Gly Pro Leu Phe Gly Ser Ala Ala Gly Glu Ser Gln Met His Leu Pro
        35                  40                  45

Pro Pro Pro Ala Ala Leu Arg Ile Arg Leu Val Phe His Thr Gln Leu
    50                  55                  60

Ala Lys Gly Ser Pro Thr Gly Arg Ile Glu Gly Leu Thr Asn Val Lys
65                  70                  75                  80

Glu Leu Tyr Gly Lys Met Ala Glu Ala Phe Arg Leu Pro Ala Ala Asn
                85                  90                  95

Val Met Phe Cys Thr Leu Asn Thr His Gln Val Asp Met Asp Lys Leu
            100                 105                 110

Leu Gly Gly Arg Ile Gly Leu Glu Asp Phe Ile Phe Ala Ser Val Lys
        115                 120                 125

Gly Gln Arg Lys Glu Val Glu Thr Phe Lys Ser Glu Glu Ala Leu Gly
    130                 135                 140

Leu Val Ile Thr Asp Asn Gly Ala Gly Tyr Ala Trp Ile Lys Arg Ile
145                 150                 155                 160

Lys Glu Gly Ser Val Tyr Asp His Ile Gln Leu Ile Ser Val Gly Ala
                165                 170                 175

Met Ile Glu Ala Ile Asn Gly Gln Ser Asp Leu Gly Cys Arg His Tyr
            180                 185                 190
```

```
Glu Val Ala Glu Leu Leu Lys Glu Leu Pro Arg Gly Arg Phe Phe Thr
            195                 200                 205

Leu Lys Leu Thr Glu Pro Arg Gly Ala Phe Asp Met Ile Ser Gln Arg
            210                 215                 220

Ser His Gly Gly His Pro Gly Ser Gly Pro Gln Ile Gly Thr Gly Arg
225                 230                 235                 240

Gly Thr Leu Arg Leu Lys Ser Arg Gly Pro Ala Thr Val Glu Asp Met
                245                 250                 255

Pro Ser Ala Phe Glu Glu Lys Ala Ile Asn Lys Val Asp Asp Leu Leu
            260                 265                 270

Glu Ser Tyr Gln Gly Ile Arg Asp Thr Glu Leu Ala Ala Arg Met Val
            275                 280                 285

Glu Leu Gly Lys Asp Lys Arg Ser Pro Asp Glu Leu Ala Glu Ala Leu
            290                 295                 300

Asp Thr Arg Leu Gly Asp Phe Ala Phe Pro Asp Val Phe Val Phe Asp
305                 310                 315                 320

Val Trp Gly Ala Ile Trp Asp Ala Lys Val Gly Arg Tyr
                325                 330

<210> SEQ ID NO 7
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 7

Met Pro Leu Gly Leu Gly Ala Arg Lys Lys Ala Pro Pro Leu Val Glu
1               5                   10                  15

Asp Glu Glu Ala Glu Pro Ser Arg Ser Gly Glu Gly Val Gly Glu Pro
            20                  25                  30

Gly Pro Leu Gly Phe Ser Ala Ala Gly Glu Ser Gln Met Gly Gly Pro
            35                  40                  45

Pro Pro Ala Ala Leu Arg Pro His Leu Val Phe His Thr Gln Leu
    50                  55                  60

Ala His Ile Ser Pro Thr Gly Arg Ile Glu Gly Phe Lys Asn Val Lys
65                  70                  75                  80

Glu Leu Tyr Gly Lys Ile Leu Glu Ala Phe Arg Leu Pro Ala Ala Glu
                85                  90                  95

Met Met Phe Cys Thr Leu Asn Thr His Lys Asn Asp Met Asp Lys Leu
            100                 105                 110

Leu Gly Gly Gln Gln Gly Leu Glu Asp Phe Ile Phe Ala His Arg Lys
            115                 120                 125

Gly Gln Arg Lys Glu Val Glu Val Ser Lys Ser Glu Glu Ala Leu Gly
130                 135                 140

Leu Thr Thr Thr Asp Asn Gly Ala Gly Tyr Ala Phe Val Lys Arg Ile
145                 150                 155                 160

Lys Glu Gly Ser Val Ile Trp His Ile Gln Leu Ile Ser Val Gly Asp
                165                 170                 175

Tyr Ile Glu Ala Ile Asn Gly Gln Ser Leu Ala Gly Cys Arg His Tyr
            180                 185                 190

Glu Val Ala Arg Asp Leu Lys Glu Leu Pro Arg Gly Arg Thr Glu Thr
            195                 200                 205

Leu Lys Leu Thr Glu Pro Arg Lys Phe Phe Asp Met Ile Ser Gln Arg
            210                 215                 220
```

Ser Ala His Gly His Pro Gly Ser Gly Pro Gln Leu Ile Thr Gly Arg
225                 230                 235                 240

Gly Thr Leu Arg Leu Arg Lys Arg Gly Pro Ala Thr Val Glu Asp Leu
            245                 250                 255

Leu Ser Ala Phe Glu Glu Lys Ala Ile Glu Met Val Asp Asp Leu Leu
        260                 265                 270

Glu Ser Tyr Met Asn Ile Arg Asp Thr Glu Leu Ala Ala Thr Gln Val
    275                 280                 285

Glu Leu Gly Lys Asp Lys Arg Asn Arg Asp Glu Leu Ala Glu Ala Leu
290                 295                 300

Asp Glu Ser Leu Gly Asp Phe Ala Phe Pro Asp Glu Thr Val Phe Asp
305                 310                 315                 320

Val Trp Gly Ala Ile Gly Val Ala Lys Val Gly Arg Tyr
                325                 330

<210> SEQ ID NO 8
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 8

Met Pro Leu Gly Leu Gly Arg Ala Lys Lys Ala Pro Pro Leu Val Glu
1               5                   10                  15

Asn Asp Glu Ala Glu Pro Ser Arg Ser Gly Leu Glu Val Gly Glu Pro
            20                  25                  30

Gly Pro Leu Gly Gly Phe Ala Ala Gly Glu Ser Gln Met Gly Leu Gly
        35                  40                  45

Pro Pro Pro Ala Ala Leu Arg Pro Arg His Val Phe His Thr Gln Leu
    50                  55                  60

Ala His Gly Ile Pro Thr Gly Arg Ile Glu Gly Phe Thr Lys Val Lys
65                  70                  75                  80

Glu Leu Tyr Gly Lys Ile Ala Leu Ala Phe Arg Leu Pro Ala Ala Glu
                85                  90                  95

Val Asn Phe Cys Thr Leu Asn Thr His Lys Val Gln Met Asp Lys Leu
            100                 105                 110

Leu Gly Gly Gln Ile Arg Leu Glu Asp Phe Ile Phe Ala His Val Ser
        115                 120                 125

Gly Gln Arg Lys Glu Val Glu Val Phe Thr Ser Glu Glu Ala Leu Gly
    130                 135                 140

Leu Thr Ile Val Asp Asn Gly Ala Gly Tyr Ala Phe Ile Trp Arg Ile
145                 150                 155                 160

Lys Glu Gly Ser Val Ile Asp Tyr Ile Gln Leu Ile Ser Val Gly Asp
                165                 170                 175

Met Ala Glu Ala Ile Asn Gly Gln Ser Leu Leu Asp Cys Arg His Tyr
            180                 185                 190

Glu Val Ala Arg Leu Glu Lys Glu Leu Pro Arg Gly Arg Thr Phe Phe
        195                 200                 205

Leu Lys Leu Thr Glu Pro Arg Lys Ala Gly Asp Met Ile Ser Gln Arg
    210                 215                 220

Ser Ala Gly His His Pro Gly Ser Gly Pro Gln Leu Gly Ile Gly Arg
225                 230                 235                 240

Gly Thr Leu Arg Leu Arg Ser Lys Gly Pro Ala Thr Val Glu Asp Leu

```
                    245             250                 255
Pro Leu Ala Phe Glu Glu Lys Ala Ile Glu Lys Met Asp Asp Leu Leu
                260             265                 270

Glu Ser Tyr Met Gly Asn Arg Asp Thr Glu Leu Ala Ala Thr Met Gln
            275                 280             285

Glu Leu Gly Lys Asp Lys Arg Asn Pro Arg Glu Leu Ala Glu Ala Leu
        290                 295             300

Asp Glu Arg Ser Gly Asp Phe Ala Phe Pro Asp Glu Phe Thr Phe Asp
305                 310             315                 320

Val Trp Gly Ala Ile Gly Asp Val Lys Val Gly Arg Tyr
                325             330

<210> SEQ ID NO 9
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 9

Met Pro Leu Gly Leu Gly Arg Arg Ala Lys Ala Pro Pro Leu Val Glu
 1               5                  10                  15

Asn Glu Asp Ala Glu Pro Ser Arg Ser Gly Leu Gly Glu Gly Glu Pro
            20                  25                  30

Gly Pro Leu Gly Gly Ser Phe Ala Gly Glu Ser Gln Met Gly Leu Pro
        35                  40                  45

Gly Pro Pro Ala Ala Leu Arg Pro Arg Leu His Phe His Thr Gln Leu
    50                  55                  60

Ala His Gly Ser Ile Thr Gly Arg Ile Glu Gly Phe Thr Asn Lys Lys
65                  70                  75                  80

Glu Leu Tyr Gly Lys Ile Ala Glu Leu Phe Arg Leu Pro Ala Ala Glu
                85                  90                  95

Val Met Met Cys Thr Leu Asn Thr His Lys Val Asp Asn Asp Lys Leu
            100                 105                 110

Leu Gly Gly Gln Ile Gly Gln Glu Asp Phe Ile Phe Ala His Val Lys
        115                 120                 125

Arg Gln Arg Lys Glu Val Glu Val Phe Lys Thr Glu Glu Ala Leu Gly
    130                 135                 140

Leu Thr Ile Thr Val Asn Gly Ala Gly Tyr Ala Phe Ile Lys Trp Ile
145                 150                 155                 160

Lys Glu Gly Ser Val Ile Asp His Tyr Gln Leu Ile Ser Val Gly Asp
                165                 170                 175

Met Ile Ala Ala Ile Asn Gly Gln Ser Leu Leu Gly Asp Arg His Tyr
            180                 185                 190

Glu Val Ala Arg Leu Leu Glu Glu Leu Pro Arg Gly Arg Thr Phe Thr
        195                 200                 205

Phe Lys Leu Thr Glu Pro Arg Lys Ala Phe Gly Met Ile Ser Gln Arg
    210                 215                 220

Ser Ala Gly Gly Ile Pro Gly Ser Gly Pro Gln Leu Gly Thr Lys Arg
225                 230                 235                 240

Gly Thr Leu Arg Leu Arg Ser Arg Leu Pro Ala Thr Val Glu Asp Leu
                245                 250                 255

Pro Ser Met Phe Glu Glu Lys Ala Ile Glu Lys Val Asn Asp Leu Leu
            260                 265                 270
```

```
Glu Ser Tyr Met Gly Ile Gln Asp Thr Glu Leu Ala Ala Thr Met Val
            275                 280                 285

Arg Leu Gly Lys Asp Lys Arg Asn Pro Asp Ser Leu Ala Glu Ala Leu
        290                 295                 300

Asp Glu Arg Leu Thr Asp Phe Ala Phe Pro Asp Glu Phe Val Val Asp
305                 310                 315                 320

Val Trp Gly Ala Ile Gly Asp Ala Trp Val Gly Arg Tyr
                325                 330

<210> SEQ ID NO 10
<211> LENGTH: 333
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 10

Met Pro Leu Gly Leu Gly Arg Arg Lys Ala Pro Pro Leu Val Glu
 1               5                  10                  15

Asn Glu Glu Asp Glu Pro Ser Arg Ser Gly Leu Gly Val Glu Glu Pro
            20                  25                  30

Gly Pro Leu Gly Gly Ser Ala Phe Gly Glu Ser Gln Met Gly Leu Pro
        35                  40                  45

Pro Gly Pro Ala Ala Leu Arg Pro Arg Leu Val His Thr Gln Leu
    50                  55                  60

Ala His Gly Ser Pro Ile Gly Arg Ile Glu Gly Phe Thr Asn Val Leu
 65                  70                  75                  80

Glu Leu Tyr Gly Lys Ile Ala Glu Ala Met Arg Leu Pro Ala Ala Glu
                85                  90                  95

Val Met Phe Asn Thr Leu Asn Thr His Lys Val Asp Met Gln Lys Leu
            100                 105                 110

Leu Gly Gly Gln Ile Gly Leu Arg Asp Phe Ile Phe Ala His Val Lys
        115                 120                 125

Gly Ser Arg Lys Glu Val Glu Val Phe Lys Ser Thr Glu Ala Leu Gly
    130                 135                 140

Leu Thr Ile Thr Asp Val Gly Ala Gly Tyr Ala Phe Ile Lys Arg Trp
145                 150                 155                 160

Lys Glu Gly Ser Val Ile Asp His Ile Tyr Leu Ile Ser Val Gly Asp
                165                 170                 175

Met Ile Glu Asp Ile Asn Gly Gln Ser Leu Leu Gly Cys Glu His Tyr
            180                 185                 190

Glu Val Ala Arg Leu Leu Lys Phe Leu Pro Arg Gly Arg Thr Phe Thr
        195                 200                 205

Leu Gly Leu Thr Glu Pro Arg Lys Ala Phe Asp His Ile Ser Gln Arg
    210                 215                 220

Ser Ala Gly Gly His Ile Gly Ser Gly Pro Gln Leu Gly Thr Gly Lys
225                 230                 235                 240

Gly Thr Leu Arg Leu Arg Ser Arg Gly Leu Ala Thr Val Glu Asp Leu
                245                 250                 255

Pro Ser Ala Met Glu Glu Lys Ala Ile Glu Lys Val Asp Asn Leu Leu
            260                 265                 270

Glu Ser Tyr Met Gly Ile Arg Gln Thr Glu Leu Ala Ala Thr Met Val
        275                 280                 285

Glu Arg Gly Lys Asp Lys Arg Asn Pro Asp Glu Ser Ala Glu Ala Leu
    290                 295                 300
```

-continued

```
Asp Glu Arg Leu Gly Thr Phe Ala Phe Pro Asp Glu Phe Val Phe Val
305                 310                 315                 320

Val Trp Gly Ala Ile Gly Asp Ala Lys Trp Gly Arg Tyr
            325                 330
```

<210> SEQ ID NO 11
<211> LENGTH: 659
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 11

```
Met Ala Glu Arg Glu Ser Gly Leu Gly Gly Ala Ala Ser Pro Pro
1               5                   10                  15

Ala Ala Ser Pro Phe Leu Gly Leu His Ile Ala Ser Pro Pro Asn Phe
                20                  25                  30

Arg Leu Thr His Asp Ile Ser Leu Glu Glu Phe Glu Asp Glu Asp Leu
            35                  40                  45

Ser Glu Ile Thr Asp Glu Cys Gly Ile Ser Leu Gln Cys Lys Asp Thr
    50                  55                  60

Leu Ser Leu Arg Pro Pro Arg Ala Gly Leu Leu Ser Ala Gly Ser Ser
65                  70                  75                  80

Gly Ser Ala Gly Ser Arg Leu Gln Ala Glu Met Leu Gln Met Asp Leu
                85                  90                  95

Ile Asp Ala Ala Gly Asp Thr Pro Gly Ala Glu Asp Asp Glu Glu Glu
            100                 105                 110

Glu Asp Asp Glu Leu Ala Ala Gln Arg Pro Gly Val Gly Pro Pro Lys
        115                 120                 125

Ala Glu Ser Asn Gln Asp Pro Ala Pro Arg Ser Gln Gly Gln Gly Pro
    130                 135                 140

Gly Thr Gly Ser Gly Asp Thr Tyr Arg Pro Lys Arg Pro Thr Thr Leu
145                 150                 155                 160

Asn Leu Phe Pro Gln Val Pro Arg Ser Gln Asp Thr Leu Asn Asn Asn
                165                 170                 175

Ser Leu Gly Lys Lys His Ser Trp Gln Asp Arg Val Ser Arg Ser Ser
            180                 185                 190

Ser Pro Leu Lys Thr Gly Glu Gln Thr Pro Pro His Glu His Ile Cys
        195                 200                 205

Leu Ser Asp Glu Leu Pro Pro Gln Gly Ser Pro Val Pro Thr Gln Asp
    210                 215                 220

Arg Gly Thr Ser Thr Asp Ser Pro Cys Arg Arg Ser Ala Ala Thr Gln
225                 230                 235                 240

Met Ala Pro Pro Ser Gly Pro Ala Thr Ala Pro Gly Gly Arg Gly
                245                 250                 255

His Ser His Arg Asp Arg Ile His Tyr Gln Ala Asp Val Arg Leu Glu
            260                 265                 270

Ala Thr Glu Glu Ile Tyr Leu Thr Pro Val Gln Arg Pro Pro Asp Pro
        275                 280                 285

Ala Glu Pro Thr Ser Thr Phe Met Pro Pro Thr Glu Ser Arg Met Ser
    290                 295                 300

Val Ser Ser Asp Pro Asp Pro Ala Ala Tyr Ser Val Thr Ala Gly Arg
305                 310                 315                 320

Pro His Pro Ser Ile Ser Glu Glu Asp Glu Gly Phe Asp Cys Leu Ser
```

```
                    325                 330                 335
Ser Pro Glu Arg Ala Glu Pro Gly Gly Trp Arg Gly Ser Leu
                340                 345                 350
Gly Glu Pro Pro Pro Pro Arg Ala Ser Leu Ser Ser Asp Thr Ser
                355                 360                 365
Ala Leu Ser Tyr Asp Ser Val Lys Tyr Thr Leu Val Val Asp Glu His
370                 375                 380
Ala Gln Leu Glu Leu Val Ser Leu Arg Pro Cys Phe Gly Asp Tyr Ser
385                 390                 395                 400
Asp Glu Ser Asp Ser Ala Thr Val Tyr Asp Asn Cys Ala Ser Ala Ser
                405                 410                 415
Ser Pro Tyr Glu Ser Ala Ile Gly Glu Glu Tyr Glu Glu Ala Pro Gln
                420                 425                 430
Pro Arg Pro Pro Thr Cys Leu Ser Glu Asp Ser Thr Pro Asp Glu Pro
                435                 440                 445
Asp Val Phe Ser Lys Lys Phe Leu Asn Val Phe Met Ser Gly Arg Ser
450                 455                 460
Arg Ser Ser Ser Ala Glu Ser Phe Gly Leu Phe Ser Cys Val Ile Asn
465                 470                 475                 480
Gly Glu Glu His Glu Gln Thr His Arg Ala Ile Phe Arg Phe Val Pro
                485                 490                 495
Arg His Glu Asp Glu Leu Glu Leu Val Asp Asp Pro Leu Leu Val
                500                 505                 510
Glu Leu Gln Ala Glu Asp Tyr Trp Tyr Glu Ala Tyr Asn Met Arg Thr
                515                 520                 525
Gly Ala Arg Gly Val Phe Pro Ala Tyr Tyr Ala Ile Glu Val Thr Lys
                530                 535                 540
Glu Pro Glu His Met Ala Ala Leu Ala Lys Asn Ser Cys Val Leu Glu
545                 550                 555                 560
Ile Ser Val Arg Gly Val Lys Ile Gly Val Lys Ala Asp Asp Ala Leu
                565                 570                 575
Glu Ala Lys Gly Asn Lys Cys Ser His Phe Phe Gln Leu Lys Asn Ile
                580                 585                 590
Ser Phe Cys Gly Tyr His Pro Lys Asn Asn Lys Tyr Phe Gly Phe Ile
                595                 600                 605
Thr Lys His Pro Ala Asp His Arg Phe Ala Cys His Val Phe Val Ser
                610                 615                 620
Glu Asp Ser Thr Lys Ala Leu Ala Glu Ser Val Gly Arg Ala Phe Gln
625                 630                 635                 640
Gln Phe Tyr Lys Gln Phe Val Glu Tyr Thr Cys Pro Thr Glu Asp Ile
                645                 650                 655
Tyr Leu Glu

<210> SEQ ID NO 12
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 12

Met Asp Glu Arg Glu Ser Gly Leu Gly Gly Gly Glu Ala Ser Pro Pro
  1               5                  10                  15

Ala Ala Ser Pro Phe Phe Gly Leu His Ile Ala Ser Pro Pro Asn Gly
```

-continued

```
                        20                  25                  30
Arg Leu Thr His Asp Ile Ser Leu Glu His Phe Glu Asp Glu Asp Leu
            35                  40                  45
Ser Glu Ile Ile Asp Glu Cys Gly Ile Ser Leu Gln Cys Leu Asp Thr
 50                  55                  60
Leu Ser Leu Arg Pro Pro Arg Met Gly Leu Leu Ser Ala Gly Ser Ser
 65                  70                  75                  80
Gly Asn Ala Gly Ser Arg Leu Gln Ala Glu Met Gln Gln Met Asp Leu
                85                  90                  95
Ile Asp Ala Ala Gly Arg Thr Pro Gly Ala Glu Asp Glu Glu Glu Ser
                100                 105                 110
Glu Asp Asp Glu Leu Ala Ala Gln Arg Thr Gly Val Gly Pro Pro Lys
            115                 120                 125
Ala Glu Ser Val Gln Asp Pro Ala Pro Arg Ser Gln Gly Trp Gly Pro
        130                 135                 140
Gly Thr Gly Ser Gly Asp Thr Ala Arg Pro Lys Arg Pro Thr Thr Leu
145                 150                 155                 160
Asn Asp Phe Pro Gln Val Pro Arg Ser Gln Asp Glu Leu Asn Asn Asn
                165                 170                 175
Ser Leu Gly Lys Lys Phe Ser Trp Gln Asp Arg Val Ser Arg Ser Gly
                180                 185                 190
Ser Pro Leu Lys Thr Gly Glu Gln Thr His Pro His Glu His Ile Cys
                195                 200                 205
Leu Ser Asp Ile Leu Pro Pro Gln Gly Ser Pro Val Pro Lys Gln Asp
        210                 215                 220
Arg Gly Thr Ser Thr Asp Ser Leu Cys Arg Arg Ser Ala Ala Thr Gln
225                 230                 235                 240
Met Met Pro Pro Ser Gly Pro Ala Thr Ala Asn Gly Gly Arg Gly
                245                 250                 255
His Ser His Arg Asp Gln Ile His Tyr Gln Ala Asp Val Arg Leu Arg
                260                 265                 270
Ala Thr Glu Glu Ile Tyr Leu Thr Pro Ser Gln Arg Pro Pro Asp Pro
            275                 280                 285
Ala Glu Pro Val Ser Thr Phe Met Pro Pro Thr Glu Ser Trp Met Ser
        290                 295                 300
Val Ser Ser Asp Pro Asp Pro Tyr Ala Tyr Ser Val Thr Ala Gly Arg
305                 310                 315                 320
Pro Ala Pro Ser Ile Ser Glu Glu Asp Glu Gly Asp Asp Cys Leu Ser
                325                 330                 335
Ser Pro Glu Arg Ala Phe Pro Pro Gly Gly Gly Trp Arg Gly Ser Gly
                340                 345                 350
Gly Glu Pro Pro Pro Pro Arg Ala His Leu Ser Ser Asp Thr Ser
                355                 360                 365
Ala Leu Ser Ile Asp Ser Val Lys Tyr Thr Leu Val Val Lys Glu His
        370                 375                 380
Ala Gln Leu Glu Leu Val Ser Met Arg Pro Cys Phe Gly Asp Tyr Ser
385                 390                 395                 400
Asp Asn Ser Asp Ser Ala Thr Val Tyr Asp Asn Gln Ala Ser Ala Ser
                405                 410                 415
Ser Pro Tyr Glu Ser Arg Ile Gly Glu Glu Tyr Glu Glu Ala Pro Ser
                420                 425                 430
Pro Arg Pro Pro Thr Cys Leu Ser Glu Thr Ser Thr Pro Asp Glu Pro
            435                 440                 445
```

```
Asp Val Phe Val Lys Lys Phe Leu Asn Val Phe Met Ser Trp Arg Ser
    450                 455                 460

Arg Ser Ser Ser Ala Glu Ser Tyr Gly Leu Phe Ser Cys Val Ile Asn
465                 470                 475                 480

Gly Ala Glu His Glu Gln Thr His Arg Ala Ile Asp Arg Phe Val Pro
                485                 490                 495

Arg His Glu Asp Glu Glu Leu Glu Val Asp Asp Pro Leu Leu Phe
                500                 505                 510

Glu Leu Gln Ala Glu Asp Tyr Trp Tyr Gly Ala Tyr Asn Met Arg Thr
        515                 520                 525

Gly Ala Arg His Val Phe Pro Ala Tyr Tyr Ala Ile Glu Ile Thr Lys
        530                 535                 540

Glu Pro Glu His Met Ala Ala Lys Ala Lys Asn Ser Cys Val Leu Glu
545                 550                 555                 560

Ile Leu Val Arg Gly Val Lys Ile Gly Val Lys Met Asp Asp Ala Leu
                565                 570                 575

Glu Ala Lys Gly Asn Asn Cys Ser His Phe Gln Leu Lys Asn Gln
            580                 585                 590

Ser Phe Cys Gly Tyr His Pro Lys Asn Arg Lys Tyr Phe Gly Phe Ile
            595                 600                 605

Thr Lys His Ser Ala Asp His Arg Phe Ala Cys His Val Thr Val Ser
    610                 615                 620

Glu Asp Ser Thr Lys Ala Leu Val Glu Ser Val Gly Arg Ala Phe Gln
625                 630                 635                 640

Gln Trp Tyr Lys Gln Phe Val Glu Tyr Thr Cys Tyr Thr Glu Asp Ile
                645                 650                 655

Tyr Leu Glu

<210> SEQ ID NO 13
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 13

Met Ala Ala Arg Glu Ser Gly Leu Gly Gly Gly Ala Asp Ser Pro Pro
1               5                   10                  15

Ala Ala Ser Pro Phe Leu Glu Leu His Ile Ala Ser Pro Pro Asn Phe
                20                  25                  30

Phe Leu Thr His Asp Ile Ser Leu Glu Glu Gly Glu Asp Glu Asp Leu
            35                  40                  45

Ser Glu Ile Thr His Glu Cys Gly Ile Ser Leu Gln Cys Lys Ile Thr
        50                  55                  60

Leu Ser Leu Arg Pro Pro Arg Ala Lys Leu Leu Ser Ala Gly Ser Ser
65              70                  75                  80

Gly Ser Leu Gly Ser Arg Leu Gln Ala Glu Met Leu Met Met Asp Leu
                85                  90                  95

Ile Asp Ala Ala Gly Asp Asn Pro Gly Ala Glu Asp Glu Glu Glu
                100                 105                 110

Gln Asp Asp Glu Leu Ala Ala Gln Arg Pro Arg Val Gly Pro Pro Lys
            115                 120                 125

Ala Glu Ser Asn Ser Asp Pro Ala Arg Ser Gln Gly Gln Thr Pro
            130                 135                 140
```

-continued

```
Gly Thr Gly Ser Gly Asp Thr Tyr Val Pro Lys Arg Pro Thr Thr Leu
145                 150                 155                 160

Asn Leu Trp Pro Gln Val Pro Arg Ser Gln Asp Thr Tyr Asn Asn Asn
            165                 170                 175

Ser Leu Gly Lys Lys His Ala Trp Gln Asp Arg Val Ser Arg Ser Ser
        180                 185                 190

Asp Pro Leu Lys Thr Gly Glu Gln Thr Pro Glu His Glu His Ile Cys
        195                 200                 205

Leu Ser Asp Glu Phe Pro Pro Gln Gly Ser Pro Val Pro Thr Gly Asp
    210                 215                 220

Arg Gly Thr Ser Thr Asp Ser Pro His Arg Arg Ser Ala Ala Thr Gln
225                 230                 235                 240

Met Ala Ile Pro Ser Gly Pro Ala Thr Ala Pro Lys Gly Arg Gly
                245                 250                 255

His Ser His Arg Asp Arg Leu His Tyr Gln Ala Asp Val Arg Leu Glu
                260                 265                 270

Met Thr Glu Glu Ile Tyr Leu Thr Pro Val Asn Arg Pro Pro Asp Pro
        275                 280                 285

Ala Glu Pro Thr Gln Thr Phe Met Pro Pro Thr Glu Ser Arg Arg Ser
    290                 295                 300

Val Ser Ser Asp Pro Asp Pro Ala Ser Tyr Ser Val Thr Ala Gly Arg
305                 310                 315                 320

Pro His Thr Ser Ile Ser Glu Glu Asp Glu Gly Phe Val Cys Leu Ser
                325                 330                 335

Ser Pro Glu Arg Ala Glu Trp Pro Gly Gly Gly Trp Arg Gly Ser Leu
            340                 345                 350

Tyr Glu Pro Pro Pro Pro Arg Ala Ser Ala Ser Ser Asp Thr Ser
            355                 360                 365

Ala Leu Ser Tyr Asp Ser Val Lys Tyr Thr Leu Val Val Asp Phe His
    370                 375                 380

Ala Gln Leu Glu Leu Val Ser Leu Gly Pro Cys Phe Gly Asp Tyr Ser
385                 390                 395                 400

Asp Glu His Asp Ser Ala Thr Val Tyr Asp Asn Cys Ile Ser Ala Ser
                405                 410                 415

Ser Pro Tyr Glu Ser Ala Lys Gly Glu Glu Tyr Glu Glu Ala Pro Gln
            420                 425                 430

Leu Arg Pro Pro Thr Cys Leu Ser Glu Asp Met Thr Pro Asp Glu Pro
            435                 440                 445

Asp Val Phe Ser Asn Lys Phe Leu Asn Val Phe Met Ser Gly Gln Ser
    450                 455                 460

Arg Ser Ser Ser Ala Glu Ser Phe Arg Leu Phe Ser Cys Val Ile Asn
465                 470                 475                 480

Gly Glu Ser His Glu Gln Thr His Arg Ala Ile Phe Thr Phe Val Pro
                485                 490                 495

Arg His Glu Asp Glu Leu Val Leu Glu Val Asp Pro Leu Leu Val
                500                 505                 510

Trp Leu Gln Ala Glu Asp Tyr Trp Tyr Glu Tyr Tyr Asn Met Arg Thr
        515                 520                 525

Gly Ala Arg Gly Ala Phe Pro Ala Tyr Tyr Ala Ile Glu Val Asp Lys
        530                 535                 540

Glu Pro Glu His Met Ala Ala Leu Glu Lys Asn Ser Cys Val Leu Glu
545                 550                 555                 560
```

```
Ile Ser Phe Arg Gly Val Lys Ile Gly Val Lys Ala Gly Asp Ala Leu
                565                 570                 575

Glu Ala Lys Gly Asn Lys His Ser His Phe Gln Leu Lys Asn Ile
            580                 585                 590

Ile Phe Cys Gly Tyr His Pro Lys Asn Asn Leu Tyr Phe Gly Phe Ile
            595                 600                 605

Thr Lys His Pro Met Asp His Arg Phe Ala Cys His Val Phe Asn Ser
        610                 615                 620

Glu Asp Ser Thr Lys Ala Leu Ala Gln Ser Val Gly Arg Ala Phe Gln
625                 630                 635                 640

Gln Phe Arg Lys Gln Phe Val Glu Tyr Thr Cys Pro Ser Glu Asp Ile
                645                 650                 655

Tyr Leu Glu

<210> SEQ ID NO 14
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 14

Met Ala Glu Ala Glu Ser Gly Leu Gly Gly Gly Ala Ala Asp Pro Pro
 1               5                  10                  15

Ala Ala Ser Pro Phe Leu Gly Glu His Ile Ala Ser Pro Pro Asn Phe
                20                  25                  30

Arg Phe Thr His Asp Ile Ser Leu Glu Glu Phe Gly Asp Glu Asp Leu
            35                  40                  45

Ser Glu Ile Thr Asp His Cys Gly Ile Ser Leu Gln Cys Lys Asp Ile
        50                  55                  60

Leu Ser Leu Arg Pro Pro Arg Ala Gly Lys Leu Ser Ala Gly Ser Ser
65                  70                  75                  80

Gly Ser Ala Leu Ser Arg Leu Gln Ala Glu Met Leu Gln Asn Asp Leu
                85                  90                  95

Ile Asp Ala Ala Gly Asp Thr Gln Gly Ala Glu Asp Glu Glu Glu Glu
                100                 105                 110

Glu Arg Asp Glu Leu Ala Ala Gln Arg Pro Gly Ser Gly Pro Pro Lys
            115                 120                 125

Ala Glu Ser Asn Gln Thr Pro Ala Pro Arg Ser Gln Gly Gln Gly Val
        130                 135                 140

Gly Thr Gly Ser Gly Asp Thr Tyr Arg Trp Lys Arg Pro Thr Thr Leu
145                 150                 155                 160

Asn Leu Phe Tyr Gln Val Pro Arg Ser Gln Asp Thr Leu Ala Asn Asn
                165                 170                 175

Ser Leu Gly Lys Lys His Ser Asp Gln Asp Arg Val Ser Arg Ser Ser
                180                 185                 190

Ser Glu Leu Lys Thr Gly Glu Gln Thr Pro Pro Phe Glu His Ile Cys
            195                 200                 205

Leu Ser Asp Glu Leu Gly Pro Gln Gly Ser Pro Val Pro Thr Gln His
        210                 215                 220

Arg Gly Thr Ser Thr Asp Ser Pro Cys Ile Arg Ser Ala Ala Thr Gln
225                 230                 235                 240

Met Ala Pro Lys Ser Gly Pro Pro Ala Thr Ala Pro Gly Leu Arg Gly
                245                 250                 255
```

-continued

```
His Ser His Arg Asp Arg Ile Met Tyr Gln Ala Asp Val Arg Leu Glu
        260                 265                 270

Ala Asn Glu Glu Ile Tyr Leu Thr Pro Val Gln Gln Pro Pro Asp Pro
    275                 280                 285

Ala Glu Pro Thr Ser Arg Phe Met Pro Pro Thr Glu Ser Arg Met Thr
290                 295                 300

Val Ser Ser Asp Pro Asp Pro Ala Ala Trp Ser Val Thr Ala Gly Arg
305                 310                 315                 320

Pro His Pro Tyr Ile Ser Glu Glu Asp Glu Gly Phe Asp Ala Leu Ser
                325                 330                 335

Ser Pro Glu Arg Ala Glu Pro Asp Gly Gly Gly Trp Arg Gly Ser Leu
                340                 345                 350

Gly Phe Pro Pro Pro Pro Arg Ala Ser Leu Gly Ser Asp Thr Ser
            355                 360                 365

Ala Leu Ser Tyr Asp His Val Lys Tyr Thr Leu Val Val Asp Glu Ile
    370                 375                 380

Ala Gln Leu Glu Leu Val Ser Leu Arg Lys Cys Phe Gly Asp Tyr Ser
385                 390                 395                 400

Asp Glu Ser Leu Ser Ala Thr Val Tyr Asp Asn Cys Ala Met Ala Ser
                405                 410                 415

Ser Pro Tyr Glu Ser Ala Ile Asn Glu Glu Tyr Glu Glu Ala Pro Gln
            420                 425                 430

Pro Gln Pro Pro Thr Cys Leu Ser Glu Asp Ser Arg Pro Asp Glu Pro
        435                 440                 445

Asp Val Phe Ser Lys Ser Phe Leu Asn Val Phe Met Ser Gly Arg Thr
    450                 455                 460

Arg Ser Ser Ser Ala Glu Ser Phe Gly Val Phe Ser Cys Val Ile Asn
465                 470                 475                 480

Gly Glu Glu Trp Glu Gln Thr His Arg Ala Ile Phe Arg Tyr Val Pro
                485                 490                 495

Arg His Glu Asp Glu Leu Glu Ala Glu Val Asp Asp Pro Leu Leu Val
            500                 505                 510

Glu Asp Gln Ala Glu Asp Tyr Trp Tyr Glu Ala Glu Asn Met Arg Thr
        515                 520                 525

Gly Ala Arg Gly Val Gly Pro Ala Tyr Tyr Ala Ile Glu Val Thr His
    530                 535                 540

Glu Pro Glu His Met Ala Ala Leu Ala Ile Asn Ser Cys Val Leu Glu
545                 550                 555                 560

Ile Ser Val Lys Gly Val Lys Ile Gly Val Lys Ala Asp Leu Ala Leu
                565                 570                 575

Glu Ala Lys Gly Asn Lys Cys Met His Phe Gln Leu Lys Asn Ile
        580                 585                 590

Ser Asn Cys Gly Tyr His Pro Lys Asn Asn Lys Gln Phe Gly Phe Ile
    595                 600                 605

Thr Lys His Pro Ala Arg His Arg Phe Ala Cys His Val Phe Val Thr
610                 615                 620

Glu Asp Ser Thr Lys Ala Leu Ala Glu Val Val Gly Arg Ala Phe Gln
625                 630                 635                 640

Gln Phe Tyr Trp Gln Phe Val Glu Tyr Thr Cys Pro Thr Tyr Asp Ile
                645                 650                 655

Tyr Leu Glu
```

<210> SEQ ID NO 15

<211> LENGTH: 659
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 15

Met Ala Glu Arg Ala Ser Gly Leu Gly Gly Ala Ala Ser Asp Pro
1               5                   10                  15

Ala Ala Ser Pro Phe Leu Gly Leu Glu Ile Ala Ser Pro Pro Asn Phe
            20                  25                  30

Arg Leu Phe His Asp Ile Ser Leu Glu Glu Phe Glu Gly Glu Asp Leu
            35                  40                  45

Ser Glu Ile Thr Asp Glu His Gly Ile Ser Leu Gln Cys Lys Asp Thr
    50                  55                      60

Ile Ser Leu Arg Pro Pro Arg Ala Gly Leu Lys Ser Ala Gly Ser Ser
65                  70                  75                  80

Gly Ser Ala Gly Leu Arg Leu Gln Ala Glu Met Leu Gln Met Met Leu
                85                  90                  95

Ile Asp Ala Ala Gly Asp Thr Pro Asn Ala Glu Asp Glu Glu Glu
                100                 105                 110

Glu Asp Gln Glu Leu Ala Ala Gln Arg Pro Gly Val Arg Pro Pro Lys
            115                 120                 125

Ala Glu Ser Asn Gln Asp Ser Ala Pro Arg Ser Gln Gly Gln Gly Pro
130                 135                 140

Thr Thr Gly Ser Gly Asp Thr Tyr Arg Pro Val Arg Pro Thr Thr Leu
145                 150                 155                 160

Asn Leu Phe Pro Trp Val Pro Arg Ser Gln Asp Thr Leu Asn Tyr Asn
                165                 170                 175

Ser Leu Gly Lys Lys His Ser Trp Ala Asp Arg Val Ser Arg Ser Ser
                180                 185                 190

Ser Pro Asp Lys Thr Gly Glu Gln Thr Pro Pro His Phe His Ile Cys
            195                 200                 205

Leu Ser Asp Glu Leu Pro Gly Gln Gly Ser Pro Val Pro Thr Gln Asp
210                 215                 220

His Gly Thr Ser Thr Asp Ser Pro Cys Arg Ile Ser Ala Ala Thr Gln
225                 230                 235                 240

Met Ala Pro Pro Lys Gly Pro Ala Thr Ala Pro Gly Gly Leu Gly
                245                 250                 255

His Ser His Arg Asp Arg Ile His Met Gln Ala Asp Val Arg Leu Glu
            260                 265                 270

Ala Thr Asn Glu Ile Tyr Leu Thr Pro Val Gln Arg Gln Pro Asp Pro
    275                 280                 285

Ala Glu Pro Thr Ser Thr Arg Met Pro Pro Thr Glu Ser Arg Met Ser
    290                 295                 300

Ser Ser Ser Asp Pro Asp Pro Ala Ala Tyr Thr Val Thr Ala Gly Arg
305                 310                 315                 320

Pro His Pro Ser Val Ser Glu Glu Asp Glu Gly Phe Asp Cys Trp Ser
                325                 330                 335

Ser Pro Glu Arg Ala Glu Pro Pro Tyr Gly Gly Trp Arg Gly Ser Leu
            340                 345                 350

Gly Glu Ala Pro Pro Pro Arg Ala Ser Leu Ser Asp Asp Thr Ser
            355                 360                 365

Ala Leu Ser Tyr Asp Ser Glu Lys Tyr Thr Leu Val Val Asp Glu His

-continued

```
                370                 375                 380
Phe Gln Leu Glu Leu Val Ser Leu Arg Pro Gly Phe Gly Asp Tyr Ser
385                 390                 395                 400

Asp Glu Ser Asp His Ala Thr Val Tyr Asp Asn Cys Ala Ser Ile Ser
                405                 410                 415

Ser Pro Tyr Glu Ser Ala Ile Gly Lys Glu Tyr Glu Ala Pro Gln
                420                 425                 430

Pro Arg Leu Pro Thr Cys Leu Ser Glu Asp Ser Thr Met Asp Glu Pro
                435                 440                 445

Asp Val Phe Ser Lys Lys Asn Leu Asn Val Phe Met Ser Gly Arg Ser
450                 455                 460

Gln Ser Ser Ser Ala Glu Ser Phe Gly Leu Arg Ser Cys Val Ile Asn
465                 470                 475                 480

Gly Glu Glu His Ser Gln Thr His Arg Ala Ile Phe Arg Phe Thr Pro
                485                 490                 495

Arg His Glu Asp Glu Leu Glu Leu Val Val Asp Pro Leu Leu Val
                500                 505                 510

Glu Leu Trp Ala Glu Asp Tyr Trp Tyr Glu Ala Tyr Tyr Met Arg Thr
                515                 520                 525

Gly Ala Arg Gly Val Phe Ala Ala Tyr Tyr Ala Ile Glu Val Thr Lys
530                 535                 540

Asp Pro Glu His Met Ala Ala Leu Ala Lys Glu Ser Cys Val Leu Glu
545                 550                 555                 560

Ile Ser Val Arg Phe Val Lys Ile Gly Val Lys Ala Asp Asp Gly Leu
                565                 570                 575

Glu Ala Lys Gly Asn Lys Cys Ser Ile Phe Phe Gln Leu Lys Asn Ile
                580                 585                 590

Ser Phe Lys Gly Tyr His Pro Lys Asn Asn Lys Tyr Leu Gly Phe Ile
                595                 600                 605

Thr Lys His Pro Ala Asp Met Arg Phe Ala Cys His Val Phe Val Ser
610                 615                 620

Asn Asp Ser Thr Lys Ala Leu Ala Glu Ser Gln Gly Arg Ala Phe Gln
625                 630                 635                 640

Gln Phe Tyr Lys Arg Phe Val Glu Tyr Thr Cys Pro Thr Glu Ser Ile
                645                 650                 655

Tyr Leu Glu

<210> SEQ ID NO 16
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 16

Met Ala Glu Arg Glu Ala Gly Leu Gly Gly Gly Ala Ala Ser Pro Asp
  1               5                  10                  15

Ala Ala Ser Pro Phe Leu Gly Leu His Glu Ala Ser Pro Pro Asn Phe
                 20                  25                  30

Arg Leu Thr Phe Asp Ile Ser Leu Glu Glu Phe Glu Asp Gly Asp Leu
             35                  40                  45

Ser Glu Ile Thr Asp Glu Cys His Ile Ser Leu Gln Cys Lys Asp Thr
         50                  55                  60

Leu Ile Leu Arg Pro Pro Arg Ala Gly Leu Leu Lys Ala Gly Ser Ser
```

-continued

```
                65                  70                  75                  80
        Gly Ser Ala Gly Ser Leu Leu Gln Ala Glu Met Leu Gln Met Asp Met
                         85                  90                  95
        Ile Asp Ala Ala Gly Asp Thr Pro Gly Asn Glu Asp Glu Glu Glu
                    100                 105                 110
        Glu Asp Asp Gln Leu Ala Ala Gln Arg Pro Gly Val Gly Arg Pro Lys
                    115                 120                 125
        Ala Glu Ser Asn Gln Asp Pro Ser Pro Arg Ser Gln Gly Gln Gly Pro
                    130                 135                 140
        Gly Val Gly Ser Gly Asp Thr Tyr Arg Pro Lys Trp Pro Thr Thr Leu
        145                 150                 155                 160
        Asn Leu Phe Pro Gln Tyr Pro Arg Ser Gln Asp Thr Leu Asn Asn Ala
                    165                 170                 175
        Ser Leu Gly Lys Lys His Ser Trp Gln Asp Arg Val Ser Arg Ser Ser
                    180                 185                 190
        Ser Pro Leu Glu Thr Gly Glu Gln Thr Pro Pro His Glu Phe Ile Cys
                    195                 200                 205
        Leu Ser Asp Glu Leu Pro Pro Gly Gly Ser Pro Val Pro Thr Gln Asp
                    210                 215                 220
        Arg His Thr Ser Thr Asp Ser Pro Cys Arg Arg Ile Ala Ala Thr Gln
        225                 230                 235                 240
        Met Ala Pro Pro Ser Lys Pro Pro Ala Thr Ala Pro Gly Gly Arg Leu
                    245                 250                 255
        His Ser His Arg Asp Arg Ile His Tyr Met Ala Asp Val Arg Leu Glu
                    260                 265                 270
        Ala Thr Glu Asn Ile Tyr Leu Thr Pro Val Gln Arg Pro Gln Asp Pro
                    275                 280                 285
        Ala Glu Pro Thr Ser Thr Phe Arg Pro Pro Thr Glu Ser Arg Met Ser
                    290                 295                 300
        Val Thr Ser Asp Pro Asp Pro Ala Ala Tyr Ser Trp Thr Ala Gly Arg
        305                 310                 315                 320
        Pro His Pro Ser Ile Tyr Glu Glu Asp Glu Gly Phe Asp Cys Leu Ala
                    325                 330                 335
        Ser Pro Glu Arg Ala Glu Pro Pro Gly Asp Gly Trp Arg Gly Ser Leu
                    340                 345                 350
        Gly Glu Pro Glu Pro Pro Arg Ala Ser Leu Ser Ser Phe Thr Ser
                    355                 360                 365
        Ala Leu Ser Tyr Asp Ser Val Gly Tyr Thr Leu Val Val Asp Glu His
                    370                 375                 380
        Ala His Leu Glu Leu Val Ser Leu Arg Pro Cys Ile Gly Asp Tyr Ser
        385                 390                 395                 400
        Asp Glu Ser Asp Ser Lys Thr Val Tyr Asp Asn Cys Ala Ser Ala Leu
                    405                 410                 415
        Ser Pro Tyr Glu Ser Ala Ile Gly Glu Met Tyr Glu Glu Ala Pro Gln
                    420                 425                 430
        Pro Arg Pro Asn Thr Cys Leu Ser Glu Asp Ser Thr Pro Gln Glu Pro
                    435                 440                 445
        Asp Val Phe Ser Lys Lys Phe Arg Asn Val Phe Met Ser Gly Arg Ser
                    450                 455                 460
        Arg Thr Ser Ser Ala Glu Ser Phe Gly Leu Phe Val Cys Val Ile Asn
        465                 470                 475                 480
        Gly Glu Glu His Glu Trp Thr His Arg Ala Ile Phe Arg Phe Val Tyr
                    485                 490                 495
```

```
Arg His Glu Asp Glu Leu Glu Leu Glu Ala Asp Asp Pro Leu Leu Val
                500                 505                 510

Glu Leu Gln Asp Glu Asp Tyr Trp Tyr Glu Ala Tyr Asn Glu Arg Thr
            515                 520                 525

Gly Ala Arg Gly Val Phe Pro Phe Tyr Ala Ile Glu Val Thr Lys
530                 535                 540

Glu Gly Glu His Met Ala Ala Leu Ala Lys Asn His Cys Val Leu Glu
545                 550                 555                 560

Ile Ser Val Arg Gly Ile Lys Ile Gly Val Lys Ala Asp Asp Ala Lys
                565                 570                 575

Glu Ala Lys Gly Asn Lys Cys Ser His Leu Phe Gln Leu Lys Asn Ile
            580                 585                 590

Ser Phe Cys Met Tyr His Pro Lys Asn Asn Lys Tyr Phe Asn Phe Ile
                595                 600                 605

Thr Lys His Pro Ala Asp His Gln Phe Ala Cys His Val Phe Val Ser
            610                 615                 620

Glu Arg Ser Thr Lys Ala Leu Ala Glu Ser Val Ser Arg Ala Phe Gln
625                 630                 635                 640

Gln Phe Tyr Lys Gln Thr Val Glu Tyr Thr Cys Pro Thr Glu Asp Val
                645                 650                 655

Tyr Leu Glu

<210> SEQ ID NO 17
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 17

Met Ala Glu Arg Glu Ser Ala Leu Gly Gly Gly Ala Ala Ser Pro Pro
 1               5                  10                  15

Asp Ala Ser Pro Phe Leu Gly Leu His Ile Glu Ser Pro Pro Asn Phe
                20                  25                  30

Arg Leu Thr His Phe Ile Ser Leu Glu Glu Phe Glu Asp Glu Gly Leu
            35                  40                  45

Ser Glu Ile Thr Asp Glu Cys Gly His Ser Leu Gln Cys Lys Asp Thr
        50                  55                  60

Leu Ser Ile Arg Pro Pro Arg Ala Gly Leu Leu Ser Lys Gly Ser Ser
 65                  70                  75                  80

Gly Ser Ala Gly Ser Arg Met Gln Ala Glu Met Leu Gln Met Asp Leu
                85                  90                  95

Asn Asp Ala Ala Gly Asp Thr Pro Gly Ala Gln Asp Glu Glu Glu
                100                 105                 110

Glu Asp Asp Glu Arg Ala Ala Gln Arg Pro Gly Val Gly Pro Ser Lys
            115                 120                 125

Ala Glu Ser Asn Gln Asp Pro Ala Thr Arg Ser Gln Gly Gln Gly Pro
        130                 135                 140

Gly Thr Val Ser Gly Asp Thr Tyr Arg Pro Lys Arg Trp Thr Thr Leu
145                 150                 155                 160

Asn Leu Phe Pro Gln Val Tyr Arg Ser Gln Asp Thr Leu Asn Asn Asn
                165                 170                 175

Ala Leu Gly Lys Lys His Ser Trp Gln Asp Asp Val Ser Arg Ser Ser
                180                 185                 190
```

-continued

```
Ser Pro Leu Lys Glu Gly Glu Gln Thr Pro Pro His Glu His Phe Cys
            195                 200                 205

Leu Ser Asp Glu Leu Pro Pro Gln His Ser Pro Val Pro Thr Gln Asp
        210                 215                 220

Arg Gly Ile Ser Thr Asp Ser Pro Cys Arg Arg Ser Lys Ala Thr Gln
225                 230                 235                 240

Met Ala Pro Pro Ser Gly Leu Pro Ala Thr Ala Pro Gly Gly Arg Gly
                245                 250                 255

Met Ser His Arg Asp Arg Ile His Tyr Gln Asn Asp Val Arg Leu Glu
            260                 265                 270

Ala Thr Glu Glu Gln Tyr Leu Thr Pro Val Gln Arg Pro Pro Arg Pro
        275                 280                 285

Ala Glu Pro Thr Ser Thr Phe Met Ser Pro Thr Glu Ser Arg Met Ser
290                 295                 300

Val Ser Thr Asp Pro Asp Pro Ala Ala Tyr Ser Val Val Ala Gly Arg
305                 310                 315                 320

Pro His Pro Ser Ile Ser Trp Glu Asp Glu Gly Phe Asp Cys Leu Ser
                325                 330                 335

Tyr Pro Glu Arg Ala Glu Pro Gly Gly Ala Trp Arg Gly Ser Leu
            340                 345                 350

Gly Glu Pro Pro Asp Pro Pro Arg Ala Ser Leu Ser Ser Asp Glu Ser
        355                 360                 365

Ala Leu Ser Tyr Asp Ser Val Lys Phe Thr Leu Val Val Asp Glu His
        370                 375                 380

Ala Gln Gly Glu Leu Val Ser Leu Arg Pro Cys Phe His Asp Tyr Ser
385                 390                 395                 400

Asp Glu Ser Asp Ser Ala Ile Val Tyr Asp Asn Cys Ala Ser Ala Ser
                405                 410                 415

Lys Pro Tyr Glu Ser Ala Ile Gly Glu Leu Glu Glu Ala Pro Gln
            420                 425                 430

Pro Arg Pro Pro Met Cys Leu Ser Glu Asp Ser Thr Pro Asp Asn Pro
        435                 440                 445

Asp Val Phe Ser Lys Lys Phe Leu Gln Val Phe Met Ser Gly Arg Ser
        450                 455                 460

Arg Ser Arg Ser Ala Glu Ser Phe Gly Leu Phe Ser Ser Val Ile Asn
465                 470                 475                 480

Gly Glu Glu His Glu Gln Val His Arg Ala Ile Phe Arg Phe Val Pro
                485                 490                 495

Trp His Glu Asp Glu Leu Glu Leu Glu Val Tyr Asp Pro Leu Leu Val
            500                 505                 510

Glu Leu Gln Ala Ala Asp Tyr Trp Tyr Glu Ala Tyr Asn Met Asp Thr
        515                 520                 525

Gly Ala Arg Gly Val Phe Pro Ala Glu Tyr Ala Ile Glu Val Thr Lys
        530                 535                 540

Glu Pro Phe His Met Ala Ala Leu Ala Lys Asn Ser Gly Val Leu Glu
545                 550                 555                 560

Ile Ser Val Arg Gly Val His Ile Gly Val Lys Ala Asp Asp Ala Leu
                565                 570                 575

Ile Ala Lys Gly Asn Lys Cys Ser His Phe Lys Gln Leu Lys Asn Ile
            580                 585                 590

Ser Phe Cys Gly Leu His Pro Lys Asn Asn Lys Tyr Phe Gly Met Ile
        595                 600                 605
```

```
Thr Lys His Pro Ala Asp His Arg Asn Ala Cys His Val Phe Val Ser
    610                 615                 620
Glu Asp Gln Thr Lys Ala Leu Ala Glu Ser Val Gly Ser Ala Phe Gln
625                 630                 635                 640
Gln Phe Tyr Lys Gln Phe Thr Glu Tyr Thr Cys Pro Thr Glu Asp Ile
                645                 650                 655
Val Leu Glu

<210> SEQ ID NO 18
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 18

Met Ala Glu Arg Glu Ser Gly Ala Gly Gly Ala Ala Ser Pro Pro
  1               5                  10                  15
Ala Asp Ser Pro Phe Leu Gly Leu His Ile Ala Glu Pro Pro Asn Phe
                 20                  25                  30
Arg Leu Thr His Asp Phe Ser Leu Glu Glu Phe Glu Asp Glu Asp Gly
             35                  40                  45
Ser Glu Ile Thr Asp Glu Cys Gly Ile His Leu Gln Cys Lys Asp Thr
 50                  55                  60
Leu Ser Leu Ile Pro Pro Arg Ala Gly Leu Leu Ser Ala Lys Ser Ser
 65                  70                  75                  80
Gly Ser Ala Gly Ser Arg Leu Leu Ala Glu Met Leu Gln Met Asp Leu
                 85                  90                  95
Ile Met Ala Ala Gly Asp Thr Pro Gly Ala Glu Asn Asp Glu Glu Glu
            100                 105                 110
Glu Asp Asp Glu Leu Gln Ala Gln Arg Pro Gly Val Gly Pro Pro Arg
        115                 120                 125
Ala Glu Ser Asn Gln Asp Pro Ala Pro Ser Ser Gln Gly Gln Gly Pro
    130                 135                 140
Gly Thr Gly Thr Gly Asp Thr Tyr Arg Pro Lys Arg Pro Val Thr Leu
145                 150                 155                 160
Asn Leu Phe Pro Gln Val Pro Trp Ser Gln Asp Thr Leu Asn Asn Asn
                165                 170                 175
Ser Tyr Gly Lys Lys His Ser Trp Gln Asp Arg Ala Ser Arg Ser Ser
            180                 185                 190
Ser Pro Leu Lys Thr Asp Glu Gln Thr Pro Pro His Glu His Ile Glu
        195                 200                 205
Leu Ser Asp Glu Leu Pro Pro Gln Gly Phe Pro Val Pro Thr Gln Asp
    210                 215                 220
Arg Gly Thr Gly Thr Asp Ser Pro Cys Arg Arg Ser Ala His Thr Gln
225                 230                 235                 240
Met Ala Pro Pro Ser Gly Pro Ile Ala Thr Ala Pro Gly Gly Arg Gly
                245                 250                 255
His Lys His Arg Asp Arg Ile His Tyr Gln Ala Leu Val Arg Leu Glu
            260                 265                 270
Ala Thr Glu Glu Ile Met Leu Thr Pro Val Gln Arg Pro Pro Asp Asn
        275                 280                 285
Ala Glu Pro Thr Ser Thr Phe Met Pro Gln Thr Glu Ser Arg Met Ser
    290                 295                 300
```

```
Val Ser Ser Arg Pro Asp Pro Ala Ala Tyr Ser Val Thr Ser Gly Arg
305                 310                 315                 320

Pro His Pro Ser Ile Ser Glu Thr Asp Glu Gly Phe Asp Cys Leu Ser
            325                 330                 335

Ser Val Glu Arg Ala Glu Pro Pro Gly Gly Tyr Arg Gly Ser Leu
        340                 345                 350

Gly Glu Pro Pro Pro Ala Pro Arg Ala Ser Leu Ser Ser Asp Thr Asp
        355                 360                 365

Ala Leu Ser Tyr Asp Ser Val Lys Tyr Glu Leu Val Val Asp Glu His
        370                 375                 380

Ala Gln Leu Phe Leu Val Ser Leu Arg Pro Cys Phe Gly Gly Tyr Ser
385                 390                 395                 400

Asp Glu Ser Asp Ser Ala Thr His Tyr Asp Asn Cys Ala Ser Ala Ser
                405                 410                 415

Ser Ile Tyr Glu Ser Ala Ile Gly Glu Glu Tyr Lys Glu Ala Pro Gln
                420                 425                 430

Pro Arg Pro Pro Thr Leu Leu Ser Glu Asp Ser Thr Pro Asp Glu Met
            435                 440                 445

Asp Val Phe Ser Lys Lys Phe Leu Asn Asn Phe Met Ser Gly Arg Ser
450                 455                 460

Arg Ser Ser Gln Ala Glu Ser Phe Gly Leu Phe Ser Cys Arg Ile Asn
465                 470                 475                 480

Gly Glu Glu His Glu Gln Thr Ser Arg Ala Ile Phe Arg Phe Val Pro
                485                 490                 495

Arg Thr Glu Asp Glu Leu Glu Leu Glu Val Asp Val Pro Leu Leu Val
                500                 505                 510

Glu Leu Gln Ala Glu Trp Tyr Trp Tyr Glu Ala Tyr Asn Met Arg Tyr
            515                 520                 525

Gly Ala Arg Gly Val Phe Pro Ala Tyr Ala Ala Ile Glu Val Thr Lys
            530                 535                 540

Glu Pro Glu Asp Met Ala Ala Leu Ala Lys Asn Ser Cys Glu Leu Glu
545                 550                 555                 560

Ile Ser Val Arg Gly Val Lys Phe Gly Val Lys Ala Asp Asp Ala Leu
                565                 570                 575

Glu Gly Lys Gly Asn Lys Cys Ser His Phe Phe His Leu Lys Asn Ile
            580                 585                 590

Ser Phe Cys Gly Tyr Ile Pro Lys Asn Asn Lys Tyr Phe Gly Phe Lys
            595                 600                 605

Thr Lys His Pro Ala Asp His Arg Phe Leu Cys His Val Phe Val Ser
            610                 615                 620

Glu Asp Ser Met Lys Ala Leu Ala Glu Ser Val Gly Arg Asn Phe Gln
625                 630                 635                 640

Gln Phe Tyr Lys Gln Phe Val Gln Tyr Thr Cys Pro Thr Glu Asp Ile
                645                 650                 655

Tyr Arg Glu

<210> SEQ ID NO 19
<211> LENGTH: 659
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 19
```

-continued

```
Met Ala Glu Arg Glu Ser Gly Leu Ala Gly Gly Ala Ala Ser Pro Pro
 1               5                  10                  15

Ala Ala Asp Pro Phe Leu Gly Leu His Ile Ala Ser Glu Pro Asn Phe
            20                  25                  30

Arg Leu Thr His Asp Ile Phe Leu Glu Glu Phe Glu Asp Glu Asp Leu
        35                  40                  45

Gly Glu Ile Thr Asp Glu Cys Gly Ile Ser His Gln Cys Lys Asp Thr
 50                  55                  60

Leu Ser Leu Arg Ile Pro Arg Ala Gly Leu Leu Ser Ala Gly Lys Ser
 65                  70                  75                  80

Gly Ser Ala Gly Ser Arg Leu Gln Leu Glu Met Leu Gln Met Asp Leu
                85                  90                  95

Ile Asp Met Ala Gly Asp Thr Pro Gly Ala Glu Asp Asn Glu Glu Glu
            100                 105                 110

Glu Asp Glu Leu Ala Gln Gln Arg Pro Gly Val Gly Pro Pro Lys
        115                 120                 125

Arg Glu Ser Asn Gln Asp Pro Ala Pro Arg Thr Gln Gly Gln Gly Pro
130                 135                 140

Gly Thr Gly Ser Val Asp Thr Tyr Arg Pro Lys Arg Pro Thr Trp Leu
145                 150                 155                 160

Asn Leu Phe Pro Gln Val Pro Arg Tyr Gln Asp Thr Leu Asn Asn Asn
                165                 170                 175

Ser Leu Ala Lys Lys His Ser Trp Gln Asp Arg Val Asp Arg Ser Ser
            180                 185                 190

Ser Pro Leu Lys Thr Gly Phe Gln Thr Pro Pro His Glu His Ile Cys
        195                 200                 205

Gly Ser Asp Glu Leu Pro Pro Gln Gly Ser His Val Pro Thr Gln Asp
210                 215                 220

Arg Gly Thr Ser Ile Asp Ser Pro Cys Arg Arg Ser Ala Ala Lys Gln
225                 230                 235                 240

Met Ala Pro Pro Ser Gly Pro Pro Leu Thr Ala Pro Gly Gly Arg Gly
                245                 250                 255

His Ser Met Arg Asp Arg Ile His Tyr Gln Ala Asp Asn Arg Leu Glu
            260                 265                 270

Ala Thr Glu Glu Ile Tyr Gln Thr Pro Val Gln Arg Pro Pro Asp Pro
        275                 280                 285

Arg Glu Pro Thr Ser Thr Phe Met Pro Pro Ser Glu Ser Arg Met Ser
290                 295                 300

Val Ser Ser Asp Thr Asp Pro Ala Ala Tyr Ser Val Thr Ala Val Arg
305                 310                 315                 320

Pro His Pro Ser Ile Ser Glu Glu Trp Glu Gly Phe Asp Cys Leu Ser
                325                 330                 335

Ser Pro Tyr Arg Ala Glu Pro Pro Gly Gly Gly Trp Ala Gly Ser Leu
            340                 345                 350

Gly Glu Pro Pro Pro Asp Arg Ala Ser Leu Ser Ser Asp Thr Ser
        355                 360                 365

Glu Leu Ser Tyr Asp Ser Val Lys Tyr Thr Phe Val Val Asp Glu His
370                 375                 380

Ala Gln Leu Glu Gly Val Ser Leu Arg Pro Cys Phe Gly Asp His Ser
385                 390                 395                 400

Asp Glu Ser Asp Ser Ala Thr Val Ile Asp Asn Cys Ala Ser Ala Ser
                405                 410                 415

Ser Pro Lys Glu Ser Ala Ile Gly Glu Glu Tyr Glu Leu Ala Pro Gln
```

-continued

```
                420               425               430
Pro Arg Pro Thr Cys Met Ser Glu Asp Ser Thr Pro Asp Glu Pro
        435               440               445
Asn Val Phe Ser Lys Lys Phe Leu Asn Val Gln Met Ser Gly Arg Ser
450               455               460
Arg Ser Ser Ser Arg Glu Ser Phe Gly Leu Phe Ser Cys Val Ser Asn
465               470               475               480
Gly Glu Glu His Glu Gln Thr His Thr Ala Ile Phe Arg Phe Val Pro
                485               490               495
Arg His Val Asp Glu Leu Glu Leu Glu Val Asp Asp Trp Leu Leu Val
                500               505               510
Glu Leu Gln Ala Glu Asp Ala Trp Tyr Glu Ala Tyr Asn Met Arg Thr
        515               520               525
Asp Ala Arg Gly Val Phe Pro Ala Tyr Tyr Glu Ile Glu Val Thr Lys
530               535               540
Glu Pro Glu His Phe Ala Ala Leu Ala Lys Asn Ser Cys Val Gly Glu
545               550               555               560
Ile Ser Val Arg Gly Val Lys Ile His Val Lys Ala Asp Asp Ala Leu
                565               570               575
Glu Ala Ile Gly Asn Lys Cys Ser His Phe Gln Lys Lys Asn Ile
        580               585               590
Ser Phe Cys Gly Tyr His Leu Lys Asn Asn Lys Tyr Phe Gly Phe Ile
        595               600               605
Met Lys His Pro Ala Asp His Arg Phe Ala Asn His Val Phe Val Ser
        610               615               620
Glu Asp Ser Thr Gln Ala Leu Ala Glu Ser Val Gly Arg Ala Arg Gln
625               630               635               640
Gln Phe Tyr Lys Gln Phe Val Glu Ser Thr Cys Pro Thr Glu Asp Ile
                645               650               655
Tyr Leu Thr
```

<210> SEQ ID NO 20
<211> LENGTH: 659
<212> TYPE: PRT
<213> ORGANISM: Artificial Sequence
<220> FEATURE:
<223> OTHER INFORMATION: Description of Artificial Sequence: Synthetic
    Sequence

<400> SEQUENCE: 20

```
Met Ala Glu Arg Glu Ser Gly Leu Gly Ala Ala Ser Pro Pro
1               5               10              15
Ala Ala Ser Asp Phe Leu Gly Leu His Ile Ala Ser Pro Glu Asn Phe
                20              25              30
Arg Leu Thr His Asp Ile Ser Phe Glu Glu Phe Glu Asp Glu Asp Leu
        35              40              45
Ser Gly Ile Thr Asp Glu Cys Gly Ile Ser Leu His Cys Lys Asp Thr
    50              55              60
Leu Ser Leu Arg Pro Ile Arg Ala Gly Leu Leu Ser Ala Gly Ser Lys
65              70              75              80
Gly Ser Ala Gly Ser Arg Leu Gln Ala Leu Met Leu Gln Met Asp Leu
                85              90              95
Ile Asp Ala Met Gly Asp Thr Pro Gly Ala Glu Asp Asp Asn Glu Glu
                100             105             110
Glu Asp Asp Glu Leu Ala Ala Arg Arg Pro Gly Val Gly Pro Pro Lys
```

-continued

```
                115                 120                 125
Ala Ser Ser Asn Gln Asp Pro Ala Pro Arg Ser Thr Gly Gln Gly Pro
    130                 135                 140
Gly Thr Gly Ser Gly Val Thr Tyr Arg Pro Lys Arg Pro Thr Thr Trp
145                 150                 155                 160
Asn Leu Phe Pro Gln Val Pro Arg Ser Tyr Asp Thr Leu Asn Asn Asn
                165                 170                 175
Ser Leu Gly Ala Lys His Ser Trp Gln Asp Arg Val Ser Asp Ser Ser
                180                 185                 190
Ser Pro Leu Lys Thr Gly Glu Glu Thr Pro Pro His Glu His Ile Cys
                195                 200                 205
Leu Phe Asp Glu Leu Pro Pro Gln Gly Ser Pro Gly Pro Thr Gln Asp
    210                 215                 220
Arg Gly Thr Ser Thr His Ser Pro Cys Arg Arg Ser Ala Ala Thr Ile
225                 230                 235                 240
Met Ala Pro Pro Ser Gly Pro Pro Ala Lys Ala Pro Gly Gly Arg Gly
                245                 250                 255
His Ser His Leu Asp Arg Ile His Tyr Gln Ala Asp Val Met Leu Glu
                260                 265                 270
Ala Thr Glu Glu Ile Tyr Leu Asn Pro Val Gln Arg Pro Pro Asp Pro
                275                 280                 285
Ala Gln Pro Thr Ser Thr Phe Met Pro Pro Thr Arg Ser Arg Met Ser
    290                 295                 300
Val Ser Ser Asp Pro Ser Pro Ala Ala Tyr Ser Val Thr Ala Gly Thr
305                 310                 315                 320
Pro His Pro Ser Ile Ser Glu Glu Asp Val Gly Phe Asp Cys Leu Ser
                325                 330                 335
Ser Pro Glu Trp Ala Glu Pro Pro Gly Gly Gly Trp Arg Tyr Ser Leu
                340                 345                 350
Gly Glu Pro Pro Pro Pro Ala Ala Ser Leu Ser Ser Asp Thr Ser
                355                 360                 365
Ala Asp Ser Tyr Asp Ser Val Lys Tyr Thr Leu Glu Val Asp Glu His
    370                 375                 380
Ala Gln Leu Glu Leu Phe Ser Leu Arg Pro Cys Phe Gly Asp Tyr Gly
385                 390                 395                 400
Asp Glu Ser Asp Ser Ala Thr Val Tyr His Asn Cys Ala Ser Ala Ser
                405                 410                 415
Ser Pro Tyr Ile Ser Ala Ile Gly Glu Glu Tyr Glu Lys Pro Gln
                420                 425                 430
Pro Arg Pro Pro Thr Cys Leu Leu Glu Asp Ser Thr Pro Asp Glu Pro
    435                 440                 445
Asp Met Phe Ser Lys Lys Phe Leu Asn Val Phe Asn Ser Gly Arg Ser
    450                 455                 460
Arg Ser Ser Ser Ala Gln Ser Phe Gly Leu Phe Ser Cys Val Ile Arg
465                 470                 475                 480
Gly Glu Glu His Glu Gln Thr His Arg Ser Ile Phe Arg Phe Val Pro
                485                 490                 495
Arg His Glu Thr Glu Leu Glu Leu Glu Val Asp Asp Pro Val Leu Val
                500                 505                 510
Glu Leu Gln Ala Glu Asp Tyr Tyr Tyr Glu Ala Tyr Asn Met Arg Thr
    515                 520                 525
Gly Asp Arg Gly Val Phe Pro Ala Tyr Tyr Ala Glu Val Thr Lys
    530                 535                 540
```

```
Glu Pro Glu His Met Phe Ala Leu Ala Lys Asn Ser Cys Val Leu Gly
545                 550                 555                 560

Ile Ser Val Arg Gly Val Lys Ile Gly His Lys Ala Asp Asp Ala Leu
                565                 570                 575

Glu Ala Lys Ile Asn Lys Cys Ser His Phe Phe Gln Leu Leu Asn Ile
            580                 585                 590

Ser Phe Cys Gly Tyr His Pro Met Asn Asn Lys Tyr Phe Gly Phe Ile
        595                 600                 605

Thr Asn His Pro Ala Asp His Arg Phe Ala Cys Gln Val Phe Val Ser
    610                 615                 620

Glu Asp Ser Thr Lys Arg Leu Ala Glu Ser Val Gly Arg Ala Phe Ser
625                 630                 635                 640

Gln Phe Tyr Lys Gln Phe Val Glu Tyr Val Cys Pro Thr Glu Asp Ile
                645                 650                 655

Tyr Leu Glu

<210> SEQ ID NO 21
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 21

Met Asp Cys Leu Cys Ile Val Thr Thr Lys Lys Tyr Arg Tyr Gln Asp
1               5                   10                  15

Glu Asp Thr Pro Pro Leu Glu His Ser Pro Ala His Leu Pro Asn Gln
                20                  25                  30

Ala Asn Ser Pro Pro Val Ile Val Asn Thr Asp Thr Leu Glu Ala Pro
            35                  40                  45

Gly Tyr Glu Leu Gln Val Asn Gly Thr Glu Gly Glu Met Glu Tyr Glu
        50                  55                  60

Glu Ile Thr Leu Glu Arg Gly Asn Ser Gly Leu Gly Phe Ser Ile Ala
65                  70                  75                  80

Gly Gly Thr Asp Asn Pro His Ile Gly Asp Asp Pro Ser Ile Phe Ile
                85                  90                  95

Thr Lys Ile Ile Pro Gly Gly Ala Ala Ala Gln Asp Gly Arg Leu Arg
                100                 105                 110

Val Asn Asp Ser Ile Leu Phe Val Asn Glu Val Asp Val Arg Glu Val
            115                 120                 125

Thr His Ser Ala Ala Val Glu Ala Leu Lys Glu Ala Gly Ser Ile Val
        130                 135                 140

Arg Leu Tyr Val Met Arg Arg Lys Pro Pro Ala Glu Lys Ile Ile Glu
145                 150                 155                 160

Ile Lys Leu Ile Lys Gly Pro Lys Gly Leu Gly Phe Ser Ile Ala Gly
                165                 170                 175

Gly Val Gly Asn Gln His Ile Pro Gly Asp Asn Ser Ile Tyr Val Thr
            180                 185                 190

Lys Ile Ile Glu Gly Gly Ala Ala His Lys Asp Gly Arg Leu Gln Ile
        195                 200                 205

Gly Asp Lys Ile Leu Ala Val Asn Ser Val Gly Leu Glu Asp Val Met
    210                 215                 220

His Glu Asp Ala Val Ala Ala Leu Lys Asn Thr Tyr Asp Val Val Tyr
225                 230                 235                 240
```

-continued

```
Leu Lys Val Ala Lys Pro Ser Asn Ala Tyr Leu Ser Asp Ser Tyr Ala
            245                 250                 255
Pro Pro Asp Ile Thr Thr Ser Tyr Ser Gln His Leu Asp Asn Glu Ile
            260                 265                 270
Ser His Ser Ser Tyr Leu Gly Thr Asp Tyr Pro Thr Ala Met Thr Pro
            275                 280                 285
Thr Ser Pro Arg Arg Tyr Ser Pro Val Ala Lys Asp Leu Leu Gly Glu
            290                 295                 300
Glu Asp Ile Pro Arg Glu Pro Arg Arg Ile Val Ile His Arg Gly Ser
305                 310                 315                 320
Thr Gly Leu Gly Phe Asn Ile Val Gly Gly Glu Asp Gly Glu Gly Ile
                    325                 330                 335
Phe Ile Ser Phe Ile Leu Ala Gly Gly Pro Ala Asp Leu Ser Gly Glu
                    340                 345                 350
Leu Arg Lys Gly Asp Gln Ile Leu Ser Val Asn Gly Val Asp Leu Arg
            355                 360                 365
Asn Ala Ser His Glu Gln Ala Ala Ile Ala Leu Lys Asn Ala Gly Gln
370                 375                 380
Thr Val Thr Ile Ile Ala Gln Tyr Lys Pro Glu Glu Tyr Ser Arg Phe
385                 390                 395                 400
Glu Ala Lys Ile His Asp Leu Arg Glu Gln Leu Met Asn Ser Ser Leu
                    405                 410                 415
Gly Ser Gly Thr Ala Ser Leu Arg Ser Asn Pro Lys Arg Gly Phe Tyr
                    420                 425                 430
Ile Arg Ala Leu Phe Asp Tyr Asp Lys Thr Lys Asp Cys Gly Phe Leu
            435                 440                 445
Ser Gln Ala Leu Ser Phe His Phe Gly Asp Val Leu His Val Ile Asp
            450                 455                 460
Ala Ser Asp Glu Glu Trp Trp Gln Ala Arg Arg Val His Ser Asp Ser
465                 470                 475                 480
Glu Thr Asp Asp Ile Gly Phe Ile Pro Ser Lys Arg Arg Val Glu Arg
                    485                 490                 495
Arg Glu Trp Ser Arg Leu Lys Ala Lys Asp Trp Gly Ser Ser Ser Gly
                    500                 505                 510
Ser Gln Gly Arg Glu Asp Ser Val Leu Ser Tyr Glu Thr Val Thr Gln
            515                 520                 525
Met Glu Val His Tyr Ala Arg Pro Ile Ile Ile Leu Gly Pro Thr Lys
            530                 535                 540
Asp Arg Ala Asn Asp Asp Leu Leu Ser Glu Phe Pro Asp Lys Phe Gly
545                 550                 555                 560
Ser Cys Val Pro His Thr Thr Arg Pro Lys Arg Glu Tyr Glu Ile Asp
                    565                 570                 575
Gly Arg Asp Tyr His Phe Val Ser Ser Arg Glu Lys Met Glu Lys Asp
                    580                 585                 590
Ile Gln Ala His Lys Phe Ile Glu Ala Gly Gln Tyr Asn Ser His Leu
            595                 600                 605
Tyr Gly Thr Ser Val Gln Ser Val Arg Glu Val Ala Glu Gln Gly Lys
            610                 615                 620
His Cys Ile Leu Asp Val Ser Ala Asn Ala Val Arg Arg Leu Gln Ala
625                 630                 635                 640
Ala His Leu His Pro Ile Ala Ile Phe Ile Arg Pro Arg Ser Leu Glu
                    645                 650                 655
```

-continued

```
Asn Val Leu Glu Ile Asn Lys Arg Ile Thr Glu Glu Gln Ala Arg Lys
            660                 665                 670

Ala Phe Asp Arg Ala Thr Lys Leu Glu Gln Glu Phe Thr Glu Cys Phe
            675                 680                 685

Ser Ala Ile Val Glu Gly Asp Ser Phe Glu Ile Tyr His Lys Val
            690                 695                 700

Lys Arg Val Ile Glu Asp Leu Ser Gly Pro Tyr Ile Trp Val Pro Ala
705                 710                 715                 720

Arg Glu Arg Leu

<210> SEQ ID NO 22
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 22

Met Ala Cys Leu Cys Ile Val Thr Thr Lys Lys Asp Arg Tyr Gln Asp
1               5                   10                  15

Glu Asp Thr Pro Pro Glu Glu His Ser Pro Ala His Leu Pro Asn Phe
            20                  25                  30

Ala Asn Ser Pro Pro Val Ile Val Asn Gly Asp Thr Leu Glu Ala Pro
            35                  40                  45

Gly Tyr Glu His Gln Val Asn Gly Thr Glu Gly Glu Met Ile Tyr Glu
    50                  55                  60

Glu Ile Thr Leu Glu Arg Gly Lys Ser Gly Leu Gly Phe Ser Ile Ala
65                  70                  75                  80

Gly Leu Thr Asp Asn Pro His Ile Gly Asp Asp Met Ser Ile Phe Ile
                85                  90                  95

Thr Lys Ile Ile Pro Asn Gly Ala Ala Ala Gln Asp Gly Arg Leu Gln
                100                 105                 110

Val Asn Asp Ser Ile Leu Phe Val Asn Arg Val Asp Val Arg Glu Val
            115                 120                 125

Thr His Ser Ser Ala Val Glu Ala Leu Lys Glu Ala Gly Thr Ile Val
            130                 135                 140

Arg Leu Tyr Val Met Arg Arg Val Pro Pro Ala Glu Lys Ile Ile Glu
145                 150                 155                 160

Ile Trp Leu Ile Lys Gly Pro Lys Gly Leu Gly Tyr Ser Ile Ala Gly
                165                 170                 175

Gly Val Gly Asn Gln Ala Ile Pro Gly Asp Asn Ser Ile Tyr Val Asp
            180                 185                 190

Lys Ile Ile Glu Gly Gly Ala Ala His Glu Asp Gly Arg Leu Gln Ile
            195                 200                 205

Gly Asp Lys Phe Leu Ala Val Asn Ser Val Gly Leu Glu Gly Val Met
            210                 215                 220

His Glu Asp Ala Val Ala Ala His Lys Asn Thr Tyr Asp Val Val Tyr
225                 230                 235                 240

Leu Ile Val Ala Lys Pro Ser Asn Ala Tyr Leu Lys Asp Ser Tyr Ala
                245                 250                 255

Pro Pro Asp Ile Thr Leu Ser Tyr Ser Gln His Leu Asp Asn Glu Met
            260                 265                 270

Ser His Ser Ser Tyr Leu Gly Thr Asp Asn Pro Thr Ala Met Thr Pro
            275                 280                 285
```

-continued

```
Thr Ser Pro Gln Arg Tyr Ser Pro Val Ala Lys Asp Leu Arg Gly Glu
    290                 295                 300
Glu Asp Ile Pro Arg Glu Pro Ser Arg Ile Val Ile His Arg Gly Ser
305                 310                 315                 320
Thr Thr Leu Gly Phe Asn Ile Val Gly Gly Glu Val Gly Glu Gly Ile
                325                 330                 335
Phe Ile Ser Phe Ile Trp Ala Gly Gly Pro Ala Asp Leu Ser Gly Tyr
            340                 345                 350
Leu Arg Lys Gly Asp Gln Ile Leu Ser Ala Asn Gly Val Asp Leu Arg
        355                 360                 365
Asn Ala Ser Asp Glu Gln Ala Ala Ile Ala Leu Lys Asn Glu Gly Gln
    370                 375                 380
Thr Val Thr Ile Ile Ala Gln Phe Lys Pro Glu Glu Tyr Ser Arg Phe
385                 390                 395                 400
Glu Gly Lys Ile His Asp Leu Arg Glu Gln Leu His Asn Ser Ser Leu
                405                 410                 415
Gly Ser Gly Thr Ala Ile Leu Arg Ser Asn Pro Lys Arg Gly Phe Lys
            420                 425                 430
Ile Arg Ala Leu Phe Asp Tyr Asp Lys Leu Lys Asp Cys Gly Phe Leu
        435                 440                 445
Ser Gln Ala Met Ser Phe His Phe Gly Asp Val Leu His Asn Ile Asp
    450                 455                 460
Ala Ser Asp Glu Glu Trp Trp Arg Ala Arg Arg Val His Ser Asp Ser
465                 470                 475                 480
Glu Ser Asp Asp Ile Gly Phe Ile Pro Ser Lys Thr Arg Val Glu Arg
                485                 490                 495
Arg Glu Trp Ser Arg Val Lys Ala Lys Asp Trp Gly Ser Ser Ser Trp
            500                 505                 510
Ser Gln Gly Arg Glu Asp Ser Val Leu Tyr Tyr Glu Thr Val Thr Gln
        515                 520                 525
Met Glu Val Ala Tyr Ala Arg Pro Ile Ile Ile Leu Gly Asp Thr Lys
    530                 535                 540
Asp Arg Ala Asn Asp Asp Leu Glu Ser Glu Phe Pro Asp Lys Phe Gly
545                 550                 555                 560
Ser Phe Val Pro His Thr Thr Arg Pro Lys Arg Gly Tyr Glu Ile Asp
                565                 570                 575
Gly Arg Asp Tyr His His Val Ser Ser Arg Glu Lys Met Glu Lys Ile
            580                 585                 590
Ile Gln Ala His Lys Phe Ile Glu Ala Lys Gln Tyr Asn Ser His Leu
        595                 600                 605
Tyr Gly Thr Leu Val Gln Ser Val Arg Glu Val Ala Glu Met Gly Lys
    610                 615                 620
His Cys Ile Leu Asp Val Ser Asn Asn Ala Val Arg Arg Leu Gln Ala
625                 630                 635                 640
Ala Gln Leu His Pro Ile Ala Ile Phe Ile Arg Arg Arg Ser Leu Glu
                645                 650                 655
Asn Val Leu Glu Ile Ser Lys Arg Ile Thr Glu Glu Gln Ala Arg Thr
            660                 665                 670
Ala Phe Asp Arg Ala Thr Lys Leu Glu Val Glu Phe Thr Glu Cys Phe
        675                 680                 685
Ser Ala Ile Trp Glu Gly Asp Ser Phe Glu Glu Ile Tyr Tyr Lys Val
    690                 695                 700
Lys Arg Val Ile Glu Asp Leu Ala Gly Pro Tyr Ile Trp Val Pro Ala
```

```
                    705                 710                 715                 720
Arg Asp Arg Leu

<210> SEQ ID NO 23
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 23

Met Asp Ala Leu Cys Ile Val Thr Thr Lys Lys Tyr Asp Tyr Gln Asp
  1               5                  10                  15

Glu Asp Thr Pro Pro Leu Phe His Ser Pro Ala His Leu Pro Asn Gln
                 20                  25                  30

Gly Asn Ser Pro Pro Val Ile Val Asn Thr His Thr Leu Glu Ala Pro
             35                  40                  45

Gly Tyr Glu Leu Ile Val Asn Gly Thr Glu Gly Met Glu Lys Glu
     50                  55                  60

Glu Ile Thr Leu Glu Arg Gly Asn Leu Gly Leu Gly Phe Ser Ile Ala
 65                  70                  75                  80

Gly Gly Met Asp Asn Pro His Ile Gly Asp Asp Pro Asn Ile Phe Ile
                 85                  90                  95

Thr Lys Ile Ile Pro Gly Gln Ala Ala Ala Gln Asp Gly Arg Leu Arg
                100                 105                 110

Arg Asn Asp Ser Ile Leu Phe Val Asn Glu Ser Asp Val Arg Glu Val
            115                 120                 125

Thr His Ser Ala Thr Val Glu Ala Leu Lys Glu Ala Gly Ser Val Val
        130                 135                 140

Arg Leu Tyr Val Met Arg Arg Lys Trp Pro Ala Glu Lys Ile Ile Glu
145                 150                 155                 160

Ile Lys Tyr Ile Lys Gly Pro Lys Gly Leu Gly Phe Ala Ile Ala Gly
                165                 170                 175

Gly Val Gly Asn Gln His Asp Pro Gly Asp Asn Ser Ile Tyr Val Thr
            180                 185                 190

Glu Ile Ile Glu Gly Gly Ala Ala His Lys Phe Gly Arg Leu Gln Ile
        195                 200                 205

Gly Asp Lys Ile Gly Ala Val Asn Ser Val Gly Leu Glu Asp His Met
    210                 215                 220

His Glu Asp Ala Val Ala Ala Leu Ile Asn Thr Tyr Asp Val Val Tyr
225                 230                 235                 240

Leu Lys Lys Ala Lys Pro Ser Asn Ala Tyr Leu Ser Leu Ser Tyr Ala
                245                 250                 255

Pro Pro Asp Ile Thr Thr Met Tyr Ser Gln His Leu Asp Asn Glu Ile
            260                 265                 270

Asn His Ser Ser Tyr Leu Gly Thr Asp Tyr Gln Thr Ala Met Thr Pro
        275                 280                 285

Thr Ser Pro Arg Ser Tyr Ser Pro Val Ala Lys Asp Leu Leu Thr Glu
    290                 295                 300

Glu Asp Ile Pro Arg Glu Pro Arg Val Ile Val Ile His Arg Gly Ser
305                 310                 315                 320

Thr Gly Trp Gly Phe Asn Ile Val Gly Gly Glu Asp Tyr Glu Gly Ile
                325                 330                 335

Phe Ile Ser Phe Ile Leu Asp Gly Gly Pro Ala Asp Leu Ser Gly Glu
```

```
                 340                 345                 350
Glu Arg Lys Gly Asp Gln Ile Leu Ser Val Phe Gly Val Asp Leu Arg
                355                 360                 365
Asn Ala Ser His Gly Gln Ala Ala Ile Ala Leu Lys Asn Ala His Gln
            370                 375                 380
Thr Val Thr Ile Ile Ala Gln Tyr Ile Pro Glu Glu Tyr Ser Arg Phe
385                 390                 395                 400
Glu Ala Leu Ile His Asp Leu Arg Glu Gln Leu Met Met Ser Ser Leu
                405                 410                 415
Gly Ser Gly Thr Ala Ser Asn Arg Ser Asn Pro Lys Arg Gly Phe Tyr
            420                 425                 430
Gln Arg Ala Leu Phe Asp Tyr Asp Lys Thr Arg Asp Cys Gly Phe Leu
                435                 440                 445
Ser Gln Ala Leu Thr Phe His Phe Gly Asp Val Leu His Val Val Asp
            450                 455                 460
Ala Ser Asp Glu Glu Trp Trp Gln Trp Arg Arg Val His Ser Asp Ser
465                 470                 475                 480
Glu Thr Tyr Asp Ile Gly Phe Ile Pro Ser Lys Arg Ala Val Glu Arg
                485                 490                 495
Arg Glu Trp Ser Arg Leu Asp Ala Lys Asp Trp Gly Ser Ser Ser Gly
            500                 505                 510
Glu Gln Gly Arg Glu Asp Ser Val Leu Ser Phe Glu Thr Val Thr Gln
        515                 520                 525
Met Glu Val His Gly Ala Arg Pro Ile Ile Ile Leu Gly Pro His Lys
        530                 535                 540
Asp Arg Ala Asn Asp Asp Leu Leu Ile Glu Phe Pro Asp Lys Phe Gly
545                 550                 555                 560
Ser Cys Lys Pro His Thr Thr Arg Pro Lys Arg Glu Leu Glu Ile Asp
                565                 570                 575
Gly Arg Asp Tyr His Phe Met Ser Ser Arg Glu Lys Met Glu Lys Asp
            580                 585                 590
Asn Gln Ala His Lys Phe Ile Glu Ala Gly Arg Tyr Asn Ser His Leu
        595                 600                 605
Tyr Gly Thr Ser Ser Gln Ser Val Arg Glu Val Ala Glu Gln Thr Lys
    610                 615                 620
His Cys Ile Leu Asp Val Ser Ala Val Ala Val Arg Arg Leu Gln Ala
625                 630                 635                 640
Ala His Trp His Pro Ile Ala Ile Phe Ile Arg Pro Tyr Ser Leu Glu
                645                 650                 655
Asn Val Leu Glu Ile Asn Ala Arg Ile Thr Glu Glu Gln Ala Arg Lys
            660                 665                 670
Asp Phe Asp Arg Ala Thr Lys Leu Glu Gln Phe Phe Thr Glu Cys Phe
        675                 680                 685
Ser Ala Ile Val Gly Gly Asp Ser Phe Glu Glu Ile Tyr His His Val
    690                 695                 700
Lys Arg Val Ile Glu Asp Leu Ser Ile Pro Tyr Ile Trp Val Pro Ala
705                 710                 715                 720
Arg Glu Lys Leu

<210> SEQ ID NO 24
<211> LENGTH: 724
<212> TYPE: PRT
<213> ORGANISM: Artificial Sequence
<220> FEATURE:
```

<223> OTHER INFORMATION: Description of Artificial Sequence: Synthetic Sequence

<400> SEQUENCE: 24

```
Met Asp Cys Ala Cys Ile Val Thr Thr Lys Lys Tyr Arg Asp Gln Asp
  1               5                  10                  15

Glu Asp Thr Pro Pro Leu Glu Glu Ser Pro Ala His Leu Pro Asn Gln
             20                  25                  30

Ala Phe Ser Pro Pro Val Ile Val Asn Thr Asp Gly Leu Glu Ala Pro
         35                  40                  45

Gly Tyr Glu Leu Gln His Asn Gly Thr Glu Gly Met Glu Tyr Ile
 50                  55                  60

Glu Ile Thr Leu Glu Arg Gly Asn Ser Lys Leu Gly Phe Ser Ile Ala
 65                  70                  75                  80

Gly Gly Thr Leu Asn Pro His Ile Gly Asp Asp Pro Ser Met Phe Ile
                 85                  90                  95

Thr Lys Ile Ile Pro Gly Gly Asn Ala Ala Gln Asp Gly Arg Leu Arg
            100                 105                 110

Val Gln Asp Ser Ile Leu Phe Val Asn Glu Val Arg Val Arg Glu Val
            115                 120                 125

Thr His Ser Ala Ala Ser Glu Ala Leu Lys Glu Ala Gly Ser Ile Thr
        130                 135                 140

Arg Leu Tyr Val Met Arg Arg Lys Pro Val Ala Glu Lys Ile Ile Glu
145                 150                 155                 160

Ile Lys Leu Trp Lys Gly Pro Lys Gly Leu Gly Phe Ser Tyr Ala Gly
                165                 170                 175

Gly Val Gly Asn Gln His Ile Ala Gly Asp Asn Ser Ile Tyr Val Thr
            180                 185                 190

Lys Asp Ile Glu Gly Gly Ala Ala His Lys Asp Glu Arg Leu Gln Ile
            195                 200                 205

Gly Asp Lys Ile Leu Phe Val Asn Ser Val Gly Leu Glu Asp Val Gly
        210                 215                 220

His Glu Asp Ala Val Ala Ala Leu Lys His Thr Tyr Asp Val Val Tyr
225                 230                 235                 240

Leu Lys Val Ile Lys Pro Ser Asn Ala Tyr Leu Ser Asp Lys Tyr Ala
                245                 250                 255

Pro Pro Asp Ile Thr Thr Ser Leu Ser Gln His Leu Asp Asn Glu Ile
            260                 265                 270

Ser Met Ser Ser Tyr Leu Gly Thr Asp Tyr Pro Asn Ala Met Thr Pro
        275                 280                 285

Thr Ser Pro Arg Arg Gln Ser Pro Val Ala Lys Asp Leu Leu Gly Arg
        290                 295                 300

Glu Asp Ile Pro Arg Glu Pro Arg Arg Ser Val Ile His Arg Gly Ser
305                 310                 315                 320

Thr Gly Leu Thr Phe Asn Ile Val Gly Gly Glu Asp Gly Val Gly Ile
                325                 330                 335

Phe Ile Ser Phe Ile Leu Ala Trp Pro Ala Asp Leu Ser Gly Glu
            340                 345                 350

Leu Tyr Lys Gly Asp Gln Ile Leu Ser Val Asn Ala Val Asp Leu Arg
        355                 360                 365

Asn Ala Ser His Glu Asp Ala Ala Ile Ala Leu Lys Asn Ala Gly Glu
        370                 375                 380

Thr Val Thr Ile Ile Ala Gln Tyr Lys Phe Glu Glu Tyr Ser Arg Phe
385                 390                 395                 400
```

Glu Ala Lys Gly His Asp Leu Arg Glu Gln Leu Met Asn His Ser Leu
            405                 410                 415

Gly Ser Gly Thr Ala Ser Leu Ile Ser Asn Pro Lys Arg Gly Phe Tyr
            420                 425                 430

Ile Lys Ala Leu Phe Asp Tyr Asp Lys Thr Lys Leu Cys Gly Phe Leu
            435                 440                 445

Ser Gln Ala Leu Ser Met His Phe Gly Asp Val Leu His Val Ile Asn
            450                 455                 460

Ala Ser Asp Glu Glu Trp Trp Gln Ala Gln Arg Val His Ser Asp Ser
465                 470                 475                 480

Glu Thr Asp Arg Ile Gly Phe Ile Pro Ser Lys Arg Arg Ser Glu Arg
            485                 490                 495

Arg Glu Trp Ser Arg Leu Lys Thr Lys Asp Trp Gly Ser Ser Ser Gly
            500                 505                 510

Ser Val Gly Arg Glu Asp Ser Val Leu Ser Tyr Trp Thr Val Thr Gln
            515                 520                 525

Met Glu Val His Tyr Tyr Arg Pro Ile Ile Leu Gly Pro Thr Ala
            530                 535                 540

Asp Arg Ala Asn Asp Asp Leu Leu Ser Asp Phe Pro Asp Lys Phe Gly
545                 550                 555                 560

Ser Cys Val Glu His Thr Thr Arg Pro Lys Arg Glu Tyr Phe Ile Asp
            565                 570                 575

Gly Arg Asp Tyr His Phe Val Gly Ser Arg Glu Lys Met Glu Lys Asp
            580                 585                 590

Ile His Ala His Lys Phe Ile Glu Ala Gly Gln Ile Asn Ser His Leu
            595                 600                 605

Tyr Gly Thr Ser Val Lys Ser Val Arg Glu Val Ala Glu Gln Gly Leu
            610                 615                 620

His Cys Ile Leu Asp Val Ser Ala Asn Met Val Arg Arg Leu Gln Ala
625                 630                 635                 640

Ala His Leu Asn Pro Ile Ala Ile Phe Ile Arg Pro Arg Gln Leu Glu
            645                 650                 655

Asn Val Leu Glu Ile Asn Lys Ser Ile Thr Glu Glu Gln Ala Arg Lys
            660                 665                 670

Ala Thr Asp Arg Ala Thr Lys Leu Glu Gln Glu Val Thr Glu Cys Phe
            675                 680                 685

Ser Ala Ile Val Glu Trp Asp Ser Phe Glu Ile Tyr His Lys Tyr
            690                 695                 700

Lys Arg Val Ile Glu Asp Leu Ser Gly Ala Tyr Ile Trp Val Pro Ala
705                 710                 715                 720

Arg Glu Arg Asp

<210> SEQ ID NO 25
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 25

Met Asp Cys Leu Ala Ile Val Thr Thr Lys Lys Tyr Arg Tyr Asp Asp
 1               5                  10                  15

Glu Asp Thr Pro Pro Leu Glu His Glu Pro Ala His Leu Pro Asn Gln
            20                  25                  30

-continued

```
Ala Asn Phe Pro Pro Val Ile Val Asn Thr Asp Thr Gly Glu Ala Pro
         35                  40                  45

Gly Tyr Glu Leu Gln Val His Gly Thr Glu Gly Glu Met Glu Tyr Glu
 50                  55                  60

Ile Ile Thr Leu Glu Arg Gly Asn Ser Gly Lys Gly Phe Ser Ile Ala
 65                  70                  75                  80

Gly Gly Thr Asp Leu Pro His Ile Gly Asp Pro Ser Ile Met Ile
                 85                  90                  95

Thr Lys Ile Ile Pro Gly Gly Ala Asn Ala Gln Asp Gly Arg Leu Arg
                100                 105                 110

Val Asn Gln Ser Ile Leu Phe Val Asn Glu Val Asp Arg Arg Glu Val
             115                 120                 125

Thr His Ser Ala Ala Val Ser Ala Leu Lys Glu Ala Gly Ser Ile Val
         130                 135                 140

Thr Leu Tyr Val Met Arg Arg Lys Pro Pro Val Glu Lys Ile Ile Glu
145                 150                 155                 160

Ile Lys Leu Ile Trp Gly Pro Lys Gly Leu Gly Phe Ser Ile Tyr Gly
                165                 170                 175

Gly Val Gly Asn Gln His Ile Pro Ala Asp Asn Ser Ile Tyr Val Thr
             180                 185                 190

Lys Ile Asp Glu Gly Gly Ala Ala His Lys Asp Gly Glu Leu Gln Ile
         195                 200                 205

Gly Asp Lys Ile Leu Ala Phe Asn Ser Val Gly Leu Glu Asp Val Met
         210                 215                 220

Gly Glu Asp Ala Val Ala Ala Leu Lys Asn His Tyr Asp Val Val Tyr
225                 230                 235                 240

Leu Lys Val Ala Ile Pro Ser Asn Ala Tyr Leu Ser Asp Ser Lys Ala
                245                 250                 255

Pro Pro Asp Ile Thr Thr Ser Tyr Leu Gln His Leu Asp Asn Glu Ile
             260                 265                 270

Ser His Met Ser Tyr Leu Gly Thr Asp Tyr Pro Thr Asn Met Thr Pro
         275                 280                 285

Thr Ser Pro Arg Arg Tyr Gln Pro Val Ala Lys Asp Leu Leu Gly Glu
290                 295                 300

Arg Asp Ile Pro Arg Glu Pro Arg Arg Ile Ser Ile His Arg Gly Ser
305                 310                 315                 320

Thr Gly Leu Gly Thr Asn Ile Val Gly Gly Asp Gly Glu Val Ile
                325                 330                 335

Phe Ile Ser Phe Ile Leu Ala Gly Trp Pro Ala Asp Leu Ser Gly Glu
             340                 345                 350

Leu Arg Tyr Gly Asp Gln Ile Leu Ser Val Asn Gly Ala Asp Leu Arg
         355                 360                 365

Asn Ala Ser His Glu Gln Asp Ala Ile Ala Leu Lys Asn Ala Gly Gln
         370                 375                 380

Glu Val Thr Ile Ile Ala Gln Tyr Lys Pro Phe Glu Tyr Ser Arg Phe
385                 390                 395                 400

Glu Ala Lys Ile Gly Asp Leu Arg Glu Gln Leu Met Asn Ser His Leu
                405                 410                 415

Gly Ser Gly Thr Ala Ser Leu Arg Ile Asn Pro Lys Arg Gly Phe Tyr
             420                 425                 430

Ile Arg Lys Leu Phe Asp Tyr Asp Lys Thr Lys Asp Leu Gly Phe Leu
         435                 440                 445
```

```
Ser Gln Ala Leu Ser Phe Met Phe Gly Asp Val Leu His Val Ile Asp
    450                 455                 460

Asn Ser Asp Glu Glu Trp Trp Gln Ala Arg Gln Val His Ser Asp Ser
465                 470                 475                 480

Glu Thr Asp Asp Arg Gly Phe Ile Pro Ser Lys Arg Val Ser Arg
                485                 490                 495

Arg Glu Trp Ser Arg Leu Lys Ala Thr Asp Trp Gly Ser Ser Gly
            500                 505                 510

Ser Gln Val Arg Glu Asp Ser Val Leu Ser Tyr Glu Trp Val Thr Gln
        515                 520                 525

Met Glu Val His Tyr Ala Tyr Pro Ile Ile Ile Leu Gly Pro Thr Lys
    530                 535                 540

Ala Arg Ala Asn Asp Asp Leu Leu Ser Glu Asp Pro Asp Lys Phe Gly
545                 550                 555                 560

Ser Cys Val Pro Glu Thr Thr Arg Pro Lys Arg Glu Tyr Glu Phe Asp
                565                 570                 575

Gly Arg Asp Tyr His Phe Val Ser Gly Arg Glu Lys Met Glu Lys Asp
                580                 585                 590

Ile Gln His His Lys Phe Ile Glu Ala Gly Gln Tyr Ile Ser His Leu
            595                 600                 605

Tyr Gly Thr Ser Val Gln Lys Val Arg Glu Val Ala Glu Gln Gly Lys
    610                 615                 620

Leu Cys Ile Leu Asp Val Ser Ala Asn Ala Met Arg Arg Leu Gln Ala
625                 630                 635                 640

Ala His Leu His Asn Ile Ala Ile Phe Ile Arg Pro Arg Ser Gln Glu
                645                 650                 655

Asn Val Leu Glu Ile Asn Lys Arg Arg Thr Glu Gln Ala Arg Lys
            660                 665                 670

Ala Phe Ser Arg Ala Thr Lys Leu Glu Gln Glu Phe Thr Glu Cys Phe
    675                 680                 685

Ser Ala Ile Val Glu Gly Val Ser Phe Glu Glu Ile Tyr His Lys Val
    690                 695                 700

Trp Arg Val Ile Glu Asp Leu Ser Gly Pro Ala Ile Trp Val Pro Ala
705                 710                 715                 720

Arg Glu Arg Leu

<210> SEQ ID NO 26
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 26

Met Asp Cys Leu Cys Ala Val Thr Thr Lys Lys Tyr Arg Tyr Gln Asp
1               5                   10                  15

Glu Asp Thr Pro Pro Leu Glu His Ser Glu Ala His Leu Pro Asn Gln
            20                  25                  30

Ala Asn Ser Phe Pro Val Ile Val Asn Thr Asp Thr Leu Gly Ala Pro
        35                  40                  45

Gly Tyr Glu Leu Gln Val Asn His Thr Glu Gly Glu Met Glu Tyr Glu
    50                  55                  60

Glu Lys Thr Leu Glu Arg Gly Asn Ser Gly Leu Leu Phe Ser Ile Ala
65                  70                  75                  80
```

-continued

```
Gly Gly Thr Asp Asn Met His Ile Gly Asp Asp Pro Ser Ile Phe Asn
                85                  90                  95
Thr Lys Ile Ile Pro Gly Ala Ala Gln Gln Asp Gly Arg Leu Arg
            100                 105                 110
Val Asn Asp Arg Ile Leu Phe Val Asn Glu Val Asp Val Ser Glu Val
        115                 120                 125
Thr His Ser Ala Ala Val Glu Thr Leu Lys Glu Ala Gly Ser Ile Val
    130                 135                 140
Arg Val Tyr Val Met Arg Arg Lys Pro Pro Ala Trp Lys Ile Ile Glu
145                 150                 155                 160
Ile Lys Leu Ile Lys Tyr Pro Lys Gly Leu Gly Phe Ser Ile Ala Ala
                165                 170                 175
Gly Val Gly Asn Gln His Ile Pro Gly Glu Asn Ser Ile Tyr Val Thr
            180                 185                 190
Lys Ile Ile Phe Gly Gly Ala Ala His Lys Asp Gly Arg Gly Gln Ile
        195                 200                 205
Gly Asp Lys Ile Leu Ala Val His Ser Val Gly Leu Glu Asp Val Met
    210                 215                 220
His Ile Asp Ala Val Ala Ala Leu Lys Asn Thr Lys Asp Val Val Tyr
225                 230                 235                 240
Leu Lys Val Ala Lys Leu Ser Asn Ala Tyr Leu Ser Asp Ser Tyr Met
                245                 250                 255
Pro Pro Asp Ile Thr Thr Ser Tyr Ser Asn His Leu Asp Asn Glu Ile
            260                 265                 270
Ser His Ser Gln Tyr Leu Gly Thr Asp Tyr Pro Thr Ala Arg Thr Pro
        275                 280                 285
Thr Ser Pro Arg Arg Tyr Ser Ser Val Ala Lys Asp Leu Leu Gly Glu
    290                 295                 300
Glu Thr Ile Pro Arg Glu Pro Arg Arg Ile Val Val His Arg Gly Ser
305                 310                 315                 320
Thr Gly Leu Gly Phe Trp Ile Val Gly Gly Glu Asp Gly Glu Gly Tyr
                325                 330                 335
Phe Ile Ser Phe Ile Leu Ala Gly Gly Ala Ala Asp Leu Ser Gly Glu
            340                 345                 350
Leu Arg Lys Asp Asp Gln Ile Leu Ser Val Asn Gly Val Glu Leu Arg
        355                 360                 365
Asn Ala Ser His Glu Gln Ala Phe Ile Ala Leu Lys Asn Ala Gly Gln
    370                 375                 380
Thr Gly Thr Ile Ala Gln Tyr Lys Pro Glu His Tyr Ser Arg Phe
385                 390                 395                 400
Glu Ala Lys Ile His Ile Leu Arg Glu Gln Leu Met Asn Ser Ser Lys
                405                 410                 415
Gly Ser Gly Thr Ala Ser Leu Arg Ser Leu Pro Lys Arg Gly Phe Tyr
            420                 425                 430
Ile Arg Ala Met Phe Asp Tyr Asp Lys Thr Lys Asp Cys Asn Phe Leu
        435                 440                 445
Ser Gln Ala Leu Ser Phe His Gln Gly Asp Val Leu His Val Ile Asp
    450                 455                 460
Ala Arg Asp Glu Glu Trp Trp Gln Ala Arg Arg Ser His Ser Asp Ser
465                 470                 475                 480
Glu Thr Asp Asp Ile Thr Phe Ile Pro Ser Lys Arg Arg Val Glu Val
                485                 490                 495
Arg Glu Trp Ser Arg Leu Lys Ala Lys Trp Trp Gly Ser Ser Ser Gly
```

-continued

```
                500             505             510
Ser Gln Gly Tyr Glu Asp Ser Val Leu Ser Tyr Glu Thr Ala Thr Gln
            515                 520                 525

Met Glu Val His Tyr Ala Arg Asp Ile Ile Ile Leu Gly Pro Thr Lys
    530                 535                 540

Asp Glu Ala Asn Asp Asp Leu Leu Ser Glu Phe Phe Asp Lys Phe Gly
545                 550                 555                 560

Ser Cys Val Pro His Gly Thr Arg Pro Lys Arg Glu Tyr Glu Ile His
                565                 570                 575

Gly Arg Asp Tyr His Phe Val Ser Ser Ile Glu Lys Met Glu Lys Asp
                580                 585                 590

Ile Gln Ala Lys Lys Phe Ile Glu Ala Gly Gln Tyr Asn Leu His Leu
            595                 600                 605

Tyr Gly Thr Ser Val Gln Ser Met Arg Glu Val Ala Glu Gln Gly Lys
    610                 615                 620

His Asn Ile Leu Asp Val Ser Ala Asn Ala Val Gln Arg Leu Gln Ala
625                 630                 635                 640

Ala His Leu His Pro Arg Ala Ile Phe Ile Arg Pro Arg Ser Leu Ser
                645                 650                 655

Asn Val Leu Glu Ile Asn Lys Arg Ile Val Glu Glu Gln Ala Arg Lys
                660                 665                 670

Ala Phe Asp Trp Ala Thr Lys Leu Glu Gln Glu Phe Thr Tyr Cys Phe
            675                 680                 685

Ser Ala Ile Val Glu Gly Asp Ala Phe Glu Glu Ile Tyr His Lys Val
    690                 695                 700

Lys Asp Val Ile Glu Asp Leu Ser Gly Pro Tyr Glu Trp Val Pro Ala
705                 710                 715                 720

Arg Glu Arg Leu
```

<210> SEQ ID NO 27
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 27

```
Met Asp Cys Leu Cys Ile Ala Thr Thr Lys Lys Tyr Arg Tyr Gln Asp
  1               5                  10                  15

Asp Asp Thr Pro Pro Leu Glu His Ser Pro Glu His Leu Pro Asn Gln
                20                  25                  30

Ala Asn Ser Pro Phe Val Ile Val Asn Thr Asp Thr Leu Glu Gly Pro
            35                  40                  45

Gly Tyr Glu Leu Gln Val Asn Gly His Glu Gly Glu Met Glu Tyr Glu
        50                  55                  60

Glu Ile Ile Leu Glu Arg Gly Asn Ser Gly Leu Gly Lys Ser Ile Ala
 65                  70                  75                  80

Gly Gly Thr Asp Asn Pro Leu Ile Gly Asp Pro Ser Ile Phe Ile
                85                  90                  95

Met Lys Ile Ile Pro Gly Gly Ala Ala Asn Asp Gly Arg Leu Arg
                100                 105                 110

Val Asn Asp Ser Gln Leu Phe Val Asn Glu Val Asp Val Arg Arg Val
            115                 120                 125

Thr His Ser Ala Ala Val Glu Ala Ser Lys Glu Ala Gly Ser Ile Val
```

```
            130                 135                 140
Arg Leu Thr Val Met Arg Arg Lys Pro Pro Ala Glu Val Ile Ile Glu
145                 150                 155                 160

Ile Lys Leu Ile Lys Gly Trp Lys Gly Leu Gly Phe Ser Ile Ala Gly
                165                 170                 175

Tyr Val Gly Asn Gln His Ile Pro Gly Asp Ala Ser Ile Tyr Val Thr
                180                 185                 190

Lys Ile Ile Glu Asp Gly Ala His Lys Asp Gly Arg Leu Glu Ile
                195                 200                 205

Gly Asp Lys Ile Leu Ala Val Asn Phe Val Gly Leu Glu Asp Val Met
            210                 215                 220

His Glu Gly Ala Val Ala Ala Leu Lys Asn Thr Tyr His Val Val Tyr
225                 230                 235                 240

Leu Lys Val Ala Lys Pro Ile Asn Ala Tyr Leu Ser Asp Ser Tyr Ala
                245                 250                 255

Lys Pro Asp Ile Thr Thr Ser Tyr Ser Gln Leu Leu Asp Asn Glu Ile
                260                 265                 270

Ser His Ser Ser Met Leu Gly Thr Asp Tyr Pro Thr Ala Met Asn Pro
            275                 280                 285

Thr Ser Pro Arg Arg Tyr Ser Pro Gln Ala Lys Asp Leu Leu Gly Glu
            290                 295                 300

Glu Asp Arg Pro Arg Glu Pro Arg Arg Ile Val Ile Ser Arg Gly Ser
305                 310                 315                 320

Thr Gly Leu Gly Phe Asn Thr Val Gly Gly Glu Asp Gly Glu Gly Ile
                325                 330                 335

Val Ile Ser Phe Ile Leu Ala Gly Gly Pro Trp Asp Leu Ser Gly Glu
            340                 345                 350

Leu Arg Lys Gly Tyr Gln Ile Leu Ser Val Asn Gly Val Asp Ala Arg
            355                 360                 365

Asn Ala Ser His Glu Gln Ala Ala Asp Ala Leu Lys Asn Ala Gly Gln
            370                 375                 380

Thr Val Glu Ile Ile Ala Gln Tyr Lys Pro Glu Glu Phe Ser Arg Phe
385                 390                 395                 400

Glu Ala Lys Ile His Asp Gly Arg Glu Gln Leu Met Asn Ser Ser Leu
                405                 410                 415

His Ser Gly Thr Ala Ser Leu Arg Ser Asn Ile Lys Arg Gly Phe Tyr
            420                 425                 430

Ile Arg Ala Leu Lys Asp Tyr Asp Lys Thr Lys Asp Cys Gly Leu Leu
            435                 440                 445

Ser Gln Ala Leu Ser Phe His Phe Met Asp Val Leu His Val Ile Asp
            450                 455                 460

Ala Ser Asn Glu Glu Trp Trp Gln Ala Arg Arg Val Gln Ser Asp Ser
465                 470                 475                 480

Glu Thr Asp Asp Ile Gly Arg Ile Pro Ser Lys Arg Arg Val Glu Arg
                485                 490                 495

Ser Glu Trp Ser Arg Leu Lys Ala Lys Asp Thr Gly Ser Ser Ser Gly
                500                 505                 510

Ser Gln Gly Arg Val Asp Ser Val Leu Ser Tyr Glu Thr Val Trp Gln
            515                 520                 525

Met Glu Val His Tyr Ala Arg Pro Tyr Ile Ile Leu Gly Pro Thr Lys
            530                 535                 540

Asp Arg Asp Asn Asp Asp Leu Leu Ser Glu Phe Pro Glu Lys Phe Gly
545                 550                 555                 560
```

```
Ser Cys Val Pro His Thr Phe Arg Pro Lys Arg Glu Tyr Glu Ile Asp
                565                 570                 575

His Arg Asp Tyr His Phe Val Ser Ser Arg Ile Lys Met Glu Lys Asp
            580                 585                 590

Ile Gln Ala His Leu Phe Ile Glu Ala Gly Gln Tyr Asn Ser Met Leu
            595                 600                 605

Tyr Gly Thr Ser Val Gln Ser Val Asn Glu Val Ala Glu Gln Gly Lys
            610                 615                 620

His Cys Gln Leu Asp Val Ser Ala Asn Ala Val Arg Ser Leu Gln Ala
625                 630                 635                 640

Ala His Leu His Pro Ile Thr Ile Phe Ile Arg Pro Arg Ser Leu Glu
                645                 650                 655

Val Val Leu Glu Ile Asn Lys Arg Ile Thr Trp Gln Ala Arg Lys
                660                 665                 670

Ala Phe Asp Arg Tyr Thr Lys Leu Glu Gln Glu Phe Thr Glu Ala Phe
                675                 680                 685

Ser Ala Ile Val Glu Gly Asp Ser Asp Glu Glu Ile Tyr His Lys Val
            690                 695                 700

Lys Arg Glu Ile Glu Asp Leu Ser Gly Pro Tyr Ile Phe Val Pro Ala
705                 710                 715                 720

Arg Glu Arg Leu
```

```
<210> SEQ ID NO 28
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 28

Met Asp Cys Leu Cys Ile Val Ala Thr Lys Lys Tyr Arg Tyr Gln Asp
  1               5                  10                  15

Glu Glu Thr Pro Pro Leu Glu His Ser Pro Ala Phe Leu Pro Asn Gln
                 20                  25                  30

Ala Asn Ser Pro Pro Gly Ile Val Asn Thr Asp Thr Leu Glu Ala His
             35                  40                  45

Gly Tyr Glu Leu Gln Val Asn Gly Thr Ile Gly Glu Met Glu Tyr Glu
         50                  55                  60

Glu Ile Thr Lys Glu Arg Gly Asn Ser Gly Leu Gly Phe Leu Ile Ala
 65                  70                  75                  80

Gly Gly Thr Asp Asn Pro His Met Gly Asp Asp Pro Ser Ile Phe Ile
                 85                  90                  95

Thr Asn Ile Ile Pro Gly Gly Ala Ala Ala Gln Gln Gly Arg Leu Arg
            100                 105                 110

Val Asn Asp Ser Ile Arg Phe Val Asn Glu Val Asp Val Arg Glu Ser
        115                 120                 125

Thr His Ser Ala Ala Val Glu Ala Leu Thr Glu Ala Gly Ser Ile Val
    130                 135                 140

Arg Leu Tyr Trp Met Arg Arg Lys Pro Pro Ala Glu Lys Tyr Ile Glu
145                 150                 155                 160

Ile Lys Leu Ile Lys Gly Pro Ala Gly Leu Gly Phe Ser Ile Ala Gly
                165                 170                 175

Gly Asp Gly Asn Gln His Ile Pro Gly Asp Asn Glu Ile Tyr Val Thr
            180                 185                 190
```

```
Lys Ile Ile Glu Gly Phe Ala Ala His Lys Asp Gly Arg Leu Gln Gly
            195                 200                 205

Gly Asp Lys Ile Leu Ala Val Asn Ser His Gly Leu Glu Asp Val Met
    210                 215                 220

His Glu Asp Ile Val Ala Ala Leu Lys Asn Thr Tyr Asp Lys Val Tyr
225                 230                 235                 240

Leu Lys Val Ala Lys Pro Ser Leu Ala Tyr Leu Ser Asp Ser Tyr Ala
                245                 250                 255

Pro Met Asp Ile Thr Thr Ser Tyr Ser Gln His Asn Asp Asn Glu Ile
                260                 265                 270

Ser His Ser Ser Tyr Gln Gly Thr Asp Tyr Pro Thr Ala Met Thr Arg
            275                 280                 285

Thr Ser Pro Arg Arg Tyr Ser Pro Val Ser Lys Asp Leu Leu Gly Glu
    290                 295                 300

Glu Asp Ile Thr Arg Glu Pro Arg Arg Ile Val Ile His Val Gly Ser
305                 310                 315                 320

Thr Gly Leu Gly Phe Asn Ile Trp Gly Gly Glu Asp Gly Glu Gly Ile
                325                 330                 335

Phe Tyr Ser Phe Ile Leu Ala Gly Gly Pro Ala Ala Leu Ser Gly Glu
                340                 345                 350

Leu Arg Lys Gly Asp Asp Ile Leu Ser Val Asn Gly Val Asp Leu Glu
            355                 360                 365

Asn Ala Ser His Glu Gln Ala Ala Ile Phe Leu Lys Asn Ala Gly Gln
    370                 375                 380

Thr Val Thr Gly Ile Ala Gln Tyr Lys Pro Glu Glu Tyr His Arg Phe
385                 390                 395                 400

Glu Ala Lys Ile His Asp Leu Ile Glu Gln Leu Met Asn Ser Ser Leu
                405                 410                 415

Gly Lys Gly Thr Ala Ser Leu Arg Ser Asn Pro Leu Arg Gly Phe Tyr
            420                 425                 430

Ile Arg Ala Leu Phe Met Tyr Asp Lys Thr Lys Asp Cys Gly Phe Asn
    435                 440                 445

Ser Gln Ala Leu Ser Phe His Phe Gly Gln Val Leu His Val Ile Asp
    450                 455                 460

Ala Ser Asp Arg Glu Trp Trp Gln Ala Arg Arg Val His Thr Asp Ser
465                 470                 475                 480

Glu Thr Asp Asp Ile Gly Phe Val Pro Ser Lys Arg Arg Val Glu Arg
                485                 490                 495

Arg Trp Trp Ser Arg Leu Lys Ala Lys Asp Trp Tyr Ser Ser Ser Gly
            500                 505                 510

Ser Gln Gly Arg Glu Ala Ser Val Leu Ser Tyr Glu Thr Val Thr Asp
    515                 520                 525

Met Glu Val His Tyr Ala Arg Pro Ile Glu Ile Leu Gly Pro Thr Lys
    530                 535                 540

Asp Arg Ala Phe Asp Asp Leu Leu Ser Glu Phe Pro Asp Gly Phe Gly
545                 550                 555                 560

Ser Cys Val Pro His Thr Thr His Pro Lys Arg Glu Tyr Glu Ile Asp
                565                 570                 575

Gly Ile Asp Tyr His Phe Val Ser Ser Arg Glu Lys Met Glu Lys Asp
            580                 585                 590

Ile Gln Ala His Lys Leu Ile Glu Ala Gly Gln Tyr Asn Ser His Met
            595                 600                 605
```

```
Tyr Gly Thr Ser Val Gln Ser Val Arg Asn Val Ala Glu Gln Gly Lys
    610                 615                 620

His Cys Ile Gln Asp Val Ser Ala Asn Ala Val Arg Arg Arg Gln Ala
625                 630                 635                 640

Ala His Leu His Pro Ile Ala Ser Phe Ile Arg Pro Arg Ser Leu Glu
                645                 650                 655

Asn Thr Leu Glu Ile Asn Lys Arg Ile Thr Glu Val Gln Ala Arg Lys
            660                 665                 670

Ala Phe Asp Arg Ala Trp Lys Leu Glu Gln Glu Phe Thr Glu Cys Tyr
        675                 680                 685

Ser Ala Ile Val Glu Gly Asp Ser Phe Ala Glu Ile Tyr His Lys Val
    690                 695                 700

Lys Arg Val Asp Glu Asp Leu Ser Gly Pro Tyr Ile Trp Glu Pro Ala
705                 710                 715                 720

Arg Glu Arg Leu

<210> SEQ ID NO 29
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 29

Met Asp Cys Leu Cys Ile Val Thr Ala Lys Lys Tyr Arg Tyr Gln Asp
  1               5                  10                  15

Glu Asp Asp Pro Pro Leu Glu His Ser Pro Ala His Glu Pro Asn Gln
                20                  25                  30

Ala Asn Ser Pro Pro Val Phe Val Asn Thr Asp Thr Leu Glu Ala Pro
            35                  40                  45

His Tyr Glu Leu Gln Val Asn Gly Thr Glu Ile Glu Met Glu Tyr Glu
        50                  55                  60

Glu Ile Thr Leu Lys Arg Gly Asn Ser Gly Leu Gly Phe Ser Leu Ala
65                  70                  75                  80

Gly Gly Thr Asp Asn Pro His Ile Met Asp Asp Pro Ser Ile Phe Ile
                85                  90                  95

Thr Lys Asn Ile Pro Gly Gly Ala Ala Ala Gln Asp Gln Arg Leu Arg
            100                 105                 110

Val Asn Asp Ser Ile Leu Arg Val Asn Glu Val Asp Val Arg Glu Val
        115                 120                 125

Ser His Ser Ala Ala Val Glu Ala Leu Lys Thr Ala Gly Ser Ile Val
    130                 135                 140

Arg Leu Tyr Val Val Arg Arg Lys Pro Pro Ala Glu Lys Ile Trp Glu
145                 150                 155                 160

Ile Lys Leu Ile Lys Gly Pro Lys Tyr Leu Gly Phe Ser Ile Ala Gly
                165                 170                 175

Gly Val Ala Asn Gln His Ile Pro Gly Asp Asn Ser Asp Tyr Val Thr
            180                 185                 190

Lys Ile Ile Glu Gly Gly Glu Ala His Lys Asp Gly Arg Leu Gln Ile
        195                 200                 205

Phe Asp Lys Ile Leu Ala Val Asn Ser Val His Leu Glu Asp Val Met
    210                 215                 220

His Glu Asp Ala Ile Ala Ala Leu Lys Asn Thr Tyr Asp Val Lys Tyr
225                 230                 235                 240
```

```
Leu Lys Val Ala Lys Pro Ser Asn Leu Tyr Leu Ser Asp Ser Tyr Ala
            245                 250                 255

Pro Pro Met Ile Thr Thr Ser Tyr Ser Gln His Leu Asn Asn Glu Ile
            260                 265                 270

Ser His Ser Ser Tyr Leu Gln Thr Asp Tyr Pro Thr Ala Met Thr Pro
            275                 280                 285

Arg Ser Pro Arg Arg Tyr Ser Pro Val Ala Ser Asp Leu Leu Gly Glu
            290                 295                 300

Glu Asp Ile Pro Thr Glu Pro Arg Arg Ile Val Ile His Arg Val Ser
305                 310                 315                 320

Thr Gly Leu Gly Phe Asn Ile Val Trp Gly Glu Asp Gly Glu Gly Ile
            325                 330                 335

Phe Ile Tyr Phe Ile Leu Ala Gly Gly Pro Ala Asp Ala Ser Gly Glu
            340                 345                 350

Leu Arg Lys Gly Asp Gln Asp Leu Ser Val Asn Gly Val Asp Leu Arg
            355                 360                 365

Glu Ala Ser His Glu Gln Ala Ala Ile Ala Phe Lys Asn Ala Gly Gln
370                 375                 380

Thr Val Thr Ile Gly Ala Gln Tyr Lys Pro Glu Glu Tyr Ser His Phe
385                 390                 395                 400

Glu Ala Lys Ile His Asp Leu Arg Ile Gln Leu Met Asn Ser Ser Leu
            405                 410                 415

Gly Ser Lys Thr Ala Ser Leu Arg Ser Asn Pro Lys Leu Gly Phe Tyr
            420                 425                 430

Ile Arg Ala Leu Phe Asp Met Asp Lys Thr Lys Asp Cys Gly Phe Leu
            435                 440                 445

Asn Gln Ala Leu Ser Phe His Phe Gly Asp Gln Leu His Val Ile Asp
            450                 455                 460

Ala Ser Asp Glu Arg Trp Trp Gln Ala Arg Arg Val His Ser Ser Ser
465                 470                 475                 480

Glu Thr Asp Asp Ile Gly Phe Ile Thr Ser Lys Arg Arg Val Glu Arg
            485                 490                 495

Arg Glu Val Ser Arg Leu Lys Ala Lys Asp Trp Gly Trp Ser Ser Gly
            500                 505                 510

Ser Gln Gly Arg Glu Asp Tyr Val Leu Ser Tyr Glu Thr Val Thr Gln
            515                 520                 525

Ala Glu Val His Tyr Ala Arg Pro Ile Ile Asp Leu Gly Pro Thr Lys
            530                 535                 540

Asp Arg Ala Asn Glu Asp Leu Leu Ser Glu Phe Pro Asp Lys Gly Gly
545                 550                 555                 560

Ser Cys Val Pro His Thr Thr Arg His Lys Arg Glu Tyr Glu Ile Asp
            565                 570                 575

Gly Arg Ile Tyr His Phe Val Ser Ser Arg Glu Lys Glu Lys Asp
            580                 585                 590

Ile Gln Ala His Lys Phe Leu Glu Ala Gly Gln Tyr Asn Ser His Leu
            595                 600                 605

Met Gly Thr Ser Val Gln Ser Val Arg Glu Asn Ala Glu Gln Gly Lys
            610                 615                 620

His Cys Ile Leu Gln Val Ser Ala Asn Ala Val Arg Arg Leu Arg Ala
625                 630                 635                 640

Ala His Leu His Pro Ile Ala Ile Ser Ile Arg Pro Arg Ser Leu Glu
            645                 650                 655

Asn Val Thr Glu Ile Asn Lys Arg Ile Thr Glu Glu Val Ala Arg Lys
```

```
                    660             665             670
Ala Phe Asp Arg Ala Thr Trp Leu Glu Gln Glu Phe Thr Glu Cys Phe
            675             680             685

Tyr Ala Ile Val Glu Gly Asp Ser Phe Glu Ala Ile Tyr His Lys Val
        690             695             700

Lys Arg Val Ile Asp Asp Leu Ser Gly Pro Tyr Ile Trp Val Glu Ala
705             710             715             720

Arg Glu Arg Leu

<210> SEQ ID NO 30
<211> LENGTH: 724
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 30

Met Asp Cys Leu Cys Ile Val Thr Thr Ala Lys Tyr Arg Tyr Gln Asp
 1               5                  10                  15

Glu Asp Thr Asp Pro Leu Glu His Ser Pro Ala His Leu Glu Asn Gln
            20                  25                  30

Ala Asn Ser Pro Pro Val Ile Phe Asn Thr Asp Thr Leu Glu Ala Pro
        35                  40                  45

Gly Gly Glu Leu Gln Val Asn Gly Thr Glu Gly His Met Glu Tyr Glu
    50                  55                  60

Glu Ile Thr Leu Glu Ile Gly Asn Ser Gly Leu Gly Phe Ser Ile Lys
65                  70                  75                  80

Gly Gly Thr Asp Asn Pro His Ile Gly Leu Asp Pro Ser Ile Phe Ile
                85                  90                  95

Thr Lys Ile Met Pro Gly Gly Ala Ala Ala Gln Asp Gly Asn Leu Arg
            100                 105                 110

Val Asn Asp Ser Ile Leu Phe Gln Asn Glu Val Asp Val Arg Glu Val
        115                 120                 125

Thr Arg Ser Ala Ala Val Glu Ala Leu Lys Glu Ser Gly Ser Ile Val
    130                 135                 140

Arg Leu Tyr Val Met Thr Arg Lys Pro Pro Ala Glu Lys Ile Ile Val
145                 150                 155                 160

Ile Lys Leu Ile Lys Gly Pro Lys Gly Trp Gly Phe Ser Ile Ala Gly
                165                 170                 175

Gly Val Gly Tyr Gln His Ile Pro Gly Asp Asn Ser Ile Ala Val Thr
            180                 185                 190

Lys Ile Ile Glu Gly Gly Ala Asp His Lys Asp Gly Arg Leu Gln Ile
        195                 200                 205

Gly Glu Lys Ile Leu Ala Val Asn Ser Val Gly Phe Glu Asp Val Met
    210                 215                 220

His Glu Asp Ala Val Gly Ala Leu Lys Asn Thr Tyr Asp Val Val His
225                 230                 235                 240

Leu Lys Val Ala Lys Pro Ser Asn Ala Ile Leu Ser Asp Ser Tyr Ala
                245                 250                 255

Pro Pro Asp Lys Thr Thr Ser Tyr Ser Gln His Leu Asp Leu Glu Ile
            260                 265                 270

Ser His Ser Ser Tyr Leu Gly Met Asp Tyr Pro Thr Ala Met Thr Pro
        275                 280                 285

Thr Asn Pro Arg Arg Tyr Ser Pro Val Ala Lys Gln Leu Leu Gly Glu
```

-continued

```
            290                 295                 300
Glu Asp Ile Pro Arg Arg Pro Arg Arg Ile Val Ile His Arg Gly Thr
305                 310                 315                 320
Thr Gly Leu Gly Phe Asn Ile Val Gly Val Glu Asp Gly Glu Gly Ile
                325                 330                 335
Phe Ile Ser Trp Ile Leu Ala Gly Gly Pro Ala Asp Leu Tyr Gly Glu
                340                 345                 350
Leu Arg Lys Gly Asp Gln Ile Ala Ser Val Asn Gly Val Asp Leu Arg
                355                 360                 365
Asn Asp Ser His Glu Gln Ala Ala Ile Ala Leu Glu Asn Ala Gly Gln
370                 375                 380
Thr Val Thr Ile Ile Phe Gln Tyr Lys Pro Glu Glu Tyr Ser Arg Gly
385                 390                 395                 400
Glu Ala Lys Ile His Asp Leu Arg Glu His Leu Met Asn Ser Ser Leu
                405                 410                 415
Gly Ser Gly Ile Ala Ser Leu Arg Ser Asn Pro Lys Arg Lys Phe Tyr
                420                 425                 430
Ile Arg Ala Leu Phe Asp Tyr Leu Lys Thr Lys Asp Cys Gly Phe Leu
                435                 440                 445
Ser Met Ala Leu Ser Phe His Phe Gly Asp Val Asn His Val Ile Asp
450                 455                 460
Ala Ser Asp Glu Glu Gln Trp Gln Ala Arg Arg Val His Ser Asp Arg
465                 470                 475                 480
Glu Thr Asp Asp Ile Gly Phe Ile Pro Thr Lys Arg Arg Val Glu Arg
                485                 490                 495
Arg Glu Trp Val Arg Leu Lys Ala Lys Asp Trp Gly Ser Trp Ser Gly
                500                 505                 510
Ser Gln Gly Arg Glu Asp Ser Tyr Leu Ser Tyr Glu Thr Val Thr Gln
                515                 520                 525
Met Ala Val His Tyr Ala Arg Pro Ile Ile Ile Asp Gly Pro Thr Lys
530                 535                 540
Asp Arg Ala Asn Asp Glu Leu Leu Ser Glu Phe Pro Asp Lys Phe Phe
545                 550                 555                 560
Ser Cys Val Pro His Thr Thr Arg Pro Gly Arg Glu Tyr Glu Ile Asp
                565                 570                 575
Gly Arg Asp His His Phe Val Ser Ser Arg Glu Lys Met Ile Lys Asp
                580                 585                 590
Ile Gln Ala His Lys Phe Ile Lys Ala Gly Gln Tyr Asn Ser His Leu
                595                 600                 605
Tyr Leu Thr Ser Val Gln Ser Val Arg Glu Val Met Glu Gln Gly Lys
                610                 615                 620
His Cys Ile Leu Asp Asn Ser Ala Asn Ala Val Arg Arg Leu Gln Gln
625                 630                 635                 640
Ala His Leu His Pro Ile Ala Ile Phe Arg Arg Pro Arg Ser Leu Glu
                645                 650                 655
Asn Val Leu Ser Ile Asn Lys Arg Ile Thr Glu Glu Gln Thr Arg Lys
                660                 665                 670
Ala Phe Asp Arg Ala Thr Lys Val Glu Gln Glu Phe Thr Glu Cys Phe
                675                 680                 685
Ser Trp Ile Val Glu Gly Asp Ser Phe Glu Glu Tyr Tyr His Lys Val
                690                 695                 700
Lys Arg Val Ile Glu Ala Leu Ser Gly Pro Tyr Ile Trp Val Pro Asp
705                 710                 715                 720
```

Arg Glu Arg Leu

<210> SEQ ID NO 31
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 31

Met Ala Asp Arg Ala Glu Met Phe Ser Leu Ser Thr Phe His Ser Leu
 1               5                  10                  15

Ser Pro Pro Gly Cys Arg Pro Pro Gln Asp Ile Ser Leu Glu Glu Phe
                20                  25                  30

Asp Asp Glu Asp Leu Ser Glu Ile Thr Asp Asp Cys Gly Leu Gly Leu
            35                  40                  45

Ser Tyr Asp Ser Asp His Cys Glu Lys Asp Ser Leu Ser Leu Gly Arg
    50                  55                  60

Ser Glu Gln Pro His Pro Ile Cys Ser Phe Gln Asp Asp Phe Gln Glu
65                  70                  75                  80

Phe Glu Met Ile Asp Asp His Gln Gly Gly His Glu Glu Glu
                85                  90                  95

Glu Glu Glu Glu Glu Glu Asp Gly Asp Arg Gln Gly Lys Ala Gly
                100                 105                 110

Gly Gly Pro Gly Ser Gln Ala Leu Ala Gly Asp Ser Leu Ile Pro Ser
            115                 120                 125

Pro Ser Leu Glu Glu Ser His Lys Leu Arg Pro Thr Thr Leu His Leu
    130                 135                 140

Thr Thr Leu Gly Ala Gln Asp Ser Leu Asn Asn Asn Asn Gly Gly Phe
145                 150                 155                 160

Thr Ser Ala Pro Pro Ser Ser Trp Gln Glu Thr Val Leu Arg Ser Pro
                165                 170                 175

Ala Gln Glu Pro Leu Lys Glu Leu Pro Ala Pro Leu Leu Pro Ala Glu
            180                 185                 190

Glu Glu Arg His Glu Val Gln Ser Leu Ala Arg Pro Gly Cys Asp Cys
        195                 200                 205

Glu Gly Asn Gln Pro Pro Glu Pro Pro Ala Ser Ser Gly Gly Ala Ser
    210                 215                 220

Pro Ser Ser Asp Pro Gly Ile Glu Ala Asp Leu Arg Ser His Ser Ser
225                 230                 235                 240

Gly Gly His Glu Gly Arg Arg Ser Ser Gln Glu Leu Ser Ser Pro Gly
                245                 250                 255

Ser Asp Ser Glu Asp Ala Gly Gly Ala Arg Leu Gly Arg Met Ile Ser
            260                 265                 270

Ser Ile Ser Glu Thr Glu Leu Glu Leu Ser Ser Asp Gly Gly Ser Ser
        275                 280                 285

Ser Gly Arg Ser Ser His Leu Thr Asn Ser Ile Glu Glu Ala Ser Ser
    290                 295                 300

Pro Ala Ser Glu Pro Glu Pro Glu Pro Glu Pro Leu His Glu Pro Pro
305                 310                 315                 320

Arg Arg Pro Ala Phe Leu Pro Val Gly Gln Asp Asp Thr Asn Ser Glu
                325                 330                 335

Tyr Glu Ser Gly Ser Glu Ser Glu Pro Asp Leu Ser Glu Asp Ala Asp
            340                 345                 350

```
Ser Pro Trp Leu Leu Ser Asn Leu Val Ser Arg Met Ile Ser Glu Gly
        355                 360                 365

Ser Ser Pro Ile Arg Cys Pro Gly Gln Cys Leu Ser Pro Ala Pro Arg
    370                 375                 380

Leu Pro Glu Glu Ala Ala Ser Gln Ala Asn Ser Val Pro Gln Asp Cys
385                 390                 395                 400

Gln Asp Pro Glu Ala Gly Pro His Val Glu Leu Val Asp Met Asp Thr
                405                 410                 415

Leu Cys Gly Pro Pro Pro Pro Ala Pro Ala Pro Arg Leu Gly Pro
                420                 425                 430

Ala Gln Pro Gly Pro Cys Leu Phe Leu Ser Asn Pro Thr Arg Asp Thr
    435                 440                 445

Ile Thr Pro Leu Trp Ala Thr Pro Gly Arg Thr Ala Arg Pro Gly Arg
450                 455                 460

Ser Cys Ser Ala Ala Cys Ser Glu Glu Glu Glu Asp Glu Glu Glu
465                 470                 475                 480

Asp Glu Glu Asp Glu Glu Asp Ala Glu Asp Ser Val Val Pro Pro Gly
                485                 490                 495

Ser Arg Thr Thr Gly Ser Thr Ala Pro Leu Asp Ala Ser Leu Val Tyr
                500                 505                 510

Asp Ala Val Lys Tyr Thr Leu Val Val Asp Glu His Thr Gln Leu Glu
            515                 520                 525

Leu Val Ser Leu Arg Arg Cys Ala Gly Leu Gly Asn Asp Ser Glu Glu
        530                 535                 540

Asp Ser Ser Cys Glu Ala Ser Glu Glu Glu Ala Gly Ala Thr Leu Leu
545                 550                 555                 560

Gly Ser Asp Gln Val Pro Glu Asp Ala Ser Pro Asp Ser Pro Asp Leu
                565                 570                 575

Thr Phe Ser Lys Lys Phe Leu Asn Val Phe Asn Ser Thr Ser Arg
                580                 585                 590

Ser Ser Ser Thr Glu Ser Phe Gly Leu Phe Ser Cys Val Xaa Asn Gly
        595                 600                 605

Glu Glu Arg Glu Gln Thr His Arg Ala Val Phe Arg Phe Ile Pro Arg
    610                 615                 620

His Pro Asp Glu Leu Glu Leu Asp Val Asp Asp Pro Val Leu Val Glu
625                 630                 635                 640

Ala Glu Glu Asp Asp Phe Trp Phe Arg Gly Phe Asn Met Arg Thr Gly
                645                 650                 655

Glu Arg Gly Val Phe Pro Ala Phe Tyr Ala His Ala Val Pro Gly Pro
            660                 665                 670

Ala Lys Asp Leu Leu Gly Ser Lys Arg Ser Pro Cys Trp Val Asp Arg
        675                 680                 685

Phe Asp Val Gln Phe Leu Gly Ser Val Glu Val Pro Cys His Gln Gly
    690                 695                 700

Asn Gly Ile Leu Cys Ala Ala Met Gln Lys Ile Ala Thr Ala Arg Lys
705                 710                 715                 720

Leu Thr Val His Leu Arg Pro Pro Ala Ser Cys Asp Leu Glu Ile Ser
                725                 730                 735

Leu Arg Gly Val Lys Leu Ser Leu Ser Gly Gly Pro Glu Phe Gln
                740                 745                 750

Arg Cys Ser His Phe Phe Gln Met Lys Asn Ile Ser Phe Cys Gly Cys
        755                 760                 765
```

```
His Pro Arg Asn Ser Cys Tyr Phe Gly Phe Ile Thr Lys His Pro Leu
        770                 775                 780

Leu Ser Arg Phe Ala Cys His Val Phe Val Ser Gln Glu Ser Met Arg
785                 790                 795                 800

Pro Val Ala Arg Ser Val Gly Arg Ala Phe Leu Glu Tyr Tyr Gln Glu
                    805                 810                 815

His Leu Ala Phe Ala Cys Pro Thr Glu Asp Ile Tyr Leu Glu
                820                 825                 830

<210> SEQ ID NO 32
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 32

Met Asp Asp Arg Ala Glu Met Phe Ser Leu Ser Glu Phe His Ser Leu
 1               5                   10                  15

Ser Pro Pro Gly Cys Phe Pro Pro Gln Asp Ile Ser Leu Glu Glu Gly
                20                  25                  30

Asp Asp Glu Asp Leu Ser Glu Ile Thr His Asp Cys Gly Leu Gly Leu
            35                  40                  45

Ser Tyr Asp Ile Asp His Cys Glu Lys Asp Ser Leu Ser Lys Gly Arg
 50                  55                  60

Ser Glu Gln Pro His Pro Ile Leu Ser Phe Gln Asp Phe Gln Glu
 65                  70                  75                  80

Phe Met Met Ile Asp Asp His Gln Gly Gly Gly Asn Glu Glu Glu Glu
                85                  90                  95

Glu Glu Glu Glu Glu Gln Glu Asp Gly Asp Arg Gln Gly Lys Ala Arg
                100                 105                 110

Gly Gly Pro Gly Ser Gln Ala Leu Ala Ser Asp Ser Leu Ile Pro Ser
            115                 120                 125

Pro Ser Leu Thr Glu Ser His Lys Leu Arg Pro Thr Thr Val His Leu
130                 135                 140

Thr Thr Leu Gly Ala Gln Asp Trp Leu Asn Asn Asn Asn Gly Gly Phe
145                 150                 155                 160

Thr Tyr Ala Pro Pro Ser Ser Trp Gln Glu Thr Ala Leu Arg Ser Pro
                165                 170                 175

Ala Gln Glu Pro Leu Asp Glu Leu Pro Ala Pro Leu Leu Pro Ala Phe
                180                 185                 190

Glu Glu Arg His Glu Val Gln Ser Leu Gly Arg Pro Gly Cys Asp Cys
                195                 200                 205

Glu Gly Asn His Pro Pro Glu Pro Pro Ala Ser Ser Gly Ile Ala Ser
            210                 215                 220

Pro Ser Ser Asp Pro Gly Ile Lys Ala Asp Leu Arg Ser His Ser Ser
225                 230                 235                 240

Gly Leu His Glu Gly Arg Arg Ser Ser Gln Glu Met Ser Ser Pro Gly
                245                 250                 255

Ser Asp Ser Glu Asp Asn Gly Gly Ala Arg Leu Gly Arg Met Ile Gln
                260                 265                 270

Ser Ile Ser Glu Thr Glu Leu Glu Leu Arg Ser Asp Gly Gly Ser Ser
            275                 280                 285

Ser Gly Arg Thr Ser His Leu Thr Asn Ser Ile Glu Glu Val Ser Ser
290                 295                 300
```

-continued

```
Pro Ala Ser Glu Pro Glu Trp Pro Glu Pro Leu His Glu Pro Pro
305                 310                 315                 320

Arg Tyr Pro Ala Phe Leu Pro Val Gly Gln Asp Ala Thr Asn Ser Glu
            325                 330                 335

Tyr Glu Ser Gly Ser Asp Ser Glu Pro Asp Leu Ser Glu Asp Ala Glu
            340                 345                 350

Ser Pro Trp Leu Leu Ser Asn Leu Val Phe Arg Met Ile Ser Glu Gly
            355                 360                 365

Ser Ser Pro Gly Arg Cys Pro Gly Gln Cys Leu Ser Pro His Pro Arg
370                 375                 380

Leu Pro Glu Glu Ala Ala Ser Ile Ala Asn Ser Val Pro Gln Asp Cys
385                 390                 395                 400

Gln Lys Pro Glu Ala Gly Pro His Val Glu Leu Leu Asp Met Asp Thr
            405                 410                 415

Leu Cys Gly Pro Pro Met Pro Ala Pro Ala Ala Pro Arg Leu Gly Asn
            420                 425                 430

Ala Gln Pro Gly Pro Cys Leu Phe Leu Gln Asn Pro Thr Arg Asp Thr
            435                 440                 445

Ile Thr Pro Arg Trp Ala Thr Pro Gly Arg Thr Ala Arg Ser Gly Arg
450                 455                 460

Ser Cys Ser Ala Ala Cys Ser Thr Glu Glu Glu Glu Asp Glu Glu Glu
465                 470                 475                 480

Asp Val Glu Asp Glu Glu Asp Ala Glu Asp Ser Trp Val Pro Pro Gly
            485                 490                 495

Ser Arg Thr Thr Gly Tyr Thr Ala Pro Leu Asp Ala Ser Leu Val Ala
            500                 505                 510

Asp Ala Val Lys Tyr Thr Leu Val Val Glu Glu His Thr Gln Leu Glu
            515                 520                 525

Leu Val Ser Phe Arg Arg Cys Ala Gly Leu Gly Asn Asp Gly Glu Glu
            530                 535                 540

Asp Ser Ser Cys Glu Ala Ser His Glu Glu Ala Gly Ala Thr Leu Leu
545                 550                 555                 560

Gly Ile Asp Gln Val Pro Glu Asp Ala Ser Pro Lys Ser Pro Asp Leu
            565                 570                 575

Thr Phe Ser Lys Lys Leu Leu Asn Val Phe Asn Ser Thr Ser Met
            580                 585                 590

Ser Ser Ser Thr Glu Ser Phe Gly Leu Asn Ser Cys Val Xaa Asn Gly
            595                 600                 605

Glu Glu Arg Gln Gln Thr His Arg Ala Val Phe Arg Phe Arg Pro Arg
610                 615                 620

His Pro Asp Glu Leu Glu Leu Ser Val Asp Asp Pro Val Leu Val Glu
625                 630                 635                 640

Ala Thr Glu Asp Asp Phe Trp Phe Arg Gly Phe Val Met Arg Thr Gly
            645                 650                 655

Glu Arg Gly Val Phe Trp Ala Phe Tyr Ala His Ala Val Pro Gly Tyr
            660                 665                 670

Ala Lys Asp Leu Leu Gly Ser Lys Arg Ala Pro Cys Trp Val Asp Arg
            675                 680                 685

Phe Asp Val Asp Phe Leu Gly Ser Val Glu Val Pro Cys Glu Gln Gly
            690                 695                 700

Asn Gly Ile Leu Cys Ala Ala Phe Gln Lys Ile Ala Thr Ala Arg Lys
705                 710                 715                 720
```

-continued

```
Leu Gly Val His Leu Arg Pro Ala Ser Cys His Leu Glu Ile Ser
                725                 730                 735

Leu Arg Gly Val Lys Ile Ser Leu Ser Gly Gly Pro Glu Phe Lys
                740                 745                 750

Arg Cys Ser His Phe Phe Gln Met Lys Leu Ile Ser Phe Cys Gly Cys
                755                 760                 765

His Pro Arg Met Ser Cys Tyr Phe Gly Phe Ile Thr Lys Asn Pro Leu
                770                 775                 780

Leu Ser Arg Phe Ala Cys His Gln Phe Val Ser Gln Glu Ser Met Arg
785                 790                 795                 800

Pro Arg Ala Arg Ser Val Gly Arg Ala Phe Leu Ser Tyr Tyr Gln Glu
                805                 810                 815

His Leu Ala Phe Ala Thr Pro Thr Glu Asp Ile Tyr Leu Glu
                820                 825                 830

<210> SEQ ID NO 33
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 33

Met Ala Ala Arg Ala Glu Met Phe Ser Leu Ser Thr Asp His Ser Leu
 1               5                  10                  15

Ser Pro Pro Gly Cys Arg Glu Pro Gln Asp Ile Ser Leu Glu Glu Phe
                20                  25                  30

Phe Asp Glu Asp Leu Ser Glu Ile Thr Asp Gly Cys Gly Leu Gly Leu
                35                  40                  45

Ser Tyr Asp Ser His His Cys Glu Lys Asp Ser Leu Ser Leu Ile Arg
        50                  55                  60

Ser Glu Gln Pro His Pro Ile Cys Lys Phe Gln Asp Phe Gln Glu
65                  70                  75                  80

Phe Glu Leu Ile Asp Asp His Gln Gly Gly His Met Glu Glu Glu
                85                  90                  95

Glu Glu Glu Glu Glu Asn Asp Gly Asp Arg Gln Gly Lys Ala Gly
                100                 105                 110

Gln Gly Pro Gly Ser Gln Ala Leu Ala Gly Arg Ser Leu Ile Pro Ser
                115                 120                 125

Pro Ser Leu Glu Ser Ser His Lys Leu Arg Pro Thr Thr Leu Thr Leu
        130                 135                 140

Thr Thr Leu Gly Ala Gln Asp Ser Val Asn Asn Asn Gly Gly Phe
145                 150                 155                 160

Thr Ser Trp Pro Pro Ser Ser Trp Gln Glu Thr Val Tyr Arg Ser Pro
                165                 170                 175

Ala Gln Glu Pro Leu Lys Ala Leu Pro Ala Pro Leu Leu Pro Ala Glu
                180                 185                 190

Asp Glu Arg His Glu Val Gln Ser Leu Ala Glu Pro Gly Cys Asp Cys
                195                 200                 205

Glu Gly Asn Gln Phe Pro Glu Pro Pro Ala Ser Ser Gly Gly Gly Ser
        210                 215                 220

Pro Ser Ser Asp Pro Gly Ile Glu His Asp Leu Arg Ser His Ser Ser
225                 230                 235                 240

Gly Gly Ile Glu Gly Arg Arg Ser Ser Gln Glu Leu Lys Ser Pro Gly
                245                 250                 255
```

-continued

```
Ser Asp Ser Glu Asp Ala Leu Gly Ala Arg Leu Gly Arg Met Ile Ser
            260                 265                 270
Met Ile Ser Glu Thr Glu Leu Glu Leu Ser Asn Asp Gly Gly Ser Ser
            275                 280                 285
Ser Gly Arg Ser Gln His Leu Thr Asn Ser Ile Glu Glu Ala Arg Ser
            290                 295                 300
Pro Ala Ser Glu Pro Glu Pro Glu Ser Glu Pro Leu His Glu Pro Pro
305                 310                 315                 320
Arg Arg Thr Ala Phe Leu Pro Val Gly Gln Asp Val Asn Ser Glu
                325                 330                 335
Tyr Glu Ser Gly Ser Glu Trp Glu Pro Asp Leu Ser Glu Asp Ala Asp
            340                 345                 350
Tyr Pro Trp Leu Leu Ser Asn Leu Val Ser Ala Met Ile Ser Glu Gly
            355                 360                 365
Ser Ser Pro Ile Asp Cys Pro Gly Gln Cys Leu Ser Pro Ala Glu Arg
            370                 375                 380
Leu Pro Glu Glu Ala Ala Ser Gln Phe Asn Ser Val Pro Gln Asp Cys
385                 390                 395                 400
Gln Asp Gly Glu Ala Gly Pro His Val Glu Leu Val His Met Asp Thr
            405                 410                 415
Leu Cys Gly Pro Pro Ile Ala Pro Ala Ala Pro Arg Leu Gly Pro
            420                 425                 430
Lys Gln Pro Gly Pro Cys Leu Phe Leu Ser Leu Pro Thr Arg Asp Thr
            435                 440                 445
Ile Thr Pro Leu Met Ala Thr Pro Gly Arg Thr Ala Arg Pro Asn Arg
450                 455                 460
Ser Cys Ser Ala Ala Cys Ser Glu Gln Glu Glu Glu Asp Glu Glu Glu
465                 470                 475                 480
Asp Glu Arg Asp Glu Glu Asp Ala Glu Asp Ser Val Ser Pro Pro Gly
                485                 490                 495
Ser Arg Thr Thr Gly Ser Val Ala Pro Leu Asp Ala Ser Leu Val Tyr
            500                 505                 510
Trp Ala Val Lys Tyr Thr Leu Val Val Asp Tyr His Thr Gln Leu Glu
            515                 520                 525
Leu Val Ser Leu Ala Arg Cys Ala Gly Leu Gly Asn Asp Ser Asp Glu
530                 535                 540
Asp Ser Ser Cys Glu Ala Ser Glu Phe Glu Ala Gly Ala Thr Leu Leu
545                 550                 555                 560
Gly Ser Gly Gln Val Pro Glu Asp Ala Ser Pro Asp His Pro Asp Leu
                565                 570                 575
Thr Phe Ser Lys Lys Phe Ile Asn Val Phe Asn Ser Thr Ser Arg
            580                 585                 590
Lys Ser Thr Glu Ser Phe Gly Leu Phe Leu Cys Val Xaa Asn Gly
            595                 600                 605
Glu Glu Arg Glu Met Thr His Arg Ala Val Phe Arg Phe Ile Asn Arg
            610                 615                 620
His Pro Asp Glu Leu Glu Leu Asp Gln Asp Pro Val Leu Val Glu
625                 630                 635                 640
Ala Glu Arg Asp Asp Phe Trp Phe Arg Gly Phe Asn Ser Arg Thr Gly
                645                 650                 655
Glu Arg Gly Val Phe Pro Thr Phe Tyr Ala His Ala Val Pro Gly Pro
            660                 665                 670
```

```
Val Lys Asp Leu Leu Gly Ser Lys Arg Ser Trp Cys Trp Val Asp Arg
            675                 680                 685

Phe Asp Val Gln Tyr Leu Gly Ser Val Glu Val Pro Cys His Ala Gly
        690                 695                 700

Asn Gly Ile Leu Cys Ala Ala Met Asp Lys Ile Ala Thr Ala Arg Lys
705                 710                 715                 720

Leu Thr Glu His Leu Arg Pro Pro Ala Ser Cys Asp Phe Glu Ile Ser
                725                 730                 735

Leu Arg Gly Val Lys Leu Gly Leu Ser Gly Gly Pro Glu Phe Gln
            740                 745                 750

His Cys Ser His Phe Phe Gln Met Lys Asn Lys Ser Phe Cys Gly Cys
        755                 760                 765

His Pro Arg Asn Leu Cys Tyr Phe Gly Phe Ile Thr Lys His Met Leu
        770                 775                 780

Leu Ser Arg Phe Ala Cys His Val Asn Val Ser Gln Glu Ser Met Arg
785                 790                 795                 800

Pro Val Gln Arg Ser Val Gly Arg Ala Phe Leu Glu Arg Tyr Gln Glu
                805                 810                 815

His Leu Ala Phe Ala Cys Ser Thr Glu Asp Ile Tyr Leu Glu
            820                 825                 830

<210> SEQ ID NO 34
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 34

Met Ala Asp Ala Ala Glu Met Phe Ser Leu Ser Thr Phe Asp Ser Leu
1               5                   10                  15

Ser Pro Pro Gly Cys Arg Pro Glu Gln Asp Ile Ser Leu Glu Glu Phe
            20                  25                  30

Asp Phe Glu Asp Leu Ser Glu Ile Thr Asp Asp Gly Gly Leu Gly Leu
        35                  40                  45

Ser Tyr Asp Ser Asp His Cys Glu Lys Asp Ser Leu Ser Leu Gly Ile
    50                  55                  60

Ser Glu Gln Pro His Pro Ile Cys Ser Lys Gln Asp Asp Phe Gln Glu
65                  70                  75                  80

Phe Glu Met Leu Asp Asp His Gln Gly Gly His Glu Met Glu Glu
                85                  90                  95

Glu Glu Glu Glu Glu Glu Asn Gly Asp Arg Gln Gly Lys Ala Gly
            100                 105                 110

Gly Gln Pro Gly Ser Gln Ala Leu Ala Gly Asp Arg Leu Ile Pro Ser
        115                 120                 125

Pro Ser Leu Glu Glu Thr His Lys Leu Arg Pro Thr Thr Leu His Val
130                 135                 140

Thr Thr Leu Gly Ala Gln Asp Ser Leu Trp Asn Asn Gly Gly Phe
145                 150                 155                 160

Thr Ser Ala Tyr Pro Ser Ser Trp Gln Glu Thr Val Leu Ala Ser Pro
                165                 170                 175

Ala Gln Glu Pro Leu Lys Glu Asp Pro Ala Pro Leu Leu Pro Ala Glu
            180                 185                 190

Glu Phe Arg His Glu Val Gln Ser Leu Ala Arg Gly Gly Cys Asp Cys
        195                 200                 205
```

```
Glu Gly Asn Gln Pro His Glu Pro Ala Ser Ser Gly Gly Ala Ile
    210                 215                 220
Pro Ser Ser Asp Pro Gly Ile Glu Ala Lys Leu Arg Ser His Ser Ser
225                 230                 235                 240
Gly Gly His Leu Gly Arg Arg Ser Ser Gln Glu Leu Ser Met Pro Gly
                245                 250                 255
Ser Asp Ser Glu Asp Ala Gly Asn Ala Arg Leu Gly Arg Met Ile Ser
            260                 265                 270
Ser Gln Ser Glu Thr Glu Leu Glu Leu Ser Ser Arg Gly Gly Ser Ser
        275                 280                 285
Ser Gly Arg Ser Ser Ser Leu Thr Asn Ser Ile Glu Glu Ala Ser Thr
    290                 295                 300
Pro Ala Ser Glu Pro Glu Pro Glu Pro Val Pro Leu His Glu Pro Pro
305                 310                 315                 320
Arg Arg Pro Trp Phe Leu Pro Val Gly Gln Asp Asp Thr Tyr Ser Glu
                325                 330                 335
Tyr Glu Ser Gly Ser Glu Ser Ala Pro Asp Leu Ser Glu Asp Ala Asp
            340                 345                 350
Ser Asp Trp Leu Leu Ser Asn Leu Val Ser Arg Glu Ile Ser Glu Gly
        355                 360                 365
Ser Ser Pro Ile Arg Phe Pro Gly Gln Cys Leu Ser Pro Ala Pro Gly
    370                 375                 380
Leu Pro Glu Glu Ala Ala Ser Gln Ala His Ser Val Pro Gln Asp Cys
385                 390                 395                 400
Gln Asp Pro Ile Ala Gly Pro His Val Glu Leu Val Asp Lys Asp Thr
                405                 410                 415
Leu Cys Gly Pro Pro Pro Leu Pro Ala Ala Pro Arg Leu Gly Pro
            420                 425                 430
Ala Met Pro Gly Pro Cys Leu Phe Leu Ser Asn Asn Thr Arg Asp Thr
        435                 440                 445
Ile Thr Pro Leu Trp Gln Thr Pro Gly Arg Thr Ala Arg Pro Gly Ser
    450                 455                 460
Ser Cys Ser Ala Ala Cys Ser Glu Glu Thr Glu Glu Asp Glu Glu Glu
465                 470                 475                 480
Asp Glu Glu Val Glu Glu Asp Ala Glu Asp Ser Val Val Trp Pro Gly
                485                 490                 495
Ser Arg Thr Thr Gly Ser Thr Tyr Pro Leu Asp Ala Ser Leu Val Tyr
            500                 505                 510
Asp Asp Val Lys Tyr Thr Leu Val Val Asp Glu Glu Thr Gln Leu Glu
        515                 520                 525
Leu Val Ser Leu Arg Gly Cys Ala Gly Leu Gly Asn Asp Ser Glu His
    530                 535                 540
Asp Ser Ser Cys Glu Ala Ser Glu Glu Ile Ala Gly Ala Thr Leu Leu
545                 550                 555                 560
Gly Ser Asp Lys Val Pro Glu Asp Ala Ser Pro Asp Ser Leu Asp Leu
                565                 570                 575
Thr Phe Ser Lys Lys Phe Leu Met Val Phe Val Asn Ser Thr Ser Arg
            580                 585                 590
Ser Asn Ser Thr Glu Ser Phe Gly Leu Phe Ser Gln Val Xaa Asn Gly
        595                 600                 605
Glu Glu Arg Glu Gln Arg His Arg Ala Val Phe Arg Phe Ile Pro Ser
    610                 615                 620
```

```
His Pro Asp Glu Leu Glu Leu Asp Val Thr Asp Pro Val Leu Val Glu
625                 630                 635                 640

Ala Glu Glu Val Asp Phe Trp Phe Arg Gly Phe Asn Met Trp Thr Gly
                645                 650                 655

Glu Arg Gly Val Phe Pro Ala Tyr Tyr Ala His Ala Val Pro Gly Pro
            660                 665                 670

Ala Ala Asp Leu Leu Gly Ser Lys Arg Ser Pro Asp Trp Val Asp Arg
            675                 680                 685

Phe Asp Val Gln Phe Glu Gly Ser Val Glu Val Pro Cys His Gln Phe
690                 695                 700

Asn Gly Ile Leu Cys Ala Ala Met Gln Gly Ile Ala Thr Ala Arg Lys
705                 710                 715                 720

Leu Thr Val Ile Leu Arg Pro Pro Ala Ser Cys Asp Leu Lys Ile Ser
                725                 730                 735

Leu Arg Gly Val Lys Leu Ser Met Ser Gly Gly Pro Glu Phe Gln
            740                 745                 750

Arg Asn Ser His Phe Phe Gln Met Lys Asn Ile Gln Phe Cys Gly Cys
            755                 760                 765

His Pro Arg Asn Ser Arg Tyr Phe Gly Phe Ile Thr Lys His Pro Ser
770                 775                 780

Leu Ser Arg Phe Ala Cys His Val Phe Thr Ser Gln Glu Ser Met Arg
785                 790                 795                 800

Pro Val Ala Val Ser Val Gly Arg Ala Phe Leu Glu Tyr Trp Gln Glu
                805                 810                 815

His Leu Ala Phe Ala Cys Pro Tyr Glu Asp Ile Tyr Leu Glu
            820                 825                 830

<210> SEQ ID NO 35
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 35

Met Ala Asp Arg Asp Glu Met Phe Ser Leu Ser Thr Phe His Glu Leu
1               5                   10                  15

Ser Pro Pro Gly Cys Arg Pro Pro Phe Asp Ile Ser Leu Glu Glu Phe
                20                  25                  30

Asp Asp Gly Asp Leu Ser Glu Ile Thr Asp Cys His Leu Gly Leu
            35                  40                  45

Ser Tyr Asp Ser Asp His Ile Glu Lys Asp Ser Leu Ser Leu Gly Arg
    50                  55                  60

Lys Glu Gln Pro His Pro Ile Cys Ser Phe Leu Asp Asp Phe Gln Glu
65                  70                  75                  80

Phe Glu Met Ile Met Asp His Gln Gly Gly Gly His Glu Glu Asn Glu
                85                  90                  95

Glu Glu Glu Glu Glu Glu Asp Gln Asp Arg Gln Gly Lys Ala Gly
            100                 105                 110

Gly Gly Arg Gly Ser Gln Ala Leu Ala Gly Asp Ser Ser Ile Pro Ser
        115                 120                 125

Pro Ser Leu Glu Glu Ser Thr Lys Leu Arg Pro Thr Thr Leu His Leu
    130                 135                 140

Val Thr Leu Gly Ala Gln Asp Ser Leu Asn Trp Asn Asn Gly Gly Phe
145                 150                 155                 160
```

```
Thr Ser Ala Pro Tyr Ser Ser Trp Gln Glu Thr Val Leu Arg Ala Pro
                165                 170                 175
Ala Gln Glu Pro Leu Lys Glu Leu Asp Ala Pro Leu Leu Pro Ala Glu
            180                 185                 190
Glu Glu Glu His Glu Val Gln Ser Leu Ala Arg Pro Phe Cys Asp Cys
        195                 200                 205
Glu Gly Asn Gln Pro Gly Pro Ala Ser Ser Gly Gly Ala Ser
    210                 215                 220
His Ser Ser Asp Pro Gly Ile Glu Ala Asp Ile Arg Ser His Ser Ser
225                 230                 235                 240
Gly Gly His Glu Lys Arg Arg Ser Ser Gln Glu Leu Ser Ser Leu Gly
                245                 250                 255
Ser Asp Ser Glu Asp Ala Gly Gly Met Arg Leu Gly Arg Met Ile Ser
                260                 265                 270
Ser Ile Asn Glu Thr Glu Leu Glu Leu Ser Ser Asp Gln Gly Ser Ser
                275                 280                 285
Ser Gly Arg Ser Ser His Arg Thr Asn Ser Ile Glu Glu Ala Ser Ser
    290                 295                 300
Ser Ala Ser Glu Pro Glu Pro Glu Pro Glu Thr Leu His Glu Pro Pro
305                 310                 315                 320
Arg Arg Pro Ala Val Leu Pro Val Gly Gln Asp Asp Thr Asn Trp Glu
                325                 330                 335
Tyr Glu Ser Gly Ser Glu Ser Glu Tyr Asp Leu Ser Glu Asp Ala Asp
                340                 345                 350
Ser Pro Ala Leu Leu Ser Asn Leu Val Ser Arg Met Asp Ser Glu Gly
                355                 360                 365
Ser Ser Pro Ile Arg Cys Glu Gly Gln Cys Leu Ser Pro Ala Pro Arg
    370                 375                 380
Phe Pro Glu Glu Ala Ala Ser Gln Ala Asn Gly Val Pro Gln Asp Cys
385                 390                 395                 400
Gln Asp Pro Glu His Gly Pro His Val Glu Leu Val Asp Met Ile Thr
                405                 410                 415
Leu Cys Gly Pro Pro Pro Ala Lys Ala Ala Pro Arg Leu Gly Pro
                420                 425                 430
Ala Gln Leu Gly Pro Cys Leu Phe Leu Ser Asn Pro Met Arg Asp Thr
            435                 440                 445
Ile Thr Pro Leu Trp Ala Asn Pro Gly Arg Thr Ala Arg Pro Gly Arg
    450                 455                 460
Gln Cys Ser Ala Ala Cys Ser Glu Glu Arg Glu Asp Glu Glu
465                 470                 475                 480
Asp Glu Glu Asp Ser Glu Asp Ala Glu Asp Ser Val Val Pro Thr Gly
                485                 490                 495
Ser Arg Thr Thr Gly Ser Thr Ala Val Leu Asp Ala Ser Leu Val Tyr
                500                 505                 510
Asp Ala Trp Lys Tyr Thr Leu Val Val Asp Glu His Tyr Gln Leu Glu
                515                 520                 525
Leu Val Ser Leu Arg Arg Ala Ala Gly Leu Gly Asn Asp Ser Glu Glu
                530                 535                 540
Glu Ser Ser Cys Glu Ala Ser Glu Glu Glu Phe Gly Ala Thr Leu Leu
545                 550                 555                 560
Gly Ser Asp Gln Gly Pro Glu Asp Ala Ser Pro Asp Ser Pro His Leu
                565                 570                 575
```

```
Thr Phe Ser Lys Lys Phe Leu Asn Ile Phe Val Asn Ser Thr Ser Arg
            580                 585                 590

Ser Ser Lys Thr Glu Ser Phe Gly Leu Phe Ser Cys Leu Xaa Asn Gly
            595                 600                 605

Glu Glu Arg Glu Gln Thr Met Arg Ala Val Phe Arg Phe Ile Pro Arg
            610                 615                 620

Asn Pro Asp Glu Leu Glu Leu Asp Val Asp Gln Pro Val Leu Val Glu
625                 630                 635                 640

Ala Glu Glu Asp Arg Phe Trp Phe Arg Gly Phe Asn Met Arg Ser Gly
                    645                 650                 655

Glu Arg Gly Val Phe Pro Ala Phe Thr Ala His Ala Val Pro Gly Pro
                    660                 665                 670

Ala Lys Val Leu Leu Gly Ser Lys Arg Ser Pro Cys Tyr Val Asp Arg
                    675                 680                 685

Phe Asp Val Gln Phe Leu Ala Ser Val Glu Val Pro Cys His Gln Gly
                    690                 695                 700

Asp Gly Ile Leu Cys Ala Ala Met Gln Lys Glu Ala Thr Ala Arg Lys
705                 710                 715                 720

Leu Thr Val His Phe Arg Pro Pro Ala Ser Cys Asp Leu Glu Gly Ser
                    725                 730                 735

Leu Arg Gly Val Lys Leu Ser Leu His Gly Gly Pro Glu Phe Gln
                    740                 745                 750

Arg Cys Ile His Phe Gln Met Lys Asn Ile Ser Lys Cys Gly Cys
                    755                 760                 765

His Pro Arg Asn Ser Cys Leu Phe Gly Phe Ile Thr Lys His Pro Leu
                    770                 775                 780

Met Ser Arg Phe Ala Cys His Val Phe Val Asn Gln Glu Ser Met Arg
785                 790                 795                 800

Pro Val Ala Arg Gln Val Gly Arg Ala Phe Leu Glu Tyr Tyr Arg Glu
                    805                 810                 815

His Leu Ala Phe Ala Cys Pro Thr Ser Asp Ile Tyr Leu Glu
                    820                 825                 830

<210> SEQ ID NO 36
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 36

Met Ala Asp Arg Ala Ala Met Phe Ser Leu Ser Thr Phe His Ser Asp
 1               5                  10                  15

Ser Pro Pro Gly Cys Arg Pro Pro Gln Glu Ile Ser Leu Glu Glu Phe
                20                  25                  30

Asp Asp Glu Phe Leu Ser Glu Ile Thr Asp Asp Cys Gly Gly Gly Leu
            35                  40                  45

Ser Tyr Asp Ser Asp His Cys His Lys Asp Ser Leu Ser Leu Gly Arg
        50                  55                  60

Ser Ile Gln Pro His Pro Ile Cys Ser Phe Gln Lys Asp Phe Gln Glu
65                  70                  75                  80

Phe Glu Met Ile Asp Leu His Gln Gly Gly His Glu Glu Glu Met
                85                  90                  95

Glu Glu Glu Glu Glu Glu Asp Gly Asn Arg Gln Gly Lys Ala Gly
                100                 105                 110
```

-continued

```
Gly Gly Pro Gln Ser Gln Ala Leu Ala Gly Asp Ser Leu Arg Pro Ser
        115                 120                 125
Pro Ser Leu Glu Glu Ser His Ser Leu Arg Pro Thr Thr Leu His Leu
130                 135                 140
Thr Val Leu Gly Ala Gln Asp Ser Leu Asn Asn Trp Asn Gly Gly Phe
145                 150                 155                 160
Thr Ser Ala Pro Pro Tyr Ser Trp Gln Glu Thr Val Leu Arg Ser Ala
                165                 170                 175
Ala Gln Glu Pro Leu Lys Glu Leu Pro Asp Pro Leu Leu Pro Ala Glu
        180                 185                 190
Glu Glu Arg Glu Glu Val Gln Ser Leu Ala Arg Pro Gly Phe Asp Cys
        195                 200                 205
Glu Gly Asn Gln Pro Pro Glu Gly Pro Ala Ser Ser Gly Gly Ala Ser
210                 215                 220
Pro His Ser Asp Pro Gly Ile Glu Ala Asp Leu Ile Ser His Ser Ser
225                 230                 235                 240
Gly Gly His Glu Gly Lys Arg Ser Ser Gln Glu Leu Ser Ser Pro Leu
                245                 250                 255
Ser Asp Ser Glu Asp Ala Gly Gly Ala Met Leu Gly Arg Met Ile Ser
                260                 265                 270
Ser Ile Ser Asn Thr Glu Leu Glu Leu Ser Ser Asp Gly Gln Ser Ser
        275                 280                 285
Ser Gly Arg Ser Ser His Leu Arg Asn Ser Ile Glu Glu Ala Ser Ser
        290                 295                 300
Pro Ser Ser Glu Pro Glu Pro Glu Pro Glu Pro Thr His Glu Pro Pro
305                 310                 315                 320
Arg Arg Pro Ala Phe Val Pro Val Gly Gln Asp Asp Thr Asn Ser Trp
                325                 330                 335
Tyr Glu Ser Gly Ser Glu Ser Glu Pro Tyr Leu Ser Glu Asp Ala Asp
                340                 345                 350
Ser Pro Trp Ala Leu Ser Asn Leu Val Ser Arg Met Ile Asp Glu Gly
        355                 360                 365
Ser Ser Pro Ile Arg Cys Pro Glu Gln Cys Leu Ser Pro Ala Pro Arg
370                 375                 380
Leu Phe Glu Glu Ala Ala Ser Gln Ala Asn Ser Gly Pro Gln Asp Cys
385                 390                 395                 400
Gln Asp Pro Glu Ala His Pro His Val Glu Leu Val Asp Met Asp Ile
                405                 410                 415
Leu Cys Gly Pro Pro Pro Ala Pro Lys Ala Pro Arg Leu Gly Pro
        420                 425                 430
Ala Gln Pro Leu Pro Cys Leu Phe Leu Ser Asn Pro Thr Met Asp Thr
        435                 440                 445
Ile Thr Pro Leu Trp Ala Thr Asn Gly Arg Thr Ala Arg Pro Gly Arg
        450                 455                 460
Ser Gln Ser Ala Ala Cys Ser Glu Glu Glu Arg Asp Glu Glu
465                 470                 475                 480
Asp Glu Glu Asp Glu Ser Asp Ala Glu Asp Ser Val Val Pro Pro Thr
                485                 490                 495
Ser Arg Thr Thr Gly Ser Thr Ala Pro Val Asp Ala Ser Leu Val Tyr
                500                 505                 510
Asp Ala Val Trp Tyr Thr Leu Val Val Asp Glu His Thr Tyr Leu Glu
        515                 520                 525
```

```
Leu Val Ser Leu Arg Arg Cys Asp Gly Leu Gly Asn Asp Ser Glu Glu
        530                 535                 540

Asp Glu Ser Cys Glu Ala Ser Glu Glu Ala Phe Ala Thr Leu Leu
545                 550                 555                 560

Gly Ser Asp Gln Val Gly Glu Asp Ala Ser Pro Asp Ser Pro Asp His
                565                 570                 575

Thr Phe Ser Lys Lys Phe Leu Asn Val Ile Val Asn Ser Thr Ser Arg
                580                 585                 590

Ser Ser Ser Lys Glu Ser Phe Gly Leu Phe Ser Cys Val Leu Asn Gly
            595                 600                 605

Glu Glu Arg Glu Gln Thr His Met Ala Val Phe Arg Phe Ile Pro Arg
        610                 615                 620

His Asn Asp Glu Leu Glu Leu Asp Val Asp Asp Gln Val Leu Val Glu
625                 630                 635                 640

Ala Glu Glu Asp Asp Arg Trp Phe Arg Gly Phe Asn Met Arg Thr Ser
                645                 650                 655

Glu Arg Gly Val Phe Pro Ala Phe Tyr Thr His Ala Val Pro Gly Pro
                660                 665                 670

Ala Lys Asp Val Leu Gly Ser Lys Arg Ser Pro Cys Trp Trp Asp Arg
            675                 680                 685

Phe Asp Val Gln Phe Leu Gly Tyr Val Glu Val Pro Cys His Gln Gly
        690                 695                 700

Asn Ala Ile Leu Cys Ala Ala Met Gln Lys Ile Asp Thr Ala Arg Lys
705                 710                 715                 720

Leu Thr Val His Leu Glu Pro Pro Ala Ser Cys Asp Leu Glu Ile Phe
                725                 730                 735

Leu Arg Gly Val Lys Leu Ser Leu Ser His Gly Gly Pro Glu Phe Gln
                740                 745                 750

Arg Cys Ser Ile Phe Phe Gln Met Lys Asn Ile Ser Phe Lys Gly Cys
            755                 760                 765

His Pro Arg Asn Ser Cys Tyr Leu Gly Phe Ile Thr Lys His Pro Leu
        770                 775                 780

Leu Met Arg Phe Ala Cys His Val Phe Val Ser Asn Glu Ser Met Arg
785                 790                 795                 800

Pro Val Ala Arg Ser Gln Gly Arg Ala Phe Leu Glu Tyr Tyr Gln Arg
                805                 810                 815

His Leu Ala Phe Ala Cys Pro Thr Glu Ser Ile Tyr Leu Glu
            820                 825                 830

<210> SEQ ID NO 37
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 37

Met Ala Asp Arg Ala Glu Ala Phe Ser Leu Ser Thr Phe His Ser Leu
 1               5                  10                  15

Asp Pro Pro Gly Cys Arg Pro Pro Gln Asp Glu Ser Leu Glu Glu Phe
                20                  25                  30

Asp Asp Glu Asp Phe Ser Glu Ile Thr Asp Asp Cys Gly Leu His Leu
            35                  40                  45

Ser Tyr Asp Ser Asp His Cys Glu Ile Asp Ser Leu Ser Leu Gly Arg
        50                  55                  60
```

```
Ser Glu Lys Pro His Pro Ile Cys Ser Phe Gln Asp Leu Phe Gln Glu
 65                  70                  75                  80

Phe Glu Met Ile Asp Asp Met Gln Gly Gly His Glu Glu Glu
                 85                  90                  95

Asn Glu Glu Glu Glu Glu Asp Gly Asp Gln Gln Gly Lys Ala Gly
            100                 105                 110

Gly Gly Pro Gly Arg Gln Ala Leu Ala Gly Asp Ser Leu Ile Ser Ser
        115                 120                 125

Pro Ser Leu Glu Glu Ser His Lys Thr Arg Pro Thr Thr Leu His Leu
    130                 135                 140

Thr Thr Val Gly Ala Gln Asp Ser Leu Asn Asn Asn Trp Gly Gly Phe
145                 150                 155                 160

Thr Ser Ala Pro Pro Ser Tyr Trp Gln Glu Thr Val Leu Arg Ser Pro
                165                 170                 175

Asp Gln Glu Pro Leu Lys Glu Leu Pro Ala Glu Leu Leu Pro Ala Glu
                180                 185                 190

Glu Glu Arg His Phe Val Gln Ser Leu Ala Arg Pro Gly Cys Gly Cys
            195                 200                 205

Glu Gly Asn Gln Pro Pro Glu Pro His Ala Ser Ser Gly Gly Ala Ser
210                 215                 220

Pro Ser Ile Asp Pro Gly Ile Glu Ala Asp Leu Arg Lys His Ser Ser
225                 230                 235                 240

Gly Gly His Glu Gly Arg Leu Ser Ser Gln Glu Leu Ser Ser Pro Gly
                245                 250                 255

Met Asp Ser Glu Asp Ala Gly Gly Ala Arg Asn Gly Arg Met Ile Ser
            260                 265                 270

Ser Ile Ser Glu Gln Glu Leu Glu Leu Ser Ser Asp Gly Gly Arg Ser
        275                 280                 285

Ser Gly Arg Ser Ser His Leu Thr Ser Ser Ile Glu Glu Ala Ser Ser
    290                 295                 300

Pro Ala Thr Glu Pro Glu Pro Glu Pro Glu Pro Leu Val Glu Pro Pro
305                 310                 315                 320

Arg Arg Pro Ala Phe Leu Trp Val Gly Gln Asp Asp Thr Asn Ser Glu
                325                 330                 335

Ala Glu Ser Gly Ser Glu Ser Glu Pro Asp Asp Ser Glu Asp Ala Asp
            340                 345                 350

Ser Pro Trp Leu Glu Ser Asn Leu Val Ser Arg Met Ile Ser Phe Gly
        355                 360                 365

Ser Ser Pro Ile Arg Cys Pro Gly Gly Cys Leu Ser Pro Ala Pro Arg
    370                 375                 380

Leu Pro His Glu Ala Ala Ser Gln Ala Asn Ser Val Ile Gln Asp Cys
385                 390                 395                 400

Gln Asp Pro Glu Ala Gly Lys His Val Glu Leu Val Asp Met Asp Thr
                405                 410                 415

Met Cys Gly Pro Pro Pro Ala Pro Ala Asn Pro Arg Leu Gly Pro
            420                 425                 430

Ala Gln Pro Gly Gln Cys Leu Phe Leu Ser Asn Pro Thr Arg Arg Thr
        435                 440                 445

Ile Thr Pro Leu Trp Ala Thr Pro Ser Arg Thr Ala Arg Pro Gly Arg
    450                 455                 460

Ser Cys Thr Ala Ala Cys Ser Glu Glu Glu Glu Val Glu Glu Glu
465                 470                 475                 480
```

-continued

```
Asp Glu Glu Asp Glu Glu Trp Ala Glu Asp Ser Val Val Pro Pro Gly
                485                 490                 495
Tyr Arg Thr Thr Gly Ser Thr Ala Pro Leu Ala Ala Ser Leu Val Tyr
            500                 505                 510
Asp Ala Val Lys Asp Thr Leu Val Val Asp Glu His Thr Gln Glu Glu
        515                 520                 525
Leu Val Ser Leu Arg Arg Cys Ala Phe Leu Gly Asn Asp Ser Glu Glu
    530                 535                 540
Asp Ser Gly Cys Glu Ala Ser Glu Glu Ala Gly His Thr Leu Leu
545                 550                 555                 560
Gly Ser Asp Gln Val Pro Ile Asp Ala Ser Pro Asp Ser Pro Asp Leu
                565                 570                 575
Lys Phe Ser Lys Lys Phe Leu Asn Val Phe Leu Asn Ser Thr Ser Arg
            580                 585                 590
Ser Ser Ser Thr Met Ser Phe Gly Leu Phe Ser Cys Val Xaa Gln Gly
        595                 600                 605
Glu Glu Arg Glu Gln Thr His Arg Arg Val Phe Arg Phe Ile Pro Arg
    610                 615                 620
His Pro Ser Glu Leu Glu Leu Asp Val Asp Asp Pro Thr Leu Val Glu
625                 630                 635                 640
Ala Glu Glu Asp Asp Phe Val Phe Arg Gly Phe Asn Met Arg Thr Gly
                645                 650                 655
Trp Arg Gly Val Phe Pro Ala Phe Tyr Ala Tyr Ala Val Pro Gly Pro
            660                 665                 670
Ala Lys Asp Leu Ala Gly Ser Lys Arg Ser Pro Cys Trp Val Glu Arg
        675                 680                 685
Phe Asp Val Gln Phe Leu Gly Ser Phe Glu Val Pro Cys His Gln Gly
    690                 695                 700
Asn Gly Gly Leu Cys Ala Ala Met Gln Lys Ile Ala His Ala Arg Lys
705                 710                 715                 720
Leu Thr Val His Leu Arg Ile Pro Ala Ser Cys Asp Leu Glu Ile Ser
                725                 730                 735
Lys Arg Gly Val Lys Leu Ser Leu Ser Gly Leu Gly Pro Glu Phe Gln
            740                 745                 750
Arg Cys Ser His Met Phe Gln Met Lys Asn Ile Ser Phe Cys Asn Cys
        755                 760                 765
His Pro Arg Asn Ser Cys Tyr Phe Gln Phe Ile Thr Lys His Pro Leu
    770                 775                 780
Leu Ser Ser Phe Ala Cys His Val Phe Val Ser Gln Thr Ser Met Arg
785                 790                 795                 800
Pro Val Ala Arg Ser Val Val Arg Ala Phe Leu Glu Tyr Tyr Gln Glu
                805                 810                 815
Trp Leu Ala Phe Ala Cys Pro Thr Glu Asp Tyr Tyr Leu Glu
            820                 825                 830

<210> SEQ ID NO 38
<211> LENGTH: 830
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 38

Met Ala Asp Arg Ala Glu Met Ala Ser Leu Ser Thr Phe His Ser Leu
 1               5                  10                  15
```

-continued

```
Ser Asp Pro Gly Cys Arg Pro Gln Asp Ile Glu Leu Glu Phe
            20                  25                  30

Asp Asp Glu Asp Leu Phe Glu Ile Thr Asp Asp Cys Gly Leu Gly Gly
        35                  40                  45

Ser Tyr Asp Ser Asp His Cys Glu Lys His Ser Leu Ser Leu Gly Arg
        50                  55                  60

Ser Glu Gln Ile His Pro Ile Cys Ser Phe Gln Asp Asp Lys Gln Glu
65                  70                  75                  80

Phe Glu Met Ile Asp Asp His Leu Gly Gly His Glu Glu Glu
                85                  90                  95

Glu Met Glu Glu Glu Glu Asp Gly Asp Arg Asn Gly Lys Ala Gly
            100                 105                 110

Gly Gly Pro Gly Ser Gln Ala Leu Ala Gly Asp Ser Leu Ile Pro Arg
            115                 120                 125

Pro Ser Leu Glu Glu Ser His Lys Leu Ser Pro Thr Thr Leu His Leu
            130                 135                 140

Thr Thr Leu Thr Ala Gln Asp Ser Leu Asn Asn Asn Val Gly Phe
145                 150                 155                 160

Thr Ser Ala Pro Pro Ser Ser Trp Gln Glu Thr Val Leu Arg Ser Pro
            165                 170                 175

Ala Tyr Glu Pro Leu Lys Glu Leu Pro Ala Pro Ala Leu Pro Ala Glu
            180                 185                 190

Glu Glu Arg His Glu Asp Gln Ser Leu Ala Arg Pro Gly Cys Asp Glu
            195                 200                 205

Glu Gly Asn Gln Pro Pro Glu Pro Pro Phe Ser Ser Gly Gly Ala Ser
            210                 215                 220

Pro Ser Ser Gly Pro Gly Ile Glu Ala Asp Leu Arg Ser Ile Ser Ser
225                 230                 235                 240

Gly Gly His Glu Gly Arg Arg Lys Ser Gln Glu Leu Ser Ser Pro Gly
            245                 250                 255

Ser Leu Ser Glu Asp Ala Gly Gly Ala Arg Leu Met Arg Met Ile Ser
            260                 265                 270

Ser Ile Ser Glu Thr Asn Leu Glu Leu Ser Ser Asp Gly Gly Ser Gln
            275                 280                 285

Ser Gly Arg Ser Ser His Leu Thr Asn Arg Ile Glu Glu Ala Ser Ser
            290                 295                 300

Pro Ala Ser Ser Pro Glu Pro Gly Pro Glu Pro Leu His Thr Pro Pro
305                 310                 315                 320

Arg Arg Pro Ala Phe Leu Pro Trp Gly Gln Asp Asp Thr Asn Ser Glu
            325                 330                 335

Tyr Tyr Ser Gly Ser Glu Ser Glu Pro Asp Leu Ala Glu Asp Ala Asp
            340                 345                 350

Ser Pro Trp Leu Leu Asp Asn Leu Val Ser Arg Met Ile Ser Glu Glu
            355                 360                 365

Ser Ser Pro Ile Arg Cys Pro Gly Gln Phe Leu Ser Pro Ala Pro Arg
            370                 375                 380

Leu Pro Glu Gly Ala Ala Ser Gln Ala Asn Ser Val Pro His Asp Cys
385                 390                 395                 400

Gln Asp Pro Glu Ala Gly Pro Ile Val Glu Leu Val Asp Met Asp Thr
            405                 410                 415

Leu Lys Gly Pro Pro Pro Pro Ala Pro Ala Ala Leu Arg Leu Gly Pro
            420                 425                 430
```

```
Ala Gln Pro Gly Pro Met Leu Phe Leu Ser Asn Pro Thr Arg Asp Asn
        435                 440                 445

Ile Thr Pro Leu Trp Ala Thr Pro Gly Gln Thr Ala Arg Pro Gly Arg
    450                 455                 460

Ser Cys Ser Arg Ala Cys Ser Glu Glu Glu Glu Asp Ser Glu Glu
465                 470                 475                 480

Asp Glu Glu Asp Glu Asp Thr Glu Asp Ser Val Val Pro Pro Gly
                485                 490                 495

Ser Val Thr Thr Gly Ser Thr Ala Pro Leu Asp Trp Ser Leu Val Tyr
            500                 505                 510

Asp Ala Val Lys Tyr Tyr Leu Val Val Asp Glu His Thr Gln Leu Ala
        515                 520                 525

Leu Val Ser Leu Arg Arg Cys Ala Gly Asp Gly Asn Asp Ser Glu Glu
    530                 535                 540

Asp Ser Ser Glu Glu Ala Ser Glu Glu Ala Gly Ala Phe Leu Leu
545                 550                 555                 560

Gly Ser Asp Gln Val Pro Glu Gly Ala Ser Pro Asp Ser Pro Asp Leu
                565                 570                 575

Thr His Ser Lys Lys Phe Leu Asn Val Phe Val Ile Ser Thr Ser Arg
            580                 585                 590

Ser Ser Ser Thr Glu Lys Phe Gly Leu Phe Ser Cys Val Xaa Asn Leu
        595                 600                 605

Glu Glu Arg Glu Gln Thr His Arg Ala Met Phe Arg Phe Ile Pro Arg
    610                 615                 620

His Pro Asp Asn Leu Glu Leu Asp Val Asp Pro Val Gln Val Glu
625                 630                 635                 640

Ala Glu Glu Asp Asp Phe Trp Arg Arg Gly Phe Asn Met Arg Thr Gly
                645                 650                 655

Glu Ser Gly Val Phe Pro Ala Phe Tyr Ala His Thr Val Pro Gly Pro
            660                 665                 670

Ala Lys Asp Leu Leu Val Ser Lys Arg Ser Pro Cys Trp Val Asp Trp
        675                 680                 685

Phe Asp Val Gln Phe Leu Gly Ser Val Tyr Val Pro Cys His Gln Gly
690                 695                 700

Asn Gly Ile Ala Cys Ala Ala Met Gln Lys Ile Ala Thr Asp Arg Lys
705                 710                 715                 720

Leu Thr Val His Leu Arg Pro Glu Ala Ser Cys Asp Leu Glu Ile Ser
                725                 730                 735

Leu Phe Gly Val Lys Leu Ser Leu Ser Gly Gly His Pro Glu Phe Gln
            740                 745                 750

Arg Cys Ser His Phe Ile Gln Met Lys Asn Ile Ser Phe Cys Gly Lys
        755                 760                 765

His Pro Arg Asn Ser Cys Tyr Phe Gly Leu Ile Thr Lys His Pro Leu
    770                 775                 780

Leu Ser Arg Met Ala Cys His Val Phe Val Ser Gln Glu Asn Met Arg
785                 790                 795                 800

Pro Val Ala Arg Ser Val Gly Gln Ala Phe Leu Glu Tyr Tyr Gln Glu
                805                 810                 815

His Arg Ala Phe Ala Cys Pro Thr Glu Asp Ile Ser Leu Glu
            820                 825                 830

<210> SEQ ID NO 39
<211> LENGTH: 830
<212> TYPE: PRT
```

<213> ORGANISM: Artificial Sequence
<220> FEATURE:
<223> OTHER INFORMATION: Description of Artificial Sequence: Synthetic
      Sequence

<400> SEQUENCE: 39

Met Ala Asp Arg Ala Glu Met Phe Ala Leu Ser Thr Phe His Ser Leu
 1               5                  10                  15

Ser Pro Asp Gly Cys Arg Pro Pro Gln Asp Ile Ser Glu Glu Glu Phe
            20                  25                  30

Asp Asp Glu Asp Leu Ser Phe Ile Thr Asp Asp Cys Gly Leu Gly Leu
        35                  40                  45

Gly Tyr Asp Ser Asp His Cys Glu Lys Asp His Leu Ser Leu Gly Arg
    50                  55                  60

Ser Glu Gln Pro Ile Pro Ile Cys Ser Phe Gln Asp Asp Phe Lys Glu
65                  70                  75                  80

Phe Glu Met Ile Asp Asp His Gln Leu Gly His Glu Glu Glu Glu Glu
                85                  90                  95

Glu Glu Met Glu Glu Glu Glu Asp Gly Asp Arg Gln Asn Lys Ala Gly
            100                 105                 110

Gly Gly Pro Gly Ser Gln Gln Leu Ala Gly Asp Ser Leu Ile Pro Ser
        115                 120                 125

Arg Ser Leu Glu Glu Ser His Lys Leu Arg Ser Thr Thr Leu His Leu
130                 135                 140

Thr Thr Leu Gly Thr Gln Asp Ser Leu Asn Asn Asn Gly Val Phe
145                 150                 155                 160

Thr Ser Ala Pro Pro Ser Ser Trp Trp Glu Thr Val Leu Arg Ser Pro
                165                 170                 175

Ala Gln Tyr Pro Leu Lys Glu Leu Pro Ala Pro Leu Ala Pro Ala Glu
            180                 185                 190

Glu Glu Arg His Glu Val Asp Ser Leu Ala Arg Pro Gly Cys Asp Cys
        195                 200                 205

Phe Gly Asn Gln Pro Pro Glu Pro Pro Ala Gly Ser Gly Gly Ala Ser
    210                 215                 220

Pro Ser Ser Asp His Gly Ile Glu Ala Asp Leu Arg Ser His Ile Ser
225                 230                 235                 240

Gly Gly His Glu Gly Arg Arg Ser Lys Gln Glu Leu Ser Ser Pro Gly
                245                 250                 255

Ser Asp Leu Glu Asp Ala Gly Gly Ala Arg Leu Gly Met Met Ile Ser
            260                 265                 270

Ser Ile Ser Glu Thr Glu Asn Glu Leu Ser Ser Asp Gly Gly Ser Ser
        275                 280                 285

Gln Gly Arg Ser Ser His Leu Thr Asn Ser Arg Glu Glu Ala Ser Ser
    290                 295                 300

Pro Ala Ser Glu Ser Glu Pro Glu Pro Glu Pro Leu His Glu Thr Pro
305                 310                 315                 320

Arg Arg Pro Ala Phe Leu Pro Val Val Gln Asp Asp Thr Asn Ser Glu
                325                 330                 335

Tyr Glu Trp Gly Ser Glu Ser Glu Pro Asp Leu Ser Tyr Asp Ala Asp
            340                 345                 350

Ser Pro Trp Leu Leu Ser Ala Leu Val Ser Arg Met Ile Ser Glu Gly
        355                 360                 365

Asp Ser Pro Ile Arg Cys Pro Gly Gln Cys Glu Ser Pro Ala Pro Arg
    370                 375                 380

```
Leu Pro Glu Glu Phe Ala Ser Gln Ala Asn Ser Val Pro Gln Gly Cys
385                 390                 395                 400

Gln Asp Pro Glu Ala Gly Pro His His Glu Leu Val Asp Met Asp Thr
            405                 410                 415

Leu Cys Ile Pro Pro Pro Ala Pro Ala Ala Pro Lys Leu Gly Pro
                420                 425                 430

Ala Gln Pro Gly Pro Cys Met Phe Leu Ser Asn Pro Thr Arg Asp Thr
            435                 440                 445

Asn Thr Pro Leu Trp Ala Thr Pro Gly Arg Gln Ala Arg Pro Gly Arg
        450                 455                 460

Ser Cys Ser Ala Arg Cys Ser Glu Glu Glu Glu Asp Glu Ser Glu
465                 470                 475                 480

Asp Glu Glu Asp Glu Glu Asp Ala Thr Asp Ser Val Val Pro Pro Gly
            485                 490                 495

Ser Arg Val Thr Gly Ser Thr Ala Pro Leu Asp Ala Trp Leu Val Tyr
            500                 505                 510

Asp Ala Val Lys Tyr Thr Tyr Val Val Asp Glu His Thr Gln Leu Glu
            515                 520                 525

Ala Val Ser Leu Arg Arg Cys Ala Gly Leu Asp Asn Asp Ser Glu Glu
530                 535                 540

Asp Ser Ser Cys Phe Ala Ser Glu Glu Glu Ala Gly Ala Thr Gly Leu
545                 550                 555                 560

Gly Ser Asp Gln Val Pro Glu Asp His Ser Pro Asp Ser Pro Asp Leu
            565                 570                 575

Thr Phe Ile Lys Lys Phe Leu Asn Val Phe Asn Lys Thr Ser Arg
                580                 585                 590

Ser Ser Ser Thr Glu Ser Leu Gly Leu Phe Ser Cys Val Xaa Asn Gly
        595                 600                 605

Met Glu Arg Glu Gln Thr His Arg Ala Val Asn Arg Phe Ile Pro Arg
        610                 615                 620

His Pro Asp Glu Gln Glu Leu Asp Val Asp Asp Pro Val Leu Arg Glu
625                 630                 635                 640

Ala Glu Glu Asp Asp Phe Trp Phe Ser Gly Phe Asn Met Arg Thr Gly
                645                 650                 655

Glu Arg Thr Val Phe Pro Ala Phe Tyr Ala His Ala Trp Pro Gly Pro
            660                 665                 670

Ala Lys Asp Leu Leu Gly Tyr Lys Arg Ser Pro Cys Trp Val Asp Arg
        675                 680                 685

Ala Asp Val Gln Phe Leu Gly Ser Val Glu Asp Pro Cys His Gln Gly
        690                 695                 700

Asn Gly Ile Leu Glu Ala Ala Met Gln Lys Ile Ala Thr Ala Phe Lys
705                 710                 715                 720

Leu Thr Val His Leu Arg Pro Pro Gly Ser Cys Asp Leu Glu Ile Ser
                725                 730                 735

Leu Arg His Val Lys Leu Ser Leu Ser Gly Gly Gly Ile Glu Phe Gln
            740                 745                 750

Arg Cys Ser His Phe Phe Lys Met Lys Asn Ile Ser Phe Cys Gly Cys
        755                 760                 765

Leu Pro Arg Asn Ser Cys Tyr Phe Gly Phe Met Thr Lys His Pro Leu
        770                 775                 780

Leu Ser Arg Phe Asn Cys His Val Phe Val Ser Gln Glu Ser Gln Arg
785                 790                 795                 800

Pro Val Ala Arg Ser Val Gly Arg Arg Phe Leu Glu Tyr Tyr Gln Glu
```

His Leu Ser Phe Ala Cys Pro Thr Glu Asp Ile Tyr Thr Glu
            820                 825                 830

<210> SEQ ID NO 40
<211> LENGTH: 829
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 40

Met Ala Asp Arg Ala Glu Met Phe Ser Ala Ser Thr Phe His Ser Leu
 1               5                  10                  15

Ser Pro Pro Asp Cys Arg Pro Pro Gln Asp Ile Ser Leu Phe Glu Phe
                20                  25                  30

Asp Asp Glu Asp Leu Ser Glu Gly Thr Asp Asp Cys Gly Leu Gly Leu
            35                  40                  45

Ser His Asp Ser Asp His Cys Glu Lys Asp Ser Ile Ser Leu Gly Arg
        50                  55                  60

Ser Glu Gln Pro His Lys Ile Cys Ser Phe Gln Asp Asp Phe Gln Leu
65                  70                  75                  80

Phe Glu Met Ile Asp Asp His Gln Gly Met Gly His Glu Glu Glu Glu
                85                  90                  95

Glu Glu Glu Asn Glu Glu Glu Asp Gly Asp Arg Gln Gly Gln Ala Gly
            100                 105                 110

Gly Gly Pro Gly Ser Gln Ala Arg Ala Gly Asp Ser Leu Ile Pro Ser
        115                 120                 125

Pro Thr Leu Glu Glu Ser His Lys Leu Arg Pro Val Thr Leu His Leu
130                 135                 140

Thr Thr Leu Gly Ala Trp Asp Ser Leu Asn Asn Asn Gly Gly Tyr
145                 150                 155                 160

Thr Ser Ala Pro Pro Ser Ser Trp Gln Ala Thr Val Leu Arg Ser Pro
                165                 170                 175

Ala Gln Glu Asp Leu Lys Glu Leu Pro Ala Pro Leu Leu Glu Ala Glu
            180                 185                 190

Glu Glu Arg His Glu Val Gln Phe Leu Ala Arg Pro Gly Cys Asp Cys
        195                 200                 205

Glu His Asn Gln Pro Pro Glu Pro Ala Ser Ile Gly Gly Ala Ser
    210                 215                 220

Pro Ser Ser Asp Pro Lys Ile Glu Ala Asp Leu Arg Ser His Ser Leu
225                 230                 235                 240

Gly Gly His Glu Gly Arg Arg Ser Ser Met Glu Leu Ser Ser Pro Gly
                245                 250                 255

Ser Asp Ser Asn Asp Ala Gly Gly Ala Arg Leu Gly Arg Gln Ile Ser
            260                 265                 270

Ser Ile Ser Glu Thr Glu Leu Arg Leu Ser Ser Asp Gly Gly Ser Ser
        275                 280                 285

Ser Ser Arg Ser Ser His Leu Thr Asn Ser Ile Thr Glu Ala Ser Ser
    290                 295                 300

Pro Ala Ser Glu Pro Val Pro Glu Pro Glu Pro Leu His Glu Pro Trp
305                 310                 315                 320

Arg Arg Pro Ala Phe Leu Pro Val Gly Tyr Asp Asp Thr Asn Ser Glu
                325                 330                 335

-continued

```
Tyr Glu Ser Ala Ser Glu Ser Glu Pro Asp Leu Ser Glu Glu Ala Asp
            340                 345                 350
Ser Pro Trp Leu Leu Ser Asn Phe Val Ser Arg Met Ile Ser Glu Gly
            355                 360                 365
Ser Gly Pro Ile Arg Cys Pro Gly Gln Cys Leu His Pro Ala Pro Arg
            370                 375                 380
Leu Pro Glu Glu Ala Lys Ser Gln Ala Asn Ser Val Pro Gln Asp Leu
385                 390                 395                 400
Gln Asp Pro Glu Ala Gly Pro His Val Met Leu Val Asp Met Asp Thr
                405                 410                 415
Leu Cys Gly Asn Pro Pro Ala Pro Ala Ala Pro Arg Gln Gly Pro
            420                 425                 430
Ala Gln Pro Gly Pro Cys Leu Arg Leu Ser Asn Pro Thr Arg Asp Thr
            435                 440                 445
Ile Ser Pro Leu Trp Ala Thr Pro Gly Arg Thr Thr Arg Pro Gly Arg
            450                 455                 460
Ser Cys Ser Ala Ala Val Ser Glu Glu Glu Glu Asp Glu Glu Trp
465                 470                 475                 480
Asp Glu Glu Asp Glu Glu Asp Ala Glu Tyr Ser Val Pro Pro Gly
                485                 490                 495
Ser Arg Thr Ala Gly Ser Thr Ala Pro Leu Asp Ala Ser Asp Val Tyr
            500                 505                 510
Asp Ala Val Lys Tyr Thr Leu Glu Val Asp Glu His Thr Gln Leu Glu
            515                 520                 525
Leu Phe Ser Leu Arg Arg Cys Ala Gly Leu Gly Gly Asp Ser Glu Glu
            530                 535                 540
Asp Ser Ser Cys Glu His Ser Glu Glu Glu Ala Gly Ala Thr Leu Ile
545                 550                 555                 560
Gly Ser Asp Gln Val Pro Glu Asp Ala Lys Pro Asp Ser Pro Asp Leu
                565                 570                 575
Thr Phe Ser Leu Lys Phe Leu Asn Val Phe Asn Ser Met Ser Arg
            580                 585                 590
Ser Ser Ser Thr Glu Ser Phe Asn Leu Phe Ser Cys Val Xaa Asn Gly
            595                 600                 605
Glu Gln Arg Glu Gln Thr His Arg Ala Val Phe Ser Phe Ile Pro Arg
610                 615                 620
His Pro Asp Glu Leu Thr Leu Asp Val Asp Asp Pro Val Leu Val Val
625                 630                 635                 640
Ala Glu Glu Asp Asp Phe Trp Phe Arg Trp Phe Asn Met Arg Thr Gly
                645                 650                 655
Glu Arg Gly Tyr Phe Pro Ala Phe Tyr Ala His Ala Val Ala Gly Pro
            660                 665                 670
Ala Lys Asp Leu Leu Gly Ser Asp Arg Ser Pro Cys Trp Val Asp Arg
            675                 680                 685
Phe Glu Val Gln Phe Leu Gly Ser Val Glu Val Phe Cys His Gln Gly
            690                 695                 700
Asn Gly Ile Leu Cys Gly Ala Met Gln Lys Ile Ala Thr Ala Arg His
705                 710                 715                 720
Leu Thr Val His Leu Arg Pro Pro Ala Ile Cys Asp Leu Glu Ile Ser
                725                 730                 735
Leu Arg Gly Lys Leu Ser Leu Ser Gly Gly Pro Lys Phe Gln Arg
            740                 745                 750
Cys Ser His Phe Phe Gln Leu Lys Asn Ile Ser Phe Cys Gly Cys His
```

```
                    755                 760                 765
Met Arg Asn Ser Cys Tyr Phe Gly Phe Ile Asn Lys His Pro Leu Leu
                770                 775                 780

Ser Arg Phe Ala Gln His Val Phe Val Ser Gln Glu Ser Met Ser Pro
785                 790                 795                 800

Val Ala Arg Ser Val Gly Arg Ala Thr Leu Glu Tyr Tyr Gln Glu His
                    805                 810                 815

Leu Ala Val Ala Cys Pro Thr Glu Asp Ile Tyr Leu Trp
                820                 825

<210> SEQ ID NO 41
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 41

Met Val Ala Leu Ser Leu Lys Ile Ser Ile Gly Asn Val Val Lys Thr
  1               5                  10                  15

Met Gln Phe Glu Pro Ser Thr Met Val Tyr Asp Ala Cys Arg Ile Ile
                 20                  25                  30

Arg Glu Arg Ile Pro Glu Ala Pro Ala Gly Pro Pro Ser Asp Phe Gly
             35                  40                  45

Leu Phe Leu Ser Asp Asp Pro Lys Lys Gly Ile Trp Leu Glu Ala
         50                  55                  60

Gly Lys Ala Leu Asp Tyr Tyr Met Leu Arg Asn Gly Asp Thr Met Glu
 65                  70                  75                  80

Tyr Arg Lys Lys Gln Arg Pro Leu Lys Ile Arg Met Leu Asp Gly Thr
                 85                  90                  95

Val Lys Thr Ile Met Val Asp Asp Ser Lys Thr Val Thr Asp Met Leu
                100                 105                 110

Met Thr Ile Cys Ala Arg Ile Gly Ile Thr Asn His Asp Glu Tyr Ser
            115                 120                 125

Leu Val Arg Glu Leu Met Glu Glu Lys Lys Glu Glu Ile Thr Gly Thr
        130                 135                 140

Leu Arg Lys Asp Lys Thr Leu Leu Arg Asp Glu Lys Lys Met Glu Lys
145                 150                 155                 160

Leu Lys Gln Lys Leu His Thr Asp Asp Glu Leu Asn Trp Leu Asp His
                165                 170                 175

Gly Arg Thr Leu Arg Glu Gln Gly Val Glu Glu His Glu Thr Leu Leu
            180                 185                 190

Leu Arg Arg Lys Phe Phe Tyr Ser Asp Gln Asn Val Asp Ser Arg Asp
        195                 200                 205

Pro Val Gln Leu Asn Leu Leu Tyr Val Gln Ala Arg Asp Asp Ile Leu
210                 215                 220

Asn Gly Ser His Pro Val Ser Phe Asp Lys Ala Cys Glu Phe Ala Gly
225                 230                 235                 240

Phe Gln Cys Gln Ile Gln Phe Gly Pro His Asn Glu Gln Lys His Lys
                245                 250                 255

Ala Gly Phe Leu Asp Leu Lys Asp Phe Leu Pro Lys Glu Tyr Val Lys
            260                 265                 270

Gln Lys Gly Glu Arg Lys Ile Phe Gln Ala His Lys Asn Cys Gly Gln
        275                 280                 285
```

-continued

```
Met Ser Glu Ile Glu Ala Lys Val Arg Tyr Val Lys Leu Ala Arg Ser
    290                 295                 300

Leu Lys Thr Tyr Gly Val Ser Phe Phe Leu Val Lys Glu Lys Met Lys
305                 310                 315                 320

Gly Lys Asn Lys Leu Val Pro Arg Leu Leu Gly Ile Thr Lys Glu Cys
                325                 330                 335

Val Met Arg Val Asp Glu Lys Thr Lys Glu Val Ile Gln Glu Trp Asn
            340                 345                 350

Leu Thr Asn Ile Lys Arg Trp Ala Ala Ser Pro Lys Ser Phe Thr Leu
        355                 360                 365

Asp Phe Gly Asp Tyr Gln Asp Gly Tyr Tyr Ser Val Gln Thr Thr Glu
    370                 375                 380

Gly Glu Gln Ile Ala Gln Leu Ile Ala Gly Tyr Ile Asp Ile Ile Leu
385                 390                 395                 400

Lys Lys Lys Lys Ser Lys Asp His Phe Gly Leu Glu Gly Asp Glu Glu
                405                 410                 415

Ser Thr Met Leu Glu Asp Ser Val Ser Pro Lys Lys Ser Thr Val Leu
            420                 425                 430

Gln Gln Gln Tyr Asn Arg Val Gly Lys Val Glu His Gly Ser Val Ala
        435                 440                 445

Leu Pro Ala Ile Met Arg Ser Gly Ala Ser Gly Pro Glu Asn Phe Gln
    450                 455                 460

Val Gly Ser Met Pro Pro Ala Gln Gln Gln Ile Thr Ser Gly Gln Met
465                 470                 475                 480

His Arg Gly His Met Pro Pro Leu Thr Ser Ala Gln Gln Ala Leu Thr
                485                 490                 495

Gly Thr Ile Asn Ser Ser Met Gln Ala Val Gln Ala Ala Gln Ala Thr
            500                 505                 510

Leu Asp Asp Phe Asp Thr Leu Pro Pro Leu Gly Gln Asp Ala Ala Ser
        515                 520                 525

Lys Ala Trp Arg Lys Asn Lys Met Asp Glu Ser Lys His Glu Ile His
    530                 535                 540

Ser Gln Val Asp Ala Ile Thr Ala Gly Thr Ala Ser Val Val Asn Leu
545                 550                 555                 560

Thr Ala Gly Asp Pro Ala Glu Thr Asp Tyr Thr Ala Val Gly Cys Ala
                565                 570                 575

Val Thr Thr Ile Ser Ser Asn Leu Thr Glu Met Ser Arg Gly Val Lys
            580                 585                 590

Leu Leu Ala Ala Leu Leu Glu Asp Glu Gly Gly Ser Gly Arg Pro Leu
        595                 600                 605

Leu Gln Ala Ala Lys Gly Leu Ala Gly Ala Val Ser Glu Leu Leu Arg
    610                 615                 620

Ser Ala Gln Pro Ala Ser Ala Glu Pro Arg Gln Asn Leu Leu Gln Ala
625                 630                 635                 640

Ala Gly Asn Val Gly Gln Ala Ser Gly Glu Leu Leu Gln Gln Ile Gly
                645                 650                 655

Glu Ser Asp Thr Asp Pro His Phe Gln Asp Ala Leu Met Gln Leu Ala
            660                 665                 670

Lys Ala Val Ala Ser Ala Ala Ala Ala Leu Val Leu Lys Ala Lys Ser
        675                 680                 685

Val Ala Gln Arg Thr Glu Asp Ser Gly Leu Gln Thr Gln Val Ile Ala
    690                 695                 700

Ala Ala Thr Gln Cys Ala Leu Ser Thr Ser Gln Leu Val Ala Cys Thr
```

-continued

```
            705                 710                 715                 720
Lys Val Val Ala Pro Thr Ile Ser Ser Pro Val Cys Gln Glu Gln Leu
                    725                 730                 735

Val Glu Ala Gly Arg Leu Val Ala Lys Ala Val Glu Gly Cys Val Ser
            740                 745                 750

Ala Ser Gln Ala Ala Thr Glu Asp Gly Gln Leu Leu Arg Gly Val Gly
        755                 760                 765

Ala Ala Ala Thr Ala Val Thr Gln Ala Leu Asn Glu Leu Leu Gln His
    770                 775                 780

Val Lys Ala His Ala Thr Gly Ala Gly Pro Ala Gly Arg Tyr Asp Gln
785                 790                 795                 800

Ala Thr Asp Thr Ile Leu Thr Val Thr Glu Asn Ile Phe Ser Ser Met
                805                 810                 815

Gly Asp Ala Gly Glu Met Val Gly Gln Ala Arg Ile Leu Ala Gln Ala
            820                 825                 830

Thr Ser Asp Leu Val Asn Ala Ile Lys Ala Asp Ala Glu Gly Glu Ser
        835                 840                 845

Asp Leu Glu Asn Ser Arg Lys Leu Leu Ser Ala Ala Lys Ile Leu Ala
    850                 855                 860

Asp Ala Thr Ala Lys Met Val Glu Ala Ala Lys Gly Ala Ala Ala His
865                 870                 875                 880

Pro Asp Ser Glu Glu Gln Gln Gln Arg Leu Arg Glu Ala Ala Glu Gly
                885                 890                 895

Leu Arg Met Ala Thr Asn Ala Ala Gln Asn Ala Ile Lys Lys Lys
            900                 905                 910

Leu Val Gln Arg Leu Glu His Ala Ala Lys Gln Ala Ala Ser Ala
        915                 920                 925

Thr Gln Thr Ile Ala Ala Ala Gln His Ala Ala Ser Thr Pro Lys Ala
    930                 935                 940

Ser Ala Gly Pro Gln Pro Leu Leu Val Gln Ser Cys Lys Ala Val Ala
945                 950                 955                 960

Glu Gln Ile Pro Leu Leu Val Gln Gly Val Arg Gly Ser Gln Ala Gln
                965                 970                 975

Pro Asp Ser Pro Ser Ala Gln Leu Ala Leu Ile Ala Ala Ser Gln Ser
            980                 985                 990

Phe Leu Gln Pro Gly Gly Lys Met Val Ala Ala Lys Ala Ser Val
        995                 1000                1005

Pro Thr Ile Gln Asp Gln Ala Ser Ala Met Gln Leu Ser Gln Cys Ala
    1010                1015                1020

<210> SEQ ID NO 42
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 42

Met Ala Ala Leu Ser Leu Lys Ile Ser Ile Gly Asp Val Val Lys Thr
1               5                   10                  15

Met Gln Phe Glu Pro Glu Thr Met Val Tyr Asp Ala Cys Arg Ile Phe
            20                  25                  30

Arg Glu Arg Ile Pro Glu Ala Pro Ala His Pro Pro Ser Asp Phe Gly
        35                  40                  45
```

-continued

```
Leu Phe Leu Ile Asp Asp Pro Lys Lys Gly Ile Trp Lys Glu Ala
 50                  55                  60

Gly Lys Ala Leu Asp Tyr Tyr Leu Arg Asn Gly Asp Thr Met Glu
 65                  70                  75                  80

Tyr Met Lys Lys Gln Arg Pro Leu Lys Ile Arg Asn Leu Asp Gly Thr
                 85                  90                  95

Val Lys Thr Ile Met Gln Asp Asp Ser Lys Thr Val Thr Asp Met Arg
            100                 105                 110

Met Thr Ile Cys Ala Arg Ile Gly Ile Ser Asn His Asp Glu Tyr Ser
            115                 120                 125

Leu Val Arg Thr Leu Met Glu Glu Lys Glu Glu Ile Val Gly Thr
            130                 135                 140

Leu Arg Lys Asp Lys Thr Leu Trp Arg Asp Glu Lys Lys Met Glu Lys
145                 150                 155                 160

Leu Tyr Gln Lys Leu His Thr Asp Asp Glu Leu Ala Trp Leu Asp His
                165                 170                 175

Gly Arg Thr Leu Arg Asp Gln Gly Val Glu Glu His Glu Thr Leu Glu
            180                 185                 190

Leu Arg Arg Lys Phe Phe Tyr Ser Asp Phe Asn Val Asp Ser Arg Asp
            195                 200                 205

Pro Val Gln Gly Asn Leu Leu Tyr Val Gln Ala Arg Asp His Ile Leu
210                 215                 220

Asn Gly Ser His Pro Val Ser Ile Asp Lys Ala Cys Glu Phe Ala Gly
225                 230                 235                 240

Phe Lys Cys Gln Ile Gln Phe Gly Pro His Asn Leu Gln Lys His Lys
                245                 250                 255

Ala Gly Phe Leu Asp Met Lys Asp Phe Leu Pro Lys Glu Tyr Val Asn
                260                 265                 270

Gln Lys Gly Glu Arg Lys Ile Phe Gln Gln His Lys Asn Cys Gly Gln
            275                 280                 285

Met Ser Glu Arg Glu Ala Lys Val Arg Tyr Val Lys Leu Ser Arg Ser
290                 295                 300

Leu Lys Thr Tyr Gly Val Ser Thr Phe Leu Val Lys Glu Lys Met Lys
305                 310                 315                 320

Gly Val Asn Lys Leu Val Pro Arg Leu Leu Gly Trp Thr Lys Glu Cys
                325                 330                 335

Val Met Arg Val Asp Tyr Lys Thr Lys Glu Val Ile Gln Glu Trp Ala
            340                 345                 350

Leu Thr Asn Ile Lys Arg Trp Ala Ala Asp Pro Lys Ser Phe Thr Leu
            355                 360                 365

Asp Phe Gly Glu Tyr Gln Asp Gly Tyr Tyr Ser Val Gln Phe Thr Glu
    370                 375                 380

Gly Glu Gln Ile Ala Gln Leu Gly Ala Gly Tyr Ile Asp Ile Ile Leu
385                 390                 395                 400

Lys His Lys Lys Ser Lys Asp His Phe Gly Leu Ile Gly Asp Glu Glu
                405                 410                 415

Ser Thr Met Leu Glu Lys Ser Val Ser Pro Lys Lys Ser Thr Val Met
            420                 425                 430

Gln Gln Gln Tyr Asn Arg Val Gly Lys Asn Glu His Gly Ser Val Ala
            435                 440                 445

Leu Pro Ala Gln Met Arg Ser Gly Ala Ser Gly Pro Glu Arg Phe Gln
450                 455                 460

Val Gly Ser Met Pro Pro Ala Ser Gln Gln Ile Thr Ser Gly Gln Met
```

```
465                 470                 475                 480
His Thr Gly His Met Pro Pro Leu Thr Ser Ala Val Gln Ala Leu Thr
                485                 490                 495
Gly Thr Ile Asn Ser Trp Met Gln Ala Val Gln Ala Ala Gln Ala Tyr
                500                 505                 510
Leu Asp Asp Phe Asp Thr Leu Pro Pro Ala Gly Gln Asp Ala Ala Ser
                515                 520                 525
Lys Ala Trp Asp Lys Asn Lys Met Asp Glu Ser Lys His Phe Ile His
                530                 535                 540
Ser Gln Val Asp Ala Ile Thr Gly Gly Thr Ala Ser Val Val Asn Leu
545                 550                 555                 560
Thr His Gly Asp Pro Ala Glu Thr Asp Tyr Thr Ile Val Gly Cys Ala
                565                 570                 575
Val Thr Thr Ile Ser Lys Asn Leu Thr Glu Met Ser Arg Gly Val Leu
                580                 585                 590
Leu Leu Ala Ala Leu Leu Glu Asp Glu Met Gly Ser Gly Arg Pro Leu
                595                 600                 605
Leu Gln Ala Asn Lys Gly Leu Ala Gly Ala Val Ser Glu Gln Leu Arg
                610                 615                 620
Ser Ala Gln Pro Ala Ser Ala Arg Pro Arg Gln Asn Leu Leu Gln Ala
625                 630                 635                 640
Ala Ser Asn Val Gly Gln Ala Ser Gly Glu Leu Thr Gln Gln Ile Gly
                645                 650                 655
Glu Ser Asp Thr Asp Val His Phe Gln Asp Ala Leu Met Gln Leu Trp
                660                 665                 670
Lys Ala Val Ala Ser Ala Ala Ala Tyr Val Leu Lys Ala Lys Ser
                675                 680                 685
Val Ala Gln Ala Thr Glu Asp Ser Gly Leu Gln Thr Gln Asp Ile Ala
                690                 695                 700
Ala Ala Thr Gln Cys Ala Leu Glu Thr Ser Gln Leu Val Ala Cys Thr
705                 710                 715                 720
Lys Phe Val Ala Pro Thr Ile Ser Ser Pro Val Gly Gln Glu Gln Leu
                725                 730                 735
Val Glu Ala Gly Arg His Val Ala Lys Ala Val Glu Gly Cys Val Ile
                740                 745                 750
Ala Ser Gln Ala Ala Thr Glu Asp Gly Lys Leu Leu Arg Gly Val Gly
                755                 760                 765
Ala Ala Ala Leu Ala Val Thr Gln Ala Leu Asn Glu Leu Met Gln His
                770                 775                 780
Val Lys Ala His Ala Thr Gly Asn Gly Pro Ala Gly Arg Tyr Asp Gln
785                 790                 795                 800
Ala Gln Asp Thr Ile Leu Thr Val Thr Glu Asn Arg Phe Ser Ser Met
                805                 810                 815
Gly Asp Ala Gly Glu Ser Val Gly Gln Ala Arg Ile Leu Ala Gln Thr
                820                 825                 830
Thr Ser Asp Leu Val Asn Ala Ile Lys Val Asp Ala Glu Gly Glu Ser
                835                 840                 845
Asp Leu Glu Trp Ser Arg Lys Leu Leu Ser Ala Ala Lys Tyr Leu Ala
                850                 855                 860
Asp Ala Thr Ala Lys Met Val Ala Ala Lys Gly Ala Ala Ala His
865                 870                 875                 880
Pro Glu Ser Glu Glu Gln Gln Gln Arg Leu Arg Phe Ala Ala Glu Gly
                885                 890                 895
```

```
Leu Arg Met Ala Thr Gly Ala Ala Gln Asn Ala Ile Lys Lys His
            900                 905                 910

Leu Val Gln Arg Leu Glu His Ala Ala Ile Gln Ala Ala Ser Ala
            915                 920                 925

Thr Gln Thr Lys Ala Ala Gln His Ala Ala Ser Thr Leu Lys Ala
            930                 935                 940

Ser Ala Gly Pro Gln Pro Leu Met Val Gln Ser Cys Lys Ala Val Ala
945                 950                 955                 960

Glu Asn Ile Pro Leu Leu Val Gln Gly Val Arg Gln Ser Gln Ala Gln
                965                 970                 975

Pro Asp Ser Pro Ser Arg Gln Leu Ala Leu Ile Ala Ala Ser Gln Thr
            980                 985                 990

Phe Leu Gln Pro Gly Gly Lys Met Val Val Ala Ala Lys Ala Ser Val
            995                1000                1005

Pro Thr Ile Trp Asp Gln Ala Ser Ala Met Gln Leu Ser Tyr Cys Ala
   1010                1015                1020
```

<210> SEQ ID NO 43
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 43

```
Met Val Asp Leu Ser Leu Lys Ile Ser Ile Gly Asn Glu Val Lys Thr
  1               5                  10                  15

Met Gln Phe Glu Pro Ser Phe Met Val Tyr Asp Ala Cys Arg Ile Ile
             20                  25                  30

Gly Glu Arg Ile Pro Glu Ala Pro Ala Gly His Pro Ser Asp Phe Gly
         35                  40                  45

Leu Phe Leu Ser Ile Asp Asp Pro Lys Lys Gly Ile Trp Leu Lys Ala
     50                  55                  60

Gly Lys Ala Leu Asp Tyr Tyr Met Met Arg Asn Gly Asp Thr Met Glu
65                  70                  75                  80

Tyr Arg Asn Lys Gln Arg Pro Leu Lys Ile Arg Met Gln Asp Gly Thr
                 85                  90                  95

Val Lys Thr Ile Met Val Arg Asp Ser Lys Thr Val Thr Asp Met Leu
            100                 105                 110

Ser Thr Ile Cys Ala Arg Ile Gly Ile Thr Thr His Asp Glu Tyr Ser
        115                 120                 125

Leu Val Arg Glu Val Met Glu Glu Lys Lys Glu Glu Ile Thr Trp Thr
    130                 135                 140

Leu Arg Lys Asp Lys Thr Leu Leu Tyr Asp Glu Lys Lys Met Glu Lys
145                 150                 155                 160

Leu Lys Ala Lys Leu His Thr Asp Asp Glu Leu Asn Asp Leu Asp His
                165                 170                 175

Gly Arg Thr Leu Arg Glu Glu Gly Val Glu His Glu Thr Leu Leu
            180                 185                 190

Phe Arg Arg Lys Phe Phe Tyr Ser Asp Gln Gly Val Asp Ser Arg Asp
        195                 200                 205

Pro Val Gln Leu His Leu Leu Tyr Val Gln Ala Arg Asp Asp Lys Leu
    210                 215                 220

Asn Gly Ser His Pro Val Ser Phe Leu Lys Ala Cys Glu Phe Ala Gly
```

-continued

```
          225                 230                 235                 240
      Phe Gln Met Gln Ile Gln Phe Gly Pro His Asn Glu Asn Lys His Lys
                      245                 250                 255
      Ala Gly Phe Leu Asp Leu Gln Asp Phe Leu Pro Lys Glu Tyr Val Lys
                      260                 265                 270
      Arg Lys Gly Glu Arg Lys Ile Phe Gln Ala Ser Lys Asn Cys Gly Gln
                      275                 280                 285
      Met Ser Glu Ile Thr Ala Lys Val Arg Tyr Val Lys Leu Ala Val Ser
                      290                 295                 300
      Leu Lys Thr Tyr Gly Val Ser Phe Trp Leu Val Lys Glu Lys Met Lys
      305                 310                 315                 320
      Gly Lys Tyr Lys Leu Val Pro Arg Leu Leu Gly Ile Ala Lys Glu Cys
                      325                 330                 335
      Val Met Arg Val Asp Glu Asp Thr Lys Glu Val Ile Gln Glu Trp Asn
                      340                 345                 350
      Glu Thr Asn Ile Lys Arg Trp Ala Ala Ser Phe Lys Ser Phe Thr Leu
                      355                 360                 365
      Asp Phe Gly Asp Gly Gln Asp Gly Tyr Tyr Ser Val Gln Thr His Glu
                      370                 375                 380
      Gly Glu Gln Ile Ala Gln Leu Ile Ile Gly Tyr Ile Asp Ile Ile Leu
      385                 390                 395                 400
      Lys Lys Leu Lys Ser Lys Asp His Phe Gly Leu Glu Met Asp Glu Glu
                      405                 410                 415
      Ser Thr Met Leu Glu Asp Asn Val Ser Pro Lys Lys Ser Thr Val Leu
                      420                 425                 430
      Arg Gln Gln Tyr Asn Arg Val Gly Lys Val Ser His Gly Ser Val Ala
                      435                 440                 445
      Leu Pro Ala Ile Thr Arg Ser Gly Ala Ser Gly Pro Glu Asn Val Gln
                      450                 455                 460
      Val Gly Ser Met Pro Pro Ala Gln Trp Gln Ile Thr Ser Gly Gln Met
      465                 470                 475                 480
      His Arg Tyr His Met Pro Pro Leu Thr Ser Ala Gln Ala Ala Leu Thr
                      485                 490                 495
      Gly Thr Ile Asn Ser Ser Asp Gln Ala Val Gln Ala Ala Gln Ala Thr
                      500                 505                 510
      Glu Asp Asp Phe Asp Thr Leu Pro Pro Leu Phe Gln Asp Ala Ala Ser
                      515                 520                 525
      Lys Ala Trp Arg Gly Asn Lys Met Asp Glu Ser Lys His Glu His His
      530                 535                 540
      Ser Gln Val Asp Ala Ile Thr Ala Ile Thr Ala Ser Val Val Asn Leu
      545                 550                 555                 560
      Thr Ala Lys Asp Pro Ala Glu Thr Asp Tyr Thr Ala Leu Gly Cys Ala
                      565                 570                 575
      Val Thr Thr Ile Ser Ser Met Leu Thr Glu Met Ser Arg Gly Val Lys
                      580                 585                 590
      Asn Leu Ala Ala Leu Leu Glu Asp Glu Gly Gln Ser Gly Arg Pro Leu
                      595                 600                 605
      Leu Gln Ala Ala Arg Gly Leu Ala Gly Ala Val Ser Glu Leu Ser Arg
                      610                 615                 620
      Ser Ala Gln Pro Ala Ser Ala Glu Thr Arg Gln Asn Leu Leu Gln Ala
      625                 630                 635                 640
      Ala Gly Val Val Gly Gln Ala Ser Gly Glu Leu Leu Trp Gln Ile Gly
                      645                 650                 655
```

```
Glu Ser Asp Thr Asp Pro Tyr Phe Gln Asp Ala Leu Met Gln Leu Ala
            660                 665                 670

Asp Ala Val Ala Ser Ala Ala Ala Leu Glu Leu Lys Ala Lys Ser
        675                 680                 685

Val Ala Gln Arg Phe Glu Asp Ser Gly Leu Gln Thr Gln Val Gly Ala
    690                 695                 700

Ala Ala Thr Gln Cys Ala Leu Ser His Ser Gln Leu Val Ala Cys Thr
705                 710                 715                 720

Lys Val Ile Ala Pro Thr Ile Ser Ser Pro Val Cys Lys Glu Gln Leu
                725                 730                 735

Val Glu Ala Gly Arg Leu Leu Ala Lys Ala Val Glu Gly Cys Val Ser
            740                 745                 750

Met Ser Gln Ala Ala Thr Glu Asp Gly Gln Asn Leu Arg Gly Val Gly
        755                 760                 765

Ala Ala Ala Thr Gln Val Thr Gln Ala Leu Asn Glu Leu Leu Arg His
    770                 775                 780

Val Lys Ala His Ala Thr Gly Ala Ser Pro Ala Gly Arg Tyr Asp Gln
785                 790                 795                 800

Ala Thr Thr Thr Ile Leu Thr Val Thr Glu Asn Ile Val Ser Ser Met
                805                 810                 815

Gly Asp Ala Gly Glu Met Trp Gly Gln Ala Arg Ile Leu Ala Gln Ala
            820                 825                 830

Tyr Ser Asp Leu Val Asn Ala Ile Lys Ala Ala Ala Glu Gly Glu Ser
        835                 840                 845

Asp Leu Glu Asn Asp Arg Lys Leu Leu Ser Ala Ala Lys Ile Glu Ala
    850                 855                 860

Asp Ala Thr Ala Lys Met Val Glu Phe Ala Lys Gly Ala Ala Ala His
865                 870                 875                 880

Pro Asp Gly Glu Glu Gln Gln Gln Arg Leu Arg Glu His Ala Glu Gly
                885                 890                 895

Leu Arg Met Ala Thr Asn Ile Ala Ala Gln Asn Ala Ile Lys Lys Lys
            900                 905                 910

Lys Val Gln Arg Leu Glu His Ala Ala Lys Leu Ala Ala Ala Ser Ala
        915                 920                 925

Thr Gln Thr Ile Met Ala Ala Gln His Ala Ala Ser Thr Pro Asn Ala
    930                 935                 940

Ser Ala Gly Pro Gln Pro Leu Leu Gln Gln Ser Cys Lys Ala Val Ala
945                 950                 955                 960

Glu Gln Arg Pro Leu Leu Val Gln Gly Val Arg Gly Thr Gln Ala Gln
                965                 970                 975

Pro Asp Ser Pro Ser Ala Val Leu Ala Leu Ile Ala Ala Ser Gln Ser
            980                 985                 990

Trp Leu Gln Pro Gly Gly Lys Met Val Ala Tyr Ala Lys Ala Ser Val
        995                 1000                1005

Pro Thr Ile Gln Ala Gln Ala Ser Ala Met Gln Leu Ser Gln Asp Ala
    1010                1015                1020

<210> SEQ ID NO 44
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence
```

```
<400> SEQUENCE: 44

Met Val Ala Ala Ser Leu Lys Ile Ser Ile Gly Asn Val Asp Lys Thr
1               5                   10                  15

Met Gln Phe Glu Pro Ser Thr Glu Val Tyr Asp Ala Cys Arg Ile Ile
            20                  25                  30

Arg Phe Arg Ile Pro Glu Ala Pro Ala Gly Pro Gly Ser Asp Phe Gly
        35                  40                  45

Leu Phe Leu Ser Asp His Asp Pro Lys Lys Gly Ile Trp Leu Glu Ile
    50                  55                  60

Gly Lys Ala Leu Asp Tyr Tyr Met Leu Lys Asn Gly Asp Thr Met Glu
65                  70                  75                  80

Tyr Arg Lys Leu Gln Arg Pro Leu Lys Ile Arg Met Leu Met Gly Thr
                85                  90                  95

Val Lys Thr Ile Met Val Asp Asn Ser Lys Thr Val Thr Asp Met Leu
            100                 105                 110

Met Gln Ile Cys Ala Arg Ile Gly Ile Thr Asn Arg Asp Glu Tyr Ser
        115                 120                 125

Leu Val Arg Glu Leu Ser Glu Lys Glu Ile Thr Gly Val
    130                 135                 140

Leu Arg Lys Asp Lys Thr Leu Leu Arg Trp Glu Lys Lys Met Glu Lys
145                 150                 155                 160

Leu Lys Gln Tyr Leu His Thr Asp Asp Glu Leu Asn Trp Ala Asp His
                165                 170                 175

Gly Arg Thr Leu Arg Glu Gln Asp Val Glu His Glu Thr Leu Leu
            180                 185                 190

Leu Glu Arg Lys Phe Phe Tyr Ser Asp Gln Asn Phe Asp Ser Arg Asp
        195                 200                 205

Pro Val Gln Leu Asn Gly Leu Tyr Val Gln Ala Arg Asp Asp Ile His
    210                 215                 220

Asn Gly Ser His Pro Val Ser Phe Asp Ile Ala Cys Glu Phe Ala Gly
225                 230                 235                 240

Phe Gln Cys Lys Ile Gln Phe Gly Pro His Asn Glu Gln Leu His Lys
                245                 250                 255

Ala Gly Phe Leu Asp Leu Lys Met Phe Leu Pro Lys Glu Tyr Val Lys
            260                 265                 270

Gln Asn Gly Glu Arg Lys Ile Phe Gln Ala His Gln Asn Cys Gly Gln
        275                 280                 285

Met Ser Glu Ile Glu Arg Lys Val Arg Tyr Val Lys Leu Ala Arg Thr
    290                 295                 300

Leu Lys Thr Tyr Gly Val Ser Phe Phe Val Val Lys Glu Lys Met Lys
305                 310                 315                 320

Gly Lys Asn Trp Leu Val Pro Arg Leu Leu Gly Ile Thr Tyr Glu Cys
                325                 330                 335

Val Met Arg Val Asp Glu Lys Ala Lys Glu Val Ile Gln Glu Trp Asn
            340                 345                 350

Leu Asp Asn Ile Lys Arg Trp Ala Ala Ser Pro Glu Ser Phe Thr Leu
        355                 360                 365

Asp Phe Gly Asp Tyr Phe Asp Gly Tyr Tyr Ser Val Gln Thr Thr Gly
    370                 375                 380

Gly Glu Gln Ile Ala Gln Leu Ile Ala His Tyr Ile Asp Ile Ile Leu
385                 390                 395                 400

Lys Lys Lys Ile Ser Lys Asp His Phe Gly Leu Glu Gly Lys Glu Glu
                405                 410                 415
```

```
Ser Thr Met Leu Glu Asp Ser Leu Ser Pro Lys Lys Ser Thr Val Leu
            420                 425                 430

Gln Met Gln Tyr Asn Arg Val Gly Lys Val Glu Asn Gly Ser Val Ala
        435                 440                 445

Leu Pro Ala Ile Met Gln Ser Gly Ala Ser Gly Pro Glu Asn Phe Arg
    450                 455                 460

Val Gly Ser Met Pro Pro Ala Gln Gln Ser Ile Thr Ser Gly Gln Met
465                 470                 475                 480

His Arg Gly Thr Met Pro Pro Leu Thr Ser Ala Gln Gln Val Leu Thr
                485                 490                 495

Gly Thr Ile Asn Ser Ser Met Trp Ala Val Gln Ala Ala Gln Ala Thr
            500                 505                 510

Leu Tyr Asp Phe Asp Thr Leu Pro Pro Leu Gly Ala Asp Ala Ala Ser
        515                 520                 525

Lys Ala Trp Arg Lys Asp Lys Met Asp Glu Ser Lys His Glu Ile Glu
530                 535                 540

Ser Gln Val Asp Ala Ile Thr Ala Gly Phe Ala Ser Val Val Asn Leu
545                 550                 555                 560

Thr Ala Gly Gly Pro Ala Glu Thr Asp Tyr Thr Ala Val His Cys Ala
                565                 570                 575

Val Thr Thr Ile Ser Ser Asn Ile Thr Glu Met Ser Arg Gly Val Lys
            580                 585                 590

Leu Lys Ala Ala Leu Leu Glu Asp Glu Gly Leu Gly Arg Pro Leu
            595                 600                 605

Leu Gln Ala Ala Lys Met Leu Ala Gly Ala Val Ser Glu Leu Leu Asn
        610                 615                 620

Ser Ala Gln Pro Ala Ser Ala Glu Pro Gln Gln Asn Leu Leu Gln Ala
625                 630                 635                 640

Ala Gly Asn Arg Gly Gln Ala Ser Gly Glu Leu Leu Gln Ser Ile Gly
                645                 650                 655

Glu Ser Asp Thr Asp Pro His Thr Gln Asp Ala Leu Met Gln Leu Ala
            660                 665                 670

Lys Val Val Ala Ser Ala Ala Ala Leu Val Trp Lys Ala Lys Ser
            675                 680                 685

Val Ala Gln Arg Thr Tyr Asp Ser Gly Leu Gln Thr Gln Val Ile Asp
    690                 695                 700

Ala Ala Thr Gln Cys Ala Leu Ser Thr Glu Gln Leu Val Ala Cys Thr
705                 710                 715                 720

Lys Val Val Phe Pro Thr Ile Ser Ser Pro Val Cys Gln Gly Gln Leu
                725                 730                 735

Val Glu Ala Gly Arg Leu Val His Lys Ala Val Glu Gly Cys Val Ser
            740                 745                 750

Ala Ile Gln Ala Ala Thr Glu Asp Gly Gln Leu Lys Arg Gly Val Gly
        755                 760                 765

Ala Ala Ala Thr Ala Leu Thr Gln Ala Leu Asn Glu Leu Leu Gln Met
        770                 775                 780

Val Lys Ala His Ala Thr Gly Ala Gly Asn Ala Gly Arg Tyr Asp Gln
785                 790                 795                 800

Ala Thr Asp Gln Ile Leu Thr Val Thr Glu Asn Ile Phe Arg Ser Met
                805                 810                 815

Gly Asp Ala Gly Glu Met Val Ser Gln Ala Arg Ile Leu Ala Gln Ala
            820                 825                 830
```

-continued

```
Thr Thr Asp Leu Val Asn Ala Ile Lys Ala Asp Val Glu Gly Glu Ser
        835                 840                 845

Asp Leu Glu Asn Ser Trp Lys Leu Leu Ser Ala Ala Lys Ile Leu Tyr
    850                 855                 860

Asp Ala Thr Ala Lys Met Val Glu Ala Asp Lys Gly Ala Ala His
865                 870                 875                 880

Pro Asp Ser Phe Glu Gln Gln Arg Leu Arg Glu Ala Gly Glu Gly
                885                 890                 895

Leu Arg Met Ala Thr Asn Ala His Ala Gln Asn Ala Ile Lys Lys Lys
                900                 905                 910

Leu Ile Gln Arg Leu Glu His Ala Ala Lys Gln Lys Ala Ala Ser Ala
            915                 920                 925

Thr Gln Thr Ile Ala Met Ala Gln His Ala Ala Ser Thr Pro Lys Asn
        930                 935                 940

Ser Ala Gly Pro Gln Pro Leu Leu Val Arg Ser Cys Lys Ala Val Ala
945                 950                 955                 960

Glu Gln Ile Ser Leu Leu Val Gln Gly Val Arg Gly Ser Thr Ala Gln
                965                 970                 975

Pro Asp Ser Pro Ser Ala Gln Val Ala Leu Ile Ala Ala Ser Gln Ser
                980                 985                 990

Phe Trp Gln Pro Gly Gly Lys Met Val Ala Ala Tyr Lys Ala Ser Val
                995                 1000                1005

Pro Thr Ile Gln Asp Ala Ala Ser Ala Met Gln Leu Ser Gln Cys Asp
    1010                1015                1020

<210> SEQ ID NO 45
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 45

Met Val Ala Leu Ala Leu Lys Ile Ser Ile Gly Asn Val Val Asp Thr
  1               5                  10                  15

Met Gln Phe Glu Pro Ser Thr Met Glu Tyr Asp Ala Cys Arg Ile Ile
                20                  25                  30

Arg Glu Phe Ile Pro Glu Ala Pro Ala Gly Pro Pro Gly Asp Phe Gly
            35                  40                  45

Leu Phe Leu Ser Asp Asp His Pro Lys Lys Gly Ile Trp Leu Glu Ala
        50                  55                  60

Ile Lys Ala Leu Asp Tyr Tyr Met Leu Arg Lys Gly Asp Thr Met Glu
65                  70                  75                  80

Tyr Arg Lys Lys Leu Arg Pro Leu Lys Ile Arg Met Leu Asp Met Thr
                85                  90                  95

Val Lys Thr Ile Met Val Asp Asp Asn Lys Thr Val Thr Asp Met Leu
                100                 105                 110

Met Thr Gln Cys Ala Arg Ile Gly Ile Thr Asn His Arg Glu Tyr Ser
            115                 120                 125

Leu Val Arg Glu Leu Met Ser Glu Lys Lys Glu Glu Ile Thr Gly Thr
        130                 135                 140

Thr Arg Lys Asp Lys Thr Leu Leu Arg Asp Val Lys Lys Met Glu Lys
145                 150                 155                 160

Leu Lys Gln Lys Trp His Thr Asp Asp Glu Leu Asn Trp Leu Tyr His
                165                 170                 175
```

-continued

```
Gly Arg Thr Leu Arg Glu Gln Gly Ala Glu His Glu Thr Leu Leu
            180                 185                 190

Leu Arg Asp Lys Phe Phe Tyr Ser Asp Gln Asn Val Glu Ser Arg Asp
        195                 200                 205

Pro Val Gln Leu Asn Leu Phe Tyr Val Gln Ala Arg Asp Asp Ile Leu
        210                 215                 220

Gly Gly Ser His Pro Val Ser Phe Asp Lys His Cys Glu Phe Ala Gly
225                 230                 235                 240

Phe Gln Cys Gln Lys Gln Phe Gly Pro His Asn Glu Gln Lys Leu Lys
                245                 250                 255

Ala Gly Phe Leu Asp Leu Lys Asp Met Leu Pro Lys Glu Tyr Val Lys
            260                 265                 270

Gln Lys Asn Glu Arg Lys Ile Phe Gln Ala His Lys Gln Cys Gly Gln
        275                 280                 285

Met Ser Glu Ile Glu Ala Arg Val Arg Tyr Val Lys Leu Ala Arg Ser
        290                 295                 300

Ser Lys Thr Tyr Gly Val Ser Phe Phe Leu Thr Lys Glu Lys Met Lys
305                 310                 315                 320

Gly Lys Asn Lys Val Val Pro Arg Leu Leu Gly Ile Thr Lys Trp Cys
                325                 330                 335

Val Met Arg Val Asp Glu Lys Thr Tyr Glu Val Ile Gln Glu Trp Asn
            340                 345                 350

Leu Thr Ala Ile Lys Arg Trp Ala Ala Ser Pro Lys Asp Phe Thr Leu
        355                 360                 365

Asp Phe Gly Asp Tyr Gln Glu Gly Tyr Tyr Ser Val Gln Thr Thr Glu
        370                 375                 380

Phe Glu Gln Ile Ala Gln Leu Ile Ala Gly Ile Asp Ile Leu
385                 390                 395                 400

Lys Lys Lys Lys His Lys Asp His Phe Gly Leu Glu Gly Asp Ile Glu
                405                 410                 415

Ser Thr Met Leu Glu Asp Ser Val Lys Pro Lys Lys Ser Thr Val Leu
            420                 425                 430

Gln Gln Leu Tyr Asn Arg Val Gly Lys Val Glu His Met Ser Val Ala
        435                 440                 445

Leu Pro Ala Ile Met Arg Asn Gly Ala Ser Gly Pro Glu Asn Phe Gln
450                 455                 460

Gln Gly Ser Met Pro Pro Ala Gln Gln Arg Thr Ser Gly Gln Met
465                 470                 475                 480

His Arg Gly His Ser Pro Pro Leu Thr Ser Ala Gln Gln Ala Thr Thr
                485                 490                 495

Gly Thr Ile Asn Ser Ser Met Gln Val Val Gln Ala Ala Gln Ala Thr
            500                 505                 510

Leu Asp Trp Phe Asp Thr Leu Pro Pro Leu Gly Gln Tyr Ala Ala Ser
        515                 520                 525

Lys Ala Trp Arg Lys Asn Ala Met Asp Glu Ser Lys His Glu Ile His
        530                 535                 540

Asp Gln Val Asp Ala Ile Thr Ala Gly Thr Glu Ser Val Val Asn Leu
545                 550                 555                 560

Thr Ala Gly Asp Phe Ala Glu Thr Asp Tyr Thr Ala Val Gly Gly Ala
                565                 570                 575

Val Thr Thr Ile Ser Ser Asn Leu His Glu Met Ser Arg Gly Val Lys
            580                 585                 590
```

-continued

```
Leu Leu Ile Ala Leu Leu Glu Asp Glu Gly Ser Lys Arg Pro Leu
            595                 600                 605
Leu Gln Ala Ala Lys Gly Met Ala Gly Ala Val Ser Glu Leu Leu Arg
            610                 615                 620
Asn Ala Gln Pro Ala Ser Ala Glu Pro Arg Arg Asn Leu Leu Gln Ala
625                 630                 635                 640
Ala Gly Asn Val Ser Gln Ala Ser Gly Glu Leu Leu Gln Gln Thr Gly
                645                 650                 655
Glu Ser Asp Thr Asp Pro His Phe Val Asp Ala Leu Met Gln Leu Ala
                660                 665                 670
Lys Ala Trp Ala Ser Ala Ala Ala Leu Val Leu Tyr Ala Lys Ser
            675                 680                 685
Val Ala Gln Arg Thr Glu Ala Ser Gly Leu Gln Thr Gln Val Ile Ala
            690                 695                 700
Asp Ala Thr Gln Cys Ala Leu Ser Thr Ser Glu Leu Val Ala Cys Thr
705                 710                 715                 720
Lys Val Val Ala Phe Thr Ile Ser Ser Pro Val Cys Gln Glu Gly Leu
                725                 730                 735
Val Glu Ala Gly Arg Leu Val Ala His Ala Val Glu Gly Cys Val Ser
            740                 745                 750
Ala Ser Ile Ala Ala Thr Glu Asp Gly Gln Leu Leu Lys Gly Val Gly
            755                 760                 765
Ala Ala Ala Thr Ala Val Leu Gln Ala Leu Asn Glu Leu Leu Gln His
770                 775                 780
Met Lys Ala His Ala Thr Gly Ala Gly Pro Asn Gly Arg Tyr Asp Gln
785                 790                 795                 800
Ala Thr Asp Thr Gln Leu Thr Val Thr Glu Asn Ile Phe Ser Arg Met
                805                 810                 815
Gly Asp Ala Gly Glu Met Val Gly Ser Ala Arg Ile Leu Ala Gln Ala
            820                 825                 830
Thr Ser Thr Leu Val Asn Ala Ile Lys Ala Asp Ala Val Gly Glu Ser
            835                 840                 845
Asp Leu Glu Asn Ser Arg Trp Leu Leu Ser Ala Ala Lys Ile Leu Ala
850                 855                 860
Tyr Ala Thr Ala Lys Met Val Glu Ala Ala Gly Ala Ala Ala His
865                 870                 875                 880
Pro Asp Ser Glu Asp Gln Gln Gln Arg Leu Arg Glu Ala Ala Phe Gly
                885                 890                 895
Leu Arg Met Ala Thr Asn Ala Ala Gly Gln Asn Ala Ile Lys Lys Lys
            900                 905                 910
Leu Val His Arg Leu Glu His Ala Ala Lys Gln Ala Ile Ala Ser Ala
            915                 920                 925
Thr Gln Thr Ile Ala Ala Lys Gln His Ala Ala Ser Thr Pro Lys Ala
            930                 935                 940
Leu Ala Gly Pro Gln Pro Leu Leu Val Gln Met Cys Lys Ala Val Ala
945                 950                 955                 960
Glu Gln Ile Pro Asn Leu Val Gln Gly Val Arg Gly Ser Gln Gln
                965                 970                 975
Pro Asp Ser Pro Ser Ala Gln Leu Arg Leu Ile Ala Ala Ser Gln Ser
            980                 985                 990
Phe Leu Ser Pro Gly Gly Lys Met Val Ala Ala Thr Ala Ser Val
            995                 1000                1005
Pro Thr Ile Gln Asp Gln Val Ser Ala Met Gln Leu Ser Gln Cys Ala
```

-continued

```
           1010                1015                1020

<210> SEQ ID NO 46
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 46

Met Val Ala Leu Ser Ala Lys Ile Ser Ile Gly Asn Val Val Lys Asp
  1               5                  10                  15

Met Gln Phe Glu Pro Ser Thr Met Val Glu Asp Ala Cys Arg Ile Ile
                 20                  25                  30

Arg Glu Arg Phe Pro Glu Ala Pro Ala Gly Pro Pro Ser Gly Phe Gly
             35                  40                  45

Leu Phe Leu Ser Asp Asp His Lys Lys Gly Ile Trp Leu Glu Ala
         50                  55                  60

Gly Ile Ala Leu Asp Tyr Tyr Met Leu Arg Asn Lys Asp Thr Met Glu
 65                  70                  75                  80

Tyr Arg Lys Lys Gln Leu Pro Leu Lys Ile Arg Met Leu Asp Gly Met
                 85                  90                  95

Val Lys Thr Ile Met Val Asp Asp Ser Asn Thr Val Thr Asp Met Leu
            100                 105                 110

Met Thr Ile Gln Ala Arg Ile Gly Ile Thr Asn His Asp Arg Tyr Ser
            115                 120                 125

Leu Val Arg Glu Leu Met Glu Ser Lys Lys Glu Glu Ile Thr Gly Thr
        130                 135                 140

Leu Thr Lys Asp Lys Thr Leu Leu Arg Asp Glu Val Lys Met Glu Lys
145                 150                 155                 160

Leu Lys Gln Lys Leu Trp Thr Asp Asp Glu Leu Asn Trp Leu Asp Tyr
                165                 170                 175

Gly Arg Thr Leu Arg Glu Gln Gly Val Ala Glu His Glu Thr Leu Leu
            180                 185                 190

Leu Arg Arg Asp Phe Phe Tyr Ser Asp Gln Asn Val Asp Glu Arg Asp
        195                 200                 205

Pro Val Gln Leu Asn Leu Leu Phe Val Gln Ala Arg Asp Asp Ile Leu
    210                 215                 220

Asn His Ser His Pro Val Ser Phe Asp Lys Ala Ile Glu Phe Ala Gly
225                 230                 235                 240

Phe Gln Cys Gln Ile Lys Phe Gly Pro His Asn Glu Gln Lys His Leu
                245                 250                 255

Ala Gly Phe Leu Asp Leu Lys Asp Phe Met Pro Lys Glu Tyr Val Lys
            260                 265                 270

Gln Lys Gly Asn Arg Lys Ile Phe Gln Ala His Lys Asn Gln Gly Gln
        275                 280                 285

Met Ser Glu Ile Glu Ala Lys Arg Arg Tyr Val Lys Leu Ala Arg Ser
    290                 295                 300

Leu Ser Thr Tyr Gly Val Ser Phe Phe Leu Val Thr Glu Lys Met Lys
305                 310                 315                 320

Gly Lys Asn Lys Leu Trp Pro Arg Leu Leu Gly Ile Thr Lys Glu Tyr
                325                 330                 335

Val Met Arg Val Asp Glu Lys Thr Lys Ala Val Ile Gln Glu Trp Asn
            340                 345                 350
```

-continued

```
Leu Thr Asn Asp Lys Arg Trp Ala Ala Ser Pro Lys Ser Glu Thr Leu
        355                 360                 365
Asp Phe Gly Asp Tyr Gln Asp Phe Tyr Tyr Ser Val Gln Thr Thr Glu
    370                 375                 380
Gly Gly Gln Ile Ala Gln Leu Ile Ala Gly Tyr His Asp Ile Ile Leu
385                 390                 395                 400
Lys Lys Lys Lys Ser Ile Asp His Phe Gly Leu Glu Gly Asp Glu Lys
                405                 410                 415
Ser Thr Met Leu Glu Asp Ser Val Ser Leu Lys Lys Ser Thr Val Leu
            420                 425                 430
Gln Gln Gln Met Asn Arg Val Gly Lys Val Glu His Gly Asn Val Ala
        435                 440                 445
Leu Pro Ala Ile Met Arg Ser Gln Ala Ser Gly Pro Glu Asn Phe Gln
    450                 455                 460
Val Arg Ser Met Pro Pro Ala Gln Gln Ile Ser Ser Gly Gln Met
465                 470                 475                 480
His Arg Gly His Met Thr Pro Leu Thr Ser Ala Gln Gln Ala Leu Val
                485                 490                 495
Gly Thr Ile Asn Ser Ser Met Gln Ala Trp Gln Ala Ala Gln Ala Thr
            500                 505                 510
Leu Asp Asp Tyr Asp Thr Leu Pro Pro Leu Gly Gln Asp Asp Ala Ser
        515                 520                 525
Lys Ala Trp Arg Lys Asn Lys Glu Asp Glu Ser Lys His Glu Ile His
    530                 535                 540
Ser Phe Val Asp Ala Ile Thr Ala Gly Thr Ala Gly Val Val Asn Leu
545                 550                 555                 560
Thr Ala Gly Asp Pro His Glu Thr Asp Tyr Thr Ala Val Gly Cys Ile
                565                 570                 575
Val Thr Thr Ile Ser Ser Asn Leu Thr Lys Met Ser Arg Gly Val Lys
            580                 585                 590
Leu Leu Ala Leu Leu Leu Glu Asp Glu Gly Ser Gly Met Pro Leu
        595                 600                 605
Leu Gln Ala Ala Lys Gly Leu Asn Gly Ala Val Ser Glu Leu Leu Arg
    610                 615                 620
Ser Gln Gln Pro Ala Ser Ala Glu Pro Arg Gln Arg Leu Leu Gln Ala
625                 630                 635                 640
Ala Gly Asn Val Gly Ser Ala Ser Gly Glu Leu Leu Gln Gln Ile Thr
                645                 650                 655
Glu Ser Asp Thr Asp Pro His Phe Gln Val Ala Leu Met Gln Leu Ala
            660                 665                 670
Lys Ala Val Trp Ser Ala Ala Ala Leu Val Leu Lys Tyr Lys Ser
        675                 680                 685
Val Ala Gln Arg Thr Glu Asp Ala Gly Leu Gln Thr Gln Val Ile Ala
    690                 695                 700
Ala Asp Thr Gln Cys Ala Leu Ser Thr Ser Gln Glu Val Ala Cys Thr
705                 710                 715                 720
Lys Val Val Ala Pro Phe Ile Ser Ser Pro Val Cys Gln Glu Gln Gly
                725                 730                 735
Val Glu Ala Gly Arg Leu Val Ala Lys His Val Glu Gly Cys Val Ser
            740                 745                 750
Ala Ser Gln Ile Ala Thr Glu Asp Gly Gln Leu Leu Arg Lys Val Gly
        755                 760                 765
Ala Ala Ala Thr Ala Val Thr Leu Ala Leu Asn Glu Leu Leu Gln His
```

```
                    770                 775                 780
Val Met Ala His Ala Thr Gly Ala Gly Pro Ala Asn Arg Tyr Asp Gln
785                 790                 795                 800

Ala Thr Asp Thr Ile Gln Thr Val Thr Glu Asn Ile Phe Ser Ser Arg
                    805                 810                 815

Gly Asp Ala Gly Glu Met Val Gly Gln Ser Arg Ile Leu Ala Gln Ala
                820                 825                 830

Thr Ser Asp Thr Val Asn Ala Ile Lys Ala Asp Ala Glu Val Glu Ser
                835                 840                 845

Asp Leu Glu Asn Ser Arg Lys Trp Leu Ser Ala Ala Lys Ile Leu Ala
            850                 855                 860

Asp Tyr Thr Ala Lys Met Val Glu Ala Lys Ala Ala Ala His
865                 870                 875                 880

Pro Asp Ser Glu Glu Asp Gln Gln Arg Leu Arg Glu Ala Ala Glu Glu
                885                 890                 895

Leu Arg Met Ala Thr Asn Ala Ala Ala Phe Asn Ala Ile Lys Lys Lys
                900                 905                 910

Leu Val Gln Gly Leu Glu His Ala Ala Lys Gln Ala Ala His Ser Ala
                915                 920                 925

Thr Gln Thr Ile Ala Ala Ala Ile His Ala Ala Ser Thr Pro Lys Ala
            930                 935                 940

Ser Lys Gly Pro Gln Pro Leu Leu Val Gln Ser Leu Lys Ala Val Ala
945                 950                 955                 960

Glu Gln Ile Pro Leu Met Val Gln Gly Val Arg Gly Ser Gln Ala Asn
                965                 970                 975

Pro Asp Ser Pro Ser Ala Gln Leu Ala Gln Ile Ala Ala Ser Gln Ser
            980                 985                 990

Phe Leu Gln Arg Gly Gly Lys Met Val Ala Ala Lys Ser Ser Val
            995                 1000                1005

Pro Thr Ile Gln Asp Gln Ala Thr Ala Met Gln Leu Ser Gln Cys Ala
    1010                1015                1020

<210> SEQ ID NO 47
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 47

Met Val Ala Leu Ser Leu Ala Ile Ser Ile Gly Asn Val Val Lys Thr
1               5                   10                  15

Asp Gln Phe Glu Pro Ser Thr Met Val Tyr Glu Ala Cys Arg Ile Ile
                20                  25                  30

Arg Glu Arg Ile Phe Glu Ala Pro Ala Gly Pro Pro Ser Asp Gly Gly
            35                  40                  45

Leu Phe Leu Ser Asp Asp Pro His Lys Gly Ile Trp Leu Glu Ala
        50                  55                  60

Gly Lys Ile Leu Asp Tyr Tyr Met Leu Arg Asn Gly Lys Thr Met Glu
65              70                  75                  80

Tyr Arg Lys Lys Gln Arg Leu Leu Lys Ile Arg Met Leu Asp Gly Thr
                85                  90                  95

Met Lys Thr Ile Met Val Asp Asp Ser Lys Asn Val Thr Asp Met Leu
            100                 105                 110
```

-continued

```
Met Thr Ile Cys Gln Arg Ile Gly Ile Thr Asn His Asp Glu Arg Ser
            115                 120                 125

Leu Val Arg Glu Leu Met Glu Glu Ser Lys Glu Glu Ile Thr Gly Thr
130                 135                 140

Leu Arg Thr Asp Lys Thr Leu Leu Arg Asp Glu Lys Val Met Glu Lys
145                 150                 155                 160

Leu Lys Gln Lys Leu His Trp Asp Asp Glu Leu Asn Trp Leu Asp His
                165                 170                 175

Tyr Arg Thr Leu Arg Glu Gln Gly Val Glu Ala His Glu Thr Leu Leu
                180                 185                 190

Leu Arg Arg Lys Asp Phe Tyr Ser Asp Gln Asn Val Asp Ser Glu Asp
            195                 200                 205

Pro Val Gln Leu Asn Leu Leu Tyr Phe Gln Ala Arg Asp Asp Ile Leu
            210                 215                 220

Asn Gly Gly His Pro Val Ser Phe Asp Lys Ala Cys His Phe Ala Gly
225                 230                 235                 240

Phe Gln Cys Gln Ile Gln Ile Gly Pro His Asn Glu Gln Lys His Lys
                245                 250                 255

Lys Gly Phe Leu Asp Leu Lys Asp Phe Leu Leu Lys Glu Tyr Val Lys
                260                 265                 270

Gln Lys Gly Glu Met Lys Ile Phe Gln Ala His Lys Asn Cys Asn Gln
            275                 280                 285

Met Ser Glu Ile Glu Ala Lys Val Gln Tyr Val Lys Leu Ala Arg Ser
290                 295                 300

Leu Lys Arg Tyr Gly Val Ser Phe Phe Leu Val Lys Ser Lys Met Lys
305                 310                 315                 320

Gly Lys Asn Lys Leu Val Thr Arg Leu Leu Gly Ile Thr Lys Glu Cys
                325                 330                 335

Trp Met Arg Val Asp Glu Lys Thr Lys Glu Tyr Ile Gln Glu Trp Asn
                340                 345                 350

Leu Thr Asn Ile Ala Arg Trp Ala Ala Ser Pro Lys Ser Phe Asp Leu
            355                 360                 365

Asp Phe Gly Asp Tyr Gln Asp Gly Glu Tyr Ser Val Gln Thr Thr Glu
            370                 375                 380

Gly Glu Phe Ile Ala Gln Leu Ile Ala Gly Tyr Ile Gly Ile Ile Leu
385                 390                 395                 400

Lys Lys Lys Lys Ser Lys His His Phe Gly Leu Glu Gly Asp Glu Glu
                405                 410                 415

Ile Thr Met Leu Glu Asp Ser Val Ser Pro Lys Lys Ser Thr Val Leu
                420                 425                 430

Gln Gln Gln Tyr Leu Arg Val Gly Lys Val Glu His Gly Ser Met Ala
            435                 440                 445

Leu Pro Ala Ile Met Arg Ser Gly Asn Ser Gly Pro Glu Asn Phe Gln
            450                 455                 460

Val Gly Gln Met Pro Pro Ala Gln Gln Ile Thr Arg Gly Gln Met
465                 470                 475                 480

His Arg Gly His Met Pro Ser Leu Thr Ser Ala Gln Gln Ala Leu Thr
                485                 490                 495

Thr Thr Ile Asn Ser Ser Met Gln Ala Val Val Ala Ala Gln Ala Thr
                500                 505                 510

Leu Asp Asp Phe Trp Thr Leu Pro Pro Leu Gly Gln Asp Ala Tyr Ser
            515                 520                 525

Lys Ala Trp Arg Lys Asn Lys Met Ala Glu Ser Lys His Glu Ile His
```

```
       530              535               540
Ser Gln Asp Asp Ala Ile Thr Ala Gly Thr Ala Ser Glu Val Asn Leu
545                 550                 555                 560

Thr Ala Gly Asp Pro Ala Phe Thr Asp Tyr Thr Ala Val Gly Cys Ala
                565                 570                 575

Gly Thr Thr Ile Ser Ser Asn Leu Thr Glu His Ser Arg Gly Val Lys
                580                 585                 590

Leu Leu Ala Ala Ile Leu Glu Asp Glu Gly Ser Gly Arg Lys Leu
            595                 600                 605

Leu Gln Ala Ala Lys Gly Leu Ala Leu Ala Val Ser Glu Leu Leu Arg
            610                 615                 620

Ser Ala Met Pro Ala Ser Ala Glu Pro Arg Gln Asn Asn Leu Gln Ala
625                 630                 635                 640

Ala Gly Asn Val Gly Gln Gln Ser Gly Glu Leu Leu Gln Gln Ile Gly
                645                 650                 655

Arg Ser Asp Thr Asp Pro His Phe Gln Asp Ser Leu Met Gln Leu Ala
                660                 665                 670

Lys Ala Val Ala Thr Ala Ala Ala Leu Val Leu Lys Ala Val Ser
            675                 680                 685

Val Ala Gln Arg Thr Glu Asp Ser Trp Leu Gln Thr Gln Val Ile Ala
690                 695                 700

Ala Ala Tyr Gln Cys Ala Leu Ser Thr Ser Gln Leu Ala Ala Cys Thr
705                 710                 715                 720

Lys Val Val Ala Pro Thr Asp Ser Ser Pro Val Cys Gln Glu Gln Leu
                725                 730                 735

Glu Glu Ala Gly Arg Leu Val Ala Lys Ala Phe Glu Gly Cys Val Ser
            740                 745                 750

Ala Ser Gln Ala Gly Thr Glu Asp Gly Gln Leu Leu Arg Gly His Gly
            755                 760                 765

Ala Ala Ala Thr Ala Val Thr Gln Ile Leu Asn Glu Leu Leu Gln His
            770                 775                 780

Val Lys Lys His Ala Thr Gly Ala Gly Pro Ala Gly Leu Tyr Asp Gln
785                 790                 795                 800

Ala Thr Asp Thr Ile Leu Met Val Thr Glu Asn Ile Phe Ser Ser Met
                805                 810                 815

Asn Asp Ala Gly Glu Met Val Gly Gln Ala Gln Ile Leu Ala Gln Ala
                820                 825                 830

Thr Ser Asp Leu Arg Asn Ala Ile Lys Ala Asp Ala Glu Gly Ser Ser
            835                 840                 845

Asp Leu Glu Asn Ser Arg Lys Leu Thr Ser Ala Ala Lys Ile Leu Ala
850                 855                 860

Asp Ala Val Ala Lys Met Val Glu Ala Ala Lys Gly Trp Ala Ala His
865                 870                 875                 880

Pro Asp Ser Glu Glu Gln Tyr Gln Arg Leu Arg Glu Ala Ala Glu Gly
                885                 890                 895

Ala Arg Met Ala Thr Asn Ala Ala Gln Asp Ala Ile Lys Lys Lys
            900                 905                 910

Leu Val Gln Arg Glu Glu His Ala Ala Lys Gln Ala Ala Phe Ala
            915                 920                 925

Thr Gln Thr Ile Ala Ala Gln Gly Ala Ala Ser Thr Pro Lys Ala
            930                 935                 940

Ser Ala His Pro Gln Pro Leu Leu Val Gln Ser Cys Ile Ala Val Ala
945                 950                 955                 960
```

-continued

```
Glu Gln Ile Pro Leu Leu Lys Gln Gly Val Arg Gly Ser Gln Ala Gln
            965                 970                 975

Leu Asp Ser Pro Ser Ala Gln Leu Ala Leu Met Ala Ala Ser Gln Ser
            980                 985                 990

Phe Leu Gln Pro Asn Gly Lys Met Val Ala Ala Lys Ala Gln Val
            995                1000                1005

Pro Thr Ile Gln Asp Gln Ala Ser Arg Met Gln Leu Ser Gln Cys Ala
       1010                1015                1020

<210> SEQ ID NO 48
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 48

Met Val Ala Leu Ser Leu Lys Ala Ser Ile Gly Asn Val Val Lys Thr
  1               5                  10                  15

Met Asp Phe Glu Pro Ser Thr Met Val Tyr Asp Glu Cys Arg Ile Ile
             20                  25                  30

Arg Glu Arg Ile Pro Phe Ala Pro Ala Gly Pro Pro Ser Asp Phe Gly
         35                  40                  45

Leu Phe Leu Ser Asp Asp Pro Lys His Gly Ile Trp Leu Glu Ala
     50                  55                  60

Gly Lys Ala Ile Asp Tyr Tyr Met Leu Arg Asn Gly Asp Lys Met Glu
 65                  70                  75                  80

Tyr Arg Lys Lys Gln Arg Pro Met Lys Ile Arg Met Leu Asp Gly Thr
                 85                  90                  95

Val Asn Thr Ile Met Val Asp Asp Ser Lys Thr Gln Thr Asp Met Leu
            100                 105                 110

Met Thr Ile Cys Ala Ser Ile Gly Ile Thr Asn His Asp Glu Tyr Thr
            115                 120                 125

Leu Val Arg Glu Leu Met Glu Glu Lys Val Glu Glu Ile Thr Gly Thr
        130                 135                 140

Leu Arg Lys Trp Lys Thr Leu Leu Arg Asp Glu Lys Lys Tyr Glu Lys
145                 150                 155                 160

Leu Lys Gln Lys Leu His Thr Ala Asp Glu Leu Asn Trp Leu Asp His
                165                 170                 175

Gly Asp Thr Leu Arg Glu Gln Gly Val Glu Glu Glu Thr Leu Leu
            180                 185                 190

Leu Arg Arg Lys Phe Phe Tyr Ser Asp Gln Asn Val Asp Ser Arg Gly
        195                 200                 205

Pro Val Gln Leu Asn Leu Leu Tyr Val His Ala Arg Asp Asp Ile Leu
    210                 215                 220

Asn Gly Ser Ile Pro Val Ser Phe Asp Lys Ala Cys Glu Lys Ala Gly
225                 230                 235                 240

Phe Gln Cys Gln Ile Gln Phe Leu Pro His Asn Glu Gln Lys His Lys
                245                 250                 255

Ala Met Phe Leu Asp Leu Lys Asp Phe Leu Pro Asn Glu Tyr Val Lys
            260                 265                 270

Gln Lys Gly Glu Arg Gln Ile Phe Gln Ala His Lys Asn Cys Gly Arg
        275                 280                 285

Met Ser Glu Ile Glu Ala Lys Val Arg Ser Val Lys Leu Ala Arg Ser
```

```
            290                 295                 300
Leu Lys Thr Thr Gly Val Ser Phe Phe Leu Val Lys Glu Val Met Lys
305                 310                 315                 320

Gly Lys Asn Lys Leu Val Pro Trp Leu Leu Gly Ile Thr Lys Glu Cys
                325                 330                 335

Val Tyr Arg Val Asp Glu Lys Thr Lys Glu Val Ala Gln Glu Trp Asn
                340                 345                 350

Leu Thr Asn Ile Lys Asp Trp Ala Ala Ser Pro Lys Ser Phe Thr Glu
                355                 360                 365

Asp Phe Gly Asp Tyr Gln Asp Gly Tyr Phe Ser Val Gln Thr Thr Glu
370                 375                 380

Gly Glu Gln Gly Ala Gln Leu Ile Ala Gly Tyr Ile Asp His Ile Leu
385                 390                 395                 400

Lys Lys Lys Lys Ser Lys Asp Ile Phe Gly Leu Glu Gly Asp Glu Glu
                405                 410                 415

Ser Lys Met Leu Glu Asp Ser Val Ser Pro Lys Leu Ser Thr Val Leu
                420                 425                 430

Gln Gln Gln Tyr Asn Met Val Gly Lys Val His Gly Ser Val Asn
                435                 440                 445

Leu Pro Ala Ile Met Arg Ser Gly Ala Gln Gly Pro Glu Asn Phe Gln
450                 455                 460

Val Gly Ser Arg Pro Pro Ala Gln Gln Gln Ile Thr Ser Ser Gln Met
465                 470                 475                 480

His Arg Gly His Met Pro Pro Thr Thr Ser Ala Gln Gln Ala Leu Thr
                485                 490                 495

Gly Val Ile Asn Ser Ser Met Gln Ala Val Gln Trp Ala Gln Ala Thr
                500                 505                 510

Leu Asp Asp Phe Asp Tyr Leu Pro Pro Leu Gly Gln Asp Ala Ala Ala
                515                 520                 525

Lys Ala Trp Arg Lys Asn Lys Met Asp Asp Ser Lys His Glu Ile His
530                 535                 540

Ser Gln Val Glu Ala Ile Thr Ala Gly Thr Ala Ser Val Phe Asn Leu
545                 550                 555                 560

Thr Ala Gly Asp Pro Ala Glu Gly Asp Tyr Thr Ala Val Gly Cys Ala
                565                 570                 575

Val His Thr Ile Ser Ser Asn Leu Thr Glu Met Ile Arg Gly Val Lys
                580                 585                 590

Leu Leu Ala Ala Leu Lys Glu Asp Glu Gly Ser Gly Arg Pro Met
                595                 600                 605

Leu Gln Ala Ala Lys Gly Leu Ala Gly Asn Val Ser Glu Leu Leu Arg
                610                 615                 620

Ser Ala Gln Gln Ala Ser Ala Glu Pro Arg Gln Asn Leu Arg Gln Ala
625                 630                 635                 640

Ala Gly Asn Val Gly Gln Ala Ser Gly Glu Leu Leu Gln Gln Ile Gly
                645                 650                 655

Glu Thr Asp Thr Asp Pro His Phe Gln Asp Ala Val Met Gln Leu Ala
                660                 665                 670

Lys Ala Val Ala Ser Trp Ala Ala Leu Val Leu Lys Ala Lys Tyr
                675                 680                 685

Val Ala Gln Arg Thr Glu Asp Ser Gly Ala Gln Thr Gln Val Ile Ala
                690                 695                 700

Ala Ala Thr Asp Cys Ala Leu Ser Thr Ser Gln Leu Val Glu Cys Thr
705                 710                 715                 720
```

```
Lys Val Val Ala Pro Thr Ile Phe Ser Pro Val Cys Gln Glu Gln Leu
                725                 730                 735

Val Gly Ala Gly Arg Leu Val Ala Lys Ala Val His Gly Cys Val Ser
            740                 745                 750

Ala Ser Gln Ala Ala Ile Glu Asp Gly Gln Leu Leu Arg Gly Val Lys
        755                 760                 765

Ala Ala Ala Thr Ala Val Thr Gln Ala Met Asn Glu Leu Leu Gln His
    770                 775                 780

Val Lys Ala Asn Ala Thr Gly Ala Gly Pro Ala Gly Arg Gln Asp Gln
785                 790                 795                 800

Ala Thr Asp Thr Ile Leu Thr Arg Thr Glu Asn Ile Phe Ser Ser Met
                805                 810                 815

Gly Ser Ala Gly Glu Met Val Gly Gln Ala Arg Thr Leu Ala Gln Ala
            820                 825                 830

Thr Ser Asp Leu Val Val Ala Ile Lys Ala Asp Ala Glu Gly Glu Trp
        835                 840                 845

Asp Leu Glu Asn Ser Arg Lys Leu Leu Tyr Ala Ala Lys Ile Leu Ala
    850                 855                 860

Asp Ala Thr Asp Lys Met Val Glu Ala Ala Lys Gly Ala Glu Ala His
865                 870                 875                 880

Pro Asp Ser Glu Glu Gln Gln Phe Arg Leu Arg Glu Ala Ala Glu Gly
                885                 890                 895

Leu Gly Met Ala Thr Asn Ala Ala Ala Gln Asn His Ile Lys Lys Lys
            900                 905                 910

Leu Val Gln Arg Leu Ile His Ala Ala Lys Gln Ala Ala Ala Ser Lys
        915                 920                 925

Thr Gln Thr Ile Ala Ala Ala Gln His Leu Ala Ser Thr Pro Lys Ala
    930                 935                 940

Ser Ala Gly Met Gln Pro Leu Leu Val Gln Ser Cys Lys Asn Val Ala
945                 950                 955                 960

Glu Gln Ile Pro Leu Leu Val Arg Gly Val Arg Gly Ser Gln Ala Gln
                965                 970                 975

Pro Ser Ser Pro Ser Ala Gln Leu Ala Leu Ile Thr Ala Ser Gln Ser
            980                 985                 990

Phe Leu Gln Pro Gly Val Lys Met Val Ala Ala Lys Ala Ser Trp
        995                 1000                1005

Pro Thr Ile Gln Asp Gln Ala Ser Ala Tyr Gln Leu Ser Gln Cys Ala
    1010                1015                1020

<210> SEQ ID NO 49
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 49

Met Val Ala Leu Ser Leu Lys Ile Ala Ile Gly Asn Val Val Lys Thr
1               5                   10                  15

Met Gln Asp Glu Pro Ser Thr Met Val Tyr Asp Ala Glu Arg Ile Ile
                20                  25                  30

Arg Glu Arg Ile Pro Glu Phe Pro Ala Gly Pro Pro Ser Asp Phe Gly
            35                  40                  45

Gly Phe Leu Ser Asp Asp Asp Pro Lys Lys His Ile Trp Leu Glu Ala
```

-continued

```
            50                      55                      60
Gly Lys Ala Leu Ile Tyr Tyr Met Leu Arg Asn Gly Asp Thr Lys Glu
 65                      70                      75                      80

Tyr Arg Lys Lys Gln Arg Pro Leu Leu Ile Arg Met Leu Asp Gly Thr
                         85                      90                      95

Val Lys Met Ile Met Val Asp Asp Ser Lys Thr Val Asn Asp Met Leu
                        100                     105                     110

Met Thr Ile Cys Ala Arg Gln Gly Ile Thr Asn His Asp Glu Tyr Ser
                        115                     120                     125

Arg Val Arg Glu Leu Met Glu Glu Lys Lys Ser Glu Ile Thr Gly Thr
                        130                     135                     140

Leu Arg Lys Asp Thr Thr Leu Leu Arg Asp Glu Lys Lys Met Val Lys
145                     150                     155                     160

Leu Lys Gln Lys Leu His Thr Asp Trp Glu Leu Asn Trp Leu Asp His
                        165                     170                     175

Gly Arg Tyr Leu Arg Glu Gln Gly Val Glu Glu His Ala Thr Leu Leu
                        180                     185                     190

Leu Arg Arg Lys Phe Phe Asp Ser Asp Gln Asn Val Asp Ser Arg Asp
                        195                     200                     205

Glu Val Gln Leu Asn Leu Leu Tyr Val Gln Phe Arg Asp Asp Ile Leu
                        210                     215                     220

Asn Gly Ser His Gly Val Ser Phe Asp Lys Ala Cys Glu Phe His Gly
225                     230                     235                     240

Phe Gln Cys Gln Ile Gln Phe Gly Ile His Asn Glu Gln Lys His Lys
                        245                     250                     255

Ala Gly Lys Leu Asp Leu Lys Asp Phe Leu Pro Lys Leu Tyr Val Lys
                        260                     265                     270

Gln Lys Gly Glu Arg Lys Met Phe Gln Ala His Lys Asn Cys Gly Gln
                        275                     280                     285

Asn Ser Glu Ile Glu Ala Lys Val Arg Tyr Gln Lys Leu Ala Arg Ser
290                     295                     300

Leu Lys Thr Tyr Arg Val Ser Phe Phe Leu Val Lys Glu Lys Ser Lys
305                     310                     315                     320

Gly Lys Asn Lys Leu Val Pro Arg Thr Leu Gly Ile Thr Lys Glu Cys
                        325                     330                     335

Val Met Val Asp Glu Lys Thr Lys Glu Val Ile Trp Glu Trp Asn
                        340                     345                     350

Leu Thr Asn Ile Lys Arg Tyr Ala Ala Ser Pro Lys Ser Phe Thr Leu
                        355                     360                     365

Ala Phe Gly Asp Tyr Gln Asp Gly Tyr Tyr Asp Val Gln Thr Thr Glu
                        370                     375                     380

Gly Glu Gln Ile Glu Gln Leu Ile Ala Gly Tyr Ile Asp Ile Phe Leu
385                     390                     395                     400

Lys Lys Lys Lys Ser Lys Asp His Gly Gly Leu Glu Gly Asp Glu Glu
                        405                     410                     415

Ser Thr His Leu Glu Asp Ser Val Ser Pro Lys Lys Ile Thr Val Leu
                        420                     425                     430

Gln Gln Gln Tyr Asn Arg Lys Gly Lys Val Glu His Gly Ser Val Ala
                        435                     440                     445

Met Pro Ala Ile Met Arg Ser Gly Ala Ser Asn Pro Glu Asn Phe Gln
                        450                     455                     460

Val Gly Ser Met Gln Pro Ala Gln Gln Gln Ile Thr Ser Gly Arg Met
465                     470                     475                     480
```

-continued

```
His Arg Gly His Met Pro Pro Leu Ser Ser Ala Gln Gln Ala Leu Thr
                485                 490                 495
Gly Thr Thr Asn Ser Ser Met Gln Ala Val Gln Ala Val Gln Ala Thr
                500                 505                 510
Leu Asp Asp Phe Asp Thr Trp Pro Leu Gly Gln Asp Ala Ala Ser
            515                 520                 525
Tyr Ala Trp Arg Lys Asn Lys Met Asp Glu Ala Lys His Glu Ile His
        530                 535                 540
Ser Gln Val Asp Asp Ile Thr Ala Gly Thr Ala Ser Val Val Glu Leu
545                 550                 555                 560
Thr Ala Gly Asp Pro Ala Glu Thr Phe Tyr Thr Ala Val Gly Cys Ala
                565                 570                 575
Val Thr Gly Ile Ser Ser Asn Leu Thr Glu Met Ser His Gly Val Lys
                580                 585                 590
Leu Leu Ala Ala Leu Leu Ile Asp Glu Gly Gly Ser Gly Arg Pro Leu
            595                 600                 605
Lys Gln Ala Ala Lys Gly Leu Ala Gly Ala Leu Ser Glu Leu Leu Arg
        610                 615                 620
Ser Ala Gln Pro Met Ser Ala Glu Pro Arg Gln Asn Leu Leu Asn Ala
625                 630                 635                 640
Ala Gly Asn Val Gly Gln Ala Ser Gln Glu Leu Leu Gln Gln Ile Gly
                645                 650                 655
Glu Ser Arg Thr Asp Pro His Phe Gln Asp Ala Leu Ser Gln Leu Ala
                660                 665                 670
Lys Ala Val Ala Ser Ala Thr Ala Ala Leu Val Leu Lys Ala Lys Ser
            675                 680                 685
Trp Ala Gln Arg Thr Glu Asp Ser Gly Leu Tyr Thr Gln Val Ile Ala
        690                 695                 700
Ala Ala Thr Gln Ala Ala Leu Ser Thr Ser Gln Leu Val Ala Asp Thr
705                 710                 715                 720
Lys Val Val Ala Pro Thr Ile Ser Glu Pro Val Cys Gln Glu Gln Leu
                725                 730                 735
Val Glu Phe Gly Arg Leu Val Ala Lys Ala Val Glu His Cys Val Ser
                740                 745                 750
Ala Ser Gln Ala Ala Thr Ile Asp Gly Gln Leu Leu Arg Gly Val Gly
            755                 760                 765
Lys Ala Ala Thr Ala Val Thr Gln Ala Leu Leu Glu Leu Leu Gln His
        770                 775                 780
Val Lys Ala His Met Thr Gly Ala Gly Pro Ala Gly Arg Tyr Asn Gln
785                 790                 795                 800
Ala Thr Asp Thr Ile Leu Thr Val Gln Glu Asn Ile Phe Ser Ser Met
                805                 810                 815
Gly Asp Arg Gly Glu Met Val Gly Gln Ala Arg Ile Ser Ala Gln Ala
                820                 825                 830
Thr Ser Asp Leu Val Asn Thr Ile Lys Ala Asp Ala Glu Gly Glu Ser
            835                 840                 845
Val Leu Glu Asn Ser Arg Lys Leu Leu Ser Trp Ala Lys Ile Leu Ala
        850                 855                 860
Asp Ala Thr Ala Tyr Met Val Glu Ala Ala Lys Gly Ala Ala Asp His
865                 870                 875                 880
Pro Asp Ser Glu Glu Gln Gln Gln Glu Leu Arg Glu Ala Ala Glu Gly
                885                 890                 895
```

-continued

```
Leu Arg Phe Ala Thr Asn Ala Ala Gln Asn Ala Gly Lys Lys Lys
            900                 905                 910

Leu Val Gln Arg Leu Glu Ile Ala Ala Lys Gln Ala Ala Ser Ala
            915                 920                 925

Lys Gln Thr Ile Ala Ala Gln His Ala Leu Ser Thr Pro Lys Ala
            930                 935                 940

Ser Ala Gly Pro Met Pro Leu Val Gln Ser Cys Lys Ala Asn Ala
945                 950                 955                 960

Glu Gln Ile Pro Leu Leu Val Gln Val Arg Gly Ser Gln Ala Gln
            965                 970                 975

Pro Asp Arg Pro Ser Ala Gln Leu Ala Leu Ile Ala Ser Ser Gln Ser
            980                 985                 990

Phe Leu Gln Pro Gly Gly Thr Met Val Ala Ala Lys Ala Ser Val
            995                 1000                1005

Val Thr Ile Gln Asp Gln Ala Ser Ala Met Trp Leu Ser Gln Cys Ala
    1010                1015                1020

<210> SEQ ID NO 50
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 50

Met Val Ala Leu Ser Leu Lys Ile Ser Ala Gly Asn Val Val Lys Thr
1               5                   10                  15

Met Gln Phe Asp Pro Ser Thr Met Val Tyr Asp Ala Cys Glu Ile Ile
            20                  25                  30

Arg Glu Arg Ile Pro Glu Ala Phe Ala Gly Pro Pro Ser Asp Phe Gly
        35                  40                  45

Leu Gly Leu Ser Asp Asp Pro Lys Lys Gly His Trp Leu Glu Ala
    50                  55                  60

Gly Lys Ala Leu Asp Ile Tyr Met Leu Arg Asn Gly Asp Thr Met Lys
65                  70                  75                  80

Tyr Arg Lys Lys Gln Arg Pro Leu Lys Leu Arg Met Leu Asp Gly Thr
                85                  90                  95

Val Lys Thr Met Met Val Asp Asp Ser Lys Thr Val Thr Asn Met Leu
            100                 105                 110

Met Thr Ile Cys Ala Arg Ile Gln Ile Thr Asn His Asp Glu Tyr Ser
        115                 120                 125

Leu Arg Arg Glu Leu Met Glu Glu Lys Lys Glu Ser Ile Thr Gly Thr
    130                 135                 140

Leu Arg Lys Asp Lys Val Leu Leu Arg Asp Glu Lys Lys Met Glu Trp
145                 150                 155                 160

Leu Lys Gln Lys Leu His Thr Asp Asp Tyr Leu Asn Trp Leu Asp His
                165                 170                 175

Gly Arg Thr Ala Arg Glu Gln Gly Val Glu Glu His Gly Asp Leu Leu
            180                 185                 190

Leu Arg Arg Lys Phe Phe Tyr Glu Asp Gln Asn Val Asp Ser Arg Asp
        195                 200                 205

Pro Phe Gln Leu Asn Leu Leu Tyr Val Gln Ala Gly Asp Asp Ile Leu
    210                 215                 220

Asn Gly Ser His Pro His Ser Phe Asp Lys Ala Cys Glu Phe Ala Ile
225                 230                 235                 240
```

```
Phe Gln Cys Gln Ile Gln Phe Gly Pro Lys Asn Glu Gln Lys His Lys
                245                 250                 255
Ala Gly Phe Met Asp Leu Lys Asp Phe Leu Pro Lys Glu Asn Val Lys
                260                 265                 270
Gln Lys Gly Glu Arg Lys Ile Gln Gln Ala His Lys Asn Cys Gly Gln
                275                 280                 285
Met Arg Glu Ile Glu Ala Lys Val Arg Tyr Val Ser Leu Ala Arg Ser
            290                 295                 300
Leu Lys Thr Tyr Gly Thr Ser Phe Phe Leu Val Lys Glu Lys Met Val
305                 310                 315                 320
Gly Lys Asn Lys Leu Val Pro Arg Leu Trp Gly Ile Thr Lys Glu Cys
                325                 330                 335
Val Met Arg Tyr Asp Glu Lys Thr Lys Glu Val Ile Gln Ala Trp Asn
                340                 345                 350
Leu Thr Asn Ile Lys Arg Trp Asp Ala Ser Pro Lys Ser Phe Thr Leu
                355                 360                 365
Asp Glu Gly Asp Tyr Gln Asp Gly Tyr Tyr Ser Phe Gln Thr Thr Glu
            370                 375                 380
Gly Glu Gln Ile Ala Gly Leu Ile Ala Gly Tyr Ile Asp Ile Ile His
385                 390                 395                 400
Lys Lys Lys Lys Ser Lys Asp His Phe Ile Leu Glu Gly Asp Glu Glu
                405                 410                 415
Ser Thr Met Lys Glu Asp Ser Val Ser Pro Lys Lys Ser Leu Val Leu
                420                 425                 430
Gln Gln Gln Tyr Asn Arg Val Met Lys Val Glu His Gly Ser Val Ala
                435                 440                 445
Leu Asn Ala Ile Met Arg Ser Gly Ala Ser Gly Gln Glu Asn Phe Gln
450                 455                 460
Val Gly Ser Met Pro Arg Ala Gln Gln Ile Thr Ser Gly Gln Ser
465                 470                 475                 480
His Arg Gly His Met Pro Pro Leu Thr Thr Ala Gln Gln Ala Leu Thr
                485                 490                 495
Gly Thr Ile Val Ser Ser Met Gln Ala Val Gln Ala Ala Trp Ala Thr
                500                 505                 510
Leu Asp Asp Phe Asp Thr Leu Tyr Pro Leu Gly Gln Asp Ala Ala Ser
                515                 520                 525
Lys Asp Trp Arg Lys Asn Lys Met Asp Glu Ser Glu His Glu Ile His
                530                 535                 540
Ser Gln Val Asp Ala Phe Thr Ala Gly Thr Ala Ser Val Val Asn Gly
545                 550                 555                 560
Thr Ala Gly Asp Pro Ala Glu Thr Asp His Thr Ala Val Gly Cys Ala
                565                 570                 575
Val Thr Thr Lys Ser Ser Asn Leu Thr Glu Met Ser Arg Leu Val Lys
                580                 585                 590
Leu Leu Ala Ala Leu Leu Glu Met Glu Gly Ser Gly Arg Pro Leu
                595                 600                 605
Leu Asn Ala Ala Lys Gly Leu Ala Gly Ala Val Gln Glu Leu Leu Arg
                610                 615                 620
Ser Ala Gln Pro Ala Arg Ala Glu Pro Arg Gln Asn Leu Leu Gln Ser
625                 630                 635                 640
Ala Gly Asn Val Gly Gln Ala Ser Gly Thr Leu Leu Gln Gln Ile Gly
                645                 650                 655
```

-continued

```
Glu Ser Asp Val Asp Pro His Phe Gln Asp Ala Leu Met Trp Leu Ala
            660                 665                 670

Lys Ala Val Ala Ser Ala Ala Tyr Ala Leu Val Leu Lys Ala Lys Ser
        675                 680                 685

Val Asp Gln Arg Thr Glu Asp Ser Gly Leu Gln Glu Gln Val Ile Ala
    690                 695                 700

Ala Ala Thr Gln Cys Phe Leu Ser Thr Ser Gln Leu Val Ala Cys Gly
705                 710                 715                 720

Lys Val Val Ala Pro Thr Ile Ser Ser His Val Cys Gln Glu Gln Leu
                725                 730                 735

Val Glu Ala Ile Arg Leu Val Ala Lys Ala Val Glu Gly Lys Val Ser
            740                 745                 750

Ala Ser Gln Ala Ala Thr Glu Leu Gly Gln Leu Leu Arg Gly Val Gly
        755                 760                 765

Ala Met Ala Thr Ala Val Thr Gln Ala Leu Asn Asn Leu Leu Gln His
    770                 775                 780

Val Lys Ala His Ala Gln Gly Ala Gly Pro Ala Gly Arg Tyr Asp Arg
785                 790                 795                 800

Ala Thr Asp Thr Ile Leu Thr Val Thr Ser Asn Ile Phe Ser Ser Met
                805                 810                 815

Gly Asp Ala Thr Glu Met Val Gly Gln Ala Arg Ile Leu Val Gln Ala
            820                 825                 830

Thr Ser Asp Leu Val Asn Ala Trp Lys Ala Asp Ala Glu Gly Glu Ser
        835                 840                 845

Asp Tyr Glu Asn Ser Arg Lys Leu Leu Ser Ala Asp Lys Ile Leu Ala
    850                 855                 860

Asp Ala Thr Ala Lys Glu Val Glu Ala Ala Lys Gly Ala Ala Ala Phe
865                 870                 875                 880

Pro Asp Ser Glu Glu Gln Gln Gln Arg Gly Arg Glu Ala Ala Glu Gly
                885                 890                 895

Leu Arg Met His Thr Asn Ala Ala Gln Asn Ala Ile Ile Lys Lys
            900                 905                 910

Leu Val Gln Arg Leu Glu His Lys Ala Lys Gln Ala Ala Ser Ala
        915                 920                 925

Thr Leu Thr Ile Ala Ala Ala Gln His Ala Ala Met Thr Pro Lys Ala
    930                 935                 940

Ser Ala Gly Pro Gln Asn Leu Leu Val Gln Ser Cys Lys Ala Val Gln
945                 950                 955                 960

Glu Gln Ile Pro Leu Leu Val Gln Gly Arg Arg Gly Ser Gln Ala Gln
                965                 970                 975

Pro Asp Ser Ser Ser Ala Gln Leu Ala Leu Ile Ala Ala Thr Gln Ser
            980                 985                 990

Phe Leu Gln Pro Gly Gly Lys Val Val Ala Ala Lys Ala Ser Val
        995                1000                1005

Pro Trp Ile Gln Asp Gln Ala Ser Ala Met Gln Tyr Ser Gln Cys Ala
   1010                1015                1020
```

<210> SEQ ID NO 51
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 51

Met Phe Leu Arg Gly Tyr Lys Arg Glu Gly Gln Val Arg Lys His Arg
1               5                   10                  15

Lys Ser Val Ala His Gly Gly Gly Leu Trp Gly Asn Cys Lys Ser Tyr
            20                  25                  30

Ala Gly Glu Ala Ala Arg Ser Leu Ile His Leu His Leu Arg Arg Ala
        35                  40                  45

Pro Ala Asp Pro Gly Phe Pro Pro Gly Glu Gln Ser Asp Met Asn Gly
    50                  55                  60

Arg Val Asp Tyr Leu Val Ser Glu Glu Ile Asn Leu Thr Arg Gly
65                  70                  75                  80

Pro Ser Gly Leu Gly Phe Asn Ile Val Gly Thr Asp Gln Gln Tyr
                85                  90                  95

Val Ser Asn Asp Ser Gly Ile Tyr Val Ser Arg Ile Lys Glu Asp Gly
            100                 105                 110

Ala Ala Ala Arg Asp Gly Arg Leu Gln Glu Gly Asp Lys Ile Leu Ser
        115                 120                 125

Val Asn Gly Gln Asp Leu Lys Asn Leu Leu His Gln Asp Ala Val Asp
    130                 135                 140

Leu Phe Arg Asn Ala Gly Tyr Ala Val Ser Leu Arg Val Gln His Arg
145                 150                 155                 160

Leu Pro Val Gln Asn Gly Pro Ile Val His Arg Gly Asp Gly Glu Pro
                165                 170                 175

Ser Gly Val Pro Val Ala Val Val Leu Leu Pro Val Phe Ala Leu Thr
            180                 185                 190

Leu Val Ala Val Trp Ala Phe Val Arg Tyr Arg Lys Gln Leu
        195                 200                 205

<210> SEQ ID NO 52
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 52

Met Ala Leu Arg Gly Tyr Lys Arg Glu Gly Gln Asp Arg Lys His Arg
1               5                   10                  15

Lys Ser Val Ala His Glu Gly Gly Leu Trp Gly Asn Cys Lys Ser Phe
            20                  25                  30

Ala Gly Glu Ala Ala Arg Ser Leu Ile Gly Leu His Leu Arg Arg Ala
        35                  40                  45

Pro Ala Asp His Gly Phe Pro Pro Gly Glu Gln Ser Asp Ile Asn Gly
    50                  55                  60

Arg Val Asp Tyr Leu Val Ser Lys Glu Glu Ile Asn Leu Thr Arg Gly
65                  70                  75                  80

Pro Leu Gly Leu Gly Phe Asn Ile Val Gly Met Asp Gln Gln Tyr
                85                  90                  95

Val Ser Asn Asp Ser Asn Ile Tyr Val Ser Arg Ile Lys Glu Asp Gln
            100                 105                 110

Ala Ala Ala Arg Asp Gly Arg Leu Gln Arg Gly Asp Lys Ile Leu Ser
        115                 120                 125

Val Asn Gly Ser Asp Leu Lys Asn Leu Leu His Gln Asp Thr Val Asp
    130                 135                 140

Leu Phe Arg Asn Ala Gly Tyr Val Val Ser Leu Arg Val Gln His Arg

-continued

```
                145                 150                 155                 160
Leu Trp Val Gln Asn Gly Pro Ile Val His Arg Tyr Asp Gly Glu Pro
                    165                 170                 175

Ser Gly Val Pro Val Asp Val Val Leu Leu Pro Val Phe Ala Leu Glu
                180                 185                 190

Leu Val Ala Val Trp Ala Phe Val Arg Phe Arg Lys Gln Leu
        195                 200                 205

<210> SEQ ID NO 53
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 53

Met Phe Ala Arg Gly Tyr Lys Arg Glu Gly Gln Val Asp Lys His Arg
  1               5                  10                  15

Lys Ser Val Ala His Gly Asp Gly Leu Trp Gly Asn Cys Lys Ser Tyr
                 20                  25                  30

Phe Gly Glu Ala Ala Arg Ser Leu Ile His Gly His Leu Arg Arg Ala
             35                  40                  45

Pro Ala Asp Pro His Phe Pro Pro Gly Glu Gln Ser Asp Met Ile Gly
     50                  55                  60

Arg Val Asp Tyr Leu Val Ser Glu Lys Glu Ile Asn Leu Thr Arg Gly
 65                  70                  75                  80

Pro Ser Leu Leu Gly Phe Asn Ile Val Gly Gly Thr Met Gln Gln Tyr
                 85                  90                  95

Val Ser Asn Asp Ser Gly Asn Tyr Val Ser Arg Ile Lys Glu Asp Gly
                100                 105                 110

Gln Ala Arg Asp Gly Arg Leu Gln Glu Arg Asp Lys Ile Leu Ser
            115                 120                 125

Val Asn Gly Gln Ser Leu Lys Asn Leu Leu His Gln Asp Ala Thr Asp
        130                 135                 140

Leu Phe Arg Asn Ala Gly Tyr Ala Trp Ser Leu Arg Val Gln His Arg
145                 150                 155                 160

Leu Pro Tyr Gln Asn Gly Pro Ile Val His Arg Gly Ala Gly Glu Pro
                    165                 170                 175

Ser Gly Val Pro Val Ala Asp Val Leu Leu Pro Val Phe Ala Leu Thr
                180                 185                 190

Glu Val Ala Val Trp Ala Phe Val Arg Tyr Phe Lys Gln Leu
        195                 200                 205

<210> SEQ ID NO 54
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 54

Met Phe Leu Ala Gly Tyr Lys Arg Glu Gly Gln Val Arg Asp His Arg
  1               5                  10                  15

Lys Ser Val Ala His Gly Gly Asp Leu Trp Gly Asn Cys Lys Ser Tyr
                 20                  25                  30

Ala Phe Glu Ala Ala Arg Ser Leu Ile His Leu Gly Leu Arg Arg Ala
```

```
                35                  40                  45
Pro Ala Asp Pro Gly His Pro Pro Gly Glu Gln Ser Asp Met Asn Ile
    50                  55                  60

Arg Val Asp Tyr Leu Val Ser Glu Glu Lys Ile Asn Leu Thr Arg Gly
 65                  70                  75                  80

Pro Ser Gly Met Gly Phe Asn Ile Val Gly Thr Asp Asn Gln Tyr
                85                  90                  95

Val Ser Asn Asp Ser Gly Ile Gln Val Ser Arg Ile Lys Glu Asp Gly
                100                 105                 110

Ala Arg Ala Arg Asp Gly Arg Leu Gln Glu Gly Ser Lys Ile Leu Ser
            115                 120                 125

Val Asn Gly Gln Asp Thr Lys Asn Leu Leu His Gln Asp Ala Val Val
    130                 135                 140

Leu Phe Arg Asn Ala Gly Tyr Ala Val Trp Leu Arg Val Gln His Arg
145                 150                 155                 160

Leu Pro Val Tyr Asn Gly Pro Ile Val His Arg Gly Asp Ala Glu Pro
                165                 170                 175

Ser Gly Val Pro Val Ala Val Asp Leu Leu Pro Val Phe Ala Leu Thr
                180                 185                 190

Leu Glu Ala Val Trp Ala Phe Val Arg Tyr Arg Phe Gln Leu
            195                 200                 205

<210> SEQ ID NO 55
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 55

Met Phe Leu Arg Ala Tyr Lys Arg Glu Gly Gln Val Arg Lys Asp Arg
  1               5                  10                  15

Lys Ser Val Ala His Gly Gly Gly Glu Trp Gly Asn Cys Lys Ser Tyr
                20                  25                  30

Ala Gly Phe Ala Ala Arg Ser Leu Ile His Leu His Gly Arg Arg Ala
            35                  40                  45

Pro Ala Asp Pro Gly Phe His Pro Gly Glu Gln Ser Asp Met Asn Gly
    50                  55                  60

Ile Val Asp Tyr Leu Val Ser Glu Glu Lys Asn Leu Thr Arg Gly
 65                  70                  75                  80

Pro Ser Gly Leu Leu Phe Asn Ile Val Gly Thr Asp Gln Met Tyr
                85                  90                  95

Val Ser Asn Asp Ser Gly Ile Tyr Asn Ser Arg Ile Lys Glu Asp Gly
                100                 105                 110

Ala Ala Gln Arg Asp Gly Arg Leu Gln Glu Gly Asp Arg Ile Leu Ser
            115                 120                 125

Val Asn Gly Gln Asp Leu Ser Asn Leu Leu His Gln Asp Ala Val Asp
    130                 135                 140

Thr Phe Arg Asn Ala Gly Tyr Ala Val Ser Val Arg Val Gln His Arg
145                 150                 155                 160

Leu Pro Val Gln Trp Gly Pro Ile Val His Arg Gly Asp Gly Tyr Pro
                165                 170                 175

Ser Gly Val Pro Val Ala Val Val Ala Leu Pro Val Phe Ala Leu Thr
                180                 185                 190
```

```
Leu Val Asp Val Trp Ala Phe Val Arg Tyr Arg Lys Glu Leu
        195                 200                 205

<210> SEQ ID NO 56
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 56

Met Phe Leu Arg Gly Ala Lys Arg Glu Gly Gln Val Arg Lys His Asp
  1               5                  10                  15

Lys Ser Val Ala His Gly Gly Leu Glu Gly Asn Cys Lys Ser Tyr
             20                  25                  30

Ala Gly Glu Phe Ala Arg Ser Leu Ile His Leu His Leu Gly Arg Ala
         35                  40                  45

Pro Ala Asp Pro Gly Phe Pro His Gly Glu Gln Ser Asp Met Asn Gly
     50                  55                  60

Arg Ile Asp Tyr Leu Val Ser Glu Glu Ile Lys Leu Thr Arg Gly
 65                  70                  75                  80

Pro Ser Gly Leu Gly Leu Asn Ile Val Gly Gly Thr Asp Gln Gln Met
                 85                  90                  95

Val Ser Asn Asp Ser Gly Ile Tyr Val Asn Arg Ile Lys Glu Asp Gly
            100                 105                 110

Ala Ala Ala Gln Asp Gly Arg Leu Gln Glu Gly Asp Lys Arg Leu Ser
        115                 120                 125

Val Asn Gly Gln Asp Leu Lys Ser Leu His Gln Asp Ala Val Asp
    130                 135                 140

Leu Thr Arg Asn Ala Gly Tyr Ala Val Ser Leu Val Val Gln His Arg
145                 150                 155                 160

Leu Pro Val Gln Asn Trp Pro Ile Val His Arg Gly Asp Gly Glu Tyr
                165                 170                 175

Ser Gly Val Pro Val Ala Val Val Leu Ala Pro Val Phe Ala Leu Thr
            180                 185                 190

Leu Val Ala Asp Trp Ala Phe Val Arg Tyr Arg Lys Gln Glu
        195                 200                 205

<210> SEQ ID NO 57
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 57

Met Phe Leu Arg Gly Tyr Ala Arg Glu Gly Gln Val Arg Lys His Arg
  1               5                  10                  15

Asp Ser Val Ala His Gly Gly Leu Trp Glu Asn Cys Lys Ser Tyr
             20                  25                  30

Ala Gly Glu Ala Phe Arg Ser Leu Ile His Leu His Leu Arg Gly Ala
         35                  40                  45

Pro Ala Asp Pro Gly Phe Pro Pro His Glu Gln Ser Asp Met Asn Gly
     50                  55                  60

Arg Val Ile Tyr Leu Val Ser Glu Glu Ile Asn Lys Thr Arg Gly
 65                  70                  75                  80
```

```
Pro Ser Gly Leu Gly Phe Leu Ile Val Gly Gly Thr Asp Gln Gln Tyr
                85                  90                  95

Met Ser Asn Asp Ser Gly Ile Tyr Val Ser Asn Ile Lys Glu Asp Gly
            100                 105                 110

Ala Ala Ala Arg Gln Gly Arg Leu Gln Glu Gly Asp Lys Ile Arg Ser
        115                 120                 125

Val Asn Gly Gln Asp Leu Lys Asn Ser Leu His Gln Asp Ala Val Asp
    130                 135                 140

Leu Phe Thr Asn Ala Gly Tyr Ala Val Ser Leu Arg Trp Gln His Arg
145                 150                 155                 160

Leu Pro Val Gln Asn Gly Tyr Ile Val His Arg Gly Asp Gly Glu Pro
                165                 170                 175

Ala Gly Val Pro Val Ala Val Val Leu Leu Asp Val Phe Ala Leu Thr
            180                 185                 190

Leu Val Ala Val Glu Ala Phe Val Arg Tyr Arg Lys Gln Leu
        195                 200                 205

<210> SEQ ID NO 58
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 58

Met Phe Leu Arg Gly Tyr Lys Ala Glu Gly Gln Val Arg Lys His Arg
 1               5                  10                  15

Lys Asp Val Ala His Gly Gly Leu Trp Gly Glu Cys Lys Ser Tyr
             20                  25                  30

Ala Gly Glu Ala Ala Phe Ser Leu Ile His Leu His Leu Arg Arg Gly
            35                  40                  45

Pro Ala Asp Pro Gly Phe Pro Pro Gly His Gln Ser Asp Met Asn Gly
        50                  55                  60

Arg Val Asp Ile Leu Val Ser Glu Glu Ile Asn Leu Lys Arg Gly
 65                 70                  75                  80

Pro Ser Gly Leu Gly Phe Asn Leu Val Gly Gly Thr Asp Gln Gln Tyr
                85                  90                  95

Val Met Asn Asp Ser Gly Ile Tyr Val Ser Arg Asn Lys Glu Asp Gly
            100                 105                 110

Ala Ala Ala Arg Asp Gln Arg Leu Gln Glu Gly Asp Lys Ile Leu Arg
        115                 120                 125

Val Asn Gly Gln Asp Leu Lys Asn Leu Ser His Gln Asp Ala Val Asp
    130                 135                 140

Leu Phe Arg Thr Ala Gly Tyr Ala Val Ser Leu Arg Val Val His Arg
145                 150                 155                 160

Leu Pro Val Gln Asn Gly Pro Trp Val His Arg Gly Asp Gly Glu Pro
                165                 170                 175

Ser Tyr Val Pro Val Ala Val Val Leu Leu Pro Ala Phe Ala Leu Thr
            180                 185                 190

Leu Val Ala Val Trp Asp Phe Val Arg Tyr Arg Lys Gln Leu
        195                 200                 205

<210> SEQ ID NO 59
<211> LENGTH: 206
<212> TYPE: PRT
<213> ORGANISM: Artificial Sequence
```

```
<220> FEATURE:
<223> OTHER INFORMATION: Description of Artificial Sequence: Synthetic
      Sequence

<400> SEQUENCE: 59

Met Phe Leu Arg Gly Tyr Lys Arg Ala Gly Gln Val Arg Lys His Arg
 1               5                  10                  15

Lys Ser Asp Ala His Gly Gly Leu Trp Gly Asn Glu Lys Ser Tyr
             20                  25                  30

Ala Gly Glu Ala Ala Arg Phe Leu Ile His Leu His Leu Arg Arg Ala
         35                  40                  45

Gly Ala Asp Pro Gly Phe Pro Pro Gly Glu His Ser Asp Met Asn Gly
     50                  55                  60

Arg Val Asp Tyr Ile Val Ser Glu Glu Ile Asn Leu Thr Lys Gly
 65                  70                  75                  80

Pro Ser Gly Leu Gly Phe Asn Ile Leu Gly Gly Thr Asp Gln Gln Tyr
                 85                  90                  95

Val Ser Met Asp Ser Gly Ile Tyr Val Ser Arg Ile Asn Glu Asp Gly
                100                 105                 110

Ala Ala Ala Arg Asp Gly Gln Leu Gln Glu Gly Asp Lys Ile Leu Ser
            115                 120                 125

Arg Asn Gly Gln Asp Leu Lys Asn Leu Leu Ser Gln Asp Ala Val Asp
        130                 135                 140

Leu Phe Arg Asn Thr Gly Tyr Ala Val Ser Leu Arg Val Gln Val Arg
145                 150                 155                 160

Leu Pro Val Gln Asn Gly Pro Ile Trp His Arg Gly Asp Gly Glu Pro
                165                 170                 175

Ser Gly Tyr Pro Val Ala Val Val Leu Pro Val Ala Ala Leu Thr
            180                 185                 190

Leu Val Ala Val Trp Ala Asp Val Arg Tyr Arg Lys Gln Leu
        195                 200                 205

<210> SEQ ID NO 60
<211> LENGTH: 206
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 60

Met Phe Leu Arg Gly Tyr Lys Arg Glu Ala Gln Val Arg Lys His Arg
 1               5                  10                  15

Lys Ser Val Asp His Gly Gly Leu Trp Gly Asn Cys Glu Ser Tyr
             20                  25                  30

Ala Gly Glu Ala Ala Arg Ser Phe Ile His Leu His Leu Arg Arg Ala
         35                  40                  45

Pro Gly Asp Pro Gly Phe Pro Pro Gly Glu Gln His Asp Met Asn Gly
     50                  55                  60

Arg Val Asp Tyr Leu Ile Ser Glu Glu Ile Asn Leu Thr Arg Lys
 65                  70                  75                  80

Pro Ser Gly Leu Gly Phe Asn Ile Val Leu Gly Thr Asp Gln Gln Tyr
                 85                  90                  95

Val Ser Asn Met Ser Gly Ile Tyr Val Ser Arg Ile Lys Asn Asp Gly
                100                 105                 110

Ala Ala Ala Arg Asp Gly Arg Gln Gln Glu Gly Asp Lys Ile Leu Ser
            115                 120                 125
```

```
Val Arg Gly Gln Asp Leu Lys Asn Leu Leu His Ser Asp Ala Val Asp
        130                 135                 140

Leu Phe Arg Asn Ala Thr Tyr Ala Val Ser Leu Arg Val Gln His Val
145                 150                 155                 160

Leu Pro Val Gln Asn Gly Pro Ile Val Trp Arg Gly Asp Gly Glu Pro
                165                 170                 175

Ser Gly Val Tyr Val Ala Val Val Leu Leu Pro Val Phe Asp Leu Thr
                180                 185                 190

Leu Val Ala Val Trp Ala Phe Glu Arg Tyr Arg Lys Gln Leu
            195                 200                 205

<210> SEQ ID NO 61
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 61

Met Pro Ser Lys Thr Lys Tyr Asn Leu Val Asp Asp Gly His Asp Leu
  1               5                  10                  15

Arg Ile Pro Leu His Asn Glu Asp Ala Phe Gln His Gly Ile Ser Phe
             20                  25                  30

Glu Ala Lys Tyr Val Gly Ser Leu Asp Val Pro Arg Pro Asn Ser Arg
         35                  40                  45

Val Glu Ile Val Ala Ala Met Arg Arg Ile Arg Tyr Glu Phe Lys Ala
     50                  55                  60

Lys Asn Ile Lys Lys Lys Val Ser Ile Met Val Ser Val Asp Gly
 65                  70                  75                  80

Val Lys Val Ile Leu Lys Lys Lys Lys Lys Lys Glu Trp Thr Trp
                 85                  90                  95

Asp Glu Ser Lys Met Leu Val Met Gln Asp Pro Ile Tyr Arg Ile Phe
            100                 105                 110

Tyr Val Ser His Asp Ser Gln Asp Leu Lys Ile Phe Ser Tyr Ile Ala
            115                 120                 125

Arg Asp Gly Ala Ser Asn Ile Phe Arg Cys Asn Val Phe Lys Ser Lys
        130                 135                 140

Lys Lys Ser Gln Ala Met Arg Ile Val Arg Thr Val Gly Gln Ala Phe
145                 150                 155                 160

Glu Val Cys His Lys Leu Ser Leu Gln His Thr Gln Asn Ala Asp
                165                 170                 175

Gly Gln Glu Asp Gly Glu Ser Glu Arg Asn Ser Asp Gly Ser Gly Asp
                180                 185                 190

Pro Gly Arg Gln Leu Thr Gly Ala Glu Arg Val Ser Thr Ala Thr Ala
            195                 200                 205

Glu Glu Thr Asp Ile Asp Ala Val Glu Val Pro Leu Pro Gly Asn Asp
        210                 215                 220

Ile Leu Glu Phe Ser Arg Gly Val Thr Asp Leu Asp Ala Ile Gly Lys
225                 230                 235                 240

Asp Gly Gly Ser His Ile Asp Thr Thr Val Ser Pro His Pro Gln Glu
                245                 250                 255

Pro Met Leu Ala Ala Ser Pro Arg Met Leu Leu Pro Ser Ser Ser Ser
                260                 265                 270

Ser Lys Pro Pro Gly Leu Gly Thr Gly Thr Pro Leu Ser Thr His His
```

```
                275                 280                 285
Gln Met Gln Leu Leu Gln Gln Leu Leu Gln Gln Gln Gln Gln Thr
            290                 295                 300

Gln Val Ala Val Ala Gln Val His Leu Leu Lys Asp Gln Leu Ala Ala
305                 310                 315                 320

Glu Ala Ala Ala Arg Leu Glu Ala Gln Ala Arg Val His Gln Leu Leu
                325                 330                 335

Leu Gln Asn Lys Asp Met Leu Gln His Ile Ser Leu Leu Val Lys Gln
            340                 345                 350

Val Gln Glu Leu Glu Leu Lys Leu Ser Gly Gln Ser Thr Met Gly Ser
        355                 360                 365

Gln Asp Ser Leu Leu Glu Ile Thr Phe Arg Ser Gly Ala Leu Pro Val
    370                 375                 380

Leu Cys Glu Ser Thr Thr Pro Lys Pro Glu Asp Leu His Ser Pro Leu
385                 390                 395                 400

Leu Gly Ala Gly Leu Ala Asp Phe Ala His Pro Val Gly Ser Pro Leu
                405                 410                 415

Gly Arg Arg Asp Cys Leu Val Lys Leu Glu Cys Phe Arg Phe Leu Pro
            420                 425                 430

Ala Glu Asp Asn Gln Pro Met Ala Gln Gly Glu Pro Leu Leu Gly Gly
        435                 440                 445

Leu Glu Leu Ile Lys Phe Arg Glu Ser Gly Ile Ala Ser Glu Tyr Glu
    450                 455                 460

Ser Asn Thr Asp Glu Ser Glu Glu Arg Asp Ser Trp Ser Gln Glu Glu
465                 470                 475                 480

Leu Pro Arg Leu Leu Asn Val Leu Gln Arg Gln Glu Leu Gly Asp Ser
                485                 490                 495

Leu Asp Asp Glu Ile Ala Val
            500

<210> SEQ ID NO 62
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 62

Met Ala Ser Lys Thr Lys Tyr Asn Leu Val Asp Glu Gly His Asp Leu
  1               5                  10                  15

Arg Ile Pro Leu His Phe Glu Asp Ala Phe Gln His Gly Ile Ser Gly
             20                  25                  30

Glu Ala Lys Tyr Val Gly Ser Leu Asp His Pro Arg Pro Asn Ser Arg
         35                  40                  45

Val Glu Ile Ile Ala Ala Met Arg Arg Ile Arg Tyr Glu Lys Lys Ala
     50                  55                  60

Lys Asn Ile Lys Lys Lys Leu Ser Ile Met Val Ser Val Asp Gly
 65                  70                  75              80

Val Met Val Ile Leu Lys Lys Lys Lys Asn Glu Trp Thr Trp
                 85                  90                  95

Asp Glu Ser Lys Met Gln Val Met Gln Asp Pro Ile Tyr Arg Ile Arg
                100                 105                 110

Tyr Val Ser His Asp Ser Gln Asp Leu Ser Ile Phe Ser Tyr Ile Ala
            115                 120                 125
```

-continued

```
Arg Asp Gly Thr Ser Asn Ile Phe Arg Cys Asn Val Phe Val Ser Lys
130                 135                 140

Lys Lys Ser Gln Ala Met Arg Trp Val Arg Thr Val Gly Gln Ala Phe
145                 150                 155                 160

Glu Tyr Cys His Lys Leu Ser Leu Gln His Thr Ala Gln Asn Ala Asp
                165                 170                 175

Gly Gln Glu Asp Gly Asp Ser Glu Arg Asn Ser Asp Gly Ser Gly Glu
            180                 185                 190

Pro Gly Arg Gln Leu Thr Gly Ala Glu Phe Val Ser Thr Ala Thr Ala
        195                 200                 205

Glu Glu Thr Gly Ile Asp Ala Val Glu Val Pro Leu Pro His Asn Asp
210                 215                 220

Ile Leu Glu Phe Ser Arg Gly Ile Thr Asp Leu Asp Ala Ile Gly Lys
225                 230                 235                 240

Asp Lys Gly Ser His Ile Asp Thr Thr Val Ser Leu His Pro Gln Glu
                245                 250                 255

Pro Met Leu Ala Ala Met Pro Arg Met Leu Leu Pro Ser Ser Ser Asn
            260                 265                 270

Ser Lys Pro Pro Gly Leu Gly Thr Gly Gln Pro Leu Ser Thr His His
        275                 280                 285

Gln Met Gln Arg Leu Gln Gln Leu Leu Gln Gln Gln Ser Gln Thr
290                 295                 300

Gln Val Ala Val Ala Gln Val Thr Leu Leu Lys Asp Gln Leu Ala Ala
305                 310                 315                 320

Glu Val Ala Ala Arg Leu Glu Ala Gln Ala Arg Trp His Gln Leu Leu
                325                 330                 335

Leu Gln Asn Lys Asp Tyr Leu Gln His Ile Ser Leu Leu Val Lys Ala
            340                 345                 350

Val Gln Glu Leu Glu Leu Lys Leu Ser Asp Gln Ser Thr Met Gly Ser
        355                 360                 365

Gln Asp Ser Glu Leu Glu Ile Thr Phe Arg Ser Gly Ala Phe Pro Val
370                 375                 380

Leu Cys Glu Ser Thr Thr Pro Gly Pro Glu Asp Leu His Ser Pro Leu
385                 390                 395                 400

Leu His Ala Gly Leu Ala Asp Phe Ala His Pro Ile Gly Ser Pro Leu
                405                 410                 415

Gly Arg Arg Asp Cys Lys Val Lys Leu Glu Cys Phe Arg Phe Leu Leu
            420                 425                 430

Ala Glu Asp Asn Gln Pro Met Ala Gln Met Glu Pro Leu Leu Gly Gly
        435                 440                 445

Leu Glu Leu Asn Lys Phe Arg Glu Ser Gly Ile Ala Ser Gln Tyr Glu
450                 455                 460

Ser Asn Thr Asp Glu Ser Glu Arg Arg Asp Ser Trp Ser Gln Glu Glu
465                 470                 475                 480

Leu Ser Arg Leu Leu Asn Val Leu Gln Arg Gln Thr Leu Gly Asp Ser
                485                 490                 495

Leu Asp Asp Glu Ile Val Val
            500
```

<210> SEQ ID NO 63
<211> LENGTH: 503
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 63

Met Pro Ala Lys Thr Lys Tyr Asn Leu Val Asp Asp His Asp Leu
1               5                   10                  15

Arg Ile Pro Leu His Asn Phe Asp Ala Phe Gln His Gly Ile Ser Phe
                20                  25                  30

Gly Ala Lys Tyr Val Gly Ser Leu Asp Val His Arg Pro Asn Ser Arg
            35                  40                  45

Val Glu Ile Val Ile Ala Met Arg Arg Ile Arg Tyr Glu Phe Leu Ala
        50                  55                  60

Lys Asn Ile Lys Lys Lys Val Met Ile Met Val Ser Val Asp Gly
65                  70                  75                  80

Val Lys Asn Ile Leu Lys Lys Lys Lys Lys Gln Trp Thr Trp
                85                  90                  95

Asp Glu Ser Lys Met Leu Arg Met Gln Asp Pro Ile Tyr Arg Ile Phe
                100                 105                 110

Ser Val Ser His Asp Ser Gln Asp Leu Lys Thr Phe Ser Tyr Ile Ala
            115                 120                 125

Arg Asp Gly Ala Val Asn Ile Phe Arg Cys Asn Val Phe Lys Trp Lys
        130                 135                 140

Lys Lys Ser Gln Ala Met Arg Ile Tyr Arg Thr Val Gly Gln Ala Phe
145                 150                 155                 160

Glu Val Ala His Lys Leu Ser Leu Gln His Thr Gln Asp Asn Ala Asp
                165                 170                 175

Gly Gln Glu Asp Gly Glu Glu Arg Asn Ser Asp Gly Ser Gly Asp
            180                 185                 190

Phe Gly Arg Gln Leu Thr Gly Ala Glu Arg Gly Ser Thr Ala Thr Ala
        195                 200                 205

Glu Glu Thr Asp His Asp Ala Val Glu Val Pro Leu Pro Gly Ile Asp
    210                 215                 220

Ile Leu Glu Phe Ser Arg Gly Val Lys Asp Leu Asp Ala Ile Gly Lys
225                 230                 235                 240

Asp Gly Leu Ser His Ile Asp Thr Thr Val Ser Pro Met Pro Gln Glu
                245                 250                 255

Pro Met Leu Ala Ala Ser Asn Arg Met Leu Leu Pro Ser Ser Ser Ser
            260                 265                 270

Gln Lys Pro Pro Gly Leu Gly Thr Gly Thr Arg Leu Ser Thr His His
        275                 280                 285

Gln Met Gln Leu Ser Gln Gln Leu Leu Gln Gln Gln Gln Thr Thr
    290                 295                 300

Gln Val Ala Val Ala Gln Val His Val Leu Lys Asp Gln Leu Ala Ala
305                 310                 315                 320

Glu Ala Trp Ala Arg Leu Glu Ala Gln Ala Arg Val Tyr Gln Leu Leu
                325                 330                 335

Leu Gln Asn Lys Asp Met Ala Gln His Ile Ser Leu Leu Val Lys Gln
            340                 345                 350

Asp Gln Glu Leu Glu Leu Lys Leu Ser Gly Glu Ser Thr Met Gly Ser
        355                 360                 365

Gln Asp Ser Leu Phe Glu Ile Thr Phe Arg Ser Gly Ala Leu Gly Val
    370                 375                 380

Leu Cys Glu Ser Thr Thr Pro Lys His Glu Asp Leu His Ser Pro Leu
385                 390                 395                 400

```
Leu Gly Ile Gly Leu Ala Asp Phe Ala His Pro Val Lys Ser Pro Leu
                405                 410                 415

Gly Arg Arg Asp Cys Leu Leu Lys Leu Glu Cys Phe Arg Phe Leu Pro
            420                 425                 430

Met Glu Asp Asn Gln Pro Met Ala Gln Gly Asn Pro Leu Leu Gly Gly
        435                 440                 445

Leu Glu Leu Ile Gln Phe Arg Glu Ser Gly Ile Ala Ser Glu Arg Glu
    450                 455                 460

Ser Asn Thr Asp Glu Ser Glu Ser Asp Ser Trp Ser Gln Glu Glu
465                 470                 475                 480

Leu Pro Thr Leu Leu Asn Val Leu Gln Arg Gln Glu Val Gly Asp Ser
            485                 490                 495

Leu Asp Asp Glu Ile Ala Trp
            500

<210> SEQ ID NO 64
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 64

Met Pro Ser Ala Thr Lys Tyr Asn Leu Val Asp Asp Gly Asp Asp Leu
 1               5                  10                  15

Arg Ile Pro Leu His Asn Glu Glu Ala Phe Gln His Gly Ile Ser Phe
            20                  25                  30

Glu Phe Lys Tyr Val Gly Ser Leu Asp Val Pro Gly Pro Asn Ser Arg
        35                  40                  45

Val Glu Ile Val Ala His Met Arg Arg Ile Arg Tyr Glu Phe Lys Ile
    50                  55                  60

Lys Asn Ile Lys Lys Lys Val Ser Lys Met Val Ser Val Asp Gly
65                  70                  75                  80

Val Lys Val Leu Leu Lys Lys Lys Lys Lys Glu Met Thr Trp
                85                  90                  95

Asp Glu Ser Lys Met Leu Val Asn Gln Asp Pro Ile Tyr Arg Ile Phe
            100                 105                 110

Tyr Gln Ser His Asp Ser Gln Asp Leu Lys Ile Arg Ser Tyr Ile Ala
        115                 120                 125

Arg Asp Gly Ala Ser Ser Ile Phe Arg Cys Asn Val Phe Lys Ser Thr
130                 135                 140

Lys Lys Ser Gln Ala Met Arg Ile Val Val Thr Val Gly Gln Ala Phe
145                 150                 155                 160

Glu Val Cys Trp Lys Leu Ser Leu Gln His Thr Gln Gln Tyr Ala Asp
                165                 170                 175

Gly Gln Glu Asp Gly Glu Ser Ala Arg Asn Ser Asp Gly Ser Gly Asp
            180                 185                 190

Pro Asp Arg Gln Leu Thr Gly Ala Glu Arg Val Glu Thr Ala Thr Ala
        195                 200                 205

Glu Glu Thr Asp Ile Phe Ala Val Glu Val Pro Leu Pro Gly Asn Gly
    210                 215                 220

Ile Leu Glu Phe Ser Arg Gly Val Thr His Leu Asp Ala Ile Gly Lys
225                 230                 235                 240

Asp Gly Gly Ile His Ile Asp Thr Thr Val Ser Pro His Lys Gln Glu
                245                 250                 255
```

```
Pro Met Leu Ala Ala Ser Pro Leu Met Leu Pro Ser Ser Ser Ser
            260                 265                 270

Ser Met Pro Pro Gly Leu Gly Thr Gly Thr Pro Asn Ser Thr His His
            275                 280                 285

Gln Met Gln Leu Leu Arg Gln Leu Leu Gln Gln Gln Gln Gln Gln Ser
            290                 295                 300

Gln Val Ala Val Ala Gln Val His Leu Thr Lys Asp Gln Leu Ala Ala
305                 310                 315                 320

Glu Ala Ala Val Arg Leu Glu Ala Gln Ala Arg Val His Trp Leu Leu
                325                 330                 335

Leu Gln Asn Lys Asp Met Leu Tyr His Ile Ser Leu Leu Val Lys Gln
            340                 345                 350

Val Ala Glu Leu Glu Leu Lys Leu Ser Gly Gln Asp Thr Met Gly Ser
            355                 360                 365

Gln Asp Ser Leu Leu Phe Ile Thr Phe Arg Ser Gly Ala Leu Pro Gly
            370                 375                 380

Leu Cys Glu Ser Thr Thr Pro Lys Pro His Asp Leu His Ser Pro Leu
385                 390                 395                 400

Leu Gly Ala Ile Leu Ala Asp Phe Ala His Pro Val Gly Lys Pro Leu
                405                 410                 415

Gly Arg Arg Asp Cys Leu Val Leu Leu Glu Cys Phe Arg Phe Leu Pro
            420                 425                 430

Ala Met Asp Asn Gln Pro Met Ala Gln Gly Glu Asn Leu Leu Gly Gly
            435                 440                 445

Leu Glu Leu Ile Lys Gln Arg Glu Ser Gly Ile Ala Ser Glu Tyr Arg
450                 455                 460

Ser Asn Thr Asp Glu Ser Glu Glu Arg Ser Ser Trp Ser Gln Glu Glu
465                 470                 475                 480

Leu Pro Arg Thr Leu Asn Val Leu Gln Arg Gln Glu Leu Val Asp Ser
                485                 490                 495

Leu Asp Asp Glu Ile Ala Val
            500

<210> SEQ ID NO 65
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 65

Met Pro Ser Lys Ala Lys Tyr Asn Leu Val Asp Asp Gly His Glu Leu
  1               5                  10                  15

Arg Ile Pro Leu His Asn Glu Asp Phe Phe Gln His Gly Ile Ser Phe
                 20                  25                  30

Glu Ala Gly Tyr Val Gly Ser Leu Asp Val Pro Arg His Asn Ser Arg
            35                  40                  45

Val Glu Ile Val Ala Ala Ile Arg Arg Ile Arg Tyr Glu Phe Lys Ala
        50                  55                  60

Leu Asn Ile Lys Lys Lys Val Ser Ile Asn Val Ser Val Asp Gly
 65                  70                  75              80

Val Lys Val Ile Gln Lys Lys Lys Lys Lys Glu Trp Arg Trp
                 85                  90                  95

Asp Glu Ser Lys Met Leu Val Met Ser Asp Pro Ile Tyr Arg Ile Phe
```

-continued

```
                  100                 105                 110
Tyr Val Thr His Asp Ser Gln Asp Leu Lys Ile Phe Val Tyr Ile Ala
            115                 120                 125
Arg Asp Gly Ala Ser Asn Trp Phe Arg Cys Asn Val Phe Lys Ser Lys
130                 135                 140
Tyr Lys Ser Gln Ala Met Arg Ile Val Arg Ala Val Gly Gln Ala Phe
145                 150                 155                 160
Glu Val Cys His Asp Leu Ser Leu Gln His Thr Gln Gln Asn Glu Asp
                165                 170                 175
Gly Gln Glu Asp Gly Glu Ser Glu Phe Asn Ser Asp Gly Ser Gly Asp
                180                 185                 190
Pro Gly Gly Gln Leu Thr Gly Ala Glu Arg Val Ser His Ala Thr Ala
                195                 200                 205
Glu Glu Thr Asp Ile Asp Ile Val Glu Val Pro Leu Pro Gly Asn Asp
            210                 215                 220
Lys Leu Glu Phe Ser Arg Gly Val Thr Asp Met Asp Ala Ile Gly Lys
225                 230                 235                 240
Asp Gly Gly Ser Asn Ile Asp Thr Thr Val Ser Pro His Pro Arg Glu
                245                 250                 255
Pro Met Leu Ala Ala Ser Pro Arg Ser Leu Leu Pro Ser Ser Ser Ser
            260                 265                 270
Ser Lys Thr Pro Gly Leu Gly Thr Gly Thr Pro Leu Val Thr His His
                275                 280                 285
Gln Met Gln Leu Leu Gln Trp Leu Leu Gln Gln Gln Gln Gln Gln Thr
            290                 295                 300
Tyr Val Ala Val Ala Gln Val His Leu Leu Ala Asp Gln Leu Ala Ala
305                 310                 315                 320
Glu Ala Ala Ala Asp Leu Glu Ala Gln Ala Arg Val His Gln Glu Leu
                325                 330                 335
Leu Gln Asn Lys Asp Met Leu Gln Phe Ile Ser Leu Leu Val Lys Gln
                340                 345                 350
Val Gln Gly Leu Glu Leu Lys Leu Ser Gly Gln Ser His Met Gly Ser
            355                 360                 365
Gln Asp Ser Leu Leu Glu Lys Thr Phe Arg Ser Gly Ala Leu Pro Val
            370                 375                 380
Met Cys Glu Ser Thr Thr Pro Lys Pro Glu Asn Leu His Ser Pro Leu
385                 390                 395                 400
Leu Gly Ala Gly Gln Ala Asp Phe Ala His Pro Val Gly Ser Arg Leu
                405                 410                 415
Gly Arg Arg Asp Cys Leu Val Lys Ser Glu Cys Phe Arg Phe Leu Pro
                420                 425                 430
Ala Glu Thr Asn Gln Pro Met Ala Gln Gly Glu Pro Val Leu Gly Gly
            435                 440                 445
Leu Glu Leu Ile Lys Phe Trp Glu Ser Gly Ile Ala Ser Glu Tyr Glu
            450                 455                 460
Tyr Asn Thr Asp Glu Ser Glu Arg Asp Ala Trp Ser Gln Glu Glu
465                 470                 475                 480
Leu Pro Arg Leu Asp Asn Val Leu Gln Arg Gln Glu Leu Gly Glu Ser
                485                 490                 495
Leu Asp Asp Glu Ile Ala Val
            500
```

<210> SEQ ID NO 66

```
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 66

Met Pro Ser Lys Thr Ala Tyr Asn Leu Val Asp Asp Gly His Asp Asp
 1               5                  10                  15

Arg Ile Pro Leu His Asn Glu Asp Ala Glu Gln His Gly Ile Ser Phe
                20                  25                  30

Glu Ala Lys Phe Val Gly Ser Leu Asp Val Pro Arg Pro Gly Ser Arg
            35                  40                  45

Val Glu Ile Val Ala Ala Met His Arg Ile Arg Tyr Glu Phe Lys Ala
        50                  55                  60

Lys Ile Ile Lys Lys Lys Val Ser Ile Met Lys Ser Val Asp Gly
 65                  70                  75                  80

Val Lys Val Ile Leu Leu Lys Lys Lys Lys Glu Trp Thr Met
                85                  90                  95

Asp Glu Ser Lys Met Leu Val Met Gln Asn Pro Ile Tyr Arg Ile Phe
                100                 105                 110

Tyr Val Ser Gln Asp Ser Gln Asp Leu Lys Ile Phe Ser Arg Ile Ala
            115                 120                 125

Arg Asp Gly Ala Ser Asn Ile Ser Arg Cys Asn Val Phe Lys Ser Lys
        130                 135                 140

Lys Thr Ser Gln Ala Met Arg Ile Val Arg Thr Trp Gly Gln Ala Phe
145                 150                 155                 160

Glu Val Cys His Lys Tyr Ser Leu Gln His Thr Gln Asn Ala Ala
                165                 170                 175

Gly Gln Glu Asp Gly Glu Ser Arg Asp Ser Asp Gly Ser Gly Asp
            180                 185                 190

Pro Gly Arg Glu Leu Thr Gly Ala Glu Arg Val Ser Thr Phe Thr Ala
        195                 200                 205

Glu Glu Thr Asp Ile Asp Ala Gly Glu Val Pro Leu Pro Gly Asn Asp
    210                 215                 220

Ile His Glu Phe Ser Arg Gly Val Thr Asp Leu Ile Ala Ile Gly Lys
225                 230                 235                 240

Asp Gly Gly Ser His Lys Asp Thr Thr Val Ser Pro His Pro Gln Leu
                245                 250                 255

Pro Met Leu Ala Ala Ser Pro Arg Met Met Leu Pro Ser Ser Ser Ser
            260                 265                 270

Ser Lys Pro Asn Gly Leu Gly Thr Gly Thr Pro Leu Ser Gln His His
        275                 280                 285

Gln Met Gln Leu Leu Gln Gln Arg Leu Gln Gln Gln Gln Gln Thr
    290                 295                 300

Gln Ser Ala Val Ala Gln Val His Leu Leu Lys Thr Gln Leu Ala Ala
305                 310                 315                 320

Glu Ala Ala Ala Arg Val Glu Ala Gln Ala Arg Val His Gln Leu Trp
                325                 330                 335

Leu Gln Asn Lys Asp Met Leu His Tyr Ser Leu Leu Val Lys Gln
            340                 345                 350

Val Gln Glu Ala Glu Leu Lys Leu Ser Gly Gln Ser Thr Asp Gly Ser
        355                 360                 365

Gln Asp Ser Leu Leu Glu Ile Glu Phe Arg Ser Gly Ala Leu Pro Val
```

-continued

```
                  370                 375                 380
Leu Phe Glu Ser Thr Thr Pro Lys Pro Glu Asp Gly His Ser Pro Leu
385                 390                 395                 400

Leu Gly Ala Gly Leu His Asp Phe Ala His Pro Val Gly Ser Pro Ile
                405                 410                 415

Gly Arg Arg Asp Cys Leu Val Lys Leu Lys Cys Phe Arg Phe Leu Pro
                420                 425                 430

Ala Glu Asp Leu Gln Pro Met Ala Gln Gly Glu Pro Leu Met Gly Gly
                435                 440                 445

Leu Glu Leu Ile Lys Phe Arg Asn Ser Gly Ile Ala Ser Glu Tyr Glu
                450                 455                 460

Ser Gln Thr Asp Glu Ser Glu Glu Arg Asp Ser Arg Ser Gln Glu Glu
465                 470                 475                 480

Leu Pro Arg Leu Leu Ser Val Leu Gln Arg Gln Glu Leu Gly Asp Thr
                485                 490                 495

Leu Asp Asp Glu Ile Ala Val
                500

<210> SEQ ID NO 67
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 67

Met Pro Ser Lys Thr Lys Ala Asn Leu Val Asp Asp Gly His Asp Leu
1               5                  10                  15

Asp Ile Pro Leu His Asn Glu Asp Ala Phe Glu His Gly Ile Ser Phe
                20                  25                  30

Glu Ala Lys Tyr Phe Gly Ser Leu Asp Val Pro Arg Pro Asn Gly Arg
                35                  40                  45

Val Glu Ile Val Ala Ala Met Arg His Ile Arg Tyr Glu Phe Lys Ala
            50                  55                  60

Lys Asn Lys Lys Lys Lys Val Ser Ile Met Val Leu Val Asp Gly
65                  70                  75                  80

Val Lys Val Ile Leu Lys Met Lys Lys Lys Lys Glu Trp Thr Trp
                85                  90                  95

Asn Glu Ser Lys Met Leu Val Met Gln Asp Gln Ile Tyr Arg Ile Phe
                100                 105                 110

Tyr Val Ser His Arg Ser Gln Asp Leu Lys Ile Phe Ser Tyr Ser Ala
                115                 120                 125

Arg Asp Gly Ala Ser Asn Ile Phe Thr Cys Asn Val Phe Lys Ser Lys
            130                 135                 140

Lys Lys Val Gln Ala Met Arg Ile Val Arg Thr Val Trp Gln Ala Phe
145                 150                 155                 160

Glu Val Cys His Lys Leu Tyr Leu Gln His Thr Gln Gln Asn Ala Asp
                165                 170                 175

Ala Gln Glu Asp Gly Glu Ser Glu Arg Asn Asp Asp Gly Ser Gly Asp
                180                 185                 190

Pro Gly Arg Gln Glu Thr Gly Ala Glu Arg Val Ser Thr Ala Phe Ala
            195                 200                 205

Glu Glu Thr Asp Ile Asp Ala Val Gly Val Pro Leu Pro Gly Asn Asp
                210                 215                 220
```

-continued

```
Ile Leu His Phe Ser Arg Gly Val Thr Asp Leu Asp Ile Ile Gly Lys
225                 230                 235                 240

Asp Gly Gly Ser His Ile Lys Thr Thr Val Ser Pro His Pro Gln Glu
            245                 250                 255

Leu Met Leu Ala Ala Ser Pro Arg Met Leu Met Pro Ser Ser Ser Ser
            260                 265                 270

Ser Lys Pro Pro Asn Leu Gly Thr Gly Thr Pro Leu Ser Thr Gln His
            275                 280                 285

Gln Met Gln Leu Leu Gln Gln Leu Arg Gln Gln Gln Gln Gln Gln Thr
290                 295                 300

Gln Val Ser Val Ala Gln Val His Leu Leu Lys Asp Thr Leu Ala Ala
305                 310                 315                 320

Glu Ala Ala Ala Arg Leu Val Ala Gln Ala Arg Val His Gln Leu Leu
                325                 330                 335

Trp Gln Asn Lys Asp Met Leu Gln His Ile Tyr Leu Leu Val Lys Gln
                340                 345                 350

Val Gln Glu Leu Ala Leu Lys Leu Ser Gly Gln Ser Thr Met Asp Ser
                355                 360                 365

Gln Asp Ser Leu Leu Glu Ile Thr Glu Arg Ser Gly Ala Leu Pro Val
370                 375                 380

Leu Cys Phe Ser Thr Thr Pro Lys Pro Glu Asp Leu Gly Ser Pro Leu
385                 390                 395                 400

Leu Gly Ala Gly Leu Ala His Phe Ala His Pro Val Gly Ser Pro Leu
                405                 410                 415

Ile Arg Arg Asp Cys Leu Val Lys Leu Glu Lys Phe Arg Phe Leu Pro
                420                 425                 430

Ala Glu Asp Asn Leu Pro Met Ala Gln Gly Glu Pro Leu Leu Met Gly
                435                 440                 445

Leu Glu Leu Ile Lys Phe Arg Glu Asn Gly Ile Ala Ser Glu Tyr Glu
            450                 455                 460

Ser Asn Gln Asp Glu Ser Glu Glu Arg Asp Ser Trp Arg Gln Glu Glu
465                 470                 475                 480

Leu Pro Arg Leu Leu Asn Ser Leu Gln Arg Gln Glu Leu Gly Asp Ser
                485                 490                 495

Thr Asp Asp Glu Ile Ala Val
            500

<210> SEQ ID NO 68
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 68

Met Pro Ser Lys Thr Lys Tyr Ala Leu Val Asp Asp Gly His Asp Leu
1               5                   10                  15

Arg Asp Pro Leu His Asn Glu Asp Ala Phe Gln His Gly Ile Ser Phe
            20                  25                  30

Glu Ala Lys Tyr Val Glu Ser Leu Asp Val Pro Arg Pro Asn Ser Phe
        35                  40                  45

Val Glu Ile Val Ala Ala Met Arg Arg Gly Arg Tyr Glu Phe Lys Ala
    50                  55                  60

Lys Asn Ile His Lys Lys Lys Val Ser Ile Met Val Ser Ile Asp Gly
65                  70                  75                  80
```

-continued

```
Val Lys Val Ile Leu Lys Lys Leu Lys Lys Lys Glu Trp Thr Trp
                 85                  90                  95

Asp Met Ser Lys Met Leu Val Met Gln Asp Pro Asn Tyr Arg Ile Phe
                100                 105                 110

Tyr Val Ser His Asp Gln Gln Asp Leu Lys Ile Phe Ser Tyr Ile Arg
            115                 120                 125

Arg Asp Gly Ala Ser Asn Ile Phe Arg Ser Asn Val Phe Lys Ser Lys
        130                 135                 140

Lys Lys Ser Thr Ala Met Arg Ile Val Arg Thr Val Gly Val Ala Phe
145                 150                 155                 160

Glu Val Cys His Lys Leu Ser Trp Gln His Thr Gln Gln Asn Ala Asp
                165                 170                 175

Gly Tyr Glu Asp Gly Glu Ser Glu Arg Asn Ser Ala Gly Ser Gly Asp
                180                 185                 190

Pro Gly Arg Gln Leu Asp Gly Ala Glu Arg Val Ser Thr Ala Thr Glu
            195                 200                 205

Glu Glu Thr Asp Ile Asp Ala Val Glu Phe Pro Leu Pro Gly Asn Asp
        210                 215                 220

Ile Leu Glu Gly Ser Arg Gly Val Thr Asp Leu Asp Ala His Gly Lys
225                 230                 235                 240

Asp Gly Gly Ser His Ile Asp Ile Thr Val Ser Pro His Pro Gln Glu
                245                 250                 255

Pro Lys Leu Ala Ala Ser Pro Arg Met Leu Leu Leu Ser Ser Ser Ser
                260                 265                 270

Ser Lys Pro Pro Gly Met Gly Thr Gly Thr Pro Leu Ser Thr His Asn
            275                 280                 285

Gln Met Gln Leu Leu Gln Gln Leu Leu Arg Gln Gln Gln Gln Gln Thr
        290                 295                 300

Gln Val Ala Ser Ala Gln Val His Leu Leu Lys Asp Gln Thr Ala Ala
305                 310                 315                 320

Glu Ala Ala Ala Arg Leu Glu Val Gln Ala Arg Val His Gln Leu Leu
                325                 330                 335

Leu Trp Asn Lys Asp Met Leu Gln His Ile Ser Tyr Leu Val Lys Gln
                340                 345                 350

Val Gln Glu Leu Glu Ala Lys Leu Ser Gly Gln Ser Thr Met Gly Asp
            355                 360                 365

Gln Asp Ser Leu Leu Glu Ile Thr Phe Glu Ser Gly Ala Leu Pro Val
        370                 375                 380

Leu Cys Glu Phe Thr Thr Pro Lys Pro Glu Asp Leu His Gly Pro Leu
385                 390                 395                 400

Leu Gly Ala Gly Leu Ala Asp His Ala His Pro Val Gly Ser Pro Leu
                405                 410                 415

Gly Ile Arg Asp Cys Leu Val Lys Leu Glu Cys Lys Arg Phe Leu Pro
                420                 425                 430

Ala Glu Asp Asn Gln Leu Met Ala Gln Gly Glu Pro Leu Leu Gly Met
            435                 440                 445

Leu Glu Leu Ile Lys Phe Arg Glu Ser Asn Ile Ala Ser Glu Tyr Glu
        450                 455                 460

Ser Asn Thr Gln Glu Ser Glu Glu Arg Asp Ser Trp Ser Arg Glu Glu
465                 470                 475                 480

Leu Pro Arg Leu Leu Asn Val Ser Gln Arg Gln Glu Leu Gly Asp Ser
                485                 490                 495
```

-continued

```
Leu Thr Asp Glu Ile Ala Val
            500

<210> SEQ ID NO 69
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 69

Met Pro Ser Lys Thr Lys Tyr Asn Ala Val Asp Asp Gly His Asp Leu
 1               5                  10                  15

Arg Ile Asp Leu His Asn Glu Asp Ala Phe Gln His Glu Ile Ser Phe
            20                  25                  30

Glu Ala Lys Tyr Val Gly Phe Leu Asp Val Pro Arg Pro Asn Ser Arg
        35                  40                  45

Gly Glu Ile Val Ala Ala Met Arg Arg Ile His Tyr Glu Phe Lys Ala
    50                  55                  60

Lys Asn Ile Lys Ile Lys Lys Val Ser Ile Met Val Ser Val Lys Gly
65                  70                  75                  80

Val Lys Val Ile Leu Lys Lys Leu Lys Lys Glu Trp Thr Trp
                85                  90                  95

Asp Glu Met Lys Met Leu Val Met Gln Asp Pro Ile Asn Arg Ile Phe
            100                 105                 110

Tyr Val Ser His Asp Ser Gln Asp Leu Lys Ile Phe Ser Tyr Ile Ala
        115                 120                 125

Ser Asp Gly Ala Ser Asn Ile Phe Arg Cys Thr Val Phe Lys Ser Lys
    130                 135                 140

Lys Lys Ser Gln Val Met Arg Ile Val Arg Thr Val Gly Gln Trp Phe
145                 150                 155                 160

Glu Val Cys His Lys Leu Ser Leu Tyr His Thr Gln Gln Asn Ala Asp
                165                 170                 175

Gly Gln Ala Asp Gly Glu Ser Glu Arg Asn Ser Asp Ser Gly Asp
            180                 185                 190

Pro Gly Arg Gln Leu Thr Glu Ala Glu Arg Val Ser Thr Ala Thr Ala
        195                 200                 205

Phe Glu Thr Asp Ile Asp Ala Val Glu Val Gly Leu Pro Gly Asn Asp
    210                 215                 220

Ile Leu Glu Phe His Arg Gly Val Thr Asp Leu Asp Ala Ile Ile Lys
225                 230                 235                 240

Asp Gly Gly Ser His Ile Asp Thr Lys Val Ser Pro His Pro Gln Glu
                245                 250                 255

Pro Met Met Ala Ala Ser Pro Arg Met Leu Leu Pro Asn Ser Ser Ser
            260                 265                 270

Ser Lys Pro Pro Gly Leu Gln Thr Gly Thr Pro Leu Ser Thr His His
        275                 280                 285

Arg Met Gln Leu Leu Gln Leu Leu Gln Ser Gln Gln Gln Thr
    290                 295                 300

Gln Val Ala Val Thr Gln Val His Leu Leu Lys Asp Gln Leu Val Ala
305                 310                 315                 320

Glu Ala Ala Arg Leu Glu Ala Trp Ala Arg Val His Gln Leu Leu
                325                 330                 335

Leu Gln Tyr Lys Asp Met Leu Gln His Ile Ser Leu Ala Val Lys Gln
            340                 345                 350
```

-continued

```
Val Gln Glu Leu Glu Leu Asp Leu Ser Gly Gln Ser Thr Met Gly Ser
        355                 360                 365
Glu Asp Ser Leu Leu Glu Ile Thr Phe Arg Phe Gly Ala Leu Pro Val
    370                 375                 380
Leu Cys Glu Ser Gly Thr Pro Lys Pro Glu Asp Leu His Ser His Leu
385                 390                 395                 400
Leu Gly Ala Gly Leu Ala Asp Phe Ile His Pro Val Gly Ser Pro Leu
                405                 410                 415
Gly Arg Lys Asp Cys Leu Val Lys Leu Glu Cys Phe Leu Phe Leu Pro
            420                 425                 430
Ala Glu Asp Asn Gln Pro Asn Ala Gln Gly Glu Pro Leu Leu Gly Gly
        435                 440                 445
Gln Glu Leu Ile Lys Phe Arg Glu Ser Gly Arg Ala Ser Glu Tyr Glu
    450                 455                 460
Ser Asn Thr Asp Ser Ser Glu Glu Arg Asp Ser Trp Ser Gln Thr Glu
465                 470                 475                 480
Leu Pro Arg Leu Leu Asn Val Leu Val Arg Gln Glu Leu Gly Asp Ser
                485                 490                 495
Leu Asp Trp Glu Ile Ala Val
            500

<210> SEQ ID NO 70
<211> LENGTH: 503
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 70

Met Pro Ser Lys Thr Lys Tyr Asn Leu Ala Asp Asp Gly His Asp Leu
1               5                   10                  15
Arg Ile Pro Asp His Asn Glu Asp Ala Phe Gln His Gly Glu Ser Phe
            20                  25                  30
Glu Ala Lys Tyr Val Gly Ser Phe Asp Val Pro Arg Pro Asn Ser Arg
        35                  40                  45
Val Gly Ile Val Ala Ala Met Arg Arg Ile Arg His Glu Phe Lys Ala
    50                  55                  60
Lys Asn Ile Lys Lys Ile Lys Val Ser Ile Met Val Ser Val Asp Lys
65                  70                  75                  80
Val Lys Val Ile Leu Lys Lys Lys Leu Lys Lys Glu Trp Thr Trp
                85                  90                  95
Asp Glu Ser Met Met Leu Val Met Gln Asp Pro Ile Tyr Asn Ile Phe
            100                 105                 110
Tyr Val Ser His Asp Ser Gln Gln Leu Lys Ile Phe Ser Tyr Ile Ala
        115                 120                 125
Arg Arg Gly Ala Ser Asn Ile Phe Arg Cys Asn Ser Phe Lys Ser Lys
    130                 135                 140
Lys Lys Ser Gln Ala Thr Arg Ile Val Arg Thr Val Gly Gln Ala Val
145                 150                 155                 160
Glu Val Cys His Lys Leu Ser Leu Gln Trp Thr Gln Gln Asn Ala Asp
                165                 170                 175
Gly Gln Glu Tyr Gly Glu Ser Gly Arg Asn Ser Asp Gly Ala Gly Asp
            180                 185                 190
Pro Gly Arg Gln Leu Thr Gly Asp Glu Arg Val Ser Thr Ala Thr Ala
```

-continued

```
                195                 200                 205
Glu Phe Thr Asp Ile Asp Ala Val Glu Val Pro Gly Pro Gly Asn Asp
    210                 215                 220
Ile Leu Glu Phe Ser His Gly Val Thr Asp Leu Asp Ala Ile Gly Ile
225                 230                 235                 240
Asp Gly Gly Ser His Ile Asp Thr Thr Lys Ser Pro His Pro Gln Glu
                245                 250                 255
Pro Met Leu Leu Ala Ser Pro Arg Met Leu Pro Ser Met Ser Ser
            260                 265                 270
Ser Lys Pro Pro Gly Leu Gly Asn Gly Thr Pro Leu Ser Thr His His
        275                 280                 285
Gln Gln Gln Leu Leu Gln Gln Leu Leu Gln Arg Gln Gln Gln Thr
    290                 295                 300
Gln Val Ala Val Ala Ser Val His Leu Leu Lys Asp Gln Leu Ala Thr
305                 310                 315                 320
Glu Ala Ala Ala Arg Leu Glu Ala Gln Val Arg Val His Gln Leu Leu
                325                 330                 335
Leu Gln Asn Trp Asp Met Leu Gln His Ile Ser Leu Leu Tyr Lys Gln
            340                 345                 350
Val Gln Glu Leu Glu Leu Lys Ala Ser Gly Gln Ser Thr Met Gly Ser
        355                 360                 365
Gln Glu Ser Leu Leu Glu Ile Thr Phe Arg Ser Phe Ala Leu Pro Val
    370                 375                 380
Leu Cys Glu Ser Thr Gly Pro Lys Pro Glu Asp Leu His Ser Pro His
385                 390                 395                 400
Leu Gly Ala Gly Leu Ala Asp Phe Ala Ile Pro Val Gly Ser Pro Leu
                405                 410                 415
Gly Arg Arg Lys Cys Leu Val Lys Leu Glu Cys Phe Arg Leu Leu Pro
            420                 425                 430
Ala Glu Asp Asn Gln Pro Met Met Gln Gly Glu Pro Leu Leu Gly Gly
        435                 440                 445
Leu Asn Leu Ile Lys Phe Arg Glu Ser Gly Ile Gln Ser Glu Tyr Glu
    450                 455                 460
Ser Asn Thr Asp Glu Arg Glu Arg Asp Ser Trp Ser Gln Glu Ser
465                 470                 475                 480
Leu Pro Arg Leu Leu Asn Val Leu Gln Thr Gln Glu Leu Gly Asp Ser
                485                 490                 495
Leu Asp Asp Val Ile Ala Val
            500

<210> SEQ ID NO 71
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 71

Glu Phe Ala Ala Ala Ser Thr Gln Pro Ala Glu Leu Ala Ser Leu Gly
1               5                   10                  15
Glu Ser Gln Ser Arg Glu Ser Leu Ser Phe Thr Ser Pro Ser Thr Ser
            20                  25                  30
Ser Glu Val Tyr Lys Ile Lys Phe Ile Phe Pro Asn Gly Asp Thr Tyr
        35                  40                  45
```

Asp Gly Asp Cys Thr Arg Thr Thr Ser Gly Ile Cys Glu Arg Asn Gly
            50                  55                  60

Thr Gly Thr His Thr Thr Pro Asn Gly Ile Val Tyr Thr Gly Ser Trp
 65                  70                  75                  80

Lys Asp Asp Lys Met Asn Gly Phe Gly Arg Leu Glu His Phe Ser Gly
                 85                  90                  95

Ala Val Tyr Glu Gly Gln Phe Lys Asp Asn Met Phe His Gly Leu Gly
                100                 105                 110

Thr Tyr Thr Phe Pro Thr Gly Ala Lys Tyr Thr Gly Asn Phe Asn Glu
            115                 120                 125

Asn Arg Val Glu Gly Glu Gly Glu Tyr Thr Asp Thr Gln Gly Leu Gln
        130                 135                 140

Trp Cys Gly Asn Phe His Phe Thr Ala Ala Pro Gly Leu Lys Leu Lys
145                 150                 155                 160

Leu Tyr Met

<210> SEQ ID NO 72
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 72

Glu Ala Ala Ala Ser Thr Gln Pro Ala Glu Asp Ala Ser Leu Gly
  1               5                  10                  15

Glu Ser Gln Ser Arg Phe Ser Leu Ser Phe Thr Ser Pro Ser Thr Gly
                 20                  25                  30

Ser Glu Val Tyr Lys Ile Lys Phe Ile His Pro Asn Gly Asp Thr Tyr
             35                  40                  45

Asp Gly Asp Ile Thr Arg Thr Thr Ser Gly Ile Cys Glu Lys Asn Gly
        50                   55                 60

Thr Gly Thr His Thr Thr Pro Leu Gly Ile Val Tyr Thr Gly Ser Trp
 65                  70                  75                  80

Lys Met Asp Lys Met Asn Gly Phe Gly Arg Leu Asn His Phe Ser Gly
                 85                  90                  95

Ala Val Tyr Glu Gly Arg Phe Lys Asp Asn Met Phe His Gly Leu Ser
                100                 105                 110

Thr Tyr Thr Phe Pro Thr Gly Ala Lys Thr Thr Gly Asn Phe Asn Glu
            115                 120                 125

Asn Arg Val Val Gly Glu Gly Glu Tyr Thr Asp Thr Gln Trp Leu Gln
        130                 135                 140

Trp Cys Gly Asn Phe His Phe Tyr Ala Ala Pro Gly Leu Lys Leu Lys
145                 150                 155                 160

Leu Ala Met

<210> SEQ ID NO 73
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 73

Glu Phe Asp Ala Ala Ser Thr Gln Pro Ala Glu Leu Glu Ser Leu Gly
  1               5                  10                  15

```
Glu Ser Gln Ser Arg Glu Phe Leu Ser Phe Thr Ser Pro Ser Thr Ser
                20                  25                  30

Gly Glu Val Tyr Lys Ile Lys Phe Ile Phe His Asn Gly Asp Thr Tyr
        35                  40                  45

Asp Gly Asp Cys Ile Arg Thr Thr Ser Gly Ile Cys Glu Arg Lys Gly
    50                  55                  60

Thr Gly Thr His Thr Thr Pro Asn Leu Ile Val Tyr Thr Gly Ser Trp
65                  70                  75                  80

Lys Asp Met Lys Met Asn Gly Phe Gly Arg Leu Glu Asn Phe Ser Gly
                85                  90                  95

Ala Val Tyr Glu Gly Gln Gln Lys Asp Asn Met Phe His Gly Leu Gly
            100                 105                 110

Arg Tyr Thr Phe Pro Thr Gly Ala Lys Tyr Ser Gly Asn Phe Asn Glu
        115                 120                 125

Asn Arg Val Glu Thr Glu Gly Tyr Thr Asp Thr Gln Gly Val Gln
    130                 135                 140

Trp Cys Gly Asn Phe His Phe Thr Trp Ala Pro Gly Leu Lys Leu Lys
145                 150                 155                 160

Leu Tyr Tyr

<210> SEQ ID NO 74
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 74

Glu Phe Ala Asp Ala Ser Thr Gln Pro Ala Glu Leu Ala Glu Leu Gly
1               5                   10                  15

Glu Ser Gln Ser Arg Glu Ser Phe Ser Phe Thr Ser Pro Ser Thr Ser
                20                  25                  30

Ser Gly Val Tyr Lys Ile Lys Phe Ile Phe Pro His Gly Asp Thr Tyr
        35                  40                  45

Asp Gly Asp Cys Thr Ile Thr Thr Ser Gly Ile Cys Glu Arg Asn Lys
    50                  55                  60

Thr Gly Thr His Thr Thr Pro Asn Gly Leu Val Tyr Thr Gly Ser Trp
65                  70                  75                  80

Lys Asp Asp Met Met Asn Gly Phe Gly Arg Leu Glu His Asn Ser Gly
                85                  90                  95

Ala Val Tyr Glu Gly Gln Phe Gln Asp Asn Met Phe His Gly Leu Gly
            100                 105                 110

Thr Arg Thr Phe Pro Thr Gly Ala Lys Tyr Thr Ser Asn Phe Asn Glu
        115                 120                 125

Asn Arg Val Glu Gly Thr Gly Glu Tyr Thr Asp Thr Gln Gly Leu Val
    130                 135                 140

Trp Cys Gly Asn Phe His Phe Thr Ala Trp Pro Gly Leu Lys Leu Lys
145                 150                 155                 160

Leu Tyr Met

<210> SEQ ID NO 75
<211> LENGTH: 163
<212> TYPE: PRT
<213> ORGANISM: Artificial Sequence
<220> FEATURE:
```

<223> OTHER INFORMATION: Description of Artificial Sequence: Synthetic
      Sequence

<400> SEQUENCE: 75

```
Glu Phe Ala Ala Asp Ser Thr Gln Pro Ala Glu Leu Ala Ser Glu Gly
 1               5                  10                  15

Glu Ser Gln Ser Arg Glu Ser Leu Phe Phe Thr Ser Pro Ser Thr Ser
             20                  25                  30

Ser Glu Gly Tyr Lys Ile Lys Phe Ile Phe Pro Asn His Asp Thr Tyr
         35                  40                  45

Asp Gly Asp Cys Thr Arg Ile Thr Ser Gly Ile Cys Glu Arg Asn Gly
     50                  55                  60

Lys Gly Thr His Thr Thr Pro Asn Gly Ile Leu Tyr Thr Gly Ser Trp
 65                  70                  75                  80

Lys Asp Asp Lys Asn Asn Gly Phe Gly Arg Leu Glu His Phe Gln Gly
                 85                  90                  95

Ala Val Tyr Glu Gly Gln Phe Lys Arg Asn Met Phe His Gly Leu Gly
            100                 105                 110

Thr Tyr Ser Phe Pro Thr Gly Ala Lys Tyr Thr Gly Thr Phe Asn Glu
        115                 120                 125

Asn Arg Val Glu Gly Glu Val Glu Tyr Thr Asp Thr Gln Gly Leu Gln
    130                 135                 140

Tyr Cys Gly Asn Phe His Phe Thr Ala Ala Gly Leu Lys Leu Lys
145                 150                 155                 160

Leu Tyr Met
```

<210> SEQ ID NO 76
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 76

```
Glu Phe Ala Ala Ala Thr Gln Pro Ala Glu Leu Ala Ser Leu Asp
 1               5                  10                  15

Glu Ser Gln Ser Arg Glu Ser Leu Ser Glu Thr Ser Pro Ser Thr Ser
             20                  25                  30

Ser Glu Val Phe Lys Ile Lys Phe Ile Phe Pro Asn Gly Gly Thr Tyr
         35                  40                  45

Asp Gly Asp Cys Thr Arg Thr His Ser Gly Ile Cys Glu Arg Asn Gly
     50                  55                  60

Thr Ile Thr His Thr Thr Pro Asn Gly Ile Val Lys Thr Gly Ser Trp
 65                  70                  75                  80

Lys Asp Asp Lys Met Leu Gly Phe Gly Arg Leu Glu His Phe Ser Met
                 85                  90                  95

Ala Val Tyr Glu Gly Gln Phe Lys Asp Gln Met Phe His Gly Leu Gly
            100                 105                 110

Thr Tyr Thr Arg Pro Thr Gly Ala Lys Tyr Thr Gly Asn Ser Asn Glu
        115                 120                 125

Asn Arg Val Glu Gly Gly Thr Tyr Thr Asp Thr Gln Gly Leu Gln
    130                 135                 140

Trp Val Gly Asn Phe His Phe Thr Ala Ala Pro Trp Leu Lys Leu Lys
145                 150                 155                 160

Leu Tyr Met
```

<210> SEQ ID NO 77
<211> LENGTH: 163
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 77

Glu Phe Ala Ala Ala Ser Ala Gln Pro Ala Glu Leu Ala Ser Leu Gly
1               5                   10                  15

Asp Ser Gln Ser Arg Glu Ser Leu Ser Phe Glu Ser Pro Ser Thr Ser
                20                  25                  30

Ser Glu Val Tyr Phe Ile Lys Phe Ile Phe Pro Asn Gly Asp Gly Tyr
            35                  40                  45

Asp Gly Asp Cys Thr Arg Thr Thr His Gly Ile Cys Glu Arg Asn Gly
        50                  55                  60

Thr Gly Ile His Thr Thr Pro Asn Gly Ile Val Tyr Lys Gly Ser Trp
65                  70                  75                  80

Lys Asp Asp Lys Met Asn Leu Phe Gly Arg Leu Glu His Phe Ser Gly
                85                  90                  95

Met Val Tyr Glu Gly Gln Phe Lys Asp Asn Phe His Gly Leu Gly
            100                 105                 110

Thr Tyr Thr Phe Gln Thr Gly Ala Lys Tyr Thr Gly Asn Phe Arg Glu
        115                 120                 125

Asn Arg Val Glu Gly Glu Gly Glu Ser Thr Asp Thr Gln Gly Leu Gln
    130                 135                 140

Trp Cys Thr Asn Phe His Phe Thr Ala Ala Pro Gly Val Lys Leu Lys
145                 150                 155                 160

Leu Tyr Met

<210> SEQ ID NO 78
<211> LENGTH: 163
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 78

Glu Phe Ala Ala Ala Ser Thr Pro Ala Glu Leu Ala Ser Leu Gly
1               5                   10                  15

Glu Asp Gln Ser Arg Glu Ser Leu Ser Phe Thr Glu Pro Ser Thr Ser
                20                  25                  30

Ser Glu Val Tyr Lys Phe Lys Phe Ile Phe Pro Asn Gly Asp Thr Gly
            35                  40                  45

Asp Gly Asp Cys Thr Arg Thr Thr Ser His Ile Cys Glu Arg Asn Gly
        50                  55                  60

Thr Gly Thr Ile Thr Thr Pro Asn Gly Ile Val Tyr Thr Lys Ser Trp
65                  70                  75                  80

Lys Asp Asp Lys Met Asn Gly Leu Gly Arg Leu Glu His Phe Ser Gly
                85                  90                  95

Ala Met Tyr Glu Gly Gln Phe Lys Asp Asn Met Asn His Gly Leu Gly
            100                 105                 110

Thr Tyr Thr Phe Pro Gln Gly Ala Lys Tyr Thr Gly Asn Phe Asn Arg
        115                 120                 125

```
Asn Arg Val Glu Gly Glu Gly Glu Tyr Ser Asp Thr Gln Gly Leu Gln
        130                 135                 140

Trp Cys Gly Thr Phe His Phe Thr Ala Ala Pro Gly Leu Val Leu Lys
145                 150                 155                 160

Leu Tyr Met

<210> SEQ ID NO 79
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 79

Glu Phe Ala Ala Ala Ser Thr Gln Ala Ala Glu Leu Ala Ser Leu Gly
  1               5                  10                  15

Glu Ser Asp Ser Arg Glu Ser Leu Ser Phe Thr Ser Glu Ser Thr Ser
             20                  25                  30

Ser Glu Val Tyr Lys Ile Phe Phe Ile Phe Pro Asn Gly Asp Thr Tyr
         35                  40                  45

Gly Gly Asp Cys Thr Arg Thr Thr Ser Gly Gly Cys Glu Arg Asn Gly
     50                  55                  60

Thr Gly Thr His Ile Thr Pro Asn Gly Ile Val Tyr Thr Gly Lys Trp
 65                  70                  75                  80

Lys Asp Asp Lys Met Asn Gly Phe Leu Arg Leu Glu His Phe Ser Gly
                 85                  90                  95

Ala Val Met Glu Gly Gln Phe Lys Asp Asn Met Phe Asn Gly Leu Gly
            100                 105                 110

Thr Tyr Thr Phe Pro Thr Gln Ala Lys Tyr Thr Gly Asn Phe Asn Glu
        115                 120                 125

Arg Arg Val Glu Gly Glu Gly Tyr Thr Ser Thr Gln Gly Leu Gln
    130                 135                 140

Trp Cys Gly Asn Thr His Phe Thr Ala Ala Pro Gly Leu Lys Val Lys
145                 150                 155                 160

Leu Tyr Met

<210> SEQ ID NO 80
<211> LENGTH: 163
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 80

Glu Phe Ala Ala Ala Ser Thr Gln Pro Asp Glu Leu Ala Ser Leu Gly
  1               5                  10                  15

Glu Ser Gln Glu Arg Glu Ser Leu Ser Phe Thr Ser Pro Phe Thr Ser
             20                  25                  30

Ser Glu Val Tyr Lys Ile Lys Gly Ile Phe Pro Asn Gly Asp Thr Tyr
         35                  40                  45

Asp His Asp Cys Thr Arg Thr Thr Ser Gly Ile Ile Glu Arg Asn Gly
     50                  55                  60

Thr Gly Thr His Thr Lys Pro Asn Gly Ile Val Tyr Thr Gly Ser Leu
 65                  70                  75                  80

Lys Asp Asp Lys Met Asn Gly Phe Gly Met Leu Glu His Phe Ser Gly
                 85                  90                  95
```

-continued

Ala Val Tyr Asn Gly Gln Phe Lys Asp Asn Met Phe His Gln Leu Gly
            100                 105                 110

Thr Tyr Thr Phe Pro Thr Gly Arg Lys Tyr Thr Gly Asn Phe Asn Glu
        115                 120                 125

Asn Ser Val Glu Gly Glu Gly Glu Tyr Thr Asp Val Gln Gly Leu Gln
    130                 135                 140

Trp Cys Gly Asn Phe Trp Phe Thr Ala Ala Pro Gly Leu Lys Leu Tyr
145                 150                 155                 160

Leu Tyr Met

<210> SEQ ID NO 81
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 81

Met Ala Gln Ala Leu Leu Val Pro Pro Gly Pro Glu Ser Phe Arg Leu
  1               5                  10                  15

Phe Thr Arg Glu Ser Leu Ala Ala Ile Glu Lys Arg Ala Ala Glu Glu
             20                  25                  30

Lys Ala Lys Lys Pro Lys Lys Glu Gln Asp Ile Asp Asp Glu Asn Lys
         35                  40                  45

Pro Lys Pro Asn Ser Asp Leu Glu Ala Gly Lys Asn Leu Pro Phe Ile
     50                  55                  60

Tyr Gly Asp Ile Pro Pro Glu Met Val Ser Glu Pro Leu Glu Asp Leu
 65                  70                  75                  80

Asp Pro Tyr Tyr Val Ser Lys Lys Thr Phe Val Val Leu Asn Lys Gly
                 85                  90                  95

Lys Ala Ile Phe Arg Phe Ser Ala Thr Ser Ala Leu Tyr Ile Leu Thr
            100                 105                 110

Pro Leu Asn Pro Val Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Leu Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Leu Ala Arg
                165                 170                 175

Gly Phe Cys Leu Glu Asp Phe Thr Phe Leu Arg Asp Pro Trp Asn Trp
            180                 185                 190

Leu Asp Phe Ser Val Ile Val Met Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ser Gln Trp Pro Pro Ser Asp Ser Ala Phe Glu
        275                 280                 285

-continued

```
Thr Asn Thr Thr Ser Tyr Phe Asn Gly Thr Met Asp Ser Asn Gly Thr
    290                 295                 300
Phe Val Asn Val Thr Met Ser Thr Phe Asn Trp Lys Asp Tyr Ile Ala
305                 310                 315                 320
Asp Asp Ser His Phe Tyr Val Leu Asp Gly Gln Lys Asp Pro Leu Leu
                325                 330                 335
Cys Gly Asn Gly Ser Asp Ala Gly Gln Cys Pro Glu Gly Tyr Ile Cys
            340                 345                 350
Val Lys Ala Gly Arg Asn Pro Asn Tyr Gly Tyr Thr Ser Phe Asp Thr
            355                 360                 365
Phe Ser Trp Ala Phe Leu Ser Leu Phe Arg Leu Met Thr Gln Asp Tyr
    370                 375                 380
Trp Glu Asn Leu Tyr Gln Leu Thr Leu Arg Ala Ala Gly Lys Thr Tyr
385                 390                 395                 400
Met Ile Phe Phe Val Leu Val Ile Phe Leu Gly Ser Phe Tyr Leu Val
                405                 410                 415
Asn Leu Ile Leu Ala Val Val Ala Met Ala Tyr Glu Glu Gln Asn Gln
            420                 425                 430
Ala Thr Leu Glu Glu Ala Glu Gln Lys Glu Ala Glu Phe Gln Gln Met
    435                 440                 445
Leu Glu Gln Leu Lys Lys Gln Gln Glu Glu Ala Gln Ala Val Ala Ala
    450                 455                 460
Ala Ser Ala Ala Ser Arg Asp Phe Ser Gly Ile Gly Gly Leu Gly Glu
465                 470                 475                 480
Leu Leu Glu Ser Ser Ser Glu Ala Ser Lys Leu Ser Ser Lys Ser Ala
            485                 490                 495
Lys Glu Trp Arg Asn Arg Arg Lys Lys Arg Arg Gln Arg Glu His Leu
            500                 505                 510
Glu Gly Asn His Arg Ala Asp Gly Asp Arg Phe Pro Lys Ser Glu Ser
            515                 520                 525
Glu Asp Ser Val Lys Arg Arg Ser Phe Leu Leu Ser Leu Asp Gly Asn
    530                 535                 540
Pro Leu Thr Gly Asp Lys Lys Leu Cys Ser Pro His Gln Ser Leu Leu
545                 550                 555                 560
Ser Ile Arg Gly Ser Leu Phe Ser Pro Arg Arg Asn Ser Lys Thr Ser
            565                 570                 575
Ile Phe Ser Phe Arg Gly Arg Ala Lys Asp Val Gly Ser Glu Asn Asp
            580                 585                 590
Phe Ala Asp Asp Glu His Ser Thr Phe Glu Asp Ser Glu Ser Arg Arg
    595                 600                 605
Asp Ser Leu Phe Val Pro His Arg Pro Gly Glu Arg Arg Asn Ser Asn
    610                 615                 620
Gly Thr Thr Thr Glu Thr Glu Val Arg Lys Arg Arg Leu Ser Ser Tyr
625                 630                 635                 640
Gln Ile Ser Met Glu Met Leu Glu Asp Ser Ser Gly Arg Gln Arg Ser
                645                 650                 655
Met Ser Ile Ala Ser Ile Leu Thr Asn Thr Met Glu Glu Leu Glu Glu
            660                 665                 670
Ser Arg Gln Lys Cys Pro Pro Cys Trp Tyr Arg Phe Ala Asn Val Phe
    675                 680                 685
Leu Ile Trp Asp Cys Cys Asp Ala Trp Leu Lys Val Lys His Leu Val
    690                 695                 700
```

```
Asn Leu Ile Val Met Asp Pro Phe Val Asp Leu Ala Ile Thr Ile Cys
705                 710                 715                 720

Ile Val Leu Asn Thr Leu Phe Met Ala Met Glu His Tyr Pro Met Thr
                725                 730                 735

Gln Gln Phe Ser Ser Val Leu Thr Val Gly Asn Leu Val Phe Thr Gly
                740                 745                 750

Ile Phe Thr Ala Glu Met Val Leu Lys Ile Ile Ala Met Asp Pro Tyr
            755                 760                 765

Tyr Tyr Phe Gln Glu Gly Trp Asn Ile Phe Asp Gly Ile Ile Val Ser
        770                 775                 780

Leu Ser Leu Met Glu Leu Gly Leu Ala Asn Val Gly Leu Ser Val
785                 790                 795                 800

Leu Arg Ser Phe Arg Leu Leu Arg Val Phe Lys Leu Ala Lys Ser Trp
                805                 810                 815

Pro Thr Leu Asn Met Leu Ile Lys Ile Ile Gly Asn Ser Val Gly Ala
                820                 825                 830

Leu Gly Asn Leu Thr Leu Val Leu Ala Ile Ile Val Phe Ile Phe Ala
            835                 840                 845

Val Val Gly Met Gln Leu Phe Gly Lys Ser Tyr Lys Glu Cys Val Cys
850                 855                 860

Lys Ile Asn Val Asp Cys Lys Leu Pro Arg Trp His Met Asn Asp Phe
865                 870                 875                 880

Phe His Ser Phe Leu Ile Val Phe Arg Val Leu Cys Gly Glu Trp Ile
                885                 890                 895

Glu Thr Met Trp Asp Cys Met Glu Val Ala Gly Gln Thr Met Cys Leu
                900                 905                 910

Ile Val Phe Met Leu Val Met Val Ile Gly Asn Leu Val Val Leu Asn
            915                 920                 925

Leu Phe Leu Ala Leu Leu Leu Ser Ser Phe Ser Ser Asp Asn Leu Ala
        930                 935                 940

Ala Thr Asp Asp Asp Asn Glu Met Asn Asn Leu Gln Ile Ala Val Gly
945                 950                 955                 960

Arg Met Gln Lys Gly Ile Asp Phe Val Lys Asn Lys Ile Arg Glu Cys
                965                 970                 975

Phe Arg Lys Ala Phe Phe Arg Lys Pro Lys Val Ile Glu Ile Gln Glu
            980                 985                 990

Gly Asn Lys Ile Asp Ser Cys Met Ser Asn Asn Thr Gly Ile Glu Ile
        995                 1000                1005

Ser Lys Glu Leu Asn Tyr Leu Lys Asp Gly Asn Gly Thr Thr Ser Gly
    1010                1015                1020

<210> SEQ ID NO 82
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 82

Met Asp Gln Ala Leu Leu Val Pro Pro Gly Pro Phe Ser Phe Arg Leu
 1               5                  10                  15

Phe Thr Arg Glu Ser Gly Ala Ala Ile Glu Lys Arg Ala Ala Glu His
                20                  25                  30

Lys Ala Lys Lys Pro Lys Lys Glu Gln Ile Ile Asp Asp Glu Asn Lys
            35                  40                  45
```

```
Pro Lys Pro Lys Ser Asp Leu Glu Ala Gly Lys Asn Leu Leu Phe Ile
 50                  55                  60

Tyr Gly Asp Ile Pro Pro Glu Asn Val Ser Glu Pro Leu Glu Asp Leu
 65                  70                  75                  80

Asp Gln Tyr Tyr Val Ser Lys Lys Thr Phe Val Arg Leu Asn Lys Gly
                 85                  90                  95

Lys Ala Ile Phe Arg Ser Ser Ala Thr Ser Ala Leu Tyr Ile Leu Val
            100                 105                 110

Pro Leu Asn Pro Val Arg Lys Ile Ala Trp Lys Ile Leu Val His Ser
        115                 120                 125

Leu Phe Ser Tyr Leu Ile Met Cys Thr Ile Leu Thr Asn Ala Val Phe
    130                 135                 140

Met Thr Leu Ser Asn Pro Pro Glu Trp Thr Lys Asn Val Glu Tyr Thr
145                 150                 155                 160

Phe Phe Gly Ile Tyr Thr Phe Glu Ser Leu Ile Gly Ile Leu Ala Arg
                165                 170                 175

Gly Phe Cys Leu Glu His Phe Thr Phe Leu Arg Asp Pro Trp Asn Ile
            180                 185                 190

Leu Asp Phe Ser Val Ile Val Met Ala Lys Val Thr Glu Phe Val Asp
        195                 200                 205

Leu Gly Asn Leu Ser Ala Leu Arg Thr Phe Arg Val Leu Met Ala Leu
    210                 215                 220

Lys Thr Ile Ser Val Ile Pro Asn Leu Lys Thr Ile Val Gly Ala Leu
225                 230                 235                 240

Ile Arg Ser Val Lys Lys Leu Ser Asp Val Met Ser Leu Thr Val Phe
                245                 250                 255

Cys Leu Ser Val Phe Thr Leu Ile Gly Leu Gln Leu Phe Met Gly Val
            260                 265                 270

Leu Arg Asn Lys Cys Ser Gln Trp Pro Trp Ser Asp Ser Ala Phe Glu
        275                 280                 285

Thr Asn Thr Tyr Ser Tyr Phe Asn Gly Thr Met Asp Ser Ala Gly Thr
    290                 295                 300

Phe Val Asn Val Thr Met Ser Asp Phe Asn Trp Lys Asp Tyr Ile Ala
305                 310                 315                 320

Asp Glu Ser His Phe Tyr Val Leu Asp Gly Gln Phe Asp Pro Leu Leu
                325                 330                 335

Cys Gly Asn Gly Ser Gly Ala Gly Gln Cys Pro Glu Gly Tyr Ile His
            340                 345                 350

Val Lys Ala Gly Arg Asn Pro Asn Tyr Ile Tyr Thr Ser Phe Asp Thr
        355                 360                 365

Phe Ser Trp Lys Phe Leu Ser Leu Phe Arg Leu Met Thr Leu Asp Tyr
    370                 375                 380

Trp Glu Asn Leu Tyr Gln Leu Met Leu Arg Ala Ala Gly Lys Thr Tyr
385                 390                 395                 400

Met Asn Phe Phe Val Leu Val Ile Phe Leu Gly Gln Phe Tyr Leu Val
                405                 410                 415

Asn Leu Ile Leu Ala Arg Val Ala Met Ala Tyr Glu Glu Gln Asn Ser
            420                 425                 430

Ala Thr Leu Glu Glu Ala Glu Gln Lys Thr Ala Glu Phe Gln Gln Met
        435                 440                 445

Leu Glu Gln Val Lys Lys Gln Gln Glu Glu Ala Gln Ala Trp Ala Ala
    450                 455                 460
```

-continued

```
Ala Ser Ala Ala Ser Arg Asp Tyr Ser Gly Ile Gly Gly Leu Gly Glu
465                 470                 475                 480

Leu Ala Glu Ser Ser Ser Glu Ala Ser Lys Leu Asp Ser Lys Ser Ala
                485                 490                 495

Lys Glu Trp Arg Asn Glu Arg Lys Lys Arg Gln Arg Glu His Phe
            500                 505                 510

Glu Gly Asn His Arg Ala Asp Gly Asp Gly Phe Pro Lys Ser Glu Ser
                515                 520                 525

Glu Asp Ser His Lys Arg Arg Ser Phe Leu Leu Ser Leu Ile Gly Asn
            530                 535                 540

Pro Leu Thr Gly Asp Lys Lys Cys Ser Pro His Gln Ser Leu Leu
545                 550                 555                 560

Ser Leu Arg Gly Ser Leu Phe Ser Pro Arg Met Ser Lys Thr Ser
                565                 570                 575

Ile Phe Ser Phe Arg Asn Arg Ala Lys Asp Val Gly Ser Glu Asn Gln
                580                 585                 590

Phe Ala Asp Asp Glu His Ser Thr Phe Arg Asp Ser Glu Ser Arg Arg
                595                 600                 605

Asp Ser Leu Ser Val Pro His Arg Pro Gly Glu Arg Arg Thr Ser Asn
                610                 615                 620

Gly Thr Thr Thr Glu Thr Glu Trp Arg Lys Arg Arg Leu Ser Ser Tyr
625                 630                 635                 640

Gln Tyr Ser Met Glu Met Leu Glu Asp Ser Ala Arg Gln Arg Ser
                645                 650                 655

Met Ser Ile Ala Ser Asp Leu Thr Asn Thr Met Glu Glu Leu Glu Phe
                660                 665                 670

Ser Arg Gln Lys Cys Pro Pro Cys Trp Gly Arg Phe Ala Asn Val Phe
                675                 680                 685

Leu Ile Trp His Cys Cys Asp Ala Trp Leu Lys Val Lys Ile Leu Val
                690                 695                 700

Asn Leu Ile Val Met Asp Pro Lys Val Asp Leu Ala Ile Thr Ile Cys
705                 710                 715                 720

Ile Leu Leu Asn Thr Leu Phe Met Ala Met Glu Met Tyr Pro Met Thr
                725                 730                 735

Gln Gln Phe Ser Ser Asn Leu Thr Val Gly Asn Leu Val Phe Thr Gln
                740                 745                 750

Ile Phe Thr Ala Glu Met Val Leu Lys Arg Ile Ala Met Asp Pro Tyr
                755                 760                 765

Tyr Tyr Phe Ser Glu Gly Trp Asn Ile Phe Asp Gly Ile Thr Val Ser
                770                 775                 780

Leu Ser Leu Met Glu Leu Gly Val Ala Asn Val Glu Gly Leu Ser Val
785                 790                 795                 800

Leu Trp Ser Phe Arg Leu Leu Arg Val Phe Lys Tyr Ala Lys Ser Trp
                805                 810                 815

Pro Thr Leu Asn Met Ala Ile Lys Ile Gly Asn Ser Val Gly Asp
                820                 825                 830

Leu Gly Asn Leu Thr Leu Val Leu Ala Glu Ile Val Phe Ile Phe Ala
                835                 840                 845

Val Val Gly Phe Gln Leu Phe Gly Lys Ser Tyr Lys Glu Gly Val Cys
                850                 855                 860

Lys Ile Asn Val Asp Cys Lys His Pro Arg Trp His Met Asn Asp Phe
865                 870                 875                 880

Phe Ile Ser Phe Leu Ile Val Phe Arg Val Leu Lys Gly Glu Trp Ile
```

```
                    885              890              895
Glu Thr Met Trp Asp Leu Met Glu Val Ala Gly Gln Thr Met Cys Met
                900              905              910
Ile Val Phe Met Leu Val Met Val Ile Asn Asn Leu Val Val Leu Asn
            915              920              925
Leu Phe Leu Gln Leu Leu Leu Ser Ser Phe Ser Ser Asp Arg Leu Ala
        930              935              940
Ala Thr Asp Asp Asn Glu Ser Asn Asn Leu Gln Ile Ala Val Gly
945              950              955              960
Arg Thr Gln Lys Gly Ile Asp Phe Val Lys Asn Val Ile Arg Glu Cys
                965              970              975
Phe Arg Lys Ala Phe Trp Arg Lys Pro Lys Val Ile Glu Ile Gln Tyr
            980              985              990
Gly Asn Lys Ile Asp Ser Cys Met Ser Ala Asn Thr Gly Ile Glu Ile
            995             1000             1005
Ser Lys Glu Asp Asn Tyr Leu Lys Asp Gly Asn Gly Thr Glu Ser Gly
   1010             1015             1020

<210> SEQ ID NO 83
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 83

Met Ala Ala Ala Leu Leu Val Pro Pro Gly Pro Glu Asp Phe Arg Leu
  1               5                  10                  15
Phe Thr Arg Glu Ser Leu Glu Ala Ile Glu Lys Arg Ala Ala Glu Glu
                 20                  25                  30
Phe Ala Lys Lys Pro Lys Lys Glu Gln Asp Gly Asp Asp Glu Asn Lys
             35                  40                  45
Pro Lys Pro Asn His Asp Leu Glu Ala Gly Lys Asn Leu Pro Ile Ile
         50                  55                  60
Tyr Gly Asp Ile Pro Pro Glu Met Lys Ser Glu Pro Leu Glu Asp Leu
 65                  70                  75                  80
Asp Pro Leu Tyr Val Ser Lys Lys Thr Phe Val Val Met Asn Lys Gly
                 85                  90                  95
Lys Ala Ile Phe Arg Phe Asn Ala Thr Ser Ala Leu Tyr Ile Leu Thr
                100                 105                 110
Gln Leu Asn Pro Val Arg Lys Ile Ala Ile Arg Ile Leu Val His Ser
            115                 120                 125
Leu Phe Ser Met Ser Ile Met Cys Thr Ile Leu Thr Asn Cys Thr Phe
        130                 135                 140
Met Thr Leu Ser Asn Pro Pro Asp Val Thr Lys Asn Val Glu Tyr Thr
145                 150                 155                 160
Phe Thr Trp Ile Tyr Thr Phe Glu Ser Leu Ile Lys Tyr Leu Ala Arg
                165                 170                 175
Gly Phe Cys Leu Glu Asp Ala Thr Phe Leu Arg Asp Pro Trp Asn Trp
            180                 185                 190
Asp Asp Phe Ser Val Ile Val Met Ala Tyr Glu Thr Glu Phe Val Asp
        195                 200                 205
Leu Gly Asn Val Phe Ala Leu Arg Thr Phe Arg Val Leu Arg Gly Leu
    210                 215                 220
```

-continued

```
Lys Thr Ile Ser Val Ile Pro Gly His Lys Thr Ile Val Gly Ala Leu
225                 230                 235                 240

Ile Gln Ile Val Lys Lys Leu Ser Asp Val Met Ile Lys Thr Val Phe
            245                 250                 255

Cys Leu Ser Val Phe Ala Met Ile Gly Leu Gln Leu Phe Met Gly Asn
                260                 265                 270

Asn Arg Asn Lys Cys Ser Gln Trp Pro Pro Gln Asp Ser Ala Phe Glu
        275                 280                 285

Thr Asn Thr Thr Arg Tyr Phe Asn Gly Thr Met Asp Ser Asn Ser Thr
    290                 295                 300

Phe Val Asn Val Thr Met Ser Thr Thr Asn Trp Lys Asp Tyr Ile Ala
305                 310                 315                 320

Asp Asp Val His Phe Tyr Val Leu Asp Gly Gln Lys Trp Pro Leu Leu
                325                 330                 335

Cys Gly Asn Gly Ser Asp Tyr Gly Gln Cys Pro Glu Gly Tyr Ile Cys
                340                 345                 350

Val Lys Ala Gly Arg Asn Pro Asn Tyr Gly Trp Thr Ser Phe Asp Thr
            355                 360                 365

Phe Ser Trp Ala Tyr Leu Ser Leu Phe Arg Leu Met Thr Gln Ala Tyr
370                 375                 380

Trp Glu Asn Leu Tyr Gln Leu Thr Asp Arg Ala Ala Gly Lys Thr Tyr
385                 390                 395                 400

Met Ile Glu Phe Val Leu Val Ile Phe Leu Gly Ser Phe Tyr Leu Val
                405                 410                 415

Asn Leu Ile Leu Ala Val Gly Ala Met Ala Tyr Glu Glu Gln Asn Gln
            420                 425                 430

His Thr Leu Glu Glu Ala Glu Gln Lys Glu Ile Glu Phe Gln Gln Met
        435                 440                 445

Leu Glu Gln Leu Lys Gln Gln Glu Ala Gln Ala Val Met Ala
    450                 455                 460

Ala Ser Ala Ala Ser Arg Asp Phe Asn Gly Ile Gly Gly Leu Gly Glu
465                 470                 475                 480

Leu Leu Gln Ser Ser Ser Glu Ala Ser Lys Leu Ser Arg Lys Ser Ala
                485                 490                 495

Lys Glu Trp Arg Asn Arg Ser Lys Lys Arg Arg Gln Arg Glu His Leu
            500                 505                 510

Thr Gly Asn His Arg Ala Asp Gly Asp Arg Val Pro Lys Ser Glu Ser
        515                 520                 525

Glu Asp Ser Val Trp Arg Arg Ser Phe Leu Leu Ser Leu Asp Tyr Asn
530                 535                 540

Pro Leu Thr Gly Asp Lys Lys Leu Ala Ser Pro His Gln Ser Leu Leu
545                 550                 555                 560

Ser Ile Asp Gly Ser Leu Phe Ser Pro Arg Arg Asn Glu Lys Thr Ser
                565                 570                 575

Ile Phe Ser Phe Arg Gly Phe Ala Lys Asp Val Gly Ser Glu Asn Asp
            580                 585                 590

Gly Ala Asp Asp Glu His Ser Thr Phe Glu His Ser Glu Ser Arg Arg
        595                 600                 605

Asp Ser Leu Phe Ile Pro His Arg Pro Gly Glu Arg Arg Asn Lys Asn
    610                 615                 620

Gly Thr Thr Thr Glu Thr Glu Val Leu Lys Arg Arg Leu Ser Ser Tyr
625                 630                 635                 640

Gln Ile Met Met Glu Met Leu Glu Asp Ser Ser Gly Asn Gln Arg Ser
```

```
                   645                 650                 655
Met Ser Ile Ala Ser Ile Gln Thr Asn Thr Met Glu Glu Leu Glu Glu
                    660                 665                 670

Arg Arg Gln Lys Cys Pro Pro Cys Trp Tyr Ser Phe Ala Asn Val Phe
                675                 680                 685

Leu Ile Trp Asp Thr Cys Asp Ala Trp Leu Lys Val Lys His Val Val
            690                 695                 700

Asn Leu Ile Val Met Asp Pro Phe Trp Asp Leu Ala Ile Thr Ile Cys
705                 710                 715                 720

Ile Val Tyr Asn Thr Leu Phe Met Ala Met Glu His Ala Pro Met Thr
                    725                 730                 735

Gln Gln Phe Ser Ser Val Asp Thr Val Gly Asn Leu Val Phe Thr Gly
                740                 745                 750

Glu Phe Thr Ala Glu Met Val Leu Lys Ile Phe Ala Met Asp Pro Tyr
            755                 760                 765

Tyr Tyr Phe Gln Gly Gly Trp Asn Ile Phe Asp Gly Ile Ile His Ser
        770                 775                 780

Leu Ser Leu Met Glu Leu Gly Leu Ile Asn Val Glu Gly Leu Ser Val
785                 790                 795                 800

Leu Arg Lys Phe Arg Leu Leu Arg Val Phe Lys Leu Leu Lys Ser Trp
                    805                 810                 815

Pro Thr Leu Asn Met Leu Met Lys Ile Ile Gly Asn Ser Val Gly Ala
                820                 825                 830

Asn Gly Asn Leu Thr Leu Val Leu Ala Ile Gln Val Phe Ile Phe Ala
            835                 840                 845

Val Val Gly Met Arg Leu Phe Gly Lys Ser Tyr Lys Glu Cys Ser Cys
        850                 855                 860

Lys Ile Asn Val Asp Cys Lys Leu Thr Arg Trp His Met Asn Asp Phe
865                 870                 875                 880

Phe His Val Phe Leu Ile Val Phe Arg Val Leu Cys Trp Glu Trp Ile
                    885                 890                 895

Glu Thr Met Trp Asp Cys Tyr Glu Val Ala Gly Gln Thr Met Cys Leu
                900                 905                 910

Ala Val Phe Met Leu Val Met Val Ile Gly Asp Leu Val Val Leu Asn
            915                 920                 925

Leu Phe Leu Ala Glu Leu Leu Ser Ser Phe Ser Ser Asp Asn Phe Ala
        930                 935                 940

Ala Thr Asp Asp Asp Asn Glu Met Gly Asn Leu Gln Ile Ala Val Gly
945                 950                 955                 960

Arg Met His Lys Gly Ile Asp Phe Val Lys Asn Lys Arg Glu Cys
                    965                 970                 975

Phe Arg Lys Ala Phe Phe Leu Pro Lys Val Ile Glu Ile Gln Glu
                980                 985                 990

Met Asn Lys Ile Asp Ser Cys Met Ser Asn Gln Thr Gly Ile Glu Ile
            995                 1000                1005

Ser Lys Glu Leu Arg Tyr Leu Asp Gly Asn Gly Thr Thr Thr Gly
     1010                1015                1020
```

<210> SEQ ID NO 84
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

```
<400> SEQUENCE: 84

Met Ala Gln Asp Leu Leu Val Pro Pro Gly Pro Glu Ser Glu Arg Leu
 1               5                  10                  15

Phe Thr Arg Glu Ser Leu Ala Phe Ile Glu Lys Arg Ala Ala Glu Glu
             20                  25                  30

Lys Gly Lys Lys Pro Lys Lys Glu Gln Asp Ile His Asp Glu Asn Lys
         35                  40                  45

Pro Lys Pro Asn Ser Ile Leu Glu Ala Gly Lys Asn Leu Pro Phe Lys
     50                  55                  60

Tyr Gly Asp Ile Pro Pro Glu Met Val Leu Glu Pro Leu Glu Asp Leu
 65                  70                  75                  80

Asp Pro Tyr Met Val Ser Lys Lys Thr Phe Val Val Leu Gln Lys Gly
                 85                  90                  95

Lys Ala Ile Phe Arg Phe Ser Arg Thr Ser Ala Leu Tyr Ile Leu Thr
            100                 105                 110

Pro Ser Asn Pro Val Arg Lys Ile Ala Ile Lys Thr Leu Val His Ser
            115                 120                 125

Leu Phe Ser Met Leu Val Met Cys Thr Ile Leu Thr Asn Cys Val Trp
    130                 135                 140

Met Thr Leu Ser Asn Pro Pro Asp Trp Tyr Lys Asn Val Glu Tyr Thr
145                 150                 155                 160

Phe Thr Gly Ala Tyr Thr Phe Glu Ser Leu Ile Lys Ile Asp Ala Arg
                165                 170                 175

Gly Phe Cys Leu Glu Asp Phe Glu Phe Leu Arg Asp Pro Trp Asn Trp
            180                 185                 190

Leu Phe Phe Ser Val Ile Val Met Ala Tyr Val Gly Glu Phe Val Asp
    195                 200                 205

Leu Gly Asn Val Ser His Leu Arg Thr Phe Arg Val Leu Arg Ala Ile
    210                 215                 220

Lys Thr Ile Ser Val Ile Pro Gly Leu Leu Thr Ile Val Gly Ala Leu
225                 230                 235                 240

Ile Gln Ser Met Lys Lys Leu Ser Asp Val Met Ile Leu Asn Val Phe
                245                 250                 255

Cys Leu Ser Val Phe Ala Leu Gln Gly Leu Gln Leu Phe Met Gly Asn
            260                 265                 270

Leu Ser Asn Lys Cys Ser Gln Trp Pro Pro Ser Thr Ser Ala Phe Glu
    275                 280                 285

Thr Asn Thr Thr Ser Val Phe Asn Gly Thr Met Asp Ser Asn Gly Trp
290                 295                 300

Phe Val Asn Val Thr Met Ser Thr Phe Tyr Trp Lys Asp Tyr Ile Ala
305                 310                 315                 320

Asp Asp Ser Ala Phe Tyr Val Leu Asp Gly Gln Lys Asp Leu Leu
                325                 330                 335

Cys Gly Asn Gly Ser Asp Ala Glu Gln Cys Pro Glu Gly Tyr Ile Cys
            340                 345                 350

Val Phe Ala Gly Arg Asn Pro Asn Tyr Gly Tyr Gly Ser Phe Asp Thr
            355                 360                 365

Phe Ser Trp Ala Phe His Ser Leu Phe Arg Leu Met Thr Gln Asp Ile
    370                 375                 380

Trp Glu Asn Leu Tyr Gln Leu Thr Leu Lys Ala Ala Gly Lys Thr Tyr
385                 390                 395                 400

Met Ile Phe Leu Val Leu Val Ile Phe Leu Gly Ser Phe Met Leu Val
```

-continued

```
                    405                 410                 415
Asn Leu Ile Leu Ala Val Val Asn Met Ala Tyr Glu Glu Gln Asn Gln
                420                 425                 430
Ala Gln Leu Glu Glu Ala Glu Gln Lys Glu Ala Arg Phe Gln Gln Met
            435                 440                 445
Leu Glu Gln Leu Lys Ser Gln Gln Glu Glu Ala Gln Ala Val Ala Thr
        450                 455                 460
Ala Ser Ala Ala Ser Arg Asp Phe Ser Val Ile Gly Gly Leu Gly Glu
465                 470                 475                 480
Leu Leu Glu Trp Ser Ser Glu Ala Ser Lys Leu Ser Ser Tyr Ser Ala
                485                 490                 495
Lys Glu Trp Arg Asn Arg Arg Ala Lys Arg Gln Arg Glu His Leu
                500                 505                 510
Glu Asp Asn His Arg Ala Asp Gly Asp Arg Phe Glu Lys Ser Glu Ser
            515                 520                 525
Glu Asp Ser Val Lys Phe Arg Ser Phe Leu Leu Ser Leu Asp Gly Gly
        530                 535                 540
Pro Leu Thr Gly Asp Lys Lys Leu Cys His Pro His Gln Ser Leu Leu
545                 550                 555                 560
Ser Ile Arg Ile Ser Leu Phe Ser Pro Arg Arg Asn Ser Leu Thr Ser
                565                 570                 575
Ile Phe Ser Phe Arg Gly Arg Met Lys Asp Val Gly Ser Glu Asn Asp
            580                 585                 590
Phe Asn Asp Asp Glu His Ser Thr Phe Glu Asp Gln Glu Ser Arg Arg
        595                 600                 605
Asp Ser Leu Phe Val Arg His Arg Pro Gly Glu Arg Arg Asn Ser Ser
610                 615                 620
Gly Thr Thr Thr Glu Thr Glu Val Arg Thr Arg Arg Leu Ser Ser Tyr
625                 630                 635                 640
Gln Ile Ser Val Glu Met Leu Glu Asp Ser Ser Gly Arg Trp Arg Ser
                645                 650                 655
Met Ser Ile Ala Ser Ile Leu Tyr Asn Thr Met Glu Glu Leu Glu Glu
            660                 665                 670
Ser Ala Gln Lys Cys Pro Pro Cys Trp Tyr Arg Asp Ala Asn Val Phe
        675                 680                 685
Leu Ile Trp Asp Cys Glu Asp Ala Trp Leu Lys Val Lys His Leu Phe
    690                 695                 700
Asn Leu Ile Val Met Asp Pro Phe Val Gly Leu Ala Ile Thr Ile Cys
705                 710                 715                 720
Ile Val Leu His Thr Leu Phe Met Ala Met Glu His Tyr Ile Met Thr
                725                 730                 735
Gln Gln Phe Ser Ser Val Leu Lys Val Gly Asn Leu Val Phe Thr Gly
            740                 745                 750
Ile Leu Thr Ala Glu Met Val Leu Lys Ile Ile Met Met Asp Pro Tyr
        755                 760                 765
Tyr Tyr Phe Gln Glu Asn Trp Asn Ile Phe Asp Gly Ile Ile Val Gln
    770                 775                 780
Leu Ser Leu Met Glu Leu Gly Leu Ala Arg Val Glu Gly Leu Ser Val
785                 790                 795                 800
Leu Arg Ser Ser Arg Leu Leu Arg Val Phe Lys Leu Ala Thr Ser Trp
                805                 810                 815
Pro Thr Leu Asn Met Leu Ile Val Ile Gly Asn Ser Val Gly Ala
            820                 825                 830
```

```
Leu Trp Asn Leu Thr Leu Val Leu Ala Ile Ile Tyr Phe Ile Phe Ala
            835                 840                 845

Val Val Gly Met Gln Ala Phe Gly Lys Ser Tyr Lys Glu Cys Val Asp
    850                 855                 860

Lys Ile Asn Val Asp Cys Lys Leu Pro Glu Trp His Met Asn Asp Phe
865                 870                 875                 880

Phe His Ser Gly Leu Ile Val Phe Arg Val Leu Cys Gly His Trp Ile
                885                 890                 895

Glu Thr Met Trp Asp Cys Met Ile Val Ala Gly Gln Thr Met Cys Leu
            900                 905                 910

Ile Lys Phe Met Leu Val Met Val Ile Gly Asn Met Val Val Leu Asn
            915                 920                 925

Leu Phe Leu Ala Leu Asn Leu Ser Ser Phe Ser Ser Asp Asn Leu Gln
    930                 935                 940

Ala Thr Asp Asp Asp Asn Glu Met Asn Arg Leu Gln Ile Ala Val Gly
945                 950                 955                 960

Arg Met Gln Ser Gly Ile Asp Phe Val Lys Asn Lys Ile Thr Glu Cys
                965                 970                 975

Phe Arg Lys Ala Phe Phe Arg Val Pro Lys Val Ile Glu Ile Gln Glu
            980                 985                 990

Gly Trp Lys Ile Asp Ser Cys Met Ser Asn Asn Tyr Gly Ile Glu Ile
            995                 1000                1005

Ser Lys Glu Leu Asn Ala Leu Lys Asp Gly Asn Gly Thr Thr Ser Asp
    1010                1015                1020

<210> SEQ ID NO 85
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 85

Met Ala Gln Ala Ala Leu Val Pro Pro Gly Pro Glu Ser Phe Asp Leu
1               5                   10                  15

Phe Thr Arg Glu Ser Leu Ala Ala Glu Glu Lys Arg Ala Ala Glu Glu
            20                  25                  30

Lys Ala Phe Lys Pro Lys Lys Glu Gln Asp Ile Asp Gly Glu Asn Lys
        35                  40                  45

Pro Lys Pro Asn Ser Asp His Glu Ala Gly Lys Asn Leu Pro Phe Ile
    50                  55                  60

Ile Gly Asp Ile Pro Pro Glu Met Val Ser Lys Pro Leu Glu Asp Leu
65                  70                  75                  80

Asp Pro Tyr Tyr Leu Ser Lys Lys Thr Phe Val Val Leu Asn Met Gly
                85                  90                  95

Lys Ala Ile Phe Arg Phe Ser Ala Asn Ser Ala Leu Tyr Ile Leu Thr
            100                 105                 110

Pro Leu Gln Pro Val Arg Lys Ile Ala Ile Lys Ile Arg Val His Ser
        115                 120                 125

Leu Phe Ser Met Leu Ile Ser Cys Thr Ile Leu Thr Asn Cys Val Phe
    130                 135                 140

Thr Thr Leu Ser Asn Pro Pro Asp Trp Thr Val Asn Val Glu Tyr Thr
145                 150                 155                 160

Phe Thr Gly Ile Trp Thr Phe Glu Ser Leu Ile Lys Ile Leu Tyr Arg
```

```
                  165                 170                 175
Gly Phe Cys Leu Glu Asp Phe Thr Ala Leu Arg Asp Pro Trp Asn Trp
                180                 185                 190

Leu Asp Asp Ser Val Ile Val Met Ala Tyr Val Thr Glu Phe Val Asp
            195                 200                 205

Leu Gly Asn Val Ser Ala Phe Arg Thr Phe Arg Val Leu Arg Ala Leu
        210                 215                 220

Gly Thr Ile Ser Val Ile Pro Gly Leu Lys His Ile Val Gly Ala Leu
225                 230                 235                 240

Ile Gln Ser Val Ile Lys Leu Ser Asp Val Met Ile Leu Thr Lys Phe
                245                 250                 255

Cys Leu Ser Val Phe Ala Leu Ile Leu Leu Gln Leu Phe Met Gly Asn
            260                 265                 270

Leu Arg Met Lys Cys Ser Gln Trp Pro Pro Ser Asp Asn Ala Phe Glu
        275                 280                 285

Thr Asn Thr Thr Ser Tyr Gln Asn Gly Thr Met Asp Ser Asn Gly Thr
    290                 295                 300

Arg Val Asn Val Thr Met Ser Thr Phe Asn Ser Lys Asp Tyr Ile Ala
305                 310                 315                 320

Asp Asp Ser His Thr Tyr Val Leu Asp Gly Gln Lys Asp Pro Val Leu
                325                 330                 335

Cys Gly Asn Gly Ser Asp Ala Gly Trp Cys Pro Glu Gly Tyr Ile Cys
            340                 345                 350

Val Lys Tyr Gly Arg Asn Pro Asn Tyr Gly Tyr Thr Ala Phe Asp Thr
        355                 360                 365

Phe Ser Trp Ala Phe Leu Asp Leu Phe Arg Leu Met Thr Gln Asp Tyr
    370                 375                 380

Glu Glu Asn Leu Tyr Gln Leu Thr Leu Arg Phe Ala Gly Lys Thr Tyr
385                 390                 395                 400

Met Ile Phe Phe Gly Leu Val Ile Phe Leu Gly Ser Phe Tyr His Val
                405                 410                 415

Asn Leu Ile Leu Ala Val Val Ala Ile Ala Tyr Glu Glu Gln Asn Gln
            420                 425                 430

Ala Thr Lys Glu Glu Ala Glu Gln Lys Glu Ala Glu Leu Gln Gln Met
        435                 440                 445

Leu Glu Gln Leu Lys Lys Met Gln Glu Glu Ala Gln Ala Val Ala Ala
    450                 455                 460

Asn Ser Ala Ala Ser Arg Asp Phe Ser Gly Gln Gly Leu Gly Glu
465                 470                 475                 480

Leu Leu Glu Ser Arg Ser Glu Ala Ser Lys Leu Ser Ser Lys Thr Ala
                485                 490                 495

Lys Glu Trp Arg Asn Arg Arg Lys Val Arg Arg Gln Arg Glu His Leu
            500                 505                 510

Glu Gly Trp His Arg Ala Asp Gly Asp Arg Phe Pro Tyr Ser Glu Ser
        515                 520                 525

Glu Asp Ser Val Lys Arg Ala Ser Phe Leu Leu Ser Leu Asp Gly Asn
    530                 535                 540

Asp Leu Thr Gly Asp Lys Lys Leu Cys Ser Glu His Gln Ser Leu Leu
545                 550                 555                 560

Ser Ile Arg Gly Phe Leu Phe Ser Pro Arg Arg Asn Ser Lys Gly Ser
                565                 570                 575

Ile Phe Ser Phe Arg Gly Arg Ala His Asp Val Gly Ser Glu Asn Asp
            580                 585                 590
```

```
Phe Ala Ile Asp Glu His Ser Thr Phe Glu Asp Ser Lys Ser Arg Arg
            595                 600                 605

Asp Ser Leu Phe Val Pro Leu Arg Pro Gly Glu Arg Arg Asn Ser Asn
610                 615                 620

Met Thr Thr Thr Glu Thr Glu Val Arg Lys Asn Arg Leu Ser Ser Tyr
625                 630                 635                 640

Gln Ile Ser Met Gln Met Leu Glu Asp Ser Ser Gly Arg Gln Ser Ser
            645                 650                 655

Met Ser Ile Ala Ser Ile Leu Thr Thr Thr Met Glu Glu Leu Glu Glu
            660                 665                 670

Ser Arg Val Lys Cys Pro Pro Cys Trp Tyr Arg Phe Trp Asn Val Phe
            675                 680                 685

Leu Ile Trp Asp Cys Cys Tyr Ala Trp Leu Lys Val Lys His Leu Val
            690                 695                 700

Ala Leu Ile Val Met Asp Pro Phe Val Asp Ala Ile Thr Ile Cys
705                 710                 715                 720

Ile Val Leu Asn Glu Leu Phe Met Ala Met Glu His Tyr Pro Phe Thr
            725                 730                 735

Gln Gln Phe Ser Ser Val Leu Thr Gly Gly Asn Leu Val Phe Thr Gly
            740                 745                 750

Ile Phe His Ala Glu Met Val Leu Lys Ile Ile Ala Ile Asp Pro Tyr
            755                 760                 765

Tyr Tyr Phe Gln Glu Gly Lys Asn Ile Phe Asp Gly Ile Ile Val Ser
            770                 775                 780

Met Ser Leu Met Glu Leu Gly Leu Ala Asn Asn Glu Gly Leu Ser Val
785                 790                 795                 800

Leu Arg Ser Phe Gln Leu Leu Arg Val Phe Lys Leu Ala Lys Arg Trp
            805                 810                 815

Pro Thr Leu Asn Met Leu Ile Lys Ser Ile Gly Asn Ser Val Gly Ala
            820                 825                 830

Leu Gly Thr Leu Thr Leu Val Leu Ala Ile Ile Val Ile Phe Ala
            835                 840                 845

Val Val Gly Met Gln Leu Trp Gly Lys Ser Tyr Lys Glu Cys Val Cys
850                 855                 860

Tyr Ile Asn Val Asp Cys Lys Leu Pro Arg Ala His Met Asn Asp Phe
865                 870                 875                 880

Phe His Ser Phe Asp Ile Val Phe Arg Val Leu Cys Gly Glu Glu Ile
            885                 890                 895

Glu Thr Met Trp Asp Cys Met Glu Phe Ala Gly Gln Thr Met Cys Leu
            900                 905                 910

Ile Val Gly Met Leu Val Met Val Ile Gly Asn Leu His Val Leu Asn
            915                 920                 925

Leu Phe Leu Ala Leu Leu Ile Ser Ser Phe Ser Ser Asp Asn Leu Ala
            930                 935                 940

Lys Thr Asp Asp Asp Asn Glu Met Asn Asn Met Gln Ile Ala Val Gly
945                 950                 955                 960

Arg Met Gln Lys Asn Ile Asp Phe Val Lys Asn Lys Ile Arg Gln Cys
            965                 970                 975

Phe Arg Lys Ala Phe Phe Arg Lys Arg Lys Val Ile Glu Ile Gln Glu
            980                 985                 990

Gly Asn Ser Ile Asp Ser Cys Met Ser Asn Asn Thr Thr Ile Glu Ile
            995                 1000                1005
```

```
Ser Lys Glu Leu Asn Tyr Val Lys Asp Gly Asn Gly Thr Thr Ser Gly
    1010                1015                1020

<210> SEQ ID NO 86
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 86

Met Ala Gln Ala Leu Ala Val Pro Pro Gly Pro Ser Phe Arg Asp
 1               5                  10                  15

Phe Thr Arg Glu Ser Leu Ala Ala Ile Phe Lys Arg Ala Ala Glu
                20                  25                  30

Lys Ala Lys Gly Pro Lys Lys Glu Gln Asp Ile Asp Asp His Asn Lys
                35                  40                  45

Pro Lys Pro Asn Ser Asp Leu Ile Ala Gly Lys Asn Leu Pro Phe Ile
    50                  55                  60

Tyr Lys Asp Ile Pro Pro Glu Met Val Ser Leu Leu Glu Asp Leu
 65                  70                  75                  80

Asp Pro Tyr Tyr Val Met Lys Lys Thr Phe Val Val Leu Asn Lys Asn
                85                  90                  95

Lys Ala Ile Phe Arg Phe Ser Ala Thr Gln Ala Leu Tyr Ile Leu Thr
                100                 105                 110

Pro Leu Asn Arg Val Arg Lys Ile Ala Ile Lys Ile Leu Ser His Ser
                115                 120                 125

Leu Phe Ser Met Leu Ile Met Thr Thr Ile Leu Thr Asn Cys Val Phe
    130                 135                 140

Met Val Leu Ser Asn Pro Pro Asp Trp Thr Lys Trp Val Glu Tyr Thr
145                 150                 155                 160

Phe Thr Gly Ile Tyr Tyr Phe Glu Ser Leu Ile Lys Ile Leu Ala Ala
                165                 170                 175

Gly Phe Cys Leu Glu Asp Phe Thr Phe Asp Arg Asp Pro Trp Asn Trp
                180                 185                 190

Leu Asp Phe Glu Val Ile Val Met Ala Tyr Val Thr Glu Gly Val Asp
                195                 200                 205

Leu Gly Asn Val Ser Ala Leu His Thr Phe Arg Val Leu Arg Ala Leu
    210                 215                 220

Lys Ile Ile Ser Val Ile Pro Gly Leu Lys Thr Lys Val Gly Ala Leu
225                 230                 235                 240

Ile Gln Ser Val Lys Leu Leu Ser Asp Val Met Ile Leu Thr Val Met
                245                 250                 255

Cys Leu Ser Val Phe Ala Leu Ile Gly Asn Gln Leu Phe Met Gly Asn
                260                 265                 270

Leu Arg Asn Gln Cys Ser Gln Trp Pro Pro Ser Asp Ser Arg Phe Glu
    275                 280                 285

Thr Asn Thr Thr Ser Tyr Phe Ser Gly Thr Met Asp Ser Asn Gly Thr
290                 295                 300

Phe Thr Asn Val Thr Met Ser Thr Phe Asn Trp Val Asp Tyr Ile Ala
305                 310                 315                 320

Asp Asp Ser His Phe Trp Val Leu Asp Gly Gln Lys Asp Pro Leu Tyr
                325                 330                 335

Cys Gly Asn Gly Ser Asp Ala Gly Gln Ala Pro Glu Gly Tyr Ile Cys
                340                 345                 350
```

-continued

```
Val Lys Ala Asp Arg Asn Pro Asn Tyr Gly Tyr Thr Ser Glu Asp Thr
        355                 360                 365
Phe Ser Trp Ala Phe Leu Ser Phe Phe Arg Leu Met Thr Gln Asp Tyr
    370                 375                 380
Trp Gly Asn Leu Tyr Gln Leu Thr Leu Arg Ala His Gly Lys Thr Tyr
385                 390                 395                 400
Met Ile Phe Phe Val Ile Val Ile Phe Leu Gly Ser Phe Tyr Leu Lys
                405                 410                 415
Asn Leu Ile Leu Ala Val Val Ala Met Leu Tyr Glu Glu Gln Asn Gln
            420                 425                 430
Ala Thr Leu Met Glu Ala Glu Gln Lys Glu Ala Glu Phe Asn Gln Met
        435                 440                 445
Leu Glu Gln Leu Lys Lys Gln Arg Glu Glu Ala Gln Ala Val Ala Ala
    450                 455                 460
Ala Thr Ala Ala Ser Arg Asp Phe Ser Gly Ile Val Gly Leu Gly Glu
465                 470                 475                 480
Leu Leu Glu Ser Ser Trp Glu Ala Ser Lys Leu Ser Ser Lys Ser Tyr
                485                 490                 495
Lys Glu Trp Arg Asn Arg Arg Lys Ala Arg Gln Arg Glu His Leu
            500                 505                 510
Glu Gly Asn Asp Arg Ala Asp Gly Asp Arg Phe Pro Lys Glu Glu Ser
        515                 520                 525
Glu Asp Ser Val Lys Arg Arg Phe Phe Leu Leu Ser Leu Asp Gly Asn
    530                 535                 540
Pro Gly Thr Gly Asp Lys Lys Leu Cys Ser Pro Ile Gln Ser Leu Leu
545                 550                 555                 560
Ser Ile Arg Gly Ser Lys Phe Ser Pro Arg Arg Asn Ser Lys Thr Leu
                565                 570                 575
Ile Phe Ser Phe Arg Gly Arg Ala Lys Met Val Gly Ser Glu Asn Asp
            580                 585                 590
Phe Ala Asp Asn Glu His Ser Thr Phe Glu Asp Ser Glu Gln Arg Arg
        595                 600                 605
Asp Ser Leu Phe Val Pro His Ser Pro Gly Glu Arg Arg Asn Ser Asn
    610                 615                 620
Gly Val Thr Thr Glu Thr Glu Val Arg Lys Arg Trp Leu Ser Ser Tyr
625                 630                 635                 640
Gln Ile Ser Met Glu Tyr Leu Glu Asp Ser Gly Arg Gln Arg Ala
                645                 650                 655
Met Ser Ile Ala Ser Ile Leu Thr Asn Asp Met Glu Glu Leu Glu Glu
            660                 665                 670
Ser Arg Gln Glu Cys Pro Pro Cys Trp Tyr Arg Phe Ala Phe Val Phe
        675                 680                 685
Leu Ile Trp Asp Cys Cys Asp Gly Trp Leu Lys Val Lys His Leu Val
    690                 695                 700
Asn His Ile Val Met Asp Pro Phe Val Asp Leu Ile Ile Thr Ile Cys
705                 710                 715                 720
Ile Val Leu Asn Thr Lys Phe Met Ala Met Glu His Tyr Pro Met Leu
                725                 730                 735
Gln Gln Phe Ser Ser Val Leu Thr Val Met Asn Leu Val Phe Thr Gly
            740                 745                 750
Ile Phe Thr Asn Glu Met Val Leu Lys Ile Ile Ala Met Gln Pro Tyr
        755                 760                 765
```

-continued

```
Tyr Tyr Phe Gln Glu Gly Trp Arg Ile Phe Asp Gly Ile Ile Val Ser
    770                 775                 780

Leu Thr Leu Met Glu Leu Gly Leu Ala Asn Val Val Gly Leu Ser Val
785                 790                 795                 800

Leu Arg Ser Phe Arg Trp Leu Arg Val Phe Lys Leu Ala Lys Ser Tyr
                805                 810                 815

Pro Thr Leu Asn Met Leu Ile Lys Ile Ala Gly Asn Ser Val Gly Ala
                820                 825                 830

Leu Gly Asn Asp Thr Leu Val Leu Ala Ile Ile Val Phe Glu Phe Ala
                835                 840                 845

Val Val Gly Met Gln Leu Phe Phe Lys Ser Tyr Lys Glu Cys Val Cys
    850                 855                 860

Lys Gly Asn Val Asp Cys Lys Leu Pro Arg Trp Ile Met Asn Asp Phe
865                 870                 875                 880

Phe His Ser Phe Leu Lys Val Phe Arg Val Leu Cys Gly Glu Trp Leu
                885                 890                 895

Glu Thr Met Trp Asp Cys Met Glu Val Met Gly Gln Thr Met Cys Leu
                900                 905                 910

Ile Val Phe Asn Leu Val Met Val Ile Gly Asn Leu Val Gln Leu Asn
                915                 920                 925

Leu Phe Leu Ala Leu Leu Leu Arg Ser Phe Ser Ser Asp Asn Leu Ala
    930                 935                 940

Ala Ser Asp Asp Asp Asn Glu Met Asn Asn Leu Thr Ile Ala Val Gly
945                 950                 955                 960

Arg Met Gln Lys Gly Val Asp Phe Val Lys Asn Lys Ile Arg Glu Ala
                965                 970                 975

Phe Arg Lys Ala Phe Phe Arg Lys Pro Asp Val Ile Glu Ile Gln Glu
                980                 985                 990

Gly Asn Lys Glu Asp Ser Cys Met Ser Asn Asn Thr Gly Phe Glu Ile
                995                 1000                1005

Ser Lys Glu Leu Asn Tyr Leu Gly Asp Gly Asn Gly Thr Thr Ser Gly
    1010                1015                1020
```

<210> SEQ ID NO 87
<211> LENGTH: 1024
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 87

```
Met Ala Gln Ala Leu Leu Ala Pro Pro Gly Pro Glu Ser Phe Arg Leu
1               5                   10                  15

Asp Thr Arg Glu Ser Leu Ala Ala Ile Glu Glu Arg Ala Ala Glu Glu
                20                  25                  30

Lys Ala Lys Lys Phe Lys Lys Glu Gln Asp Ile Asp Asp Glu Gly Lys
            35                  40                  45

Pro Lys Pro Asn Ser Asp Leu Glu His Gly Lys Asn Leu Pro Phe Ile
    50                  55                  60

Tyr Gly Ile Ile Pro Pro Glu Met Val Ser Glu Pro Lys Glu Asp Leu
65                  70                  75                  80

Asp Pro Tyr Tyr Val Ser Leu Lys Thr Phe Val Val Leu Asn Lys Gly
                85                  90                  95

Met Ala Ile Phe Arg Phe Ser Ala Thr Ser Asn Leu Tyr Ile Leu Thr
                100                 105                 110
```

-continued

```
Pro Leu Asn Pro Gln Arg Lys Ile Ala Ile Lys Ile Leu Val Arg Ser
            115                 120                 125
Leu Phe Ser Met Leu Ile Met Cys Ser Ile Leu Thr Asn Cys Val Phe
130                 135                 140
Met Thr Thr Ser Asn Pro Pro Asp Trp Thr Lys Asn Trp Glu Tyr Thr
145                 150                 155                 160
Phe Thr Gly Ile Tyr Thr Tyr Glu Ser Leu Ile Lys Ile Leu Ala Arg
                165                 170                 175
Ala Phe Cys Leu Glu Asp Phe Thr Phe Leu Asp Asp Pro Trp Asn Trp
            180                 185                 190
Leu Asp Phe Ser Glu Ile Val Met Ala Tyr Val Thr Glu Phe Phe Asp
            195                 200                 205
Leu Gly Asn Val Ser Ala Leu Arg Gly Phe Arg Val Leu Arg Ala Leu
    210                 215                 220
Lys Thr His Ser Val Ile Pro Gly Leu Lys Thr Ile Ile Gly Ala Leu
225                 230                 235                 240
Ile Gln Ser Val Lys Lys Ser Asp Val Met Ile Leu Thr Val Phe
                245                 250                 255
Leu Leu Ser Val Phe Ala Leu Ile Gly Leu Met Leu Phe Met Gly Asn
            260                 265                 270
Leu Arg Asn Lys Asn Ser Gln Trp Pro Pro Ser Asp Ser Ala Gln Glu
        275                 280                 285
Thr Asn Thr Thr Ser Tyr Phe Asn Arg Thr Met Asp Ser Asn Gly Thr
    290                 295                 300
Phe Val Ser Val Thr Met Ser Thr Phe Asn Trp Lys Thr Tyr Ile Ala
305                 310                 315                 320
Asp Asp Ser His Phe Tyr Trp Leu Asp Gly Gln Lys Asp Pro Leu Leu
                325                 330                 335
Tyr Gly Asn Gly Ser Asp Ala Gly Gln Cys Ala Glu Gly Tyr Ile Cys
            340                 345                 350
Val Lys Ala Gly Asp Asn Pro Asn Tyr Gly Tyr Thr Ser Phe Glu Thr
            355                 360                 365
Phe Ser Trp Ala Phe Leu Ser Leu Gly Arg Leu Met Thr Gln Asp Tyr
370                 375                 380
Trp Glu His Leu Tyr Gln Leu Thr Leu Arg Ala Ala Ile Lys Thr Tyr
385                 390                 395                 400
Met Ile Phe Phe Val Leu Lys Ile Phe Leu Gly Ser Phe Tyr Leu Val
                405                 410                 415
Leu Leu Ile Leu Ala Val Val Ala Met Ala Met Glu Glu Gln Asn Gln
            420                 425                 430
Ala Thr Leu Glu Asn Ala Glu Gln Lys Glu Ala Glu Phe Gln Arg Met
            435                 440                 445
Leu Glu Gln Leu Lys Lys Gln Gln Ser Glu Ala Gln Ala Val Ala Ala
    450                 455                 460
Ala Ser Thr Ala Ser Arg Asp Phe Ser Gly Ile Gly Val Leu Gly Glu
465                 470                 475                 480
Leu Leu Glu Ser Ser Ser Trp Ala Ser Lys Leu Ser Ser Lys Ser Ala
            485                 490                 495
Tyr Glu Trp Arg Asn Arg Arg Lys Lys Arg Ala Gln Arg Glu His Leu
            500                 505                 510
Glu Gly Asn His Asp Ala Asp Gly Asp Arg Phe Pro Lys Ser Phe Ser
        515                 520                 525
```

-continued

```
Glu Asp Ser Val Lys Arg Arg Ser Gly Leu Leu Ser Leu Asp Gly Asn
    530                 535                 540

Pro Leu His Gly Asp Lys Lys Leu Cys Ser Pro His Ile Ser Leu Leu
545                 550                 555                 560

Ser Ile Arg Gly Ser Leu Lys Ser Pro Arg Arg Asn Ser Lys Thr Ser
                565                 570                 575

Leu Phe Ser Phe Arg Gly Arg Ala Lys Asp Met Gly Ser Glu Asn Asp
            580                 585                 590

Phe Ala Asp Asp Asn His Ser Thr Phe Glu Asp Ser Glu Ser Gln Arg
            595                 600                 605

Asp Ser Leu Phe Val Pro His Arg Arg Gly Glu Arg Arg Asn Ser Asn
        610                 615                 620

Gly Thr Ser Thr Glu Thr Glu Val Arg Lys Arg Arg Thr Ser Ser Tyr
625                 630                 635                 640

Gln Ile Ser Met Glu Met Val Glu Asp Ser Ser Gly Arg Gln Arg Ser
                645                 650                 655

Trp Ser Ile Ala Ser Ile Leu Thr Asn Thr Tyr Glu Glu Leu Glu Glu
            660                 665                 670

Ser Arg Gln Lys Ala Pro Pro Cys Trp Tyr Arg Phe Ala Asn Asp Phe
        675                 680                 685

Leu Ile Trp Asp Cys Cys Asp Ala Glu Leu Lys Val Lys His Leu Val
    690                 695                 700

Asn Leu Phe Val Met Asp Pro Phe Val Asp Leu Ala Gly Thr Ile Cys
705                 710                 715                 720

Ile Val Leu Asn Thr Leu His Met Ala Met Glu His Tyr Pro Met Thr
                725                 730                 735

Ile Gln Phe Ser Ser Val Leu Thr Val Gly Lys Leu Val Phe Thr Gly
            740                 745                 750

Ile Phe Thr Ala Leu Met Val Leu Lys Ile Ile Ala Met Asp Met Tyr
        755                 760                 765

Tyr Tyr Phe Gln Glu Gly Trp Asn Asn Phe Asp Gly Ile Ile Val Ser
770                 775                 780

Leu Ser Gln Met Glu Leu Gly Leu Ala Asn Val Glu Arg Leu Ser Val
785                 790                 795                 800

Leu Arg Ser Phe Arg Leu Ser Arg Val Phe Lys Leu Ala Lys Ser Trp
                805                 810                 815

Thr Thr Leu Asn Met Leu Ile Lys Ile Ile Val Asn Ser Val Gly Ala
            820                 825                 830

Leu Gly Asn Leu Trp Leu Val Leu Ala Ile Ile Val Phe Ile Tyr Ala
        835                 840                 845

Val Val Gly Met Gln Leu Phe Gly Ala Ser Tyr Lys Glu Cys Val Cys
    850                 855                 860

Lys Ile Asp Val Asp Cys Lys Leu Pro Arg Trp His Glu Asn Asp Phe
865                 870                 875                 880

Phe His Ser Phe Leu Ile Phe Phe Arg Val Leu Cys Gly Glu Trp Ile
                885                 890                 895

Gly Thr Met Trp Asp Cys Met Glu Val Ala His Gln Thr Met Cys Leu
            900                 905                 910

Ile Val Phe Met Ile Val Met Val Ile Gly Asn Leu Val Val Lys Asn
        915                 920                 925

Leu Phe Leu Ala Leu Leu Leu Ser Leu Phe Ser Ser Asp Asn Leu Ala
    930                 935                 940

Ala Thr Met Asp Asp Asn Glu Met Asn Asn Leu Gln Asn Ala Val Gly
```

```
                    945                 950                 955                 960
Arg Met Gln Lys Gly Ile Gln Phe Val Lys Asn Lys Ile Arg Glu Cys
                965                 970                 975

Arg Arg Lys Ala Phe Phe Arg Lys Pro Lys Ser Ile Glu Ile Gln Glu
            980                 985                 990

Gly Asn Lys Ile Thr Ser Cys Met Ser Asn Asn Thr Gly Ile Val Ile
        995                1000                1005

Ser Lys Glu Leu Asn Tyr Leu Lys Trp Gly Asn Gly Thr Thr Ser Gly
   1010                1015                1020

<210> SEQ ID NO 88
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 88

Met Ala Gln Ala Leu Leu Val Ala Pro Gly Pro Glu Ser Phe Arg Leu
 1               5                  10                  15

Phe Asp Arg Glu Ser Leu Ala Ala Ile Glu Lys Glu Ala Ala Glu Glu
            20                  25                  30

Lys Ala Lys Lys Pro Phe Lys Glu Gln Asp Ile Asp Asp Glu Asn Gly
        35                  40                  45

Pro Lys Pro Asn Ser Asp Leu Glu Ala His Lys Asn Leu Pro Phe Ile
    50                  55                  60

Tyr Gly Asp Lys Pro Pro Glu Met Val Ser Glu Pro Leu Leu Asp Leu
65                  70                  75                  80

Asp Pro Tyr Tyr Val Ser Lys Met Thr Phe Val Val Leu Asn Lys Gly
                85                  90                  95

Lys Asn Ile Phe Arg Phe Ser Ala Thr Ser Ala Gln Tyr Ile Leu Thr
            100                 105                 110

Pro Leu Asn Pro Val Ser Lys Ile Ala Ile Lys Ile Leu Val His Thr
        115                 120                 125

Leu Phe Ser Met Leu Ile Met Cys Thr Val Leu Thr Asn Cys Val Phe
    130                 135                 140

Met Thr Leu Trp Asn Pro Pro Asp Trp Thr Lys Asn Val Tyr Tyr Thr
145                 150                 155                 160

Phe Thr Gly Ile Tyr Thr Phe Ala Ser Leu Ile Lys Ile Leu Ala Arg
                165                 170                 175

Gly Asp Cys Leu Glu Asp Phe Thr Phe Leu Arg Glu Pro Trp Asn Trp
            180                 185                 190

Leu Asp Phe Ser Val Phe Val Met Ala Tyr Val Thr Glu Phe Val Gly
        195                 200                 205

Leu Gly Asn Val Ser Ala Leu Arg Thr His Arg Val Leu Arg Ala Leu
    210                 215                 220

Lys Thr Ile Ile Val Ile Pro Gly Leu Lys Thr Ile Val Lys Ala Leu
225                 230                 235                 240

Ile Gln Ser Val Lys Lys Leu Leu Asp Val Met Ile Leu Thr Val Phe
                245                 250                 255

Cys Met Ser Val Phe Ala Leu Ile Gly Leu Gln Asn Phe Met Gly Asn
            260                 265                 270

Leu Arg Asn Lys Cys Gln Gln Trp Pro Pro Ser Asp Ser Ala Phe Arg
        275                 280                 285
```

```
Thr Asn Thr Thr Ser Tyr Phe Asn Gly Ser Met Asp Ser Asn Gly Thr
    290                 295                 300

Phe Val Asn Thr Thr Met Ser Thr Phe Asn Trp Lys Asp Val Ile Ala
305                 310                 315                 320

Asp Asp Ser His Phe Tyr Val Trp Asp Gly Gln Lys Asp Pro Leu Leu
                325                 330                 335

Cys Tyr Asn Gly Ser Asp Ala Gly Gln Cys Pro Ala Gly Tyr Ile Cys
            340                 345                 350

Val Lys Ala Gly Arg Asp Pro Asn Tyr Gly Tyr Thr Ser Phe Asp Glu
        355                 360                 365

Phe Ser Trp Ala Phe Leu Ser Leu Phe Phe Leu Met Thr Gln Asp Tyr
    370                 375                 380

Trp Glu Asn Gly Tyr Gln Leu Thr Leu Arg Ala Ala Gly His Thr Tyr
385                 390                 395                 400

Met Ile Phe Phe Val Leu Val Lys Phe Leu Gly Ser Phe Tyr Leu Val
                405                 410                 415

Asn Met Ile Leu Ala Val Val Ala Met Ala Tyr Asn Glu Gln Asn Gln
            420                 425                 430

Ala Thr Leu Glu Glu Gln Glu Gln Lys Glu Ala Glu Phe Gln Gln Arg
        435                 440                 445

Leu Glu Gln Leu Lys Lys Gln Gln Glu Ser Ala Gln Ala Val Ala Ala
    450                 455                 460

Ala Ser Ala Thr Ser Arg Asp Phe Ser Gly Ile Gly Gly Val Gly Glu
465                 470                 475                 480

Leu Leu Glu Ser Ser Ser Glu Trp Ser Lys Leu Ser Ser Lys Ser Ala
                485                 490                 495

Lys Tyr Trp Arg Asn Arg Arg Lys Arg Arg Ala Arg Glu His Leu
            500                 505                 510

Glu Gly Asn His Arg Asp Asp Gly Asp Arg Phe Pro Lys Ser Glu Glu
        515                 520                 525

Glu Asp Ser Val Lys Arg Arg Ser Phe Phe Leu Ser Leu Asp Gly Asn
    530                 535                 540

Pro Leu Thr His Asp Lys Lys Leu Cys Ser Pro His Gln Ile Leu Leu
545                 550                 555                 560

Ser Ile Arg Gly Ser Leu Phe Lys Pro Arg Arg Asn Ser Lys Thr Ser
                565                 570                 575

Ile Leu Ser Phe Arg Gly Arg Ala Lys Asp Val Met Ser Glu Asn Asp
            580                 585                 590

Phe Ala Asp Asp Glu Asn Ser Thr Phe Glu Asp Ser Glu Ser Arg Gln
        595                 600                 605

Asp Ser Leu Phe Val Pro His Arg Pro Arg Glu Arg Arg Asn Ser Asn
    610                 615                 620

Gly Thr Thr Ser Glu Thr Glu Val Arg Lys Arg Arg Leu Thr Ser Tyr
625                 630                 635                 640

Gln Ile Ser Met Glu Met Leu Val Asp Ser Gly Arg Gln Arg Ser
                645                 650                 655

Met Trp Ile Ala Ser Ile Leu Thr Asn Thr Met Tyr Glu Leu Glu Glu
            660                 665                 670

Ser Arg Gln Lys Cys Ala Pro Cys Trp Tyr Arg Phe Ala Asn Val Asp
        675                 680                 685

Leu Ile Trp Asp Cys Cys Asp Ala Trp Glu Lys Val Lys His Leu Val
    690                 695                 700

Asn Leu Ile Phe Met Asp Pro Phe Val Asp Leu Ala Ile Gly Ile Cys
```

-continued

```
            705                 710                 715                 720
Ile Val Leu Asn Thr Leu Phe His Ala Met Glu His Tyr Pro Met Thr
                725                 730                 735

Gln Ile Phe Ser Ser Val Leu Thr Val Gly Asn Lys Val Phe Thr Gly
                740                 745                 750

Ile Phe Thr Ala Glu Leu Val Leu Lys Ile Ile Ala Met Asp Pro Met
                755                 760                 765

Tyr Tyr Phe Gln Glu Gly Trp Asn Ile Asn Asp Gly Ile Ile Val Ser
            770                 775                 780

Leu Ser Leu Gln Glu Leu Gly Leu Ala Asn Val Glu Gly Arg Ser Val
785                 790                 795                 800

Leu Arg Ser Phe Arg Leu Leu Ser Val Phe Lys Leu Ala Lys Ser Trp
                805                 810                 815

Pro Val Leu Asn Met Leu Ile Lys Ile Gly Trp Ser Val Gly Ala
                820                 825                 830

Leu Gly Asn Leu Thr Tyr Val Leu Ala Ile Ile Val Phe Ile Phe Asp
                835                 840                 845

Val Val Gly Met Gln Leu Phe Gly Lys Glu Tyr Lys Glu Cys Val Cys
    850                 855                 860

Lys Ile Asn Phe Asp Cys Lys Leu Pro Arg Trp His Met Gly Asp Phe
865                 870                 875                 880

Phe His Ser Phe Leu Ile Val His Arg Val Leu Cys Gly Glu Trp Ile
                885                 890                 895

Glu Ile Met Trp Asp Cys Met Glu Val Ala Gly Lys Thr Met Cys Leu
                900                 905                 910

Ile Val Phe Met Leu Leu Met Val Ile Gly Asn Leu Val Val Leu Met
            915                 920                 925

Leu Phe Leu Ala Leu Leu Leu Ser Ser Asn Ser Ser Asp Asn Leu Ala
    930                 935                 940

Ala Thr Asp Gln Asp Asn Glu Met Asn Asn Leu Gln Ile Arg Val Gly
945                 950                 955                 960

Arg Met Gln Lys Gly Ile Asp Ser Val Lys Asn Lys Ile Arg Glu Cys
                965                 970                 975

Phe Thr Lys Ala Phe Phe Arg Lys Pro Lys Val Val Glu Ile Gln Glu
                980                 985                 990

Gly Asn Lys Ile Asp Trp Cys Met Ser Asn Asn Thr Gly Ile Glu Tyr
            995                 1000                1005

Ser Lys Glu Leu Asn Tyr Leu Lys Asp Ala Asn Gly Thr Thr Ser Gly
    1010                1015                1020
```

<210> SEQ ID NO 89
<211> LENGTH: 1024
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 89

```
Met Ala Gln Ala Leu Leu Val Pro Ala Gly Pro Glu Ser Phe Arg Leu
  1                 5                  10                  15

Phe Thr Asp Glu Ser Leu Ala Ala Ile Glu Lys Arg Glu Ala Glu Glu
                20                  25                  30

Lys Ala Lys Lys Pro Lys Phe Glu Gln Asp Ile Asp Asp Glu Asn Lys
        35                  40                  45
```

```
Gly Lys Pro Asn Ser Asp Leu Glu Ala Gly His Asn Leu Pro Phe Ile
 50                  55                  60

Tyr Gly Asp Ile Ile Pro Glu Met Val Ser Glu Pro Leu Glu Lys Leu
 65                      70                  75                  80

Asp Pro Tyr Tyr Val Ser Lys Lys Leu Phe Val Leu Asn Lys Gly
                     85                  90                  95

Lys Ala Met Phe Arg Phe Ser Ala Thr Ser Ala Leu Asn Ile Leu Thr
                100                 105                 110

Pro Leu Asn Pro Val Arg Gln Ile Ala Ile Lys Ile Leu Val His Ser
                115                 120                 125

Arg Phe Ser Met Leu Ile Met Cys Thr Ile Ser Thr Asn Cys Val Phe
                130                 135                 140

Met Thr Leu Ser Thr Pro Pro Asp Trp Thr Lys Asn Val Glu Val Thr
145                 150                 155                 160

Phe Thr Gly Ile Tyr Thr Phe Glu Trp Leu Ile Lys Ile Leu Ala Arg
                165                 170                 175

Gly Phe Tyr Leu Glu Asp Phe Thr Phe Leu Arg Asp Ala Trp Asn Trp
                180                 185                 190

Leu Asp Phe Ser Val Ile Asp Met Ala Tyr Val Thr Glu Phe Val Asp
                195                 200                 205

Glu Gly Asn Val Ser Ala Leu Arg Thr Phe Phe Val Leu Arg Ala Leu
    210                 215                 220

Lys Thr Ile Ser Gly Ile Pro Gly Leu Lys Thr Ile Val Gly His Leu
225                 230                 235                 240

Ile Gln Ser Val Lys Lys Leu Ser Ile Val Met Ile Leu Thr Val Phe
                245                 250                 255

Cys Leu Lys Val Phe Ala Leu Ile Gly Leu Gln Leu Leu Met Gly Asn
                260                 265                 270

Leu Arg Asn Lys Cys Ser Met Trp Pro Pro Ser Asp Ser Ala Phe Glu
    275                 280                 285

Asn Asn Thr Thr Ser Tyr Phe Asn Gly Thr Gln Asp Ser Asn Gly Thr
    290                 295                 300

Phe Val Asn Val Arg Met Ser Thr Phe Asn Trp Lys Asp Tyr Ser Ala
305                 310                 315                 320

Asp Asp Ser His Phe Tyr Val Leu Thr Gly Gln Lys Asp Pro Leu Leu
                325                 330                 335

Cys Gly Val Gly Ser Asp Ala Gly Gln Cys Pro Glu Trp Tyr Ile Cys
                340                 345                 350

Val Lys Ala Gly Arg Asn Tyr Asn Tyr Gly Tyr Thr Ser Phe Asp Thr
                355                 360                 365

Ala Ser Trp Ala Phe Leu Ser Leu Phe Arg Asp Met Thr Gln Asp Tyr
    370                 375                 380

Trp Glu Asn Leu Glu Gln Leu Thr Leu Arg Ala Ala Gly Lys Phe Tyr
385                 390                 395                 400

Met Ile Phe Phe Val Leu Val Ile Gly Leu Gly Ser Phe Tyr Leu Val
                405                 410                 415

Asn Leu His Leu Ala Val Val Ala Met Ala Tyr Glu Ile Gln Asn Gln
                420                 425                 430

Ala Thr Leu Glu Glu Ala Lys Gln Lys Glu Ala Glu Phe Gln Gln Met
    435                 440                 445

Met Glu Gln Leu Lys Lys Gln Gln Glu Glu Asn Gln Ala Val Ala Ala
450                 455                 460

Ala Ser Ala Ala Gln Arg Asp Phe Ser Gly Ile Gly Gly Leu Arg Glu
```

-continued

```
465                 470                 475                 480
Leu Leu Glu Ser Ser Glu Ala Thr Lys Leu Ser Lys Ser Ala
                485                 490                 495
Lys Glu Val Arg Asn Arg Lys Lys Arg Gln Trp Glu His Leu
            500                 505                 510
Glu Gly Asn His Arg Ala Tyr Gly Asp Arg Phe Pro Lys Ser Glu Ser
            515                 520                 525
Ala Asp Ser Val Lys Arg Arg Ser Phe Leu Asp Ser Leu Asp Gly Asn
530                 535                 540
Pro Leu Thr Gly Glu Lys Lys Leu Cys Ser Pro His Gln Ser Phe Leu
545                 550                 555                 560
Ser Ile Arg Gly Ser Leu Phe Ser Gly Arg Arg Asn Ser Lys Thr Ser
            565                 570                 575
Ile Phe His Phe Arg Gly Arg Ala Lys Asp Val Gly Ile Glu Asn Asp
            580                 585                 590
Phe Ala Asp Asp Glu His Lys Thr Phe Glu Asp Ser Glu Ser Arg Arg
            595                 600                 605
Leu Ser Leu Phe Val Pro His Arg Pro Gly Met Arg Arg Asn Ser Asn
            610                 615                 620
Gly Thr Thr Thr Asn Thr Glu Val Arg Lys Arg Arg Leu Ser Gln Tyr
625                 630                 635                 640
Gln Ile Ser Met Glu Met Leu Glu Arg Ser Gly Arg Gln Arg Ser
            645                 650                 655
Met Ser Ser Ala Ser Ile Leu Thr Asn Thr Met Glu Thr Leu Glu Glu
            660                 665                 670
Ser Arg Gln Lys Cys Pro Val Cys Trp Tyr Arg Phe Ala Asn Val Phe
            675                 680                 685
Trp Ile Trp Asp Cys Cys Asp Ala Trp Leu Tyr Val Lys His Leu Val
            690                 695                 700
Asn Leu Ile Val Ala Asp Pro Phe Val Asp Leu Ala Ile Thr Asp Cys
705                 710                 715                 720
Ile Val Leu Asn Thr Leu Phe Met Glu Met Glu His Tyr Pro Met Thr
                725                 730                 735
Gln Gln Gly Ser Ser Val Leu Thr Val Gly Asn Leu His Phe Thr Gly
            740                 745                 750
Ile Phe Thr Ala Glu Met Ile Leu Lys Ile Ile Ala Met Asp Pro Tyr
            755                 760                 765
Lys Tyr Phe Gln Glu Gly Trp Asn Ile Phe Leu Gly Ile Ile Val Ser
770                 775                 780
Leu Ser Leu Met Met Leu Gly Leu Ala Asn Val Glu Gly Leu Asn Val
785                 790                 795                 800
Leu Arg Ser Phe Arg Leu Leu Arg Gln Phe Lys Leu Ala Lys Ser Trp
            805                 810                 815
Pro Thr Arg Asn Met Leu Ile Lys Ile Ile Gly Asn Thr Val Gly Ala
            820                 825                 830
Leu Gly Asn Leu Thr Leu Trp Leu Ala Ile Ile Val Phe Ile Phe Ala
            835                 840                 845
Tyr Val Gly Met Gln Leu Phe Gly Lys Ser Ala Lys Glu Cys Val Cys
            850                 855                 860
Lys Ile Asn Val Glu Cys Lys Leu Pro Arg Trp His Met Asn Phe Phe
865                 870                 875                 880
Phe His Ser Phe Leu Ile Val Phe Gly Val Leu Cys Gly Glu Trp Ile
                885                 890                 895
```

```
Glu Thr His Trp Asp Cys Met Glu Val Ala Gly Gln Ile Met Cys Leu
            900                 905                 910

Ile Val Phe Met Leu Val Lys Val Ile Gly Asn Leu Val Val Leu Asn
            915                 920                 925

Met Phe Leu Ala Leu Leu Leu Ser Ser Phe Asn Ser Asp Asn Leu Ala
            930                 935                 940

Ala Thr Asp Asp Gln Asn Glu Met Asn Asn Leu Gln Ile Ala Arg Gly
945                 950                 955                 960

Arg Met Gln Lys Gly Ile Asp Phe Ser Lys Asn Lys Ile Arg Glu Cys
                965                 970                 975

Phe Arg Thr Ala Phe Phe Arg Lys Pro Lys Val Ile Val Ile Gln Glu
            980                 985                 990

Gly Asn Lys Ile Asp Ser Trp Met Ser Asn Asn Thr Gly Ile Glu Ile
            995                 1000                1005

Tyr Lys Glu Leu Asn Tyr Leu Lys Asp Gly Ala Gly Thr Thr Ser Gly
    1010                1015                1020

<210> SEQ ID NO 90
<211> LENGTH: 1024
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 90

Met Ala Gln Ala Leu Leu Val Pro Pro Ala Pro Glu Ser Phe Arg Leu
 1               5                  10                  15

Phe Thr Arg Asp Ser Leu Ala Ala Ile Glu Lys Arg Ala Glu Glu Glu
                20                  25                  30

Lys Ala Lys Lys Pro Lys Lys Phe Gln Asp Ile Asp Asp Glu Asn Lys
            35                  40                  45

Pro Gly Pro Asn Ser Asp Leu Glu Ala Gly Lys His Leu Pro Phe Ile
    50                  55                  60

Tyr Gly Asp Ile Pro Ile Glu Met Val Ser Glu Pro Leu Glu Asp Lys
65                  70                  75                  80

Asp Pro Tyr Tyr Val Ser Lys Lys Thr Leu Val Val Leu Asn Lys Gly
                85                  90                  95

Lys Ala Ile Met Arg Phe Ser Ala Thr Ser Ala Leu Tyr Asn Leu Thr
            100                 105                 110

Pro Leu Asn Pro Val Arg Lys Gln Ala Ile Lys Ile Leu Val His Ser
            115                 120                 125

Leu Arg Ser Met Leu Ile Met Cys Thr Ile Leu Ser Asn Cys Val Phe
    130                 135                 140

Met Thr Leu Ser Asn Thr Pro Asp Trp Thr Lys Asn Val Glu Tyr Val
145                 150                 155                 160

Phe Thr Gly Ile Tyr Thr Phe Glu Ser Trp Ile Lys Ile Leu Ala Arg
                165                 170                 175

Gly Phe Cys Tyr Glu Asp Phe Thr Phe Leu Arg Asp Pro Ala Asn Trp
            180                 185                 190

Leu Asp Phe Ser Val Ile Val Asp Ala Tyr Val Thr Glu Phe Val Asp
            195                 200                 205

Leu Glu Asn Val Ser Ala Leu Arg Thr Phe Arg Phe Leu Arg Ala Leu
    210                 215                 220

Lys Thr Ile Ser Val Gly Pro Gly Leu Lys Thr Ile Val Gly Ala His
```

-continued

```
            225                 230                 235                 240
Ile Gln Ser Val Lys Lys Leu Ser Asp Ile Met Ile Leu Thr Val Phe
                    245                 250                 255
Cys Leu Ser Lys Phe Ala Leu Ile Gly Leu Gln Leu Phe Leu Gly Asn
                    260                 265                 270
Leu Arg Asn Lys Cys Ser Gln Met Pro Pro Ser Asp Ser Ala Phe Glu
                    275                 280                 285
Thr Gln Thr Thr Ser Tyr Phe Asn Gly Thr Met Arg Ser Asn Gly Thr
            290                 295                 300
Phe Val Asn Val Thr Ser Ser Thr Phe Asn Trp Lys Asp Tyr Ile Thr
305                 310                 315                 320
Asp Asp Ser His Phe Tyr Val Leu Asp Val Gln Lys Asp Pro Leu Leu
                    325                 330                 335
Cys Gly Asn Trp Ser Asp Ala Gly Gln Cys Pro Glu Gly Ala Ile Cys
                    340                 345                 350
Val Lys Ala Gly Arg Asn Pro Asp Tyr Gly Tyr Thr Ser Phe Asp Thr
                    355                 360                 365
Phe Glu Trp Ala Phe Leu Ser Leu Phe Arg Leu Phe Thr Gln Asp Tyr
            370                 375                 380
Trp Glu Asn Leu Tyr Gly Leu Thr Leu Arg Ala Ala Gly Lys Thr His
385                 390                 395                 400
Met Ile Phe Phe Val Leu Val Ile Phe Ile Gly Ser Phe Tyr Leu Val
                    405                 410                 415
Asn Leu Ile Lys Ala Val Val Ala Met Ala Tyr Glu Leu Asn Gln
                    420                 425                 430
Ala Thr Leu Glu Glu Ala Glu Met Lys Glu Ala Glu Phe Gln Gln Met
            435                 440                 445
Leu Asn Gln Leu Lys Lys Gln Gln Glu Glu Ala Arg Ala Val Ala Ala
450                 455                 460
Ala Ser Ala Ala Ser Ser Asp Phe Ser Gly Ile Gly Gly Leu Gly Thr
465                 470                 475                 480
Leu Leu Glu Ser Ser Ser Glu Ala Ser Val Leu Ser Ser Lys Ser Ala
                    485                 490                 495
Lys Glu Trp Trp Asn Arg Arg Lys Lys Arg Arg Gln Arg Tyr His Leu
                    500                 505                 510
Glu Gly Asn His Arg Ala Asp Ala Asp Arg Phe Pro Lys Ser Glu Ser
            515                 520                 525
Glu Glu Ser Val Lys Arg Arg Ser Phe Leu Leu Phe Leu Asp Gly Asn
530                 535                 540
Pro Leu Thr Gly Asp Gly Lys Leu Cys Ser Pro His Gln Ser Leu His
545                 550                 555                 560
Ser Ile Arg Gly Ser Leu Phe Ser Pro Ile Arg Asn Ser Lys Thr Ser
                    565                 570                 575
Ile Phe Ser Lys Arg Gly Arg Ala Lys Asp Val Gly Ser Leu Asn Asp
                    580                 585                 590
Phe Ala Asp Asp Glu His Ser Met Phe Glu Asp Ser Glu Ser Arg Arg
            595                 600                 605
Asp Asn Leu Phe Val Pro His Arg Pro Gly Glu Gln Arg Asn Ser Asn
610                 615                 620
Gly Thr Thr Thr Glu Arg Glu Val Arg Lys Arg Arg Leu Ser Ser Ser
625                 630                 635                 640
Gln Ile Ser Met Glu Met Leu Glu Asp Thr Ser Gly Arg Gln Arg Ser
                    645                 650                 655
```

```
Met Ser Ile Val Ser Ile Leu Thr Asn Thr Met Glu Glu Trp Glu Glu
            660                 665                 670

Ser Arg Gln Lys Cys Pro Pro Tyr Trp Tyr Arg Phe Ala Asn Val Phe
        675                 680                 685

Leu Ala Trp Asp Cys Cys Asp Ala Trp Leu Lys Asp Lys His Leu Val
    690                 695                 700

Asn Leu Ile Val Met Glu Pro Phe Val Asp Leu Ala Ile Thr Ile Phe
705                 710                 715                 720

Ile Val Leu Asn Thr Leu Phe Met Ala Gly Glu His Tyr Pro Met Thr
                725                 730                 735

Gln Gln Phe His Ser Val Leu Thr Val Gly Asn Leu Val Ile Thr Gly
            740                 745                 750

Ile Phe Thr Ala Glu Met Val Lys Lys Ile Ile Ala Met Asp Pro Tyr
        755                 760                 765

Tyr Leu Phe Gln Glu Gly Trp Asn Ile Phe Asp Met Ile Ile Val Ser
    770                 775                 780

Leu Ser Leu Met Glu Asn Gly Leu Ala Asn Val Glu Gly Leu Ser Gln
785                 790                 795                 800

Leu Arg Ser Phe Arg Leu Leu Arg Val Arg Lys Leu Ala Lys Ser Trp
                805                 810                 815

Pro Thr Leu Ser Met Leu Ile Lys Ile Ile Gly Asn Ser Thr Gly Ala
            820                 825                 830

Leu Gly Asn Leu Thr Leu Val Val Ala Ile Ile Val Phe Ile Phe Ala
        835                 840                 845

Val Trp Gly Met Gln Leu Phe Gly Lys Ser Tyr Tyr Glu Cys Val Cys
    850                 855                 860

Lys Ile Asn Val Asp Ala Lys Leu Pro Arg Trp His Met Asn Asp Asp
865                 870                 875                 880

Phe His Ser Phe Leu Ile Val Phe Arg Glu Leu Cys Gly Glu Trp Ile
                885                 890                 895

Glu Thr Met Phe Asp Cys Met Glu Val Ala Gly Gln Thr Gly Cys Leu
            900                 905                 910

Ile Val Phe Met Leu Val Met His Ile Gly Asn Leu Val Val Leu Asn
        915                 920                 925

Leu Ile Leu Ala Leu Leu Leu Ser Ser Phe Ser Lys Asp Asn Leu Ala
    930                 935                 940

Ala Thr Asp Asp Asp Leu Glu Met Asn Asn Leu Gln Ile Ala Val Met
945                 950                 955                 960

Arg Met Gln Lys Gly Ile Asp Phe Val Asn Asn Lys Ile Arg Glu Cys
                965                 970                 975

Phe Arg Lys Gln Phe Arg Lys Pro Lys Val Ile Glu Arg Gln Glu
            980                 985                 990

Gly Asn Lys Ile Asp Ser Cys Ser Asn Asn Thr Gly Ile Glu Ile
        995                 1000                1005

Ser Thr Glu Leu Asn Tyr Leu Lys Asp Gly Asn Val Thr Thr Ser Gly
    1010                1015                1020
```

<210> SEQ ID NO 91
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence -continued

```
<400> SEQUENCE: 91

Met Ala His Arg Lys Leu Glu Ser Val Gly Ser Gly Met Leu Asp His
 1               5                   10                  15

Arg Val Arg Pro Gly Pro Val Pro His Ser Gln Glu Pro Glu Ser Glu
             20                  25                  30

Asp Met Glu Leu Pro Leu Glu Gly Tyr Val Pro Glu Gly Leu Glu Leu
         35                  40                  45

Ala Ala Leu Arg Pro Glu Ser Pro Ala Pro Glu Glu Gln Glu Cys His
     50                  55                  60

Asn His Ser Pro Asp Gly Asp Ser Ser Asp Tyr Val Asn Asn Thr
 65                  70                  75                  80

Ser Glu Glu Glu Asp Tyr Asp Glu Gly Leu Pro Glu Glu Glu Glu Gly
                 85                  90                  95

Ile Thr Tyr Tyr Ile Arg Tyr Cys Pro Glu Asp Asp Ser Tyr Leu Glu
             100                 105                 110

Gly Met Asp Cys Asn Gly Glu Glu Tyr Leu Ala His Ser Ala His Pro
         115                 120                 125

Val Asp Thr Asp Glu Cys Gln Glu Ala Val Glu Glu Trp Thr Asp Ser
    130                 135                 140

Ala Gly Pro His Pro His Gly His Glu Ala Glu Gly Ser Gln Asp Tyr
145                 150                 155                 160

Pro Asp Gly Gln Leu Pro Ile Pro Glu Asp Glu Pro Ser Val Leu Glu
                165                 170                 175

Ala His Asp Gln Glu Glu Asp Gly His Tyr Cys Ala Ser Lys Glu Gly
            180                 185                 190

Tyr Gln Asp Tyr Tyr Pro Glu Glu Ala Asn Gly Asn Thr Gly Ala Ser
        195                 200                 205

Pro Tyr Arg Leu Arg Arg Gly Asp Gly Asp Leu Glu Asp Gln Glu Glu
    210                 215                 220

Asp Ile Asp Gln Ile Val Ala Glu Ile Lys Met Ser Leu Ser Met Thr
225                 230                 235                 240

Ser Ile Thr Ser Ala Ser Glu Ala Ser Pro Glu His Gly Pro Glu Pro
                245                 250                 255

Gly Pro Glu Asp Ser Val Glu Ala Cys Pro Pro Ile Lys Ala Ser Cys
            260                 265                 270

Ser Pro Ser Arg His Glu Ala Arg Pro Lys Ser Leu Asn Leu Leu Pro
        275                 280                 285

Glu Ala Lys His Pro Gly Asp Pro Gln Arg Gly Phe Lys Pro Lys Thr
    290                 295                 300

Arg Thr Pro Glu Glu Arg Leu Lys Trp Pro His Glu Gln Val Cys Asn
305                 310                 315                 320

Gly Leu Glu Gln Pro Arg Lys Gln Gln Arg Ser Asp Leu Asn Gly Pro
                325                 330                 335

Val Asp Asn Asn Asn Ile Pro Glu Thr Lys Lys Val Ala Ser Phe Pro
            340                 345                 350

Ser Phe Val Ala Val Pro Gly Pro Cys Glu Pro Glu Asp Leu Ile Asp
        355                 360                 365

Gly Ile Ile Phe Ala Ala Asn Tyr Leu Gly Ser Thr Gln Leu Leu Ser
    370                 375                 380

Glu Arg Asn Pro Ser Lys Asn Ile Arg Met Met Gln Ala Gln Glu Ala
385                 390                 395                 400

Val Ser Arg Val Lys Arg Met Gln Lys Ala Ala Lys Ile Lys Lys Lys
                405                 410                 415
```

-continued

```
Ala Asn Ser Glu Gly Asp Ala Gln Thr Leu Thr Glu Val Asp Leu Phe
            420                 425                 430

Ile Ser Thr Gln Arg Ile Lys Val Leu Asn Ala Asp Thr Gln Glu Thr
        435                 440                 445

Met Met Asp His Ala Leu Arg Thr Ile Ser Tyr Ile Ala Asp Ile Gly
    450                 455                 460

Asn Ile Val Val Leu Met Ala Arg Arg Met Pro Arg Ser Ala Ser
465                 470                 475                 480

Gln Asp Cys Ile Glu Thr Thr Pro Gly Ala Gln Glu Gly Lys Lys Gln
                485                 490                 495

Tyr Lys Met Ile Cys His Val Phe Glu Ser Glu Asp Ala Gln Leu Ile
            500                 505                 510

Ala Gln Ser Ile Gly Gln Ala Phe Ser Val Ala Tyr Gln Glu Phe Leu
        515                 520                 525

Arg Ala Asn Gly Ile Asn Pro Glu Asp Leu Ser Gln Lys Glu Tyr Ser
    530                 535                 540

Asp Ile Ile Asn Thr Gln Glu Met Tyr Asn Asp Asp Leu Ile His Phe
545                 550                 555                 560

Ser Asn Ser Glu Asn Cys Lys Glu Leu Gln Leu Glu Lys His Lys Gly
                565                 570                 575

Glu Ile Leu Gly Val Val Val Glu Ser Gly Trp Gly Ser Ile Leu
            580                 585                 590

Pro Thr Val Ile Leu Ala Asn Met Met Asn Gly Pro Ala Ala Arg
        595                 600                 605

Ser Gly Lys Leu Ser Ile Gly Asp Gln Ile Met Ser Ile Asn Gly Thr
    610                 615                 620

Ser Leu Val Gly Leu Pro Leu Ala Thr Cys Gln Gly Ile Ile Lys Gly
625                 630                 635                 640

Leu Lys Asn Gln Thr Gln Val Lys Leu Asn Ile Val Ser Cys Pro Pro
                645                 650                 655

Val Thr Thr Val Leu Ile Lys Arg Pro Asp Leu Lys Tyr Gln Leu Gly
            660                 665                 670

Phe Ser Val Gln Asn Gly Ile Ile Cys Ser Leu Met Arg Gly Gly Ile
        675                 680                 685

Ala Glu Arg Gly Gly Val Arg Val Gly His Arg Ile Ile Glu Ile Asn
    690                 695                 700

Gly Gln Ser Val Val Ala Thr His His Glu Lys Ile Val Gln Ala Leu
705                 710                 715                 720

Ser Asn Ser Val Gly Glu Ile His Met Lys Thr Met Pro Ala Ala Met
                725                 730                 735

Phe Arg Leu Leu Thr Gly Gln Glu Thr Pro Leu Tyr Ile
            740                 745

<210> SEQ ID NO 92
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 92

Met Asp His Arg Lys Leu Glu Ser Val Gly Ser Glu Met Leu Asp His
  1               5                  10                  15

Arg Val Arg Pro Gly Phe Val Pro His Ser Gln Glu Pro Glu Ser Gly
```

-continued

```
            20                  25                  30
Asp Met Glu Leu Pro Leu Glu Gly Tyr His Pro Gly Leu Glu Leu
                35                  40                  45
Ala Ala Leu Ile Pro Glu Ser Pro Ala Pro Glu Gln Lys Cys His
     50                  55                  60
Asn His Ser Pro Asp Gly Asp Leu Ser Ser Asp Tyr Val Asn Asn Thr
 65                  70                  75                  80
Ser Met Glu Glu Asp Tyr Asp Glu Gly Leu Pro Asn Glu Glu Glu Gly
                 85                  90                  95
Ile Thr Tyr Tyr Ile Gln Tyr Cys Pro Glu Asp Ser Tyr Leu Arg
                100                 105                 110
Gly Met Asp Cys Asn Gly Glu Glu Tyr Ser Ala His Ser Ala His Pro
            115                 120                 125
Val Asp Thr Thr Glu Cys Gln Glu Ala Val Glu Glu Trp Val Asp Ser
 130                 135                 140
Ala Gly Pro His Pro His Gly Trp Glu Ala Glu Gly Ser Gln Asp Tyr
145                 150                 155                 160
Pro Tyr Gly Gln Leu Pro Ile Pro Glu Asp Glu Ala Ser Val Leu Glu
                165                 170                 175
Ala His Asp Gln Glu Asp Asp Gly His Tyr Cys Ala Ser Lys Glu Glu
            180                 185                 190
Tyr Gln Asp Tyr Tyr Pro Glu Glu Ala Phe Gly Asn Thr Gly Ala Ser
                195                 200                 205
Pro Tyr Arg Gly Arg Gly Asp Gly Asp Leu Glu Asp His Glu Glu
            210                 215                 220
Asp Ile Asp Gln Ile Val Ala Ile Ile Lys Met Ser Leu Ser Met Thr
225                 230                 235                 240
Ser Lys Thr Ser Ala Ser Glu Ala Ser Pro Glu Leu Gly Pro Glu Pro
                245                 250                 255
Gly Pro Glu Asp Ser Met Glu Ala Cys Pro Pro Ile Lys Ala Ser Asn
            260                 265                 270
Ser Pro Ser Arg His Glu Ala Arg Pro Gln Ser Leu Asn Leu Leu Pro
        275                 280                 285
Glu Ala Lys Arg Pro Gly Asp Pro Gln Arg Gly Phe Lys Ser Lys Thr
 290                 295                 300
Arg Thr Pro Glu Glu Arg Leu Thr Trp Pro His Glu Gln Val Cys Asn
305                 310                 315                 320
Gly Val Glu Gln Pro Arg Lys Gln Gln Arg Ser Trp Leu Asn Gly Pro
                325                 330                 335
Val Asp Asn Asn Asn Tyr Pro Glu Thr Lys Lys Val Ala Ser Phe Ala
            340                 345                 350
Ser Phe Val Ala Val Pro Gly Pro Cys Asp Pro Glu Asp Leu Ile Asp
        355                 360                 365
Gly Ile Ile Glu Ala Ala Asn Tyr Leu Gly Ser Thr Gln Phe Leu Ser
    370                 375                 380
Glu Arg Asn Pro Ser Lys Asn Gly Arg Met Met Gln Ala Gln Glu Ala
385                 390                 395                 400
Val His Arg Val Lys Arg Met Gln Lys Ala Ala Ile Ile Lys Lys Lys
                405                 410                 415
Ala Asn Ser Glu Gly Lys Ala Gln Thr Leu Thr Glu Val Asp Leu Leu
            420                 425                 430
Ile Ser Thr Gln Arg Ile Lys Val Leu Met Ala Asp Thr Gln Glu Thr
        435                 440                 445
```

```
Met Met Asp Asn Ala Leu Arg Thr Ile Ser Tyr Ile Ala Gln Ile Gly
        450                 455                 460

Asn Ile Val Val Leu Met Ala Ser Arg Arg Met Pro Arg Ser Ala Ser
465                 470                 475                 480

Gln Thr Cys Ile Glu Thr Thr Pro Gly Ala Gln Val Gly Lys Lys Gln
                485                 490                 495

Tyr Lys Met Ile Cys Trp Val Phe Glu Ser Glu Asp Ala Gln Leu Tyr
                500                 505                 510

Ala Gln Ser Ile Gly Gln Ala Phe Ser Ala Ala Tyr Gln Glu Phe Leu
            515                 520                 525

Arg Ala Asn Asp Ile Asn Pro Glu Asp Leu Ser Gln Lys Phe Tyr Ser
530                 535                 540

Asp Ile Ile Asn Thr Gln Gly Tyr Asn Asp Asp Leu Ile His Phe
545                 550                 555                 560

Ser His Ser Glu Asn Cys Lys Glu Leu Gln Leu Ile Lys His Lys Gly
                565                 570                 575

Glu Ile Leu Gly Val Lys Val Val Glu Ser Gly Trp Gly Ser Ile Met
                580                 585                 590

Pro Thr Val Ile Leu Ala Asn Met Met Gln Gly Gly Pro Ala Ala Arg
                595                 600                 605

Ser Gly Lys Arg Ser Ile Gly Asp Gln Ile Met Ser Ile Ser Gly Thr
610                 615                 620

Ser Leu Val Gly Leu Pro Leu Thr Thr Cys Gln Gly Ile Ile Lys Gly
625                 630                 635                 640

Leu Val Asn Gln Thr Gln Val Lys Leu Asn Ile Trp Ser Cys Pro Pro
                645                 650                 655

Val Thr Thr Val Leu Tyr Lys Arg Pro Asp Leu Lys Tyr Gln Leu Ala
                660                 665                 670

Phe Ser Val Gln Asn Gly Ile Ile Cys Asp Leu Met Arg Gly Gly Ile
            675                 680                 685

Ala Glu Arg Glu Gly Val Arg Val Gly His Arg Ile Ile Phe Ile Asn
        690                 695                 700

Gly Gln Ser Val Val Ala Thr His His Glu Lys Ile Val Gln Ala Leu
705                 710                 715                 720

Ser Ile Ser Val Gly Glu Ile His Met Lys Thr Lys Pro Ala Ala Met
                725                 730                 735

Phe Arg Leu Leu Thr Leu Gln Glu Thr Pro Leu Tyr Ile
            740                 745

<210> SEQ ID NO 93
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 93

Met Ala Ala Arg Lys Leu Glu Ser Val Gly Ser Gly Asp Leu Asp His
1               5                   10                  15

Arg Val Arg Pro Gly Pro Glu Pro His Ser Gln Glu Pro Glu Ser Glu
            20                  25                  30

Phe Met Glu Leu Pro Leu Glu Gly Tyr Val Gly Glu Gly Leu Glu Leu
        35                  40                  45

Ala Ala Leu Arg His Glu Ser Pro Ala Pro Glu Glu Gln Glu Ile His
```

-continued

```
              50                      55                      60
Asn His Ser Pro Asp Gly Asp Ser Lys Ser Asp Tyr Val Asn Asn Thr
 65                      70                      75                      80
Ser Glu Leu Glu Asp Tyr Asp Glu Gly Leu Pro Glu Met Glu Glu Gly
                         85                      90                      95
Ile Thr Tyr Tyr Ile Arg Asn Cys Pro Glu Asp Ser Tyr Leu Glu
                        100                     105                     110
Gln Met Asp Cys Asn Gly Glu Glu Tyr Leu Arg His Ser Ala His Pro
                        115                     120                     125
Val Asp Thr Asp Ser Cys Gln Glu Ala Val Glu Glu Trp Thr Thr Ser
                        130                     135                     140
Ala Gly Pro His Pro His Gly His Val Ala Glu Gly Ser Gln Asp Tyr
145                     150                     155                     160
Pro Asp Trp Gln Leu Pro Ile Pro Glu Asp Glu Pro Tyr Val Leu Glu
                        165                     170                     175
Ala His Asp Gln Glu Glu Ala Gly His Tyr Cys Ala Ser Lys Glu Gly
                        180                     185                     190
Asp Gln Asp Tyr Tyr Pro Glu Glu Ala Asn Glu Asn Thr Gly Ala Ser
                        195                     200                     205
Pro Tyr Arg Leu Phe Arg Gly Asp Gly Asp Leu Glu Asp Gln Gly Glu
                        210                     215                     220
Asp Ile Asp Gln Ile Val Ala Glu His Lys Met Ser Leu Ser Met Thr
225                     230                     235                     240
Ser Ile Ile Ser Ala Ser Glu Ala Ser Pro Glu His Lys Pro Glu Pro
                        245                     250                     255
Gly Pro Glu Asp Ser Val Leu Ala Cys Pro Pro Ile Lys Ala Ser Cys
                        260                     265                     270
Met Pro Ser Arg His Glu Ala Arg Pro Lys Asn Leu Asn Leu Leu Pro
                        275                     280                     285
Glu Ala Lys His Gln Gly Asp Pro Gln Arg Gly Phe Lys Pro Arg Thr
                        290                     295                     300
Arg Thr Pro Glu Glu Arg Leu Lys Ser Pro His Glu Gln Val Cys Asn
305                     310                     315                     320
Gly Leu Thr Gln Pro Arg Lys Gln Gln Arg Ser Asp Val Asn Gly Pro
                        325                     330                     335
Val Asp Asn Asn Asn Ile Trp Glu Thr Lys Lys Val Ala Ser Phe Pro
                        340                     345                     350
Tyr Phe Val Ala Val Pro Gly Pro Cys Glu Ala Glu Asp Leu Ile Asp
                        355                     360                     365
Gly Ile Ile Phe Asp Ala Asn Tyr Leu Gly Ser Thr Gln Leu Glu Ser
                        370                     375                     380
Glu Arg Asn Pro Ser Lys Asn Ile Phe Met Met Gln Ala Gln Glu Ala
385                     390                     395                     400
Val Ser Gly Val Lys Arg Met Gln Lys Ala Ala Lys His Lys Lys Lys
                        405                     410                     415
Ala Asn Ser Glu Gly Asp Ile Gln Thr Leu Thr Glu Val Asp Leu Phe
                        420                     425                     430
Lys Ser Thr Gln Arg Ile Lys Val Leu Asn Leu Asp Thr Gln Glu Thr
                        435                     440                     445
Met Met Asp His Met Leu Arg Thr Ile Ser Tyr Ile Ala Asp Asn Gly
                        450                     455                     460
Asn Ile Val Val Leu Met Ala Arg Gln Arg Met Pro Arg Ser Ala Ser
465                     470                     475                     480
```

```
Gln Asp Arg Ile Glu Thr Thr Pro Gly Ala Gln Glu Ser Lys Lys Gln
                485                 490                 495

Tyr Lys Met Ile Cys His Thr Phe Glu Ser Glu Asp Ala Gln Leu Ile
            500                 505                 510

Val Gln Ser Ile Gly Gln Ala Phe Ser Val Trp Tyr Gln Glu Phe Leu
        515                 520                 525

Arg Ala Asn Gly Tyr Asn Pro Glu Asp Leu Ser Gln Lys Glu Ala Ser
    530                 535                 540

Asp Ile Ile Asn Thr Gln Glu Met Asp Asn Asp Leu Ile His Phe
545                 550                 555                 560

Ser Asn Glu Glu Asn Cys Lys Glu Leu Gln Leu Glu Phe His Lys Gly
                565                 570                 575

Glu Ile Leu Gly Val Val Gly Val Glu Ser Gly Trp Gly Ser Ile Leu
            580                 585                 590

His Thr Val Ile Leu Ala Asn Met Met Asn Ile Gly Pro Ala Ala Arg
        595                 600                 605

Ser Gly Lys Leu Lys Ile Gly Asp Gln Ile Met Ser Ile Asn Leu Thr
    610                 615                 620

Ser Leu Val Gly Leu Pro Leu Ala Met Cys Gln Gly Ile Ile Lys Gly
625                 630                 635                 640

Leu Lys Gln Gln Thr Gln Val Lys Leu Asn Ile Val Arg Cys Pro Pro
                645                 650                 655

Val Thr Thr Val Leu Ile Ser Arg Pro Asp Leu Lys Tyr Gln Leu Gly
            660                 665                 670

Thr Ser Val Gln Asn Gly Ile Ile Cys Ser Val Met Arg Gly Gly Ile
        675                 680                 685

Ala Glu Arg Gly Trp Val Arg Val Gly His Arg Ile Ile Glu Tyr Asn
    690                 695                 700

Gly Gln Ser Val Val Ala Thr Ala Ala Glu Lys Ile Val Gln Ala Leu
705                 710                 715                 720

Ser Asn Asp Val Gly Glu Ile His Met Lys Thr Met Glu Ala Ala Met
                725                 730                 735

Phe Arg Leu Leu Thr Gly Phe Glu Thr Pro Leu Tyr Ile
            740                 745

<210> SEQ ID NO 94
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 94

Met Ala His Ala Lys Leu Glu Ser Val Gly Ser Gly Met Asp Asp His
 1               5                  10                  15

Arg Val Arg Pro Gly Pro Val Glu His Ser Gln Glu Pro Glu Ser Glu
            20                  25                  30

Asp Phe Glu Leu Pro Leu Glu Gly Tyr Val Pro Gly Leu Glu Leu
        35                  40                  45

Ala Ala Leu Arg Pro His Ser Pro Ala Pro Glu Gln Glu Cys Ile
    50                  55                  60

Asn His Ser Pro Asp Gly Asp Ser Ser Lys Asp Tyr Val Asn Asn Thr
65                  70                  75                  80

Ser Glu Glu Leu Asp Tyr Asp Glu Gly Leu Pro Glu Glu Met Glu Gly
```

-continued

```
                85                  90                  95
Ile Thr Tyr Tyr Ile Arg Tyr Asn Pro Glu Asp Asp Ser Tyr Leu Glu
                    100                 105                 110

Gly Gln Asp Cys Asn Gly Glu Glu Tyr Leu Ala Arg Ser Ala His Pro
            115                 120                 125

Val Asp Thr Asp Glu Ser Gln Glu Ala Val Glu Glu Trp Thr Asp Thr
    130                 135                 140

Ala Gly Pro His Pro His Gly His Glu Val Glu Gly Ser Gln Asp Tyr
145                 150                 155                 160

Pro Asp Gly Trp Leu Pro Ile Pro Glu Asp Glu Pro Ser Tyr Leu Glu
                165                 170                 175

Ala His Asp Gln Glu Glu Asp Ala His Tyr Cys Ala Ser Lys Glu Gly
            180                 185                 190

Tyr Asp Asp Tyr Tyr Pro Glu Glu Ala Asn Gly Glu Thr Gly Ala Ser
        195                 200                 205

Pro Tyr Arg Leu Arg Phe Gly Asp Gly Asp Leu Glu Asp Gln Glu Gly
    210                 215                 220

Asp Ile Asp Gln Ile Val Ala Glu Ile His Met Ser Leu Ser Met Thr
225                 230                 235                 240

Ser Ile Thr Ile Ala Ser Glu Ala Ser Pro Glu His Gly Lys Glu Pro
                245                 250                 255

Gly Pro Glu Asp Ser Val Glu Leu Cys Pro Pro Ile Lys Ala Ser Cys
            260                 265                 270

Ser Met Ser Arg His Glu Ala Arg Pro Lys Ser Asn Asn Leu Leu Pro
        275                 280                 285

Glu Ala Lys His Pro Gln Asp Pro Gln Arg Gly Phe Lys Pro Lys Arg
    290                 295                 300

Arg Thr Pro Glu Glu Arg Leu Lys Trp Ser His Glu Gln Val Cys Asn
305                 310                 315                 320

Gly Leu Glu Thr Pro Arg Lys Gln Gln Arg Ser Asp Leu Val Gly Pro
                325                 330                 335

Val Asp Asn Asn Asn Ile Pro Trp Thr Lys Lys Val Ala Ser Phe Pro
            340                 345                 350

Ser Tyr Val Ala Val Pro Gly Pro Cys Glu Pro Ala Asp Leu Ile Asp
        355                 360                 365

Gly Ile Ile Phe Ala Asp Asn Tyr Leu Gly Ser Thr Gln Leu Leu Glu
    370                 375                 380

Glu Arg Asn Pro Ser Lys Asn Ile Arg Phe Met Gln Ala Gln Glu Ala
385                 390                 395                 400

Val Ser Arg Gly Lys Arg Met Gln Lys Ala Ala Lys Ile His Lys Lys
                405                 410                 415

Ala Asn Ser Glu Gly Asp Ala Ile Thr Leu Thr Glu Val Asp Leu Phe
            420                 425                 430

Ile Lys Thr Gln Arg Ile Lys Val Leu Asn Ala Leu Thr Gln Glu Thr
        435                 440                 445

Met Met Asp His Ala Met Arg Thr Ile Ser Tyr Ile Ala Asp Ile Asn
    450                 455                 460

Asn Ile Val Val Leu Met Ala Arg Arg Gln Met Pro Arg Ser Ala Ser
465                 470                 475                 480

Gln Asp Cys Arg Glu Thr Thr Pro Gly Ala Gln Glu Gly Ser Lys Gln
                485                 490                 495

Tyr Lys Met Ile Cys His Val Thr Glu Ser Glu Asp Ala Gln Leu Ile
            500                 505                 510
```

-continued

Ala Val Ser Ile Gly Gln Ala Phe Ser Val Ala Trp Gln Glu Phe Leu
        515                 520                 525

Arg Ala Asn Gly Ile Tyr Pro Glu Asp Leu Ser Gln Lys Glu Tyr Ala
    530                 535                 540

Asp Ile Ile Asn Thr Gln Glu Met Tyr Asp Asp Leu Ile His Phe
545                 550                 555                 560

Ser Asn Ser Phe Asn Cys Lys Glu Leu Gln Leu Glu Lys Gly Lys Gly
                565                 570                 575

Glu Ile Leu Gly Val Val His Glu Ser Gly Trp Gly Ser Ile Leu
            580                 585                 590

Pro Ile Val Ile Leu Ala Asn Met Met Asn Gly Lys Pro Ala Ala Arg
            595                 600                 605

Ser Gly Lys Leu Ser Leu Gly Asp Gln Ile Met Ser Ile Asn Gly Met
    610                 615                 620

Ser Leu Val Gly Leu Pro Leu Ala Thr Asn Gln Gly Ile Ile Lys Gly
625                 630                 635                 640

Leu Lys Asn Arg Thr Gln Val Lys Leu Asn Ile Val Ser Ser Pro Pro
                645                 650                 655

Val Thr Thr Val Leu Ile Lys Thr Pro Asp Leu Lys Tyr Gln Leu Gly
            660                 665                 670

Phe Val Val Gln Asn Gly Ile Ile Cys Ser Leu Trp Arg Gly Gly Ile
            675                 680                 685

Ala Glu Arg Gly Gly Tyr Arg Val Gly His Arg Ile Ile Glu Ile Ala
        690                 695                 700

Gly Gln Ser Val Val Ala Thr Ala His Asp Lys Ile Val Gln Ala Leu
705                 710                 715                 720

Ser Asn Ser Glu Gly Glu Ile His Met Lys Thr Met Pro Phe Ala Met
                725                 730                 735

Phe Arg Leu Leu Thr Gly Gln Gly Thr Pro Leu Tyr Ile
            740                 745

<210> SEQ ID NO 95
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 95

Met Ala His Arg Ala Leu Glu Ser Val Gly Ser Gly Met Leu Glu His
1               5                   10                  15

Arg Val Arg Pro Gly Pro Val Pro Phe Ser Gln Glu Pro Glu Ser Glu
            20                  25                  30

Asp Met Gly Leu Pro Leu Glu Gly Tyr Val Pro Glu His Leu Glu Leu
        35                  40                  45

Ala Ala Leu Arg Pro Glu Ile Pro Ala Pro Glu Glu Gln Glu Cys His
    50                  55                  60

Lys His Ser Pro Asp Gly Asp Ser Ser Leu Tyr Val Asn Asn Thr
65                  70                  75                  80

Ser Glu Glu Glu Met Tyr Asp Glu Gly Leu Pro Glu Glu Asn Gly
                85                  90                  95

Ile Thr Tyr Tyr Ile Arg Tyr Cys Gln Glu Asp Asp Ser Tyr Leu Glu
            100                 105                 110

Gly Met Arg Cys Asn Gly Glu Glu Tyr Leu Ala His Thr Ala His Pro

-continued

```
            115                 120                 125
Val Asp Thr Asp Glu Cys Val Glu Ala Val Glu Glu Trp Thr Asp Ser
130                 135                 140

Trp Gly Pro His Pro His Gly His Glu Ala Tyr Gly Ser Gln Asp Tyr
145                 150                 155                 160

Pro Asp Gly Gln Ala Pro Ile Pro Glu Asp Glu Pro Ser Val Asp Glu
                165                 170                 175

Ala His Asp Gln Glu Glu Asp Gly Glu Tyr Cys Ala Ser Lys Glu Gly
                180                 185                 190

Tyr Gln Phe Tyr Tyr Pro Glu Ala Asn Gly Asn Gly Gly Ala Ser
        195                 200                 205

Pro Tyr Arg Leu Arg Arg His Asp Gly Asp Leu Glu Asp Gln Glu Glu
        210                 215                 220

Ile Ile Asp Gln Ile Val Ala Glu Ile Lys Lys Ser Leu Ser Met Thr
225                 230                 235                 240

Ser Ile Thr Ser Leu Ser Glu Ala Ser Pro Glu His Gly Pro Met Pro
                245                 250                 255

Gly Pro Glu Asp Ser Val Glu Ala Asn Pro Pro Ile Lys Ala Ser Cys
                260                 265                 270

Ser Pro Gln Arg His Glu Ala Arg Pro Lys Ser Leu Arg Leu Leu Pro
                275                 280                 285

Glu Ala Lys His Pro Gly Ser Pro Gln Arg Gly Phe Lys Pro Lys Thr
                290                 295                 300

Thr Thr Pro Glu Glu Arg Leu Lys Trp Pro Val Glu Gln Val Cys Asn
305                 310                 315                 320

Gly Leu Glu Gln Trp Arg Lys Gln Gln Arg Ser Asp Leu Asn Tyr Pro
                325                 330                 335

Val Asp Asn Asn Asn Ile Pro Glu Ala Lys Lys Val Ala Ser Phe Pro
                340                 345                 350

Ser Phe Asp Ala Val Pro Gly Pro Cys Glu Pro Glu Glu Leu Ile Asp
                355                 360                 365

Gly Ile Ile Phe Ala Ala Phe Tyr Leu Gly Ser Thr Gln Leu Leu Ser
                370                 375                 380

Gly Arg Asn Pro Ser Lys Asn Ile Arg Met His Gln Ala Gln Glu Ala
385                 390                 395                 400

Val Ser Arg Val Ile Arg Met Gln Lys Ala Ala Lys Ile Lys Leu Lys
                405                 410                 415

Ala Asn Ser Glu Gly Asp Ala Gln Met Leu Thr Glu Val Asp Leu Phe
                420                 425                 430

Ile Ser Asn Gln Arg Ile Lys Val Leu Asn Ala Asp Gln Gln Glu Thr
                435                 440                 445

Met Met Asp His Ala Leu Ser Thr Ile Ser Tyr Ile Ala Asp Ile Gly
                450                 455                 460

Thr Ile Val Val Leu Met Ala Arg Arg Arg Val Pro Arg Ser Ala Ser
465                 470                 475                 480

Gln Asp Cys Ile Trp Thr Thr Pro Gly Ala Gln Glu Gly Lys Tyr Gln
                485                 490                 495

Tyr Lys Met Ile Cys His Val Phe Ala Ser Glu Asp Ala Gln Leu Ile
                500                 505                 510

Ala Gln Asp Ile Gly Gln Ala Phe Ser Val Ala Tyr Glu Glu Phe Leu
                515                 520                 525

Arg Ala Asn Gly Ile Asn Phe Glu Asp Leu Ser Gln Lys Glu Tyr Ser
                530                 535                 540
```

-continued

```
Gly Ile Ile Asn Thr Gln Glu Met Tyr Asn His Asp Leu Ile His Phe
545                 550                 555                 560

Ser Asn Ser Glu Ile Cys Lys Glu Leu Gln Leu Glu Lys His Leu Gly
            565                 570                 575

Glu Ile Leu Gly Val Val Val Met Ser Gly Trp Gly Ser Ile Leu
        580                 585                 590

Pro Thr Asn Ile Leu Ala Asn Met Met Asn Gly Gly Gln Ala Ala Arg
            595                 600                 605

Ser Gly Lys Leu Ser Ile Arg Asp Gln Ile Met Ser Ile Asn Gly Thr
        610                 615                 620

Thr Leu Val Gly Leu Pro Leu Ala Thr Cys Val Gly Ile Ile Lys Gly
625                 630                 635                 640

Leu Lys Asn Gln Trp Gln Val Lys Leu Asn Ile Val Ser Cys Tyr Pro
                645                 650                 655

Val Thr Thr Val Leu Ile Lys Arg Ala Asp Leu Lys Tyr Gln Leu Gly
            660                 665                 670

Phe Ser Asp Gln Asn Gly Ile Ile Cys Ser Leu Met Glu Gly Gly Ile
        675                 680                 685

Ala Glu Arg Gly Gly Val Phe Val Gly His Arg Ile Ile Glu Ile Asn
690                 695                 700

His Gln Ser Val Val Ala Thr Ala His Glu Ile Ile Val Gln Ala Leu
705                 710                 715                 720

Ser Asn Ser Val Lys Glu Ile His Met Lys Thr Met Pro Ala Leu Met
                725                 730                 735

Phe Arg Leu Leu Thr Gly Gln Glu Met Pro Leu Tyr Ile
            740                 745

<210> SEQ ID NO 96
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 96

Met Ala His Arg Lys Ala Glu Ser Val Gly Ser Gly Met Leu Asp Asp
 1               5                  10                  15

Arg Val Arg Pro Gly Pro Val Pro His Glu Gln Glu Pro Glu Ser Glu
            20                  25                  30

Asp Met Glu Phe Pro Leu Glu Gly Tyr Val Pro Glu Gly Gly Glu Leu
        35                  40                  45

Ala Ala Leu Arg Pro Glu Ser His Ala Pro Glu Glu Gln Glu Cys His
    50                  55                  60

Asn Ile Ser Pro Asp Gly Asp Ser Ser Asp Lys Val Asn Asn Thr
 65                  70                  75                  80

Ser Glu Glu Glu Asp Leu Asp Glu Gly Leu Pro Glu Glu Glu Met
                85                  90                  95

Ile Thr Tyr Tyr Ile Arg Tyr Cys Pro Asn Asp Asp Ser Tyr Leu Glu
            100                 105                 110

Gly Met Asp Gln Asn Gly Glu Glu Tyr Leu Ala His Ser Arg His Pro
        115                 120                 125

Val Asp Thr Asp Glu Cys Gln Ser Ala Val Glu Glu Trp Thr Asp Ser
    130                 135                 140

Ala Thr Pro His Pro His Gly His Glu Ala Glu Val Ser Gln Asp Tyr
```

-continued

```
145                 150                 155                 160
Pro Asp Gly Gln Leu Trp Ile Pro Glu Asp Glu Pro Ser Val Leu Tyr
                165                 170                 175
Ala His Asp Gln Glu Asp Gly His Ala Cys Ala Ser Lys Glu Gly
            180                 185                 190
Tyr Gln Asp Asp Tyr Pro Glu Glu Ala Asn Gly Asn Thr Glu Ala Ser
                195                 200                 205
Pro Tyr Arg Leu Arg Arg Gly Phe Gly Asp Leu Glu Asp Gln Glu Glu
            210                 215                 220
Asp Gly Asp Gln Ile Val Ala Glu Ile Lys Met His Leu Ser Met Thr
225                 230                 235                 240
Ser Ile Thr Ser Ala Ile Glu Ala Ser Pro Glu His Gly Pro Glu Lys
                245                 250                 255
Gly Pro Glu Asp Ser Val Glu Ala Cys Leu Pro Ile Lys Ala Ser Cys
            260                 265                 270
Ser Pro Ser Met His Glu Ala Arg Pro Lys Ser Leu Asn Asn Leu Pro
            275                 280                 285
Glu Ala Lys His Pro Gly Asp Gln Gln Arg Gly Phe Lys Pro Lys Thr
            290                 295                 300
Arg Arg Pro Glu Glu Arg Leu Lys Trp Pro His Ser Gln Val Cys Asn
305                 310                 315                 320
Gly Leu Glu Gln Pro Thr Lys Gln Gln Arg Ser Asp Leu Asn Gly Val
                325                 330                 335
Val Asp Asn Asn Asn Ile Pro Glu Thr Trp Lys Val Ala Ser Phe Pro
                340                 345                 350
Ser Phe Val Tyr Val Pro Gly Pro Cys Glu Pro Glu Asp Ala Ile Asp
            355                 360                 365
Gly Ile Ile Phe Ala Ala Asn Asp Leu Gly Ser Thr Gln Leu Leu Ser
    370                 375                 380
Glu Glu Asn Pro Ser Lys Asn Ile Arg Met Met Phe Ala Gln Glu Ala
385                 390                 395                 400
Val Ser Arg Val Lys Gly Met Gln Lys Ala Ala Lys Ile Lys Lys His
                405                 410                 415
Ala Asn Ser Glu Gly Asp Ala Gln Thr Ile Thr Glu Val Asp Leu Phe
            420                 425                 430
Ile Ser Thr Lys Arg Ile Lys Val Leu Asn Ala Asp Thr Leu Glu Thr
            435                 440                 445
Met Met Asp His Ala Leu Arg Met Ile Ser Tyr Ile Ala Asp Ile Gly
    450                 455                 460
Asn Asn Val Val Leu Met Ala Arg Arg Met Gln Arg Ser Ala Ser
465                 470                 475                 480
Gln Asp Cys Ile Glu Arg Thr Pro Gly Ala Gln Glu Gly Lys Lys Ser
            485                 490                 495
Tyr Lys Met Ile Cys His Val Phe Glu Thr Glu Asp Ala Gln Leu Ile
            500                 505                 510
Ala Gln Ser Val Gly Gln Ala Phe Ser Val Ala Tyr Gln Trp Phe Leu
    515                 520                 525
Arg Ala Asn Gly Ile Asn Pro Tyr Asp Leu Ser Gln Lys Glu Tyr Ser
530                 535                 540
Asp Ala Ile Asn Thr Gln Glu Met Tyr Asn Asp Glu Leu Ile His Phe
545                 550                 555                 560
Ser Asn Ser Glu Asn Phe Lys Glu Leu Gln Leu Glu Lys His Lys His
            565                 570                 575
```

-continued

```
Glu Ile Leu Gly Val Val Val Glu Ile Gly Trp Gly Ser Ile Leu
            580                 585                 590

Pro Thr Val Lys Leu Ala Asn Met Met Asn Gly Gly Pro Leu Ala Arg
            595                 600                 605

Ser Gly Lys Leu Ser Ile Gly Met Gln Ile Met Ser Ile Asn Gly Thr
            610                 615                 620

Ser Asn Val Gly Leu Pro Leu Ala Thr Cys Gln Gln Ile Ile Lys Gly
625                 630                 635                 640

Leu Lys Asn Gln Thr Arg Val Lys Leu Asn Ile Val Ser Cys Pro Ser
                645                 650                 655

Val Thr Thr Val Leu Ile Lys Arg Pro Thr Leu Lys Tyr Gln Leu Gly
            660                 665                 670

Phe Ser Val Val Asn Gly Ile Ile Cys Ser Leu Met Arg Trp Gly Ile
            675                 680                 685

Ala Glu Arg Gly Gly Val Arg Tyr Gly His Arg Ile Ile Glu Ile Asn
            690                 695                 700

Gly Ala Ser Val Val Ala Thr Ala His Glu Lys Asp Val Gln Ala Leu
705                 710                 715                 720

Ser Asn Ser Val Gly Phe Ile His Met Lys Thr Met Pro Ala Ala Gly
                725                 730                 735

Phe Arg Leu Leu Thr Gly Gln Glu Thr His Leu Tyr Ile
            740                 745

<210> SEQ ID NO 97
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 97

Met Ala His Arg Lys Leu Ala Ser Val Gly Ser Gly Met Leu Asp His
1               5                   10                  15

Asp Val Arg Pro Gly Pro Val Pro His Ser Glu Glu Pro Glu Ser Glu
            20                  25                  30

Asp Met Glu Leu Phe Leu Glu Gly Tyr Val Pro Glu Gly Leu Gly Leu
        35                  40                  45

Ala Ala Leu Arg Pro Glu Ser Pro His Pro Glu Glu Gln Glu Cys His
    50                  55                  60

Asn His Ile Pro Asp Gly Asp Ser Ser Asp Tyr Lys Asn Asn Thr
65                  70                  75                  80

Ser Glu Glu Glu Asp Tyr Leu Glu Gly Leu Pro Glu Glu Glu Glu Gly
                85                  90                  95

Met Thr Tyr Tyr Ile Arg Tyr Cys Pro Glu Asn Asp Ser Tyr Leu Glu
            100                 105                 110

Gly Met Asp Cys Gln Gly Glu Glu Tyr Leu Ala His Ser Ala Arg Pro
        115                 120                 125

Val Asp Thr Asp Glu Cys Gln Glu Ser Val Glu Glu Trp Thr Asp Ser
    130                 135                 140

Ala Gly Thr His Pro His Gly His Glu Ala Glu Gly Val Gln Asp Tyr
145                 150                 155                 160

Pro Asp Gly Gln Leu Pro Trp Pro Glu Asp Glu Pro Ser Val Leu Glu
                165                 170                 175

Tyr His Asp Gln Glu Glu Asp Gly His Tyr Ala Ala Ser Lys Glu Gly
```

-continued

```
            180                 185                 190
Tyr Gln Asp Tyr Asp Pro Glu Glu Ala Asn Gly Asn Thr Gly Glu Ser
            195                 200                 205
Pro Tyr Arg Leu Arg Arg Gly Asp Phe Asp Leu Glu Asp Gln Glu Glu
210                 215                 220
Asp Ile Gly Gln Ile Val Ala Glu Ile Lys Met Ser His Ser Met Thr
225                 230                 235                 240
Ser Ile Thr Ser Ala Ser Ile Ala Ser Pro Glu His Gly Pro Glu Pro
                245                 250                 255
Lys Pro Glu Asp Ser Val Glu Ala Cys Pro Leu Ile Lys Ala Ser Cys
                260                 265                 270
Ser Pro Ser Arg Met Glu Ala Arg Pro Lys Ser Leu Asn Leu Asn Pro
                275                 280                 285
Glu Ala Lys His Pro Gly Asp Pro Arg Arg Gly Phe Lys Pro Lys Thr
                290                 295                 300
Arg Thr Ser Glu Glu Arg Leu Lys Trp Pro His Glu Thr Val Cys Asn
305                 310                 315                 320
Gly Leu Glu Gln Pro Arg Val Gln Gln Arg Ser Asp Leu Asn Gly Pro
                325                 330                 335
Trp Asp Asn Asn Ile Pro Glu Thr Lys Tyr Val Ala Ser Phe Pro
                340                 345                 350
Ser Phe Val Ala Ala Pro Gly Pro Cys Glu Pro Glu Asp Leu Asp Asp
                355                 360                 365
Gly Ile Ile Phe Ala Ala Asn Tyr Glu Gly Ser Thr Gln Leu Leu Ser
                370                 375                 380
Glu Arg Phe Pro Ser Lys Asn Ile Arg Met Met Gln Gly Gln Glu Ala
385                 390                 395                 400
Val Ser Arg Val Lys Arg His Gln Lys Ala Ala Lys Ile Lys Lys Lys
                405                 410                 415
Ile Asn Ser Glu Gly Asp Ala Gln Thr Leu Lys Glu Val Asp Leu Phe
                420                 425                 430
Ile Ser Thr Gln Leu Ile Lys Val Leu Asn Ala Asp Thr Gln Met Thr
                435                 440                 445
Met Met Asp His Ala Leu Arg Thr Asn Ser Tyr Ile Ala Asp Ile Gly
450                 455                 460
Asn Ile Gln Val Leu Met Ala Arg Arg Met Pro Ser Ser Ala Ser
465                 470                 475                 480
Gln Asp Cys Ile Glu Thr Val Pro Gly Ala Gln Gly Lys Lys Gln
                485                 490                 495
Trp Lys Met Ile Cys His Val Phe Glu Ser Tyr Asp Ala Gln Leu Ile
                500                 505                 510
Ala Gln Ser Ile Ala Gln Ala Phe Ser Val Ala Tyr Gln Glu Asp Leu
                515                 520                 525
Arg Ala Asn Gly Ile Asn Pro Glu Glu Leu Ser Gln Lys Glu Tyr Ser
                530                 535                 540
Asp Ile Phe Asn Thr Gln Glu Met Tyr Asn Asp Gly Ile His Phe
545                 550                 555                 560
Ser Asn Ser Glu Asn Cys His Glu Leu Gln Leu Glu Lys His Lys Gly
                565                 570                 575
Ile Ile Leu Gly Val Val Val Glu Ser Lys Trp Gly Ser Ile Leu
                580                 585                 590
Pro Thr Val Ile Met Ala Asn Met Met Asn Gly Gly Pro Ala Asn Arg
                595                 600                 605
```

-continued

```
Ser Gly Lys Leu Ser Ile Gly Asp Arg Ile Met Ser Ile Asn Gly Thr
610                 615                 620

Ser Leu Ser Gly Leu Pro Leu Ala Thr Cys Gln Gly Thr Ile Lys Gly
625                 630                 635                 640

Leu Lys Asn Gln Thr Gln Trp Lys Leu Asn Ile Val Ser Cys Pro Pro
                645                 650                 655

Tyr Thr Thr Val Leu Ile Lys Arg Pro Asp Ala Lys Tyr Gln Leu Gly
                660                 665                 670

Phe Ser Val Gln Asp Gly Ile Ile Cys Ser Leu Met Arg Gly Glu Ile
                675                 680                 685

Ala Glu Arg Gly Gly Val Arg Val Phe His Arg Ile Ile Glu Ile Asn
690                 695                 700

Gly Gln Gly Val Val Ala Thr Ala His Glu Lys Ile His Gln Ala Leu
705                 710                 715                 720

Ser Asn Ser Val Gly Glu Lys His Met Lys Thr Met Pro Ala Ala Met
                725                 730                 735

Leu Arg Leu Leu Thr Gly Gln Glu Thr Pro Met Tyr Ile
                740                 745

<210> SEQ ID NO 98
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 98

Met Ala His Arg Lys Leu Glu Ala Val Gly Ser Gly Met Leu Asp His
1               5                   10                  15

Arg Asp Arg Pro Gly Pro Val Pro His Ser Gln Phe Pro Glu Ser Glu
                20                  25                  30

Asp Met Glu Leu Pro Gly Glu Gly Tyr Val Pro Glu Gly Leu Glu His
            35                  40                  45

Ala Ala Leu Arg Pro Glu Ser Pro Ala Ile Glu Glu Gln Glu Cys His
        50                  55                  60

Asn His Ser Lys Asp Gly Asp Ser Ser Asp Tyr Val Leu Asn Thr
65                  70                  75                  80

Ser Glu Glu Glu Asp Tyr Asp Met Gly Leu Pro Glu Glu Glu Gly
                85                  90                  95

Ile Asn Tyr Tyr Ile Arg Tyr Cys Pro Glu Asp Gln Ser Tyr Leu Glu
                100                 105                 110

Gly Met Asp Cys Asn Arg Glu Glu Tyr Leu Ala His Ser Ala His Ser
            115                 120                 125

Val Asp Thr Asp Glu Cys Gln Glu Ala Thr Glu Trp Thr Asp Ser
        130                 135                 140

Ala Gly Pro Val Pro His Gly His Glu Ala Glu Gly Ser Trp Asp Tyr
145                 150                 155                 160

Pro Asp Gly Gln Leu Pro Ile Tyr Glu Asp Glu Pro Ser Val Leu Glu
                165                 170                 175

Ala Ala Asp Gln Glu Glu Asp Gly His Tyr Cys Asp Ser Lys Glu Gly
            180                 185                 190

Tyr Gln Asp Tyr Glu Glu Glu Ala Asn Gly Asn Thr Gly Ala Phe
        195                 200                 205

Pro Tyr Arg Leu Arg Arg Gly Asp Gly Gly Leu Glu Asp Gln Glu Glu
```

```
                210                 215                 220
Asp Ile Asp His Ile Val Ala Glu Ile Lys Met Ser Leu Ile Met Thr
225                 230                 235                 240

Ser Ile Thr Ser Ala Ser Glu Lys Ser Pro Glu His Gly Pro Glu Pro
                245                 250                 255

Gly Leu Glu Asp Ser Val Glu Ala Cys Pro Pro Met Lys Ala Ser Cys
                260                 265                 270

Ser Pro Ser Arg His Asn Ala Arg Pro Lys Ser Leu Asn Leu Leu Gln
                275                 280                 285

Glu Ala Lys His Pro Gly Asp Pro Gln Ser Gly Phe Lys Pro Lys Thr
290                 295                 300

Arg Thr Pro Thr Glu Arg Leu Lys Trp Pro His Glu Gln Trp Cys Asn
305                 310                 315                 320

Gly Leu Glu Gln Pro Arg Lys Tyr Gln Arg Ser Asp Leu Asn Gly Pro
                325                 330                 335

Val Ala Asn Asn Asn Ile Pro Glu Thr Lys Lys Asp Ala Ser Phe Pro
                340                 345                 350

Ser Phe Val Ala Val Glu Gly Pro Cys Glu Pro Glu Asp Leu Ile Phe
                355                 360                 365

Gly Ile Ile Phe Ala Ala Asn Tyr Leu His Ser Thr Gln Leu Leu Ser
370                 375                 380

Glu Arg Asn Ile Ser Lys Asn Ile Arg Met Met Gln Ala Lys Glu Ala
385                 390                 395                 400

Val Ser Arg Val Lys Arg Met Leu Lys Ala Ala Lys Ile Lys Lys Lys
                405                 410                 415

Ala Met Ser Glu Gly Asp Ala Gln Thr Leu Thr Asn Val Asp Leu Phe
                420                 425                 430

Ile Ser Thr Gln Arg Gln Lys Val Leu Asn Ala Asp Thr Gln Glu Arg
                435                 440                 445

Met Met Asp His Ala Leu Arg Thr Ile Thr Tyr Ile Ala Asp Ile Gly
450                 455                 460

Asn Ile Val Trp Leu Met Ala Arg Arg Met Pro Arg Tyr Ala Ser
465                 470                 475                 480

Gln Asp Cys Ile Glu Thr Thr Ala Gly Ala Gln Glu Gly Lys Lys Gln
                485                 490                 495

Tyr Asp Met Ile Cys His Val Phe Glu Ser Glu Ala Gln Leu Ile
                500                 505                 510

Ala Gln Ser Ile Gly Phe Ala Phe Ser Val Ala Tyr Gln Glu Phe Gly
                515                 520                 525

Arg Ala Asn Gly Ile Asn Pro Glu Asp His Ser Gln Lys Glu Tyr Ser
530                 535                 540

Asp Ile Ile Ile Thr Gln Glu Met Tyr Asn Asp Leu Lys His Phe
545                 550                 555                 560

Ser Asn Ser Glu Asn Cys Lys Leu Leu Gln Leu Glu Lys His Lys Gly
                565                 570                 575

Glu Met Leu Gly Val Val Val Glu Ser Gly Asn Gly Ser Ile Leu
                580                 585                 590

Pro Thr Val Ile Leu Gln Asn Met Met Asn Gly Pro Ala Ala Ser
                595                 600                 605

Ser Gly Lys Leu Ser Ile Gly Asp Gln Thr Met Ser Ile Asn Gly Thr
                610                 615                 620

Ser Leu Val Val Leu Pro Leu Ala Thr Cys Gln Gly Ile Trp Lys Gly
625                 630                 635                 640
```

-continued

```
Leu Lys Asn Gln Thr Gln Val Tyr Leu Asn Ile Val Ser Cys Pro Pro
                645                 650                 655

Val Ala Thr Val Leu Ile Lys Arg Pro Asp Leu Asp Tyr Gln Leu Gly
            660                 665                 670

Phe Ser Val Gln Asn Glu Ile Ile Cys Ser Leu Met Arg Gly Gly Phe
        675                 680                 685

Ala Glu Arg Gly Gly Val Arg Val Gly Gly Arg Ile Ile Glu Ile Asn
    690                 695                 700

Gly Gln Ser His Val Ala Thr His Glu Lys Ile Val Ile Ala Leu
705                 710                 715                 720

Ser Asn Ser Val Gly Glu Ile Lys Met Lys Thr Met Pro Ala Ala Met
                725                 730                 735

Phe Leu Leu Leu Thr Gly Gln Glu Thr Pro Leu Met Ile
                740                 745

<210> SEQ ID NO 99
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 99

Met Ala His Arg Lys Leu Glu Ser Ala Gly Ser Gly Met Leu Asp His
  1               5                   10                  15

Arg Val Asp Pro Gly Pro Val Pro His Ser Gln Glu Glu Ser Glu
                20                  25                  30

Asp Met Glu Leu Pro Leu Phe Gly Tyr Val Pro Glu Gly Leu Glu Leu
            35                  40                  45

Gly Ala Leu Arg Pro Glu Ser Pro Ala Pro His Glu Gln Glu Cys His
        50                  55                  60

Asn His Ser Pro Ile Gly Asp Ser Ser Ser Asp Tyr Val Asn Lys Thr
 65                  70                  75                  80

Ser Glu Glu Glu Asp Tyr Asp Glu Leu Leu Pro Glu Glu Glu Gly
                85                  90                  95

Ile Thr Met Tyr Ile Arg Tyr Cys Pro Glu Asp Asn Tyr Leu Glu
            100                 105                 110

Gly Met Asp Cys Asn Gly Gln Glu Tyr Leu Ala His Ser Ala His Pro
        115                 120                 125

Arg Asp Thr Asp Glu Cys Gln Glu Ala Val Ser Glu Trp Thr Asp Ser
    130                 135                 140

Ala Gly Pro His Thr His Gly His Glu Ala Glu Gly Ser Gln Val Tyr
145                 150                 155                 160

Pro Asp Gly Gln Leu Pro Ile Pro Trp Asp Glu Pro Ser Val Leu Glu
                165                 170                 175

Ala His Tyr Gln Glu Glu Asp Gly His Tyr Cys Ala Ala Lys Glu Gly
            180                 185                 190

Tyr Gln Asp Tyr Tyr Pro Asp Glu Ala Asn Gly Asn Thr Gly Ala Ser
        195                 200                 205

Glu Tyr Arg Leu Arg Arg Gly Asp Gly Asp Phe Glu Asp Gln Glu Glu
    210                 215                 220

Asp Ile Asp Gln Gly Val Ala Glu Ile Lys Met Ser Leu Ser His Thr
225                 230                 235                 240

Ser Ile Thr Ser Ala Ser Glu Ala Ile Pro Glu His Gly Pro Glu Pro
```

```
                    245                 250                     255
Gly Pro Lys Asp Ser Val Glu Ala Cys Pro Pro Ile Leu Ala Ser Cys
            260                 265                 270

Ser Pro Ser Arg His Glu Met Arg Pro Lys Ser Leu Asn Leu Leu Pro
            275                 280                 285

Asn Ala Lys His Pro Gly Asp Pro Gln Arg Gln Phe Lys Pro Lys Thr
            290                 295                 300

Arg Thr Pro Glu Arg Arg Leu Lys Trp Pro His Glu Gln Val Ser Asn
305                 310                 315                 320

Gly Leu Glu Gln Pro Arg Lys Gln Thr Arg Ser Asp Leu Asn Gly Pro
                325                 330                 335

Val Asp Val Asn Asn Ile Pro Glu Thr Lys Lys Val Trp Ser Phe Pro
            340                 345                 350

Ser Phe Val Ala Val Pro Tyr Pro Cys Glu Pro Glu Asp Leu Ile Asp
            355                 360                 365

Ala Ile Ile Phe Ala Ala Asn Tyr Leu Gly Asp Thr Gln Leu Leu Ser
            370                 375                 380

Glu Arg Asn Pro Glu Lys Asn Ile Arg Met Met Gln Ala Gln Phe Ala
385                 390                 395                 400

Val Ser Arg Val Lys Arg Met Gln Gly Ala Ala Lys Ile Lys Lys Lys
                405                 410                 415

Ala Asn His Glu Gly Asp Ala Gln Thr Leu Thr Glu Ile Asp Leu Phe
            420                 425                 430

Ile Ser Thr Gln Arg Ile Leu Val Leu Asn Ala Asp Thr Gln Glu Thr
            435                 440                 445

Asn Met Asp His Ala Leu Arg Thr Ile Ser Gln Ile Ala Asp Ile Gly
            450                 455                 460

Asn Ile Val Val Arg Met Ala Arg Arg Met Pro Arg Ser Ser Ser
465                 470                 475                 480

Gln Asp Cys Ile Glu Thr Thr Pro Thr Ala Gln Glu Gly Lys Lys Gln
                485                 490                 495

Tyr Lys Val Ile Cys His Val Phe Glu Ser Glu Asp Trp Gln Leu Ile
            500                 505                 510

Ala Gln Ser Ile Gly Gln Tyr Phe Ser Val Ala Tyr Gln Glu Phe Leu
            515                 520                 525

Ala Ala Asn Gly Ile Asn Pro Glu Asp Leu Asp Gln Lys Glu Tyr Ser
            530                 535                 540

Asp Ile Ile Asn Glu Gln Glu Met Tyr Asn Asp Leu Ile Phe Phe
545                 550                 555                 560

Ser Asn Ser Glu Asn Cys Lys Glu Gly Gln Leu Glu Lys His Lys Gly
                565                 570                 575

Glu Ile His Gly Val Val Val Glu Ser Gly Trp Ile Ser Ile Leu
            580                 585                 590

Pro Thr Val Ile Leu Ala Lys Met Met Asn Gly Gly Pro Ala Ala Arg
            595                 600                 605

Leu Gly Lys Leu Ser Ile Gly Asp Gln Ile Asn Ser Ile Asn Gly Thr
            610                 615                 620

Ser Leu Val Gly Gln Pro Leu Ala Thr Cys Gln Gly Ile Ile Arg Gly
625                 630                 635                 640

Leu Lys Asn Gln Thr Gln Val Lys Ser Asn Ile Val Ser Cys Pro Pro
                645                 650                 655

Val Thr Val Val Leu Ile Lys Arg Pro Asp Leu Lys Trp Gln Leu Gly
            660                 665                 670
```

```
Phe Ser Val Gln Asn Gly Tyr Ile Cys Ser Leu Met Arg Gly Gly Ile
            675                 680                 685

Asp Glu Arg Gly Gly Val Arg Val Gly His Glu Ile Ile Glu Ile Asn
        690                 695                 700

Gly Gln Ser Val Phe Ala Thr Ala His Glu Lys Ile Val Gln Gly Leu
705                 710                 715                 720

Ser Asn Ser Val Gly Glu Ile His His Lys Thr Met Pro Ala Ala Met
                725                 730                 735

Phe Arg Ile Leu Thr Gly Gln Glu Thr Pro Leu Tyr Lys
            740                 745

<210> SEQ ID NO 100
<211> LENGTH: 749
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 100

Met Ala His Arg Lys Leu Glu Ser Val Ala Ser Gly Met Leu Asp His
1               5                   10                  15

Arg Val Arg Asp Gly Pro Val Pro His Ser Gln Glu Pro Phe Ser Glu
            20                  25                  30

Asp Met Glu Leu Pro Leu Glu His Tyr Val Pro Glu Gly Leu Glu Leu
        35                  40                  45

Ala Ile Leu Arg Pro Glu Ser Pro Ala Pro Glu Lys Gln Glu Cys His
    50                  55                  60

Asn His Ser Pro Asp Leu Asp Ser Ser Ser Asp Tyr Val Asn Asn Met
65                  70                  75                  80

Ser Glu Glu Glu Asp Tyr Asp Glu Gly Asn Pro Glu Glu Glu Glu Gly
                85                  90                  95

Ile Thr Tyr Gln Ile Arg Tyr Cys Pro Glu Asp Asp Ser Arg Leu Glu
            100                 105                 110

Gly Met Asp Cys Asn Gly Glu Ser Tyr Leu Ala His Ser Ala His Pro
        115                 120                 125

Val Thr Thr Asp Glu Cys Gln Glu Ala Val Glu Val Trp Thr Asp Ser
    130                 135                 140

Ala Gly Pro His Pro Trp Gly His Glu Ala Glu Gly Ser Gln Asp Ala
145                 150                 155                 160

Pro Asp Gly Gln Leu Pro Ile Pro Glu Glu Glu Pro Ser Val Leu Glu
                165                 170                 175

Ala His Asp Phe Glu Glu Asp Gly His Tyr Cys Ala Ser Gly Glu Gly
            180                 185                 190

Tyr Gln Asp Tyr Tyr Pro Glu His Ala Asn Gly Asn Thr Gly Ala Ser
        195                 200                 205

Pro Ile Arg Leu Arg Arg Gly Asp Gly Asp Leu Lys Asp Gln Glu Glu
    210                 215                 220

Asp Ile Asp Gln Ile Leu Ala Glu Ile Lys Met Ser Leu Ser Met Met
225                 230                 235                 240

Ser Ile Thr Ser Ala Ser Glu Ala Ser Asn Glu His Gly Pro Glu Pro
                245                 250                 255

Gly Pro Glu Gln Ser Val Glu Ala Cys Pro Ile Lys Arg Ser Cys
            260                 265                 270

Ser Pro Ser Arg His Glu Ala Ser Pro Lys Ser Leu Asn Leu Leu Pro
```

```
                275                 280                 285
Glu Thr Lys His Pro Gly Asp Pro Gln Arg Gly Val Lys Pro Lys Thr
        290                 295                 300
Arg Thr Pro Glu Glu Trp Leu Lys Trp Pro His Glu Gln Val Cys Tyr
305                 310                 315                 320
Gly Leu Glu Gln Pro Arg Lys Gln Gln Ala Ser Asp Leu Asn Gly Pro
                325                 330                 335
Val Asp Asn Asp Asn Ile Pro Glu Thr Lys Lys Val Ala Glu Phe Pro
        340                 345                 350
Ser Phe Val Ala Val Pro Gly Phe Cys Glu Pro Glu Asp Leu Ile Asp
        355                 360                 365
Gly Gly Ile Phe Ala Ala Asn Tyr Leu Gly Ser His Gln Leu Leu Ser
370                 375                 380
Glu Arg Asn Pro Ser Ile Asn Ile Arg Met Met Gln Ala Gln Glu Lys
385                 390                 395                 400
Val Ser Arg Val Lys Arg Met Gln Lys Leu Ala Lys Ile Lys Lys Lys
                405                 410                 415
Ala Asn Ser Met Gly Asp Ala Gln Thr Leu Thr Glu Val Asn Leu Phe
        420                 425                 430
Ile Ser Thr Gln Arg Ile Lys Gln Leu Asn Ala Asp Thr Gln Glu Thr
        435                 440                 445
Met Arg Asp His Ala Leu Arg Thr Ile Ser Tyr Ser Ala Asp Ile Gly
450                 455                 460
Asn Ile Val Val Leu Thr Ala Arg Arg Arg Met Pro Arg Ser Ala Val
465                 470                 475                 480
Gln Asp Cys Ile Glu Thr Thr Pro Gly Trp Gln Glu Gly Lys Lys Gln
                485                 490                 495
Tyr Lys Met Tyr Cys His Val Phe Glu Ser Glu Asp Ala Ala Leu Ile
                500                 505                 510
Ala Gln Ser Ile Gly Gln Ala Asp Ser Val Ala Tyr Gln Glu Phe Leu
        515                 520                 525
Arg Glu Asn Gly Ile Asn Pro Glu Asp Leu Ser Phe Lys Glu Tyr Ser
        530                 535                 540
Asp Ile Ile Asn Thr Gly Glu Met Tyr Asn Asp Asp Leu Ile His His
545                 550                 555                 560
Ser Asn Ser Glu Asn Cys Lys Glu Leu Ile Leu Glu Lys His Lys Gly
                565                 570                 575
Glu Ile Leu Lys Val Val Val Glu Ser Gly Trp Gly Leu Ile Leu
                580                 585                 590
Pro Thr Val Ile Leu Ala Asn Asn Met Asn Gly Gly Pro Ala Ala Arg
        595                 600                 605
Ser Gln Lys Leu Ser Ile Gly Asp Gln Ile Met Arg Ile Asn Gly Thr
        610                 615                 620
Ser Leu Val Gly Leu Ser Leu Ala Thr Cys Gln Gly Ile Ile Lys Thr
625                 630                 635                 640
Leu Lys Asn Gln Thr Gln Val Lys Leu Val Ile Val Ser Cys Pro Pro
                645                 650                 655
Val Thr Thr Trp Leu Ile Lys Arg Pro Asp Leu Lys Tyr Tyr Leu Gly
        660                 665                 670
Phe Ser Val Gln Asn Gly Ile Ala Cys Ser Leu Met Arg Gly Gly Ile
        675                 680                 685
Ala Asp Arg Gly Gly Val Arg Val Gly His Arg Glu Ile Glu Ile Asn
690                 695                 700
```

```
Gly Gln Ser Val Val Phe Thr Ala His Glu Lys Ile Val Gln Ala Gly
705                 710                 715                 720

Ser Asn Ser Val Gly Glu Ile His Met His Thr Met Pro Ala Ala Met
                725                 730                 735

Phe Arg Leu Ile Thr Gly Gln Glu Thr Pro Leu Tyr Ile
            740                 745
```

<210> SEQ ID NO 101
<211> LENGTH: 200
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 101

```
Met Phe Arg Lys Gly Lys Lys Arg His Ser Ser Ser Ser Gln Ser
 1               5                  10                  15

Ser Glu Ile Ser Thr Lys Ser Lys Ser Val Asp Ser Ser Leu Gly Gly
                20                  25                  30

Leu Ser Arg Ser Ser Thr Val Ala Ser Leu Asp Thr Asp Ser Thr Lys
            35                  40                  45

Ser Ser Gly Gln Ser Asn Ser Asn Leu Asp Thr Cys Ala Glu Phe Arg
 50                  55                  60

Ile Lys Tyr Val Gly Ala Ile Glu Lys Leu Ala Val Ser Glu Gly Lys
 65                  70                  75                  80

Ser Leu Glu Gly Pro Leu Asp Leu Ile Asn Tyr Ile Asp Val Ala Gln
                85                  90                  95

Gln Asp Gly Lys Leu Pro Phe Val Pro Leu Glu Glu Phe Ile Leu
            100                 105                 110

Gly Val Ser Lys Tyr Gly Ile Lys Val Ser Thr Thr Asp Gln His Gly
            115                 120                 125

Val Leu His Arg His Ala Leu Tyr Leu Ile Ile Arg Met Val Cys Tyr
130                 135                 140

Asp Asp Gly Leu Gly Ala Gly Lys Ser Leu Leu Ala Leu Lys Thr Thr
145                 150                 155                 160

Asp Ala Ser Asn Glu Glu Tyr Ser Leu Trp Val Tyr Gln Cys Asn Ser
                165                 170                 175

Leu Glu Gln Ala Gln Ala Ile Cys Lys Val Leu Ser Thr Ala Phe Asp
            180                 185                 190

Ser Val Leu Thr Ser Asp Lys Ser
            195                 200
```

<210> SEQ ID NO 102
<211> LENGTH: 200
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 102

```
Met Ala Arg Lys Gly Lys Lys Arg His Ser Ser Asp Ser Ser Gln Ser
 1               5                  10                  15

Ser Glu Ile Ser Thr Glu Ser Lys Ser Val Asp Ser Ser Leu Gly Phe
                20                  25                  30

Leu Ser Arg Ser Ser Thr Val Ala Ser Gly Asp Thr Asp Ser Thr Lys
            35                  40                  45
```

```
Ser Ser Gly His Ser Asn Ser Asn Leu Asp Thr Cys Ala Ile Phe Arg
         50                  55                  60

Ile Lys Tyr Val Gly Ala Ile Lys Lys Leu Ala Val Ser Glu Gly Lys
 65                  70                  75                  80

Ser Met Glu Gly Pro Leu Asp Leu Ile Asn Tyr Asn Asp Val Ala Gln
                 85                  90                  95

Gln Asp Gly Lys Leu Gln Phe Val Pro Leu Glu Glu Phe Ile Arg
                100                 105                 110

Gly Val Ser Lys Tyr Gly Ile Lys Val Thr Thr Thr Asp Gln His Gly
                115                 120                 125

Val Leu His Val His Ala Leu Tyr Leu Ile Ile Arg Met Trp Cys Tyr
130                 135                 140

Asp Asp Gly Leu Gly Ala Gly Tyr Ser Leu Leu Ala Leu Lys Thr Thr
145                 150                 155                 160

Asp Asp Ser Asn Glu Glu Tyr Ser Leu Trp Val Glu Gln Cys Asn Ser
                165                 170                 175

Leu Glu Gln Ala Gln Phe Ile Cys Lys Val Leu Ser Thr Ala Phe Gly
                180                 185                 190

Ser Val Leu Thr Ser Asp Lys Ser
                195                 200

<210> SEQ ID NO 103
<211> LENGTH: 200
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 103

Met Phe Ala Lys Gly Lys Lys Arg His Ser Ser Asp Ser Gln Ser
  1               5                  10                  15

Ser Glu Ile Ser Thr Lys Glu Lys Ser Val Asp Ser Ser Leu Gly Gly
                 20                  25                  30

Phe Ser Arg Ser Ser Thr Val Ala Ser Leu Gly Thr Asp Ser Thr Lys
                 35                  40                  45

Ser Ser Gly Gln His Asn Ser Asn Leu Asp Thr Cys Ala Glu Ile Arg
         50                  55                  60

Ile Lys Tyr Val Gly Ala Ile Glu Leu Ala Val Ser Glu Gly Lys
 65                  70                  75                  80

Ser Leu Met Gly Pro Leu Asp Leu Ile Asn Tyr Ile Asn Val Ala Gln
                 85                  90                  95

Gln Asp Gly Lys Leu Pro Gln Val Pro Leu Glu Glu Phe Ile Leu
                100                 105                 110

Arg Val Ser Lys Tyr Gly Ile Lys Val Ser Ser Thr Asp Gln His Gly
                115                 120                 125

Val Leu His Arg Thr Ala Leu Tyr Leu Ile Ile Arg Met Val Val Tyr
130                 135                 140

Asp Asp Gly Leu Gly Ala Gly Lys Trp Leu Leu Ala Leu Lys Thr Thr
145                 150                 155                 160

Asp Ala Tyr Asn Glu Glu Tyr Ser Leu Trp Val Tyr Ala Cys Asn Ser
                165                 170                 175

Leu Glu Gln Ala Gln Ala Asp Cys Lys Val Leu Ser Thr Ala Phe Asp
                180                 185                 190

Glu Val Leu Thr Ser Asp Lys Ser
```

<210> SEQ ID NO 104
<211> LENGTH: 200
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 104

Met Phe Arg Ala Gly Lys Lys Arg His Ser Ser Ser Asp Gln Ser
1               5                   10                  15

Ser Glu Ile Ser Thr Lys Ser Glu Ser Val Asp Ser Ser Leu Gly Gly
            20                  25                  30

Leu Phe Arg Ser Ser Thr Val Ala Ser Leu Asp Gly Asp Ser Thr Lys
        35                  40                  45

Ser Ser Gly Gln Ser His Ser Asn Leu Asp Thr Cys Ala Glu Phe Ile
    50                  55                  60

Ile Lys Tyr Val Gly Ala Ile Glu Lys Lys Ala Val Ser Glu Gly Lys
65                  70                  75                  80

Ser Leu Glu Leu Pro Leu Asp Leu Ile Asn Tyr Ile Asp Met Ala Gln
                85                  90                  95

Gln Asp Gly Lys Leu Pro Phe Asn Pro Leu Glu Glu Phe Ile Leu
            100                 105                 110

Gly Gln Ser Lys Tyr Gly Ile Lys Val Ser Thr Arg Asp Gln His Gly
        115                 120                 125

Val Leu His Arg His Ser Leu Tyr Leu Ile Ile Arg Met Val Cys Thr
    130                 135                 140

Asp Asp Gly Leu Gly Ala Gly Lys Ser Val Leu Ala Leu Lys Thr Thr
145                 150                 155                 160

Asp Ala Ser Trp Glu Glu Tyr Ser Leu Trp Val Tyr Gln Tyr Asn Ser
                165                 170                 175

Leu Glu Gln Ala Gln Ala Ile Ala Lys Val Leu Ser Thr Ala Phe Asp
            180                 185                 190

Ser Asp Leu Thr Ser Asp Lys Ser
        195                 200

<210> SEQ ID NO 105
<211> LENGTH: 200
<212> TYPE: PRT
<213> ORGANISM: Artificial Sequence
<220> FEATURE:
<223> OTHER INFORMATION: Description of Artificial Sequence: Synthetic Sequence

<400> SEQUENCE: 105

Met Phe Arg Lys Ala Lys Lys Arg His Ser Ser Ser Ser Asp Ser
1               5                   10                  15

Ser Glu Ile Ser Thr Lys Ser Lys Glu Val Asp Ser Ser Leu Gly Gly
            20                  25                  30

Leu Ser Phe Ser Ser Thr Val Ala Ser Leu Asp Thr Gly Ser Thr Lys
        35                  40                  45

Ser Ser Gly Gln Ser Asn His Asn Leu Asp Thr Cys Ala Glu Phe Arg
    50                  55                  60

Lys Lys Tyr Val Gly Ala Ile Glu Lys Leu Leu Val Ser Glu Gly Lys
65                  70                  75                  80

Ser Leu Glu Gly Met Leu Asp Leu Ile Asn Tyr Ile Asp Val Asn Gln

```
                    85                  90                  95
Gln Asp Gly Lys Leu Pro Phe Val Gln Leu Glu Glu Phe Ile Leu
                100                 105                 110

Gly Val Arg Lys Tyr Gly Ile Lys Val Ser Thr Thr Ser Gln His Gly
                115                 120                 125

Val Leu His Arg His Ala Thr Tyr Leu Ile Ile Arg Met Val Cys Tyr
        130                 135                 140

Val Asp Gly Leu Gly Ala Gly Lys Ser Leu Trp Ala Leu Lys Thr Thr
145                 150                 155                 160

Asp Ala Ser Asn Tyr Glu Tyr Ser Leu Trp Val Tyr Gln Cys Ala Ser
                165                 170                 175

Leu Glu Gln Ala Gln Ala Ile Cys Asp Val Leu Ser Thr Ala Phe Asp
                180                 185                 190

Ser Val Glu Thr Ser Asp Lys Ser
        195                 200

<210> SEQ ID NO 106
<211> LENGTH: 200
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 106

Met Phe Arg Lys Gly Ala Lys Arg His Ser Ser Ser Ser Ser Gln Asp
 1               5                  10                  15

Ser Glu Ile Ser Thr Lys Ser Lys Ser Glu Asp Ser Ser Leu Gly Gly
                20                  25                  30

Leu Ser Arg Phe Ser Thr Val Ala Ser Leu Asp Thr Asp Gly Thr Lys
        35                  40                  45

Ser Ser Gly Gln Ser Asn Ser His Leu Asp Thr Cys Ala Glu Phe Arg
    50                  55                  60

Ile Ile Tyr Val Gly Ala Ile Glu Lys Leu Ala Lys Ser Glu Gly Lys
65                  70                  75                  80

Ser Leu Glu Gly Pro Met Asp Leu Ile Asn Tyr Ile Asp Val Ala Asn
                85                  90                  95

Gln Asp Gly Lys Leu Pro Phe Val Pro Gln Glu Glu Glu Phe Ile Leu
                100                 105                 110

Gly Val Ser Arg Tyr Gly Ile Lys Val Ser Thr Thr Asp Ser His Gly
                115                 120                 125

Val Leu His Arg His Ala Leu Thr Leu Ile Ile Arg Met Val Cys Tyr
        130                 135                 140

Asp Val Gly Leu Gly Ala Gly Lys Ser Leu Leu Trp Leu Lys Thr Thr
145                 150                 155                 160

Asp Ala Ser Asn Glu Tyr Tyr Ser Leu Trp Val Tyr Gln Cys Asn Ala
                165                 170                 175

Leu Glu Gln Ala Gln Ala Ile Cys Lys Asp Leu Ser Thr Ala Phe Asp
                180                 185                 190

Ser Val Leu Glu Ser Asp Lys Ser
        195                 200

<210> SEQ ID NO 107
<211> LENGTH: 200
<212> TYPE: PRT
<213> ORGANISM: Artificial Sequence
<220> FEATURE:
```

-continued

<223> OTHER INFORMATION: Description of Artificial Sequence: Synthetic
      Sequence

<400> SEQUENCE: 107

Met Phe Arg Lys Gly Lys Ala Arg His Ser Ser Ser Ser Gln Ser
 1               5                  10                  15

Asp Glu Ile Ser Thr Lys Ser Lys Ser Val Glu Ser Ser Leu Gly Gly
             20                  25                  30

Leu Ser Arg Ser Phe Thr Val Ala Ser Leu Asp Thr Asp Ser Gly Lys
         35                  40                  45

Ser Ser Gly Gln Ser Asn Ser Asn His Asp Thr Cys Ala Glu Phe Arg
     50                  55                  60

Ile Lys Ile Val Gly Ala Ile Glu Lys Leu Ala Val Lys Glu Gly Lys
 65                  70                  75                  80

Ser Leu Glu Gly Pro Leu Leu Leu Ile Asn Tyr Ile Asp Val Ala Gln
                 85                  90                  95

Met Asp Gly Lys Leu Pro Phe Val Pro Leu Asn Glu Glu Phe Ile Leu
            100                 105                 110

Gly Val Ser Lys Gln Gly Ile Lys Val Ser Thr Thr Asp Gln Arg Gly
        115                 120                 125

Val Leu His Arg His Ala Leu Tyr Ser Ile Ile Arg Met Val Cys Tyr
    130                 135                 140

Asp Asp Thr Leu Gly Ala Gly Lys Ser Leu Leu Ala Val Lys Thr Thr
145                 150                 155                 160

Asp Ala Ser Asn Glu Glu Trp Ser Leu Trp Val Tyr Gln Cys Asn Ser
                165                 170                 175

Tyr Glu Gln Ala Gln Ala Ile Cys Lys Val Ala Ser Thr Ala Phe Asp
            180                 185                 190

Ser Val Leu Thr Asp Asp Lys Ser
        195                 200

<210> SEQ ID NO 108
<211> LENGTH: 200
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 108

Met Phe Arg Lys Gly Lys Lys Ala His Ser Ser Ser Ser Gln Ser
 1               5                  10                  15

Ser Asp Ile Ser Thr Lys Ser Lys Ser Val Asp Glu Ser Leu Gly Gly
             20                  25                  30

Leu Ser Arg Ser Ser Phe Val Ala Ser Leu Asp Thr Asp Ser Thr Gly
         35                  40                  45

Ser Ser Gly Gln Ser Asn Ser Asn Leu His Thr Cys Ala Glu Phe Arg
     50                  55                  60

Ile Lys Tyr Ile Gly Ala Ile Glu Lys Leu Ala Val Ser Lys Gly Lys
 65                  70                  75                  80

Ser Leu Glu Gly Pro Leu Asp Met Ile Asn Tyr Ile Asp Val Ala Gln
                 85                  90                  95

Gln Asn Gly Lys Leu Pro Phe Val Pro Leu Glu Gln Glu Phe Ile Leu
            100                 105                 110

Gly Val Ser Lys Tyr Arg Ile Lys Val Ser Thr Thr Asp Gln His Ser
        115                 120                 125

```
Val Leu His Arg His Ala Leu Tyr Leu Thr Ile Arg Met Val Cys Tyr
    130                 135                 140

Asp Asp Gly Val Gly Ala Gly Lys Ser Leu Leu Ala Leu Trp Thr Thr
145                 150                 155                 160

Asp Ala Ser Asn Glu Glu Tyr Tyr Leu Trp Val Tyr Gln Cys Asn Ser
                    165                 170                 175

Leu Ala Gln Ala Gln Ala Ile Cys Lys Val Leu Asp Thr Ala Phe Asp
                180                 185                 190

Ser Val Leu Thr Ser Glu Lys Ser
            195                 200

<210> SEQ ID NO 109
<211> LENGTH: 200
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 109

Met Phe Arg Lys Gly Lys Lys Arg Ala Ser Ser Ser Ser Gln Ser
  1               5                  10                  15

Ser Glu Asp Ser Thr Lys Ser Lys Ser Val Asp Ser Glu Leu Gly Gly
                 20                  25                  30

Leu Ser Arg Ser Ser Thr Phe Ala Ser Leu Asp Thr Asp Ser Thr Lys
             35                  40                  45

Gly Ser Gly Gln Ser Asn Ser Asn Leu Asp His Cys Ala Glu Phe Arg
     50                  55                  60

Ile Lys Tyr Val Ile Ala Ile Glu Lys Leu Ala Val Ser Glu Lys Lys
 65                  70                  75                  80

Ser Leu Glu Gly Pro Leu Asp Leu Leu Asn Tyr Ile Asp Val Ala Gln
                 85                  90                  95

Gln Asp Met Lys Leu Pro Phe Val Pro Leu Glu Glu Asn Phe Ile Leu
                100                 105                 110

Gly Val Ser Lys Tyr Gly Gln Lys Val Ser Thr Thr Asp Gln His Gly
            115                 120                 125

Arg Leu His Arg His Ala Leu Tyr Leu Ile Ser Arg Met Val Cys Tyr
    130                 135                 140

Asp Asp Gly Leu Thr Ala Gly Lys Ser Leu Leu Ala Leu Lys Val Thr
145                 150                 155                 160

Asp Ala Ser Asn Glu Glu Tyr Ser Trp Trp Val Tyr Gln Cys Asn Ser
                    165                 170                 175

Leu Glu Tyr Ala Gln Ala Ile Cys Lys Val Leu Ser Ala Ala Phe Asp
                180                 185                 190

Ser Val Leu Thr Ser Asp Asp Ser
            195                 200

<210> SEQ ID NO 110
<211> LENGTH: 200
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 110

Met Phe Arg Lys Gly Lys Lys Arg His Ala Ser Ser Ser Ser Gln Ser
  1               5                  10                  15
```

-continued

```
Ser Glu Ile Asp Thr Lys Ser Lys Ser Val Asp Ser Ser Glu Gly Gly
             20                  25                  30

Leu Ser Arg Ser Ser Thr Val Phe Ser Leu Asp Thr Asp Ser Thr Lys
         35                  40                  45

Ser Gly Gly Gln Ser Asn Ser Asn Leu Asp Thr His Ala Glu Phe Arg
     50                  55                  60

Ile Lys Tyr Val Gly Ile Ile Glu Lys Leu Ala Val Ser Glu Gly Leu
 65                  70                  75                  80

Ser Leu Glu Gly Pro Leu Asp Leu Ile Met Tyr Ile Asp Val Ala Gln
                 85                  90                  95

Gln Asp Gly Asn Leu Pro Phe Val Pro Leu Glu Glu Glu Gln Ile Leu
            100                 105                 110

Gly Val Ser Lys Tyr Gly Ile Arg Val Ser Thr Thr Asp Gln His Gly
        115                 120                 125

Val Ser His Arg His Ala Leu Tyr Leu Ile Ile Thr Met Val Cys Tyr
    130                 135                 140

Asp Asp Gly Leu Gly Val Gly Lys Ser Leu Leu Ala Leu Lys Thr Trp
145                 150                 155                 160

Asp Ala Ser Asn Glu Glu Tyr Ser Leu Tyr Val Tyr Gln Cys Asn Ser
                165                 170                 175

Leu Glu Gln Asp Gln Ala Ile Cys Lys Val Leu Ser Thr Glu Phe Asp
            180                 185                 190

Ser Val Leu Thr Ser Asp Lys Phe
        195                 200

<210> SEQ ID NO 111
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 111

Met Thr Thr Pro Asn Lys Thr Pro Gly Ala Asp Pro Lys Gln Leu
 1               5                  10                  15

Glu Arg Thr Gly Thr Val Arg Glu Ile Gly Ser Gln Ala Val Trp Ser
             20                  25                  30

Leu Ser Ser Cys Lys Pro Gly Phe Gly Val Asp Gln Leu Arg Asp Asp
         35                  40                  45

Asn Leu Glu Thr Tyr Trp Gln Ser Asp Gly Ser Gln Pro His Leu Val
     50                  55                  60

Asn Ile Gln Phe Arg Arg Lys Thr Thr Val Lys Thr Leu Cys Ile Tyr
 65                  70                  75                  80

Ala Asp Tyr Lys Ser Asp Glu Ser Tyr Thr Pro Ser Lys Ile Ser Val
                 85                  90                  95

Arg Val Gly Asn Asn Phe His Asn Leu Gln Glu Ile Arg Gln Leu Glu
            100                 105                 110

Leu Val Glu Pro Ser Gly Trp Ile His Val Pro Leu Thr Asp Asn His
        115                 120                 125

Lys Lys Pro Thr Arg Thr Phe Met Ile Gln Ile Ala Val Leu Ala Asn
    130                 135                 140

His Gln Asn Gly Arg Asp Thr His Met Arg Gln Ile Lys Ile Tyr Thr
145                 150                 155                 160

Pro Val Glu Glu Ser Ser Ile Gly Lys Phe Pro Arg Cys Thr Thr Ile
                165                 170                 175
```

```
Asp Phe Met Met Tyr Arg Ser Ile Arg
            180                 185
```

```
<210> SEQ ID NO 112
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 112
```

```
Met Ala Thr Pro Asn Lys Thr Pro Pro Gly Ala Glu Pro Lys Gln Leu
 1               5                  10                  15

Glu Arg Thr Gly Thr Phe Arg Glu Ile Gly Ser Gln Ala Val Trp Gly
                20                  25                  30

Leu Ser Ser Cys Lys Pro Gly Phe Gly His Asp Gln Leu Arg Asp Asp
            35                  40                  45

Asn Leu Glu Ile Tyr Trp Gln Ser Asp Gly Ser Gln Pro Lys Leu Val
 50                  55                  60

Asn Ile Gln Phe Arg Arg Lys Leu Thr Val Lys Thr Leu Cys Ile Tyr
 65                  70                  75                  80

Ala Met Tyr Lys Ser Asp Glu Ser Tyr Thr Pro Asn Lys Ile Ser Val
                85                  90                  95

Arg Val Gly Asn Asn Gln His Asn Leu Gln Glu Ile Arg Gln Leu Arg
                100                 105                 110

Leu Val Glu Pro Ser Gly Trp Ile His Ser Pro Leu Thr Asp Asn His
            115                 120                 125

Lys Lys Pro Val Arg Thr Phe Met Ile Gln Ile Ala Val Trp Ala Asn
130                 135                 140

His Gln Asn Gly Arg Asp Thr Tyr Met Arg Gln Ile Lys Ile Tyr Thr
145                 150                 155                 160

Pro Ala Glu Glu Ser Ser Ile Gly Lys Phe Pro Asp Cys Thr Thr Ile
                165                 170                 175

Asp Phe Met Met Tyr Glu Ser Ile Arg
            180                 185
```

```
<210> SEQ ID NO 113
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 113
```

```
Met Thr Ala Pro Asn Lys Thr Pro Pro Gly Ala Asp Asp Lys Gln Leu
 1               5                  10                  15

Glu Arg Thr Gly Thr Val Glu Ile Gly Ser Gln Ala Val Trp Ser
                20                  25                  30

Phe Ser Ser Cys Lys Pro Gly Phe Gly Val Gly Gln Leu Arg Asp Asp
            35                  40                  45

Asn Leu Glu Thr His Trp Gln Ser Asp Gly Ser Gln Pro His Ile Val
 50                  55                  60

Asn Ile Gln Phe Arg Arg Lys Thr Lys Val Lys Thr Leu Cys Ile Tyr
 65                  70                  75                  80

Ala Asp Leu Lys Ser Asp Glu Ser Tyr Thr Pro Ser Met Ile Ser Val
                85                  90                  95
```

```
Arg Val Gly Asn Asn Phe Asn Asn Leu Gln Glu Ile Arg Gln Leu Glu
            100                 105                 110

Gln Val Glu Pro Ser Gly Trp Ile His Val Arg Leu Thr Asp Asn His
        115                 120                 125

Lys Lys Pro Thr Ser Thr Phe Met Ile Gln Ile Ala Val Leu Thr Asn
130                 135                 140

His Gln Asn Gly Arg Asp Thr His Val Arg Gln Ile Lys Ile Tyr Thr
145                 150                 155                 160

Pro Val Trp Glu Ser Ser Ile Gly Lys Phe Pro Arg Tyr Thr Thr Ile
                165                 170                 175

Asp Phe Met Met Tyr Arg Ala Ile Arg
            180                 185

<210> SEQ ID NO 114
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 114

Met Thr Thr Ala Asn Lys Thr Pro Pro Gly Ala Asp Pro Asp Gln Leu
1               5                   10                  15

Glu Arg Thr Gly Thr Val Arg Phe Ile Gly Ser Gln Ala Val Trp Ser
            20                  25                  30

Leu Gly Ser Cys Lys Pro Gly Phe Gly Val Asp His Leu Arg Asp Asp
        35                  40                  45

Asn Leu Glu Thr Tyr Ile Gln Ser Asp Gly Ser Gln Pro His Leu Lys
    50                  55                  60

Asn Ile Gln Phe Arg Arg Lys Thr Thr Leu Lys Thr Leu Cys Ile Tyr
65                  70                  75                  80

Ala Asp Tyr Met Ser Asp Glu Ser Tyr Thr Pro Ser Lys Asn Ser Val
                85                  90                  95

Arg Val Gly Asn Asn Phe His Gln Leu Gln Glu Ile Arg Gln Leu Glu
            100                 105                 110

Leu Arg Glu Pro Ser Gly Trp Ile His Val Pro Ser Thr Asp Asn His
        115                 120                 125

Lys Lys Pro Thr Arg Thr Phe Met Ile Gln Ile Ala Val Leu Ala Val
130                 135                 140

His Gln Asn Gly Arg Asp Thr His Met Trp Gln Ile Lys Ile Tyr Thr
145                 150                 155                 160

Pro Val Glu Tyr Ser Ser Ile Gly Lys Phe Pro Arg Cys Ala Thr Ile
                165                 170                 175

Asp Phe Met Met Tyr Arg Ser Asp Arg
            180                 185

<210> SEQ ID NO 115
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 115

Met Thr Thr Pro Ala Lys Thr Pro Pro Gly Ala Asp Pro Lys Asp Leu
1               5                   10                  15
```

```
Glu Arg Thr Gly Thr Val Arg Glu Glu Gly Ser Gln Ala Val Trp Ser
         20                  25                  30

Leu Ser Phe Cys Lys Pro Gly Phe Gly Val Asp Gln Gly Arg Asp Asp
     35                  40                  45

Asn Leu Glu Thr Tyr Trp His Ser Asp Gly Ser Gln Pro His Leu Val
 50                  55                  60

Ile Ile Gln Phe Arg Arg Lys Thr Thr Val Leu Thr Leu Cys Ile Tyr
 65                  70                  75                  80

Ala Asp Tyr Lys Met Asp Glu Ser Tyr Thr Pro Ser Lys Ile Asn Val
             85                  90                  95

Arg Val Gly Asn Asn Phe His Asn Gln Gln Glu Ile Arg Gln Leu Glu
             100                 105                 110

Leu Val Arg Pro Ser Gly Trp Ile His Val Pro Leu Ser Asp Asn His
         115                 120                 125

Lys Lys Pro Thr Arg Thr Thr Met Ile Gln Ile Ala Val Leu Ala Asn
 130                 135                 140

Val Gln Asn Gly Arg Asp Thr His Met Arg Trp Ile Lys Ile Tyr Thr
145                 150                 155                 160

Pro Val Glu Glu Tyr Ser Ile Gly Lys Phe Pro Arg Cys Thr Ala Ile
             165                 170                 175

Asp Phe Met Met Tyr Arg Ser Ile Asp
             180                 185

<210> SEQ ID NO 116
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 116

Met Thr Thr Pro Asn Ala Thr Pro Pro Gly Ala Asp Pro Lys Gln Asp
 1               5                  10                  15

Glu Arg Thr Gly Thr Val Arg Glu Ile Glu Ser Gln Ala Val Trp Ser
             20                  25                  30

Leu Ser Ser Phe Lys Pro Gly Phe Gly Val Asp Gln Leu Gly Asp Asp
         35                  40                  45

Asn Leu Glu Thr Tyr Trp Gln His Asp Gly Ser Gln Pro His Leu Val
 50                  55                  60

Asn Lys Gln Phe Arg Arg Lys Thr Thr Val Lys Leu Leu Cys Ile Tyr
 65                  70                  75                  80

Ala Asp Tyr Lys Ser Met Glu Ser Tyr Thr Pro Ser Lys Ile Ser Asn
             85                  90                  95

Arg Val Gly Asn Asn Phe His Asn Leu Arg Glu Ile Arg Gln Leu Glu
             100                 105                 110

Leu Val Glu Ser Ser Gly Trp Ile His Val Pro Leu Thr Thr Asn His
         115                 120                 125

Lys Lys Pro Thr Arg Thr Phe Val Ile Gln Ile Ala Val Leu Ala Asn
 130                 135                 140

His Trp Asn Gly Arg Asp Thr His Met Arg Gln Tyr Lys Ile Tyr Thr
145                 150                 155                 160

Pro Val Glu Glu Ser Ala Ile Gly Lys Phe Pro Arg Cys Thr Thr Asp
             165                 170                 175

Asp Phe Met Met Tyr Arg Ser Ile Arg
```

```
                180             185

<210> SEQ ID NO 117
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 117

Met Thr Thr Pro Asn Lys Ala Pro Pro Gly Ala Asp Pro Lys Gln Leu
 1               5                  10                  15

Asp Arg Thr Gly Thr Val Arg Glu Ile Gly Glu Gln Ala Val Trp Ser
            20                  25                  30

Leu Ser Ser Cys Phe Pro Gly Phe Gly Val Asp Gln Leu Arg Gly Asp
        35                  40                  45

Asn Leu Glu Thr Tyr Trp Gln Ser His Gly Ser Gln Pro His Leu Val
    50                  55                  60

Asn Ile Ile Phe Arg Arg Lys Thr Thr Val Lys Thr Lys Cys Ile Tyr
65                  70                  75                  80

Ala Asp Tyr Lys Ser Asp Leu Ser Tyr Thr Pro Ser Lys Ile Ser Val
                85                  90                  95

Met Val Gly Asn Asn Phe His Asn Leu Gln Asn Ile Arg Gln Leu Glu
            100                 105                 110

Leu Val Glu Pro Gln Gly Trp Ile His Val Pro Leu Thr Asp Arg His
        115                 120                 125

Lys Lys Pro Thr Arg Thr Phe Met Ser Gln Ile Ala Val Leu Ala Asn
    130                 135                 140

His Gln Thr Gly Arg Asp Thr His Met Arg Gln Ile Val Ile Tyr Thr
145                 150                 155                 160

Pro Val Glu Glu Ser Ser Trp Gly Lys Phe Pro Arg Cys Thr Thr Ile
                165                 170                 175

Tyr Phe Met Met Tyr Arg Ser Ile Arg
            180                 185

<210> SEQ ID NO 118
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 118

Met Thr Thr Pro Asn Lys Thr Ala Pro Gly Ala Asp Pro Lys Gln Leu
 1               5                  10                  15

Glu Asp Thr Gly Thr Val Arg Glu Ile Gly Ser Glu Ala Val Trp Ser
            20                  25                  30

Leu Ser Ser Cys Lys Phe Gly Phe Gly Val Asp Gln Leu Arg Asp Gly
        35                  40                  45

Asn Leu Glu Thr Tyr Trp Gln Ser Asp His Ser Gln Pro His Leu Val
    50                  55                  60

Asn Ile Gln Ile Arg Arg Lys Thr Thr Val Lys Thr Leu Lys Ile Tyr
65                  70                  75                  80

Ala Asp Tyr Lys Ser Asp Glu Leu Tyr Thr Pro Ser Lys Ile Ser Val
                85                  90                  95

Arg Met Gly Asn Asn Phe His Asn Leu Gln Glu Asn Arg Gln Leu Glu
```

```
                100                 105                 110
Leu Val Glu Pro Ser Gln Trp Ile His Val Pro Leu Thr Asp Asn Arg
            115                 120                 125

Lys Lys Pro Thr Arg Thr Phe Met Ile Ser Ile Ala Val Leu Ala Asn
        130                 135                 140

His Gln Asn Thr Arg Asp Thr His Met Arg Gln Ile Lys Val Tyr Thr
145                 150                 155                 160

Pro Val Glu Glu Ser Ser Ile Trp Lys Phe Pro Arg Cys Thr Thr Ile
                165                 170                 175

Asp Tyr Met Met Tyr Arg Ser Ile Arg
            180                 185

<210> SEQ ID NO 119
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 119

Met Thr Thr Pro Asn Lys Thr Pro Ala Gly Ala Asp Pro Lys Gln Leu
  1               5                  10                  15

Glu Arg Asp Gly Thr Val Arg Glu Ile Gly Ser Gln Glu Val Trp Ser
            20                  25                  30

Leu Ser Cys Lys Pro Phe Phe Gly Val Asp Gln Leu Arg Asp Asp
        35                  40                  45

Gly Leu Glu Thr Tyr Trp Gln Ser Asp Gly His Gln Pro His Leu Val
    50                  55                  60

Asn Ile Gln Phe Ile Arg Lys Thr Thr Val Lys Thr Leu Cys Lys Tyr
65                  70                  75                  80

Ala Asp Tyr Lys Ser Asp Glu Ser Leu Thr Pro Ser Lys Ile Ser Val
                85                  90                  95

Arg Val Met Asn Asn Phe His Asn Leu Gln Glu Ile Asn Gln Leu Glu
            100                 105                 110

Leu Val Glu Pro Ser Gly Gln Ile His Val Pro Leu Thr Asp Asn His
        115                 120                 125

Arg Lys Pro Thr Arg Thr Phe Met Ile Gln Ser Ala Val Leu Ala Asn
    130                 135                 140

His Gln Asn Gly Thr Asp Thr His Met Arg Gln Ile Lys Ile Val Thr
145                 150                 155                 160

Pro Val Glu Glu Ser Ser Ile Gly Trp Phe Pro Arg Cys Thr Thr Ile
                165                 170                 175

Asp Phe Tyr Met Tyr Arg Ser Ile Arg
            180                 185

<210> SEQ ID NO 120
<211> LENGTH: 185
<212> TYPE: PRT
<213> ORGANISM: Artificial Sequence
<220> FEATURE:
<223> OTHER INFORMATION: Description of Artificial Sequence: Synthetic
      Sequence

<400> SEQUENCE: 120

Met Thr Thr Pro Asn Lys Thr Pro Pro Ala Ala Asp Pro Lys Gln Leu
  1               5                  10                  15

Glu Arg Thr Asp Thr Val Arg Glu Ile Gly Ser Gln Ala Glu Trp Ser
```

```
                    20                  25                  30
Leu Ser Ser Cys Lys Pro Gly Gly Val Asp Gln Leu Arg Asp Asp
            35                  40                  45
Asn His Glu Thr Tyr Trp Gln Ser Asp Gly Ser Ile Pro His Leu Val
    50                  55                  60
Asn Ile Gln Phe Arg Lys Lys Thr Thr Val Lys Thr Leu Cys Ile Leu
65                  70                  75                  80
Ala Asp Tyr Lys Ser Asp Glu Ser Tyr Met Pro Ser Lys Ile Ser Val
                85                  90                  95
Arg Val Gly Gln Asn Phe His Asn Leu Gln Glu Ile Arg Arg Leu Glu
            100                 105                 110
Leu Val Glu Pro Ser Gly Trp Ser His Val Pro Leu Thr Asp Asn His
        115                 120                 125
Lys Thr Pro Thr Arg Thr Phe Met Ile Gln Ile Val Val Leu Ala Asn
    130                 135                 140
His Gln Asn Gly Arg Trp Thr His Met Arg Gln Ile Lys Ile Tyr Tyr
145                 150                 155                 160
Pro Val Glu Glu Ser Ser Ile Gly Lys Ala Pro Arg Cys Thr Thr Ile
                165                 170                 175
Asp Phe Met Asp Tyr Arg Ser Ile Arg
                180                 185

<210> SEQ ID NO 121
<211> LENGTH: 50
<212> TYPE: PRT
<213> ORGANISM: human

<400> SEQUENCE: 121

Lys Asn Trp Arg Leu Lys Asn Ile Asn Ser Ile Asn Phe Asp Asn Pro
1               5                   10                  15
Val Tyr Gln Lys Thr Thr Glu Asp Glu Val His Ile Cys His Asn Gln
            20                  25                  30
Asp Gly Tyr Ser Tyr Pro Ser Arg Gln Met Val Ser Leu Glu Asp Asp
        35                  40                  45
Val Ala
    50

<210> SEQ ID NO 122
<211> LENGTH: 54
<212> TYPE: PRT
<213> ORGANISM: mouse

<400> SEQUENCE: 122

Arg Asn Trp Gln His Lys Asn Met Lys Ser Met Asn Phe Asp Asn Pro
1               5                   10                  15
Val Tyr Leu Lys Thr Thr Glu Glu Asp Leu Ser Ile Asp Ile Gly Arg
            20                  25                  30
His Ser Ala Ser Val Gly His Thr Tyr Pro Ala Ile Ser Val Val Ser
        35                  40                  45
Thr Asp Asp Asp Leu Ala
    50

<210> SEQ ID NO 123
<211> LENGTH: 62
<212> TYPE: PRT
<213> ORGANISM: human

<400> SEQUENCE: 123
```

```
Thr Lys His Arg Arg Leu Gln Ser Ser Phe Thr Ala Phe Ala Asn Ser
 1               5                  10                 15

His Tyr Ser Ser Arg Leu Gly Ser Ala Ile Phe Ser Ser Gly Asp Asp
            20                  25                  30

Leu Gly Glu Asp Asp Glu Asp Ala Pro Met Ile Thr Gly Phe Ser Asp
        35                  40                  45

Asp Val Pro Met Ala Ala Ala Arg Val Asp Leu Gln Pro Ser
    50                  55                  60
```

<210> SEQ ID NO 124
<211> LENGTH: 57
<212> TYPE: PRT
<213> ORGANISM: mouse

<400> SEQUENCE: 124

```
Trp Arg Asn Trp Lys Arg Lys Asn Thr Lys Ser Met Asn Phe Asp Asn
 1               5                  10                 15

Pro Val Tyr Arg Lys Thr Thr Glu Glu Glu Glu Asp Glu Leu His
            20                  25                  30

Ile Gly Arg Thr Ala Gln Ile Gly His Val Tyr Pro Ala Arg Val Ala
        35                  40                  45

Leu Ser Leu Glu Asp Asp Gly Leu Pro
    50                  55
```

<210> SEQ ID NO 125
<211> LENGTH: 116
<212> TYPE: PRT
<213> ORGANISM: mouse

<400> SEQUENCE: 125

```
Trp Arg Asn Trp Lys Arg Lys Asn Thr Lys Ser Met Asn Phe Asp Asn
 1               5                  10                 15

Pro Val Tyr Arg Lys Thr Thr Glu Glu Glu Glu Asp Glu Leu His
            20                  25                  30

Ile Gly Arg Thr Ala Gln Ile Gly His Val Tyr Pro Ala Ala Ile Ser
        35                  40                  45

Asn Tyr Asp Arg Pro Leu Trp Ala Glu Pro Cys Leu Gly Glu Thr Arg
    50                  55                  60

Asp Leu Glu Asp Pro Ala Pro Ala Leu Lys Glu Leu Phe Val Leu Pro
65                  70                  75                  80

Gly Glu Pro Arg Ser Gln Leu His Gln Leu Pro Lys Asn Pro Leu Ser
                85                  90                  95

Glu Leu Pro Val Val Lys Cys Lys Arg Val Ala Leu Ser Leu Glu Asp
            100                 105                 110

Asp Gly Leu Pro
        115
```

<210> SEQ ID NO 126
<211> LENGTH: 97
<212> TYPE: PRT
<213> ORGANISM: human

<400> SEQUENCE: 126

```
Gly Ser Leu Leu Pro Ala Leu Pro Lys Leu Pro Ser Leu Ser Ser Leu
 1               5                  10                 15

Val Lys Pro Ser Glu Asn Gly Asn Gly Val Thr Phe Arg Ser Gly Ala
            20                  25                  30
```

-continued

```
Asp Leu Asn Met Asp Ile Gly Val Ser Gly Phe Gly Pro Glu Thr Ala
         35                  40                  45

Ile Asp Arg Ser Met Ala Met Ser Glu Asp Phe Val Met Glu Met Gly
 50                  55                  60

Lys Gln Pro Ile Ile Phe Glu Asn Pro Met Tyr Ser Ala Arg Asp Ser
 65                  70                  75                  80

Ala Val Lys Val Val Gln Pro Ile Gln Val Thr Val Ser Glu Asn Val
                 85                  90                  95

Asp

<210> SEQ ID NO 127
<211> LENGTH: 204
<212> TYPE: PRT
<213> ORGANISM: human

<400> SEQUENCE: 127

Gly Ser Leu Leu Pro Ala Leu Pro Lys Leu Pro Ser Leu Ser Ser Leu
 1               5                  10                  15

Val Lys Pro Ser Glu Asn Gly Asn Gly Val Thr Phe Arg Ser Gly Ala
                 20                  25                  30

Asp Leu Asn Met Asp Ile Gly Val Ser Gly Phe Gly Pro Glu Thr Ala
         35                  40                  45

Ile Asp Arg Ser Met Ala Met Ser Glu Asp Phe Val Met Glu Met Gly
 50                  55                  60

Lys Gln Pro Ile Ile Phe Glu Asn Pro Met Tyr Ser Ala Arg Asp Ser
 65                  70                  75                  80

Ala Val Lys Val Val Gln Pro Ile Gln Val Thr Val Ser Glu Asn Val
                 85                  90                  95

Asp Asn Lys Asn Tyr Gly Ser Pro Ile Asn Pro Ser Glu Ile Val Pro
                100                 105                 110

Glu Thr Asn Pro Thr Ser Pro Ala Asp Gly Thr Gln Val Thr Lys
             115                 120                 125

Trp Asn Leu Phe Lys Arg Lys Ser Lys Gln Thr Thr Asn Phe Glu Asn
130                 135                 140

Pro Ile Tyr Ala Gln Met Glu Asn Glu Gln Lys Glu Ser Val Ala Ala
145                 150                 155                 160

Thr Pro Pro Pro Ser Pro Ser Leu Pro Ala Lys Pro Lys Pro Pro Ser
                165                 170                 175

Arg Arg Asp Pro Thr Pro Thr Tyr Ser Ala Thr Glu Asp Thr Phe Lys
                180                 185                 190

Asp Thr Ala Asn Leu Val Lys Glu Asp Ser Glu Val
            195                 200

<210> SEQ ID NO 128
<211> LENGTH: 103
<212> TYPE: PRT
<213> ORGANISM: human

<400> SEQUENCE: 128

Gly Ser Pro Ile Asn Pro Ser Glu Ile Val Pro Glu Thr Asn Pro Thr
 1               5                  10                  15

Ser Pro Ala Ala Asp Gly Thr Gln Val Thr Lys Trp Asn Leu Phe Lys
                 20                  25                  30

Arg Lys Ser Lys Gln Thr Thr Asn Phe Glu Asn Pro Ile Tyr Ala Gln
         35                  40                  45

Met Glu Asn Glu Gln Lys Glu Ser Val Ala Ala Thr Pro Pro Pro Ser
```

-continued

```
                50                  55                  60
Pro Ser Leu Pro Ala Lys Pro Lys Pro Pro Ser Arg Arg Asp Pro Thr
 65                  70                  75                  80

Pro Thr Tyr Ser Ala Thr Glu Asp Thr Phe Lys Asp Thr Ala Asn Leu
                 85                  90                  95

Val Lys Glu Asp Ser Glu Val
            100

<210> SEQ ID NO 129
<211> LENGTH: 76
<212> TYPE: PRT
<213> ORGANISM: human

<400> SEQUENCE: 129

Val Gln Gly Ala Lys Gly Phe Gln His Gln Arg Met Thr Asn Gly Ala
 1               5                   10                  15

Met Asn Val Glu Ile Gly Asn Pro Thr Tyr Lys Met Tyr Glu Gly Gly
                 20                  25                  30

Glu Pro Asp Asp Val Gly Gly Leu Leu Asp Ala Asp Phe Ala Leu Asp
             35                  40                  45

Pro Asp Lys Pro Thr Asn Phe Thr Asn Pro Val Tyr Ala Thr Leu Tyr
         50                  55                  60

Met Gly Gly His Gly Ser Arg His Ser Leu Ala Ser
 65                  70                  75

<210> SEQ ID NO 130
<211> LENGTH: 38
<212> TYPE: PRT
<213> ORGANISM: human

<400> SEQUENCE: 130

Val Gln Gly Ala Lys Gly Phe Gln His Gln Arg Met Thr Asn Gly Ala
 1               5                   10                  15

Met Asn Val Glu Ile Gly Asn Pro Thr Tyr Lys Met Tyr Glu Gly Gly
                 20                  25                  30

Glu Pro Asp Asp Val Gly
             35

<210> SEQ ID NO 131
<211> LENGTH: 68
<212> TYPE: PRT
<213> ORGANISM: human

<400> SEQUENCE: 131

Ser Ala Arg Asp Ser Ala Val Lys Val Val Gln Pro Ile Gln Val Thr
 1               5                   10                  15

Val Ser Glu Asn Val Asp Asn Lys Asn Tyr Gly Ser Pro Ile Asn Pro
                 20                  25                  30

Ser Glu Ile Val Pro Glu Thr Asn Pro Thr Ser Pro Ala Ala Asp Gly
             35                  40                  45

Thr Gln Val Thr Lys Trp Asn Leu Phe Lys Arg Lys Ser Lys Gln Thr
         50                  55                  60

Thr Asn Phe Glu
 65

<210> SEQ ID NO 132
<211> LENGTH: 97
<212> TYPE: PRT
<213> ORGANISM: human
```

-continued

```
<400> SEQUENCE: 132

Val Gln Gly Ala Lys Gly Phe Gln His Gln Arg Met Thr Asn Gly Ala
  1               5                  10                  15

Met Asn Val Glu Ile Gly Asn Pro Thr Tyr Lys Met Tyr Glu Gly Gly
             20                  25                  30

Glu Pro Asp Asp Val Gly Gly Leu Leu Asp Ala Asp Phe Ala Leu Asp
         35                  40                  45

Pro Asp Lys Pro Thr Asn Phe Thr Asn Pro Val Tyr Ala Thr Leu Tyr
     50                  55                  60

Met Gly Gly His Gly Ser Arg His Ser Leu Ala Ser Thr Asp Glu Lys
 65                  70                  75                  80

Arg Glu Leu Leu Gly Arg Gly Pro Glu Asp Glu Ile Gly Asp Pro Leu
                 85                  90                  95

Ala
```

LDL RECEPTOR SIGNALING PATHWAYS

The research carried out in the subject application was supported in part by grants from the National Institutes of Health (HL20948 and HL63762). The government may have rights in any patent issuing on this application.

INTRODUCTION

1. Field of the Invention

The field of the invention is methods for inducing and detecting LDL receptor signaling.

2. Background of the Invention

The members of the low density lipoprotein (LDL) receptor gene family bind a broad spectrum of extracellular ligands. Traditionally, they had been regarded as mere cargo receptors that promote the endocytosis and lysosomal delivery of these ligands. However, recent genetic experiments in mice have revealed critical functions for LDL receptor family members in the transmission of extracellular signals and the activation of intracellular tyrosine kinases. This process regulates neuronal migration and is crucial for brain development. Signaling through these receptors requires the interaction of their cytoplasmic tails with the intracellular adaptor proteins Disabled-1 (Dab1) and FE65 (2,3). Here, we disclose an extended set of cytoplasmic polypeptides that can participate in signal transmission by the LDL receptor gene family. Most of these novel polypeptides are adaptor or scaffold polypeptides that contain PID or PDZ domains and function in the regulation of cellular kinases, including tyrosine kinases, serine/threonine kinases (e.g. microtubule associated protein (MAP) kinases) and lipid kinases (e.g. PI kinases), cell adhesion, vesicle trafficking, or neurotransmission. We also show that binding of Dab1 competes with receptor internalization indicating a mechanism by which signaling through this class of receptors might be regulated.

SUMMARY OF THE INVENTION

The invention provides methods and compositions for detecting and modulating, including inducing and suppressing, signal transduction through LDL receptors.

In a particular embodiment, the methods involve specifically detecting a stress that alters a functional interaction of an LDL receptor binding polypeptide with an LDL receptor interaction domain, the method comprising steps (a) introducing a predetermined stress into a system which provides a physical interaction of an LDL receptor binding polypeptide with an LDL receptor intracellular binding polypeptide interaction domain, whereby the system provides a stress-biased interaction of the binding polypeptide and the interaction domain, wherein the absence of the stress, the system provides an unbiased interaction of the binding polypeptide and the interaction domain; and (b) detecting the stress-biased interaction of the binding polypeptide and the interaction domain, wherein a difference between the stress-biased and unbiased interactions indicates that the stress alters the interaction of the binding polypeptide and the interaction domain. The binding polypeptide is independently selected from SEMCAP-1, JIP-1, PSD-95, JIP-2, Talin, OMP25, CAPON, PIP4,5 kinase, Na channel brain 3, Mint1, ICAP-1 and APC subunit10; and the receptor may be selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin. In panicula embodiments, the binding polypeptides and receptors are of natural sequence, preferably human sequence. In particular embodiments, the system is a cell expressing both the binding polypeptide and the interaction domain or an in vitro, cell-free mixture comprising a determined amount of the binding polypeptide and the interaction domain; exemplary systems include two-hybrid, biochemical pull-down, fluorescent polarization and solid phase binding assays.

The compositions of the invention, useful in the subject methods, include the subject binding polypeptides and mixtures consisting essentially of an LDL receptor binding polypeptide and an LDL receptor interaction domain, wherein the receptor may be independently selected from VLDLR, ApoER2, LDLR, LRP, MEGF7 and Megalin. Other aspects of the invention include nucleic acids encoding the disclosed binding polypeptides, antibodies which specifically bind them, and methods of use.

DETAILED DESCRIPTION OF PARTICULAR EMBODIMENTS OF THE INVENTION

The invention provides methods and compositions for inducing and detecting signal transduction through LDL receptors. In a particular embodiment, the methods involve specifically detecting a stress that alters a functional interaction of a low density lipoprotein (LDL) receptor binding polypeptide with an LDL receptor interaction domain.

The binding polypeptide is independently selected from SEMCAP-1, JIP-1, PSD-95, JIP-2, Talin, OMP25, CAPON, PIP4,5 kinase, Na channel brain 3, Mint1, ICAP-1 and APC subunit 10. These names are used generically to refer to polypeptides which comprise, or have sequence similarity to, the corresponding disclosed parental sequences, wherein the sequence similarity is at least 50%, preferably at least 80%, more preferably at least 90%, more preferably at least 95%, most preferably 100%, and specifically bind a specifically disclosed LDL receptor cytoplasmic domain (tail), as measured in one or more of the disclosed interaction assays. The polypeptides comprise, and the similarity or identity extends over at least 10, preferably at least 15, more preferably at least 25, more preferably at least 35, more preferably at least 50 contiguous residues and most preferably over the entire polypeptide sequence.

For disclosed polymeric genuses, "percent (%) sequence identity over a specified window size W" with respect to parental sequences is defined as the percentage of residues in any window of W residues in the candidate sequence that are identical with the residues in the parent sequence, after aligning the sequences and introducing gaps, if necessary, to achieve the maximum percent sequence identity. The % identity values are generated by WU-BLAST-2.0 a19 obtained from Altschul et al., J. Mol. Biol., 215: 403–410 (1990); http://blast.wustl.edu/blast/README.html. WU-BLAST-2.0a19 which uses several search parameters, all of which are set to the default values. The HSP S and HSP S2 parameters are dynamic values and are established by the program itself depending upon the composition of the particular sequence and composition of the particular database against which the sequence of interest is being searched; however, the values may be adjusted to increase sensitivity. Hence, a % sequence identity value is determined by the number of matching identical residues divided by the window size W for which the percent identity is reported. Exemplary species are readily generated by mutating the corresponding parental sequences and confirming LDL receptor interaction domain binding. For example, SEMCAP1 polypeptides defined by SEQ ID NOS:2–10 exemplify an active (demonstrating LDL receptor interaction domain binding) 90% genus around parental sequence SEQ ID NO: 1 (see table 1).

TABLE 1

LDL Receptor Binding Polypeptides

| Name | Similar Genbank Accession Nos. | Parental Sequence | Active 90% Species |
|---|---|---|---|
| SEMCAP-1 | gb\|AF104358.1\|AF104358 (m)<br>gb\|AF089817.1\|AF089817 (r)<br>gb\|AF089816.1\|AF089816 (h) | SEQ ID NO: 1 | SEQ ID NOS: 1–10 |
| JIP-1 | gb\|AF054611.1\|AF054611 (m)<br>gb\|AF109772.1\|AF109772 (r)<br>gb\|AF074091.1\|AF074091 (h)<br>gb\|AF003115.1\|MMAF003115<br>(isoforms/splice variants) | SEQ ID NO: 11 | SEQ ID NOS: 11–20 |
| PSD-95 | dbj\|D50621.1\|MUSPSD95SP (m)<br>gb\|M96853.1\|RATPSD95A (r)<br>gb\|U83192.1\|HSU83192 (h) | SEQ ID NO: 21 | SEQ ID NOS: 21–30 |
| JIP-2 | gb\|AF218778.1\|AF218778 (h)<br>emb\|AL021708.1\|HSU56K21<br>(isoforms/splice variants) | SEQ ID NO: 31 | SEQ ID NOS: 31–40 |
| Talin | gb\|AF177198.1\|AF177198<br>(h ortholog) | SEQ ID NO: 41 | SEQ ID NOS: 41–50 |
| OMP25 | gb\|AF107295.1\|AF107295 (r) | SEQ ID NO: 51 | SEQ ID NOS: 51–60 |
| CAPON | gb\|AF037071.1\|AF037071 (r)<br>dbj\|AB007933.2\|AB007933<br>(partial h) | SEQ ID NO: 61 | SEQ ID NOS: 61–70 |
| PIP4, 5 kinase | EST gb\|AA544527.1\|AA544527 (m) | SEQ ID NO: 71 | SEQ ID NOS: 71–80 |
| Na channel brain 3 | gb\|L42341.1\|MUSSOCHA<br>(m, homolog)<br>ref\|NM_013119.1\|<br>(r, homolog)<br>dbj\|AB037777.1\|AB037777<br>(partial h, homolog) | SEQ ID NO: 81 | SEQ ID NOS: 81–90 |
| Mint1 | gb\|L34676.1\|MUSX11P (m)<br>gb\|AF029107.1\|AF029107 (r)<br>ref\|NM_005503.1\| (h) | SEQ ID NO: 91 | SEQ ID NOS: 91–100 |
| ICAP-1 | ref\|NM_008403.1\| (m)<br>ref\|NM_004763.1\| (h) | SEQ ID NO: 101 | SEQ ID NOS: 101–110 |
| APC subunit10 | dbj\|AB012109.1\|AB012109 (h) | SEQ ID NO: 111 | SEQ ID NOS: 111–120 |

The LDL receptor interaction domain comprises or has sequence similarity to a natural LDL receptor cytoplasmic tail portion, wherein the sequence similarity is at least 50%, more preferably at least 70%, more preferably at least 80%, more preferably at least 90%, more preferably at least 95% and most preferably 100%, wherein the domain is sufficient to provide a specific binding target for the binding polypeptide, comparable to that provided by the corresponding cytoplasmic tail portion of the receptor, as measured in one or more of the disclosed interaction assays. The domains comprise, and the similarity or identity extends over at least 10, preferably at least 15, more preferably at least 25, more preferably at least 35, more preferably at least 50 contiguous residues and most preferably over the entire domain sequence. The receptor is preferably selected from a natural very low density lipoprotein receptor (VLDLR, such as human, mouse and chicken sequences), apolipoprotein E receptor-2 (ApoER2, such as human and mouse sequences), low density lipoprotein receptor (LDLR, such as human, mouse, rat, xenopus, hamster, rabbit, bovine and pig sequences), low density lipoprotein receptor related protein (LRP, such as human, mouse and chicken sequences), MEGF7 (such as human and rat sequences) and Megalin (such as human, rat, C. elegans and Drosophila sequences), which are known in the art and accessible from public genetic depositories such as Genbank. Unless noted otherwise by context, the term LDL receptor, as used herein, is used generically to refer to members of the LDL receptor gene family.

In one embodiment, the method comprises the steps of (a) introducing a predetermined stress into a system which provides a physical interaction of an LDL receptor binding polypeptide with an LDL receptor intracellular binding polypeptide interaction domain, whereby the system provides a stress-biased interaction of the binding polypeptide and the interaction domain, wherein the absence of the stress, the system provides an unbiased interaction of the binding polypeptide and the interaction domain; and (b) detecting the stress-biased interaction of the binding polypeptide and the interaction domain, wherein a difference between the stress-biased and unbiased interactions indicates that the stress alters the interaction of the binding polypeptide and the interaction domain.

A wide variety of systems may be used in the methods. For example, in particular embodiments, the system is a cell or animal expressing both the binding polypeptide and the interaction domain or an in vitro, cell-free mixture comprising a determined amount of the binding polypeptide and the interaction domain; exemplary systems include two-hybrid, biochemical pull-down, fluorescent polarization and solid phase binding assays. Similarly, a wide variety of stresses may be assayed or evaluated, including chemical agents, such as candidate drugs, toxins, contaminants, etc.; radiation such as ultraviolet rays and x-rays; infection such as viral or bacterial infection including cellular transformation, etc.

The particular method used to detect the interaction of the binding polypeptide and the interaction domain will depend on the nature of the assay, so long as the interaction is specifically detected. For example, depending on if and how the binding polypeptide and/or the interaction domains are labeled, the interaction readout may be measured by changes in fluorescence, optical density, gel shifts, radiation, etc. In a particular embodiment, the system provides a tau phosphorylation readout for the binding of the LDL receptor binding polypeptide and the LDL receptor interaction domain.

The compositions of the invention, useful in the subject methods, include the subject binding polypeptides and mixtures comprising predetermined amounts of a disclosed low density lipoprotein (LDL) receptor binding polypeptide and a disclosed LDL receptor interaction domain, particularly wherein one, preferably both of these components are isolated and mixtures consisting essentially of both components, i.e. wherein other components of the mixture (except for an assayed stress) do not significantly influence the interaction of these two components. Other aspects of the invention include nucleic acids encoding the disclosed binding polypeptides, antibodies which specifically bind them, and methods of use.

Subject polypeptides consisting of the disclosed parental sequences or fragments thereof are isolated, i.e. unaccompanied by at least some of the material with which it is associated in its natural state, preferably constituting at least about 0.5%, preferably at least about 5%, more preferably at least about 50% by weight of total polypeptide present in a given sample, and a pure polypeptide constitutes at least about 90%, and preferably at least about 99% by weight of the total polypeptide in a given sample, as are preferred subject polypeptides comprising other than parental sequence. In addition the subject polypeptides consisting of the disclosed parental sequences or fragments thereof have corresponding-polypeptide-specific antibody binding, elicitation or binding or elicitation inhibitory activity, e.g. elicit specific antibody in a heterologous host, etc. In a particular embodiment, the subject polypeptide fragments provide specific antigens and/or immunogens, especially when coupled to carrier proteins. For example, peptides are covalently coupled to keyhole limpet antigen (KLH) and the conjugate is emulsified in Freunds complete adjuvant. Laboratory rabbits are immunized according to conventional protocol and bled. The presence of specific antibodies is assayed by solid phase inmmunosorbant assays using immobilized corresponding polypeptide, see, e.g. Table 2.

TABLE 2

Immunogenic polypeptides eliciting specific rabbit polyclonal antibody: Polypeptide-KLH conjugates immunized per protocol described above.

| Polypeptide Sequence | Immunogenicity |
| --- | --- |
| SEQ ID NO:71, residues 7–16 | +++ |
| SEQ ID NO:71, residues 16–25 | +++ |
| SEQ ID NO:71, residues 23–31 | +++ |
| SEQ ID NO:71, residues 29–38 | +++ |
| SEQ ID NO:71, residues 39–46 | +++ |
| SEQ ID NO:71, residues 44–51 | +++ |
| SEQ ID NO:71, residues 51–60 | +++ |
| SEQ ID NO:71, residues 55–62 | +++ |
| SEQ ID NO:71, residues 58–66 | +++ |
| SEQ ID NO:71, residues 69–78 | +++ |
| SEQ ID NO:71, residues 78–88 | +++ |
| SEQ ID NO:71, residues 87–96 | +++ |
| SEQ ID NO:71, residues 99–108 | +++ |
| SEQ ID NO:71, residues 104–114 | +++ |
| SEQ ID NO:71, residues 116–128 | +++ |
| SEQ ID NO:71, residues 130–138 | +++ |

TABLE 2-continued

Immunogenic polypeptides eliciting specific rabbit polyclonal antibody: Polypeptide-KLH conjugates immunized per protocol described above.

| Polypeptide Sequence | Immunogenicity |
| --- | --- |
| SEQ ID NO:71, residues 141–149 | +++ |
| SEQ ID NO:71, residues 150–159 | +++ |
| SEQ ID NO:71, residues 159–168 | +++ |

In addition to direct synthesis, the subject polypeptides can also be expressed in cell and cell-free systems (e.g. Jermutus L, et al., Curr Opin Biotechnol. 1998 October;9 (5):534–48) from encoding polynucleotides, such as the corresponding parent polynucleotides or naturally-encoding polynucleotides isolated with degenerate oligonucleotide primers and probes generated from the subject polypeptide sequences ("GCG" software, Genetics Computer Group, Inc, Madison Wis.) or polynucleotides optimized for selected expression systems made by back-translating the subject polypeptides according to computer algorithms (e.g. Holler et al. (1993) Gene 136, 323–328; Martin et al. (1995) Gene 154, 150–166). Hence, the polypeptides may be synthesized, produced by recombinant technology, or purified from cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to the subject polypeptides, methods of identifying and making such agents, and their use. For example, specific binding agents are useful in a variety of diagnostic and industrial applications and include somatically recombined polypeptide receptors like specific antibodies or T-cell antigen receptors (see, e.g Harlow and Lane (1988) Antibodies, A Laboratory Manual, Cold Spring Harbor Laboratory), intracellular binding agents identified with assays such as one-, two- and three-hybrid screens, non-natural intracellular binding agents identified in screens of chemical libraries such as described below, etc. Accordingly, the invention provides complementarity determining region (CDR) sequences and libraries of such sequences. Generally, the CDR polypeptides are expressed and used as the binding domain of an immunoglobulin or fragment thereof.

The invention provides polynucleotides encoding the disclosed polypeptides, which polynucleotides may be joined to other components such as labels or other polynucleotide sequences (i.e. they may be part of larger sequences) and are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant polynucleotides comprising natural sequence contain such sequence at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bases, most preferably fewer than

EXAMPLES, PROTOCOLS AND EXPERIMENTAL PROCEDURES

I. High-Throughput In Vitro Fluorescence Polarization Assay

Reagents:
 LDL Receptor Interaction Domain peptide (size minimized, rhodamine-labeled; final conc.=1–5 nM)
 Binding Polypeptide (final conc.=100–200 nM)
 Buffer: 10 mM HEPES, 10 mM NaCl, 6 mM magnesium chloride, pH 7.6

Protocol:
1. Add 90 microliters of receptor peptide/binding polypeptide mixture to each well of a 96-well microtiter plate.
2. Add 10 microliters of test compound per well.
3. Shake 5 min and within 5 minutes determine amount of fluorescence polarization by using a Fluorolite FPM-2 Fluorescence Polarization Microtiter System (Dynatech Laboratories, Inc).

II. Conformnational Sensor—ELISA Format Assay

Buffer and Solution Preparation:
1. 10×Assay Buffer:
   100 mL of 1M Hepes
   300 mL of 5M NaCl
   20 mL of 1M MgCl
   Add MQ H2O to 1L
2. Master Mix of peptide/protein
   Protein: Glutathione-S-transferase/binding polypeptide fusion protein: final conc=100 nM
   LDL Receptor Interaction Domain peptide (size minimized, biotinylated; final conc.=1 uM)
   Add Assay Buffer and H2O to bring to final volume: final buffer conc=1×
3. Antibody Mix:
   anti-GST, rabbit (final con.=1:10,000)
   anti-rabbit-HRP (final conc.=1:10,000)
   Add T-TBS to bring to final volume: final buffer conc=1×

Procedure:
1. Make 50 mL of Master Mix (see 2 above) of appropriate peptide/polypeptide combinations (use 50 mL polypropylene tubes). Incubate for 1 hr at RT
2. Add 95 uL of Master Mix to each well of a 96-well plate Reacti-Bind Streptavidin-Coated, White Polystyrene Plates (#15118B), which have been blocked by Super-Blocking Reagent from Pierce.
3. Transfer 5 uL of each test compound (stock=60 uM) to each well of the plate
4. Incubate plate for 1 hr at RT
5. While incubating, make rabbit anti-GST antibody and anti-rabbit-HRP Antibody Mix (see 3 above). Incubate on ice for 1 hr.
6. Wash plates 3× with H2O thoroughly
7. Add 100 uL of Antibody Mix into each well of the plate
8. Incubate for 1 hr at RT
9. Wash 3× with H2O
10. Dilute Supersignal substrate (mixed Luminol and peroxide) in 1:2 H2O and then add 100 uL into each well
11. Shake 3–5 min. Read chemiluminescence.

III. High-Throughput In Vitro Binding Assay.

A. Reagents:
 Neutralite Avidin: 20 $\mu$g/ml in PBS.
 Blocking buffer: 5% BSA, 0.5% Tween 20 in PBS; 1 hour at room temperature.
 Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.
 $^{33}$P LDL Receptor Interaction Domain 10× stock: $10^{-8}$–$10^{-6}$ M "cold" interaction domain supplemented with 200,000–250,000 cpm of labeled interaction domain (Beckman counter). Place in the 4° C. microfridge during screening.
 Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (MB #1017128), 10 mg APMSF (BMB #917575), and 2mM NaVO$_3$ (Sigma #S-6508) in 10 ml of PBS.
 Binding Polypeptide: $10^{-7}$–$10^{-5}$ M biotinylated binding polypeptide in PBS.

B. Preparation of assay plates:
 Coat with 120 $\mu$l of stock N-Avidin per well overnight at 4° C.
 Wash 2 times with 200 $\mu$l PBS.
 Block with 150 $\mu$l of blocking buffer.
 Wash 2 times with 200 $\mu$l PBS.

C. Assay:
 Add 40 $\mu$l assay buffer/well.
 Add 10 $\mu$l compound or extract.
 Add 10 $\mu$l $^{33}$P-interaction domain(20–25,000 cpm/0.1–10 pmoles/well=$10^{-9}$–$10^{-7}$ M final conc).
 Shake at 25° C. for 15 minutes.
 Incubate additional 45 minutes at 25° C.
 Add 40 $\mu$M biotinylated binding polypeptide (0.1–10 pmoles/40 ul in assay buffer)
 Incubate 1 hour at room temperature.
 Stop the reaction by washing 4 times with 200 $\mu$M PBS.
 Add 150 $\mu$M scintillation cocktail.
 Count in Topcount.

D. Controls for all assays (located on each plate):
 a. Non-specific binding
 b. Soluble (non-biotinylated binding polypeptide) at 80% inhibition.

IV. Parental Binding Polypeptide Interaction with Natureal Sequence Interaction Domains Materials Restriction endonucleases and other DNA modifying enzymes (T4 DNA ligase, calf intenstinal alkaline phosphatase) were purchased from Boehringer Mannheim and New England Biolabs (Beverly, Mass.). The Taq polymerase and the TAKARA LA PCR Kit were obtained from Perkin Elmer and PANVERA, respectively. Glutathione-agarose was purchased from Sigma, Protease Inhibitor Cocktail from Boehringer Mannheim. The MATCH-MAKER LexA two-hybrid system used and yeast culture media were obtained from CLONTECH. Antibodies against LRP (13) and Megalin (11) have been described previously. Human LDL was iodinated using the iodine monochloride method (14).

Yeast Plasmid Construction and the Two-hybrid Assay

All LDL receptor family cytoplasmic tail LexA fusion proteins were constructed using the pLexA vector (MATCHMAKER system, CLONTECH). The cytoplasmic domains and Dab1 were amplified by PCR from human and mouse brain 1st strand cDNA or cDNA clones. PCR products were subcloned into the EcoRI and NcoI sites of pLexA for the Megalin and VLDL Receptor, and into EcoRI and BarnHI sites for the other receptors. The Dab-1 cDNA (2) was transferred via EcoRi and SaII into the EcoRI and XhoI digested prey plasmid pB42AD (MATCHMAKER system, CLONTECH). All constructs were sequenced after cloning, and all bait vectors were tested for self-activation. Bait and prey vectors were cotransfected into yeast cells (leucine auxotrophic strain EGY48) using the LiAc method as described in the MATCHMAKER manual (CLONTECH). The two-hybrid assay used two reporters (LEU2 and lacZ) under the control of LexA operators. Cells were spread on selective plates (His-;Leu-;Trp-) and grown for 3 days. Single clones were grown on selective plates in patches and harvested after 2–3 days. To recover DNA from yeast, cells were resuspended in 50 μl STES (0.5M NaCl, 0.2M Tris-HCl pH 7.6, 0.01M EDTA, 1% SDS). Glass beads were added and the cells vortexed vigorously. After addition of 20 μl H2O and 60 μl phenol/chloroform cells were vortexed for 1 more minute and centrifuged (14,000×g, 5 min). The aqueous phase was collected and the DNA was precipitated with EtOH. DNA from positive clones was retransformed into DH5α and checked by DNA sequencing. Yeast mating was performed after transformation of LexA plasmids into the yeast strain YM4271 following the instructions in the MATCHMAKER manual (CLONTECH).

Generation and Purification of Glutahione-S-transferase (GST)-fusion Proteins

GST-fusion plasmids of Dab1 and FE65 have been described previously (2). Positive clones derived from the yeast two-hybrid screen were cloned into pGEX-4T1 (Pharmacia) using the flanking EcoRI and XhoI restriction sites and verified by sequencing. Fusion proteins were expressed in BL21 or BL21 codon+ bacteria (Stratagene) following induction by 1 mM isopropyl-thio-D-galactopyranoside for 5h. Proteins were recovered by Triton lysis (phosphate buffered saline (PBS) with 1% Triton X-100, and Protease Inhibitor cocktail) and purified using glutathione-agarose beads.

In Vitro Binding Assay

Liver and kidney membrane extracts were prepared as described previously (15). Lysates were incubated with 50 μl of glutathione-agarose and 10 μg of the respective purified GST-fusion protein for 6 h at 4° C. Glutathione beads were washed rapidly three times in 150 mM NaCl, 10 mM Tris-HCl pH 7.5, 2 mM each MgC12, CaC12, and MnC12 for 10 min. SDS sample buffer was added to the supernatant or beads. Proteins were separated by electrophoresis on 4% (for Megalin) and 8% (for LRP) SDS-polyacrylamide gel electrophoresis under nonreducing conditions and analyzed by immunoblotting using specific antibodies (11,13) and ECL detection.

In Situ Hybridization

Templates used for in situ hybridization were amplified from mouse cDNA clones for LRP, Megalin, and ApoER2, and from the yeast-two-hybrid clones using the pB42AD2 primer in combination with primers specific for individual interacting clone (meg8, Semcap-1; meg11, Jip-1; meg20, Jip-2). PCR products were cloned into pCR2.1-TOPO or pCRII-TOPO (Invitrogen) and sequenced. For each labeling reaction, 0.5 μg of linearized template was transcribed using T7 RNA polymerase (Ambion, Tex.) and 100 μCi of 33P-UTP (Amersham).

Time-mated wild-type female mice at 13.5 days post coitum were anaesthetized with metofane and perfused via the left ventricle with PBS followed by 4% paraformaldehyde. Whole embryos were immersed overnight in 4% paraformaldehyde at 4° C., and subsequently transferred to PBS. The tissue was placed in 70% ethanol, dehydrated through graded ethanol solutions, cleared in xylene, and infused with paraffin. Sagittal sections were cut at 5 μm intervals and mounted on Vectabond-treated slides (Vector Laboratories).

In situ hybridization was performed on adjacent sections to determine the expression pattern of ApoER2, LRP, Megalin, SEMCAP-1, JIP-1 and JIP-2. Xylene was used to remove paraffin. Sections were then rehydrated through graded ethanol solutions, refixed in 4% paraformaldehyde, digested with Pronase (20 μg/ml Pronase for 7.5 min), and acetylated (0.1 M triethanolamine-HCL [pH 7.5]/0.25% acetic anhydride for 5 min). Slides were hybridized for 12 hr at 55° C. in a solution containing 50% formamide, 0.3% dextrane sulfate, 1× Denhardt's solution, 0.5 mg/ml tRNA, and 7.5×106 cpm/ml riboprobe. After hybridization, slides were washed in 5×SSC/100 mM DTT at 65° C. for 30 min, and covered with K.5 nuclear emulsion (Ilford) before exposure at 4° C. for 21 to 35 days.

Cell Lines and Tissue Culture

Cell lines containing the wild type LDL-Receptor (TR715-19) and the LDL receptor containing a stop codon in the cytoplasmic domain at position 807 (TR807-3) have been published previously (16,17). The plasmid pcDNA3.1/ZEO DAB555 contains the mouse Dab1 cDNA under control of the CMV promoter in the pcDNA3.1/ZEO(+) vector (Invitrogen) and was used to create Dab1 overexpressing cell lines derived from TR715-19 and TR807-3, designated TR 3097 and TR 3098, respectively. Multiple clones were generated after transfection and Zeocin selection and analyzed for levels of LDLR and Dab1 expression by immunoblotting using specific antibodies and ECL detection. All cell lines were maintained in Dulbecco's rninimal essential medium (DMEM) with 100 units/ml penicillin, and 100 μg/ml streptomycin sulfate, supplemented with 5% (v/v) fetal calf serum (Life Technologies, Inc., Grand Island, N.Y.).

Cellular Binding and Degradation Assays

For uptake, binding, and degradation assays, the cells were plated in 6-well plates at a cell density of 60,000 cells/well in Medium A (1:1 mixture of Dulbecco's minimal essential medium and Ham's F-12 medium) supplemented with 100 units/ml penicillin, 100 μg/ml streptomycin sulfate, and with 5% (v/v) fetal calf serum. On day 2, the cells were washed twice with PBS and re-fed with medium A containing 5% (v/v) newborn calf lipoprotein-deficient serum, 10 μM compactin, and 100 μM mevalonate. On day 3 the cells were washed twice with PBS and switched to medium B (Dulbecco's modified Eagle's medium (minus glutamine) containing 2 mg/ml fatty acid-free bovine serum albumin) with $^{125}$I-LDL. After 1, 3, and 5 h, the medium and the cells were harvested and surface binding, uptake, and degradation were measured as previously described (17).

Results

To identify other adaptor proteins besides Dab1 and FE65 that interact with the cytoplasmic tails of LDL receptor family members we performed a series of yeast-two-hybrid screens of various tail bait constructs against a panel of commercially available libraries (described in detail in 'Methods'). The genes that were identified in these screens and that survived specificity testing include natural murine homologs of the parental sequences shown in Table I. Most of these genes have known functions that are related to cell adhesion, cell activation, reorganization of the cytoskeleton and neurotransmission. Dab1 has previously been shown to bind to the cytoplasmic tails of LDL receptor family members (2,3). JIP-1 and JIP-2 are scaffolding proteins for components of the Jun N-terminal Kinase (JNK) signaling pathway (18) and JIP-1 was recently shown to also interact with p190 rhoGEF (19). SEMCAP-1 is an adaptor protein that can bind to the cytoplasmic tails of membrane proteins such as SemF (20) and LDL receptor family members, but also to the cytoplasmic and membrane associated regulation of G-protein signaling (RGS) protein GAIP (21). Mint1, or X11, is another scaffold protein that interacts with the cytoplasmic tail of the amyloid precursor protein (APP) via its phosphotyrosine binding (PTB) domain, and with the presynaptic protein Munc-18 via its amino terminus (22). Munc-18 is necessary for synaptic vesicle exocytosis (23). CAPON is a PTB domain containing adaptor protein that was shown to bind neuronal nitric oxide synthase (nNOS) and is thought to dislodge nNOS from the postsynaptic density protein PSD-95, thus inactivating the enzyme (24). PSD-95, a scaffolding protein that organizes active components of the postsynaptic neurotransmission machinery such as glutamate receptors, K-channels, kinases and nNOS into functional microdomains (25) was also found to interact directly with LDL receptor family tails. Although it does not contain a PTB domain, the integrin cytoplasmic domain associated protein-1 (ICAP-1) binds to an NPxY sequence motif in the integrin tail (26,27) and thus presumably also to the NPxY motifs that are present in the cytoplasmic tails of all LDL receptor family members (2). Omp25 is an outer mitochondrial membrane protein that contains a PDZ domain and thereby interacts with the inositol phosphatase synaptojanin, a protein thought to be involved in the recycling of synaptic vesicles (28). Another protein that is homologous to phosphatidyl inositol 4,5 kinase and therefore is presumably involved in inositol metabolism was also identified in our screen. A close homologue of the cytoskeletal protein talin, the α subunit of the brain-specific sodium channel 3 and APC10, a component of the anaphase promoting complex also bound directly to LDL receptor family tails by yeast-two-hybrid interaction.

Next, we determined the binding specificity of each of the proteins that had been identified in the initial screens against a panel of bait constructs containing the whole or part of the cytoplasmic tails of the presently known LDL receptor family members. The tail sequences contained in these bait constructs are shown in Table 3.

TABLE 3

LDL receptor two-hybrid bait sequences

| Bait Sequence | Sequence Source | Source Residues |
| --- | --- | --- |
| SEQ ID NO:121 | LDLR human | 2431–2583 |
| SBQ ID NO:122 | VLDLR mouse | 2477–2641 |
| SEQ ID NO:123 | LR11 human | 6557–6714 |
| SEQ ID NO:124 | ApoER2– mouse | 1925–2104 |
| SEQ ID NO:125 | ApoER2+ mouse | 2642–2998 |
| SEQ ID NO:126 | MegA human | 13457–14073 |
| SEQ ID NO:127 | Meg human | 13457–13748 |
| SEQ ID NO:128 | MegC human | 13761–14073 |
| SEQ ID NO:129 | MegB human | 13682–13886 |
| SEQ ID NO:130 | LRPA human | 13808–13921 |
| SEQ ID NO:131 | LRPB human | 13808–14035 |
| SEQ ID NO:132 | LRP human | 13808–14103 |

The ApoER2 tail was tested with (+) and without (−) its alternatively spliced insert. For Megalin and for LRP the complete tails and parts thereof containing a single NPxY motif were tested separately. Dab1 bound strongly to all the LDL receptor family tails, but only to one of the NPxY motifs in the LRP and Megalin tail (LRPB and MegA, respectively). LRP and Megalin have the longest cytoplasmic tails that contain several potential adaptor binding motifs and thus bound most of the proteins. In contrast, the LDL receptor and the VLDL receptor bound only Dab1 (2, 3). Interestingly, the ApoER2 tail containing the alternatively spliced insert bound the scaffold proteins JIP-1, JIP-2 and PSD-95, while the tail without this insert did not. This suggests that the alternative splicing of the ApoER2 tail has important regulatory functions and may determine the ability of ApoER2 to activate MAP kinase dependent signals.

Next, we sought to determine whether the protein interactions we had found in the yeast-two-hybrid screen could be reproduced by a different approach, such as a biochemical pull-down assay. The respective cDNA fragments were cut out from the yeast prey vector and cloned into a bacterial GST expression vector. GST fusion proteins were incubated with membrane extracts from liver (LRP) and kidney (Megalin). GST alone served as a negative control, Dab1 and FE65 served as positive controls for interactions of fusion proteins with LRP. Binding of FE65 was specific for LRP, Dab1 bound to both receptors, consistent with the two-hybrid results. All other fusion proteins tested, with the exception of the talin homologue and Mint-1, bound to both native Megalin and LRP in membrane extracts.

Our experiments so far have revealed a spectrum of cytoplasmic adaptor or scaffold proteins that can interact with the cytoplasmic tails of LDL receptor family members in vivo. In the case of Dab1, there is strong genetic and biochemical evidence that binding of this protein to the tails of the VLDL receptor and ApoER2 is absolutely required for the transmission of a critical developmental signal to migrating neurons (2,3,10). However, as we have shown, Dab1 not only interacted with these two receptors, but in fact bound tightly to the tails of all known members of the LDL receptor gene family. Whether these interactions occur only under in vitro conditions or also take place in vivo was not known. To address this question we examined the effect of Dab1 expression on the activity of the LDL receptor in cultured cells. Chinese hamster ovary (CHO) cells expressing the wild type human LDL receptor with or without its cytoplasmic tail (Chen et al., 1990) were transfected with a Dab1 expression plasmid. Stable cell lines that expressed approximately equal amounts of Dab1 were selected. All four cell lines were then tested for their ability to bind, internalize and degrade $^{125}$I labeled human LDL. Cell lines expressing the human LDL receptor without a cytoplasmic tail bound, internalized and degraded the human LDL to the same extent, whether Dab1 was present or not. In contrast, CHO cells expressing the wild type human LDL receptor bound approximately 2 times more LDL on their surface when Dab1 was present. Cellular uptake was not significantly affected by Dab1 expression, although the degradation rate was slightly reduced. These findings indicate that Dab1 binds to a site in the LDL receptor tail that overlaps with the endocytosis signal, and thereby increases the surface pool of the receptor by competing with the assembly of the endocytosis complex.

Our yeast-two-hybrid screen has revealed a number of other scaffold and adaptor proteins that function in cellular signaling cascades in which Dab1 is not yet known to be involved. Two of these proteins, JIP-1 and JIP-2, serve as scaffolding proteins for MAP kinases, and SEMCAP-1 is an adaptor protein that can also bind to the C-terminus of the GTPase activating RGS protein GAIP. Membrane-associated SEMCAP-1 colocalizes with clathrin and is primarily found in vesicles just underneath the plasma membrane, a compartment where LDL receptor family members also reside. In addition to the demonstrated role of LDL receptor family members and Dab1 in cellular tyrosine kinase signaling, recruitment of MAP kinases and interactions with RGS proteins considerably expands the functional roles of this class of cell surface receptors. We tested whether LDL receptor gene family members are expressed together with these adaptors and may thus functionally interact with them in vivo. We used in situ hybridization to compare the expression pattern of ApoER2, LRP and Megalin with that of SEMCAP-1, JIP-1 and JIP-2 during embryonic development of the brain, a time period in which these LDL receptor family members perform critical functions. At E13.5 ApoER2 was expressed throughout the brain in a pattern almost identical to that of JIP-1 and JIP-2. SEMCAP-1 also showed a largely overlapping expression pattern. Notably, JIP-1 and JIP-2 were predominantly expressed in the more superficial cortical plate, while SEMCAP-1 was mainly expressed in the subventricular zone and in the population of migrating neurons in the developing cortex. ApoER2 was present throughout the cortex. In contrast, LRP expression in the developing brain was comparatively low and restricted mainly to the choroid plexus, and Megalin was almost exclusively expressed in the ventricular zone. SEMCAP-1 and JIP-1 were expressed in the structures as LRP and Megalin.

NUMERICAL REFERENCES

2. Trommsdorff, M., Borg, J. P., Margolis, B., and Herz, J. (1998) J Biol Chem 273(50), 33556–60
3. Trommsdorff, M., Gotthardt, M., Hiesberger, T., Shelton, J., Stockinger, W., Nimpf, J., Hammer, R. E., Richardson, J. A., and Herz, J. (1999) Cell 97(6), 689–701
11. Willnow, T. E., Hilpert, J., Armstrong, S. A., Rohlmann, A., Hammer, R. E., Burns, D. K., and Herz, J. (1996) Proc Natl Acad Sci U S A 93(16), 8460–4
13. Herz, J., Hamann, U., Rogne, S., Myklebost, O., Gausepohl, H., and Stanley, K. K. (1988) Embo J 7(13), 4119–27
14. Goldstein, J. L., Basu, S. K., and Brown, M. S. (1983) Methods Enzymol 98, 241–60
15. Kowal, R. C., Herz, J., Weisgraber, K. H., Mahley, R. W., Brown, M. S., and Goldstein, J. L. (1990) J Biol Chem 265(18), 10771–9
16. van Driel, I. R., Goldstein, J. L., Sudhof, T. C., and Brown, M. S. (1987) J Biol Chem 262(36), 17443–9
17. Chen, W. -J., Goldstein, J. L., and Brown, M. S. (1990) J.Biol.Chem. 265, 3116–3123
18. Yasuda, J., Whitmarsh, A. J., Cavanagh, J., Sharma, M., and Davis, R. J. (1999) Mol Cell Biol 19(10), 7245–54
19. Meyer, D., Liu, A., and Margolis, B. (1999) J Biol Chem 274(49), 35113–8
20. Wang, L. H., Kalb, R. G., and Strittmatter, S. M. (1999) J Biol Chem 274(20), 14137–46
21. De Vries, et al.. (1998) Proc Natl Acad Sci U S A 95(21), 12340–5
22. Okamoto, M., and Sudhof, T. C. (1997) J Biol Chem 272(50), 31459–64
23. Hata, Y., Slaughter, C. A., and Sudhof, T. C. (1993) Nature 366(6453), 347–51
24. Jaffrey, S. R., Snowman, A. M., Eliasson, M. J., Cohen, N. A., and Snyder, S. H. (1998) Neuron 20(1), 115–24
25. Sheng, M., and Pak, D. T. (1999) Ann N Y Acad Sci 868, 483–93
26. Zhang, X. A., and Hemler, M. E. (1999) J Biol Chem 274(1), 11–9
27. Chang, D. D., Wong, C., Smith, H., and Liu, J. (1997) J Cell Biol 138(5), 1149–57
28. Nemoto, Y., and De Camilli, P. (1999) Embo J 18(11), 2991–3006
29. Jimenez, B., et al. (2000) Nat Med 6(1), 41–8.

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for identifying a candidate drug which may alter low density liproprotein (LDL) receptor function by altering aninteraction of the LDL receptor with a native interacellular LDL receptor binding polypeptide, the method comprising steps:

providing a system which comprises the binding polypeptide and a corresponding binding polypeptide interaction domain of the LDL receptor, introducing a test compound into the system and detecting a resultant level of binding between the binding polypeptide and the interaction domain, wherein a difference in the level of binding as compared to that of the system without the test compound indicates that the compound is a candidate drug, wherein the binding polypeptide is PSD-95 (postsynaptic density-95).

2. A method according to claim 1, wherein the system is a two-hybrid assay.

3. A method according to claim 1, wherein the system is a biochemical pull-down assay.

4. A method according to claim 1, wherein the system is a high-throughput, in vitro fluorescent polarization assay.

5. A method according to claim 1, wherein the system is a high-throughput, in vitro fluorescent binding assay.

6. A method according to claim 1, wherein the system is a high-throughput, conformational sensor-solid-phase chemiluminescence assay.

7. A method according to claim 1, wherein the system is a cell expressing both the binding polypeptide and the interaction domain.

8. A method according to claim 1, wherein the system is an in vitro, cell-free mixture comprising a determined amount of the binding polypeptide and the interaction domain.

9. A method according to claim 1, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

10. A method according to claim 2, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

11. A method according to claim 3, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

12. A method according to claim 4, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

13. A method according to claim 5, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

14. A method according to claim 6, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

15. A method according to claim 7, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

16. A method according to claim 8, wherein the LDL receptor is selected from very low density lipoprotein receptor (VLDLR), apolipoprotein E receptor-2 (ApoER2), low density lipoprotein receptor (LDLR), low density lipoprotein receptor related protein (LRP), MEGF7 and Megalin.

* * * * *

UNITED STATES PATENT AND TRADEMARK OFFICE
CERTIFICATE OF CORRECTION

PATENT NO.    : 6,428,967 B1
DATED         : August 6, 2002
INVENTOR(S)   : Herz et al.

It is certified that error appears in the above-identified patent and that said Letters Patent is hereby corrected as shown below:

<u>Column 371,</u>
Line 27, "aninteraction" should be -- an interaction --.
Line 48, between "in vitro" and "binding assay" should be -- solid-phase --

Signed and Sealed this

Twenty-fourth Day of December, 2002

JAMES E. ROGAN
*Director of the United States Patent and Trademark Office*